US009626650B2

(12) United States Patent
Hwang et al.

(10) Patent No.: US 9,626,650 B2
(45) Date of Patent: Apr. 18, 2017

(54) COST-EFFECTIVE RESOURCE APPORTIONMENT TECHNOLOGIES SUITABLE FOR FACILITATING THERAPIES

(75) Inventors: Eun Young Hwang, San Francisco, CA (US); Roderick A. Hyde, Redmond, WA (US); Muriel Y. Ishikawa, Livermore, CA (US); Jordin T. Kare, Seattle, WA (US); Dennis J. Rivet, Chesapeake, VA (US); Elizabeth A. Sweeney, Seattle, WA (US); Clarence T. Tegreene, Mercer Island, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/066,442

(22) Filed: Apr. 14, 2011

(65) Prior Publication Data

US 2012/0265544 A1    Oct. 18, 2012

Related U.S. Application Data

(63) Continuation-in-part of application No. 13/066,444, filed on Apr. 14, 2011, and a continuation-in-part of
(Continued)

(51) Int. Cl.
*G06Q 10/10* (2012.01)
*G06F 19/00* (2011.01)
*G06Q 50/24* (2012.01)

(52) U.S. Cl.
CPC ......... *G06Q 10/10* (2013.01); *G06F 19/3456* (2013.01); *G06F 19/3462* (2013.01); *G06Q 50/24* (2013.01)

(58) Field of Classification Search
CPC ..... G06Q 10/10; G06Q 50/24; G06F 19/3456
(Continued)

(56) References Cited

U.S. PATENT DOCUMENTS 5,485,827 A * 1/1996 Zapol et al. ............. 128/200.14
5,537,314 A    7/1996 Kanter
(Continued)

FOREIGN PATENT DOCUMENTS

WO    WO 03-050646 A2    6/2003

OTHER PUBLICATIONS

Claassen, Dirk et al.; "Money for medication: financial incentives to improve medication adherence in assertive outreach"; The Psychiatrist, Psychiatric Bulletin; 2007; pp. 4-7; vol. 31.
(Continued)

*Primary Examiner* — Minnah Seoh

(57) ABSTRACT

Configuration technologies for apportioning resources and communicating indications of potential or actual incentives based on one or more measurements or other objective indications that therapeutic components have been administered to an individual, other attributes of the therapeutic components or the individual, or other such determinants. Techniques for apportioning resources cost-effectively (between providers and other parties, e.g.) and for facilitating or handling implementations thereof or output therefrom.

27 Claims, 22 Drawing Sheets

Related U.S. Application Data application No. 13/066,441, filed on Apr. 14, 2011, and a continuation-in-part of application No. 13/066,454, filed on Apr. 14, 2011, and a continuation-in-part of application No. 13/066,445, filed on Apr. 14, 2011, and a continuation-in-part of application No. 13/066,443, filed on Apr. 14, 2011.

(58) Field of Classification Search
USPC ........................................................ 705/2–3
See application file for complete search history.

(56) References Cited

U.S. PATENT DOCUMENTS

| | | |
|---|---|---|
| 5,544,044 A | 8/1996 | Leatherman |
| 5,576,952 A | 11/1996 | Stutman et al. |
| 5,601,811 A | 2/1997 | Gallagher et al. |
| 5,676,138 A | 10/1997 | Zawilinski |
| 5,724,983 A | 3/1998 | Selker et al. |
| 5,755,741 A | 5/1998 | Vogel |
| 5,771,261 A | 6/1998 | Anbar |
| 5,915,241 A | 6/1999 | Giannini |
| 5,978,693 A | 11/1999 | Hamilton et al. |
| 5,991,731 A | 11/1999 | Colon et al. |
| 6,007,986 A | 12/1999 | Sadee |
| 6,011,835 A | 1/2000 | Rathore et al. |
| 6,025,128 A | 2/2000 | Veltri et al. |
| 6,035,230 A | 3/2000 | Kang et al. |
| 6,041,737 A | 3/2000 | Hennigan |
| 6,061,657 A | 5/2000 | Whiting-O'Keefe |
| 6,064,318 A | 5/2000 | Kirchner, III et al. |
| 6,117,087 A | 9/2000 | Kamm et al. |
| 6,136,801 A | 10/2000 | Kell |
| 6,151,586 A | 11/2000 | Brown |
| 6,168,563 B1 | 1/2001 | Brown |
| 6,179,793 B1 | 1/2001 | Rothman et al. |
| 6,198,383 B1 | 3/2001 | Sekura et al. |
| 6,198,695 B1 | 3/2001 | Kirton et al. |
| 6,208,974 B1 | 3/2001 | Campbell et al. |
| 6,216,104 B1 | 4/2001 | Moshfeghi et al. |
| 6,234,964 B1 | 5/2001 | Iliff |
| 6,240,394 B1 | 5/2001 | Uecker et al. |
| 6,245,511 B1 | 6/2001 | Gulati |
| 6,246,992 B1 | 6/2001 | Brown |
| 6,261,101 B1 | 7/2001 | Benitz et al. |
| 6,263,243 B1 | 7/2001 | Lang |
| 6,268,145 B1 | 7/2001 | Hoffman et al. |
| 6,282,516 B1 | 8/2001 | Giuliani |
| 6,292,688 B1 | 9/2001 | Patton |
| 6,305,943 B1 | 10/2001 | Pougatchev et al. |
| 6,306,614 B1 | 10/2001 | Romaschin et al. |
| 6,312,378 B1 | 11/2001 | Bardy |
| 6,317,731 B1 | 11/2001 | Luciano |
| 6,324,393 B1 | 11/2001 | Doshay |
| 6,329,153 B1 | 12/2001 | Stein et al. |
| 6,332,502 B1 | 12/2001 | Mills et al. |
| 6,336,048 B1 | 1/2002 | Bonnet |
| 6,336,903 B1 | 1/2002 | Bardy |
| 6,347,239 B1 | 2/2002 | Arnold et al. |
| 6,352,053 B1 | 3/2002 | Records et al. |
| 6,358,201 B1 | 3/2002 | Childre et al. |
| 6,366,848 B1 | 4/2002 | Gustavsson |
| 6,371,931 B1 | 4/2002 | Guillen |
| 6,375,038 B1 | 4/2002 | Daansen et al. |
| 6,379,393 B1 | 4/2002 | Mavroidis et al. |
| 6,383,135 B1 | 5/2002 | Chikovani et al. |
| 6,393,404 B2 | 5/2002 | Waters et al. |
| 6,402,371 B2 | 6/2002 | Pompei et al. |
| 6,413,223 B1 | 7/2002 | Yang et al. |
| 6,434,534 B1 | 8/2002 | Walker et al. |
| 6,442,421 B1 | 8/2002 | Le Van Quyen et al. |
| 6,461,830 B1 | 10/2002 | Parrott |
| 6,473,646 B2 | 10/2002 | Sun et al. |
| 6,478,737 B2 | 11/2002 | Bardy |
| 6,494,579 B1 | 12/2002 | Weiss |
| 6,505,051 B1 | 1/2003 | Alperovich et al. |
| 6,514,200 B1 | 2/2003 | Khouri |
| 6,520,919 B1 | 2/2003 | Nunome et al. |
| 6,533,724 B2 | 3/2003 | McNair |
| 6,542,767 B1 | 4/2003 | McNichols et al. |
| 6,552,531 B1 | 4/2003 | Fey et al. |
| 6,561,811 B2 | 5/2003 | Rapoza et al. |
| 6,566,064 B1 | 5/2003 | Shiraki et al. |
| 6,569,095 B2 | 5/2003 | Eggers |
| 6,575,169 B2 | 6/2003 | McMichael |
| 6,581,606 B2 | 6/2003 | Kutzko et al. |
| 6,581,607 B2 | 6/2003 | Kutzko et al. |
| 6,585,518 B1 | 7/2003 | Jenkins et al. |
| 6,600,949 B1 | 7/2003 | Turcott |
| 6,613,573 B1 | 9/2003 | Cohen |
| 6,623,972 B2 | 9/2003 | Malin et al. |
| 6,638,217 B1 | 10/2003 | Liberman |
| 6,643,646 B2 | 11/2003 | Su et al. |
| 6,645,142 B2 | 11/2003 | Braig et al. |
| 6,651,592 B2 | 11/2003 | Maddox et al. |
| 6,655,583 B2 | 12/2003 | Walsh et al. |
| 6,656,116 B2 | 12/2003 | Kim et al. |
| 6,658,323 B2 | 12/2003 | Tedesco et al. |
| 6,659,959 B2 | 12/2003 | Brockway et al. |
| 6,663,846 B1 | 12/2003 | McCombs et al. |
| 6,671,548 B1 | 12/2003 | Mouchawar et al. |
| 6,689,069 B2 | 2/2004 | Bratteli et al. |
| 6,694,177 B2 | 2/2004 | Eggers et al. |
| 6,699,124 B2 | 3/2004 | Suchocki |
| 6,699,188 B2 | 3/2004 | Wessel |
| 6,718,007 B1 | 4/2004 | James |
| 6,731,976 B2 | 5/2004 | Penn et al. |
| 6,739,508 B2 | 5/2004 | Ushioda et al. |
| 6,740,042 B1 | 5/2004 | Lerner et al. |
| 6,750,053 B1 | 6/2004 | Widrig Opalsky et al. |
| 6,752,145 B1 | 6/2004 | Bonney et al. |
| 6,755,783 B2 | 6/2004 | Cosentino et al. |
| 6,770,029 B2 | 8/2004 | Iliff |
| 6,817,980 B2 | 11/2004 | Iliff |
| 6,839,678 B1 | 1/2005 | Schmidt et al. |
| 6,852,086 B2 | 2/2005 | Atlas et al. |
| 6,879,959 B1 | 4/2005 | Chapman et al. |
| 6,881,192 B1 | 4/2005 | Park |
| 6,882,278 B2 | 4/2005 | Winings et al. |
| 6,884,223 B2 | 4/2005 | Kleibohmer et al. |
| 6,893,396 B2 | 5/2005 | Schulze et al. |
| 6,895,307 B2 | 5/2005 | Gardner, Jr. |
| 6,901,347 B1 | 5/2005 | Murray et al. |
| 6,920,372 B2 | 7/2005 | Nickerson et al. |
| 6,926,667 B2 | 8/2005 | Khouri |
| 6,926,668 B2 | 8/2005 | Bardy |
| 6,941,466 B2 | 9/2005 | Mastrianni |
| 6,942,616 B2 | 9/2005 | Kerr, II |
| 6,942,619 B2 | 9/2005 | Toda |
| 6,942,626 B2 | 9/2005 | Salisbury et al. |
| 6,952,678 B2 | 10/2005 | Williams et al. |
| 6,968,375 B1 | 11/2005 | Brown |
| 6,973,371 B1 | 12/2005 | Benouali |
| 6,975,231 B2 | 12/2005 | Lane et al. |
| 6,975,232 B1 | 12/2005 | McKenna |
| 6,978,177 B1 | 12/2005 | Chen et al. |
| 6,978,182 B2 | 12/2005 | Mazar et al. |
| 6,979,293 B2 | 12/2005 | Hansmann et al. |
| 6,980,851 B2 | 12/2005 | Zhu et al. |
| 6,980,958 B1 | 12/2005 | Surwit et al. |
| 6,980,960 B2 | 12/2005 | Hajdukiewicz et al. |
| 6,983,178 B2 | 1/2006 | Fine et al. |
| 6,984,207 B1 | 1/2006 | Sullivan et al. |
| 6,988,088 B1 | 1/2006 | Mukkulainen et al. |
| 6,988,132 B2 | 1/2006 | Horvitz |
| 6,988,498 B2 | 1/2006 | Berthon-Jones et al. |
| 6,989,891 B2 | 1/2006 | Braig et al. |
| 6,998,230 B1 | 2/2006 | Schantz et al. |
| 7,003,346 B2 | 2/2006 | Singer |
| 7,004,907 B2 | 2/2006 | Banet et al. |
| 7,016,854 B2 | 3/2006 | Himes |
| 7,024,234 B2 | 4/2006 | Margulies et al. |
| 7,027,871 B2 | 4/2006 | Burnes et al. |
| 7,027,935 B2 | 4/2006 | Shimase et al. |

(56) References Cited

U.S. PATENT DOCUMENTS

| | | |
|---|---|---|
| 7,035,684 B2 | 4/2006 | Lee |
| 7,037,273 B2 | 5/2006 | Zhu et al. |
| 7,041,468 B2 | 5/2006 | Drucker et al. |
| 7,047,083 B2 | 5/2006 | Gunderson et al. |
| 7,054,688 B1 | 5/2006 | Uhrenius et al. |
| 7,058,591 B2 | 6/2006 | Guiliani et al. |
| 7,062,312 B2 | 6/2006 | Gonzales et al. |
| 7,063,782 B2 | 6/2006 | Wayment et al. |
| 7,072,842 B2 | 7/2006 | Provost et al. |
| 7,079,035 B2 | 7/2006 | Bock et al. |
| 7,086,269 B2 | 8/2006 | Sauder et al. |
| 7,086,399 B2 | 8/2006 | Makinson et al. |
| 7,087,903 B2 | 8/2006 | Balan et al. |
| 7,103,154 B1 | 9/2006 | Cannon et al. |
| 7,107,095 B2 | 9/2006 | Manolas |
| 7,117,653 B2 | 10/2006 | Yakushigawa et al. |
| 7,118,531 B2 | 10/2006 | Krill |
| 7,120,592 B1 | 10/2006 | Lewis |
| 7,122,322 B2 | 10/2006 | Timms |
| 7,125,681 B2 | 10/2006 | Knuth et al. |
| 7,127,253 B2 | 10/2006 | Chen |
| 7,127,370 B2 | 10/2006 | Kelly, Jr. et al. |
| 7,128,713 B2 | 10/2006 | Moehring et al. |
| 7,128,877 B2 | 10/2006 | Quay et al. |
| 7,132,238 B2 | 11/2006 | Danengberg |
| 7,138,240 B2 | 11/2006 | Barak et al. |
| 7,141,016 B2 | 11/2006 | Lykke et al. |
| 7,155,281 B1 | 12/2006 | Fayram |
| 7,162,437 B2 | 1/2007 | Shaak et al. |
| 7,165,033 B1 | 1/2007 | Liberman |
| 7,166,063 B2 | 1/2007 | Rahman et al. |
| 7,170,823 B2 | 1/2007 | Fabricius et al. |
| 7,171,251 B2 | 1/2007 | Sarussi et al. |
| 7,174,302 B2 | 2/2007 | Patricelli et al. |
| 7,177,684 B1 | 2/2007 | Kroll et al. |
| 7,177,686 B1 | 2/2007 | Turcott |
| 7,179,612 B2 | 2/2007 | Fischer et al. |
| 7,181,054 B2 | 2/2007 | Zaleski |
| 7,184,963 B1 | 2/2007 | Shannon |
| 7,185,650 B2 | 3/2007 | Huber et al. |
| 7,194,301 B2 | 3/2007 | Jenkins et al. |
| 7,194,416 B1 | 3/2007 | Provost et al. |
| 7,195,598 B2 | 3/2007 | Fuchs et al. |
| 7,200,431 B2 | 4/2007 | Franco et al. |
| 7,200,652 B2 | 4/2007 | Cheston et al. |
| 7,211,397 B2 | 5/2007 | Mikolajczyk et al. |
| 7,222,075 B2 | 5/2007 | Petrushin |
| 7,223,237 B2 | 5/2007 | Shelchuk |
| 7,223,246 B2 | 5/2007 | Don |
| 7,225,013 B2 | 5/2007 | Geva et al. |
| 7,226,415 B2 | 6/2007 | Haddad et al. |
| 7,226,422 B2 | 6/2007 | Hatlestsad et al. |
| 7,226,792 B2 | 6/2007 | Roberts et al. |
| 7,233,015 B2 | 6/2007 | Roberts |
| 7,233,913 B2 | 6/2007 | Scroggie et al. |
| 7,242,308 B2 | 7/2007 | Ulrich et al. |
| 7,246,619 B2 | 7/2007 | Truschel et al. |
| 7,248,171 B2 | 7/2007 | Mishelevich |
| 7,249,263 B2 | 7/2007 | Chaudhari et al. |
| 7,250,855 B2 | 7/2007 | Suenbuel et al. |
| 7,252,959 B2 | 8/2007 | Rand |
| 7,254,432 B2 | 8/2007 | Fine |
| 7,254,563 B1 | 8/2007 | Gelfer |
| 7,255,987 B1 | 8/2007 | Andersson et al. |
| 7,257,365 B2 | 8/2007 | He et al. |
| 7,258,534 B2 | 8/2007 | Fathallah et al. |
| 7,258,666 B2 | 8/2007 | Brown |
| 7,261,690 B2 | 8/2007 | Teller et al. |
| 7,264,591 B2 | 9/2007 | Brown |
| 7,269,476 B2 | 9/2007 | Ratnakar |
| 7,271,728 B2 | 9/2007 | Taylor et al. |
| 7,271,896 B2 | 9/2007 | Chan et al. |
| 7,272,212 B2 | 9/2007 | Eberle et al. |
| 7,272,435 B2 | 9/2007 | Rowlandson |
| 7,273,277 B2 | 9/2007 | Sarver |
| 7,275,867 B2 | 10/2007 | Lee |
| 7,280,858 B2 | 10/2007 | Al-Ali et al. |
| 7,282,028 B2 | 10/2007 | Kim et al. |
| 7,283,962 B2 | 10/2007 | Meyerhoff et al. |
| 7,285,090 B2 | 10/2007 | Stivoric et al. |
| 7,287,031 B1 | 10/2007 | Karpf et al. |
| 7,289,927 B2 | 10/2007 | Bedard et al. |
| 7,289,949 B2 | 10/2007 | Warner et al. |
| 7,293,645 B2 | 11/2007 | Harper et al. |
| 7,295,890 B2 | 11/2007 | Jean-Pierre |
| 7,297,108 B2 | 11/2007 | Iliff |
| 7,297,280 B2 | 11/2007 | Krivitski et al. |
| 7,298,256 B2 | 11/2007 | Sato et al. |
| 7,299,944 B2 | 11/2007 | Roady et al. |
| 7,304,580 B2 | 12/2007 | Sullivan et al. |
| 7,305,262 B2 | 12/2007 | Brodnick et al. |
| 7,308,292 B2 | 12/2007 | Colvin et al. |
| 7,314,411 B2 | 1/2008 | Lannert et al. |
| 7,315,825 B2 | 1/2008 | Rosenfeld et al. |
| 7,319,386 B2 | 1/2008 | Collins, Jr. et al. |
| 7,321,862 B2 | 1/2008 | Rosenfeld et al. |
| 7,330,101 B2 | 2/2008 | Sekura |
| 7,331,928 B2 | 2/2008 | Seki et al. |
| 7,334,541 B2 | 2/2008 | Reiter |
| 7,335,106 B2 | 2/2008 | Johnson |
| 7,335,166 B2 | 2/2008 | Faupel et al. |
| 7,340,293 B2 | 3/2008 | McQuilkin |
| 7,340,296 B2 | 3/2008 | Stahmann et al. |
| 7,340,393 B2 | 3/2008 | Mitsuyoshi |
| 7,346,522 B1 | 3/2008 | Baylor et al. |
| 7,347,200 B2 | 3/2008 | Jones et al. |
| 7,356,364 B1 | 4/2008 | Bullock et al. |
| 7,359,866 B2 | 4/2008 | Farat |
| 7,361,306 B2 | 4/2008 | Bote Bote |
| 7,366,571 B2 | 4/2008 | Armstrong |
| 7,369,476 B2 | 5/2008 | Kravtchenko et al. |
| 7,369,919 B2 | 5/2008 | Vonk et al. |
| 7,373,318 B2 | 5/2008 | Kutsumi et al. |
| 7,375,640 B1 | 5/2008 | Plost |
| 7,376,700 B1 | 5/2008 | Clark et al. |
| 7,379,885 B1 | 5/2008 | Zakim |
| 7,380,707 B1 | 6/2008 | Fredman |
| 7,382,263 B2 | 6/2008 | Danowski et al. |
| 7,386,595 B1 | 6/2008 | Bloomer, Jr. et al. |
| 7,389,245 B1 | 6/2008 | Ashford et al. |
| 7,395,103 B2 | 7/2008 | Cappo et al. |
| 7,395,214 B2 | 7/2008 | Shillingburg |
| 7,395,216 B2 | 7/2008 | Rosenfeld et al. |
| 7,396,511 B2 | 7/2008 | Fujii et al. |
| 7,397,380 B1 | 7/2008 | Smolsky |
| 7,398,248 B2 | 7/2008 | Phillips et al. |
| 7,399,276 B1 | 7/2008 | Brown et al. |
| 7,400,257 B2 | 7/2008 | Rivas |
| 7,404,796 B2 | 7/2008 | Ginsberg |
| 7,406,480 B2 | 7/2008 | Seibel et al. |
| 7,407,762 B2 | 8/2008 | Auersperg |
| 7,412,396 B1 | 8/2008 | Haq |
| 7,414,534 B1 | 8/2008 | Kroll et al. |
| 7,415,447 B2 | 8/2008 | Shiffman et al. |
| 7,416,544 B2 | 8/2008 | Sakaguchi et al. |
| 7,418,400 B1 | 8/2008 | Lorenz |
| 7,421,410 B1 | 9/2008 | Schechtman et al. |
| 7,427,266 B2 | 9/2008 | Ayer et al. |
| 7,430,515 B1 | 9/2008 | Wolfe et al. |
| 7,430,554 B1 | 9/2008 | Heisinger, Jr. |
| 7,433,834 B2 | 10/2008 | Joao |
| 7,434,541 B2 | 10/2008 | Kates |
| 7,435,225 B2 | 10/2008 | Hietala |
| 7,437,195 B2 | 10/2008 | Policker et al. |
| 7,442,180 B2 | 10/2008 | Vitello et al. |
| 7,447,643 B1 | 11/2008 | Olson et al. |
| 7,448,249 B1 | 11/2008 | Smith |
| 7,451,648 B2 | 11/2008 | Brisson et al. |
| 7,453,982 B1 | 11/2008 | Klausz et al. |
| 7,455,973 B2 | 11/2008 | Fischer et al. |
| 7,458,889 B2 | 12/2008 | Gauselmann |
| 7,459,286 B1 | 12/2008 | Hazen et al. |
| 7,465,273 B2 | 12/2008 | Friedman |
| 7,465,551 B2 | 12/2008 | Blumenthal et al. |

(56) References Cited

U.S. PATENT DOCUMENTS

| | | | |
|---|---|---|---|
| 7,467,842 B2 | 12/2008 | Silverbrook | |
| 7,468,040 B2 | 12/2008 | Hartley et al. | |
| 7,469,679 B2 | 12/2008 | Puckett et al. | |
| 7,470,508 B2 | 12/2008 | Bastian et al. | |
| 7,473,534 B2 | 1/2009 | Carney et al. | |
| 7,477,051 B2 | 1/2009 | Tse et al. | |
| 7,477,147 B2 | 1/2009 | Fitzgibbon | |
| 7,478,061 B1 | 1/2009 | Spreng et al. | |
| 7,480,032 B2 | 1/2009 | Braig et al. | |
| 7,480,543 B2 | 1/2009 | Bautista et al. | |
| 7,483,253 B2 | 1/2009 | Schumacher | |
| 7,483,670 B2 | 1/2009 | Walker et al. | |
| 7,483,838 B1 | 1/2009 | Marks | |
| 7,485,472 B2 | 2/2009 | Nowak et al. | |
| 7,486,040 B2 | 2/2009 | DeJohn | |
| 7,487,774 B2 | 2/2009 | Acker | |
| 7,488,291 B2 | 2/2009 | Cho et al. | |
| 7,489,143 B2 | 2/2009 | Konno et al. | |
| 7,489,458 B2 | 2/2009 | Su et al. | |
| 7,490,048 B2 | 2/2009 | Joao | |
| 7,490,086 B2 | 2/2009 | Joao | |
| 7,491,493 B2 | 2/2009 | Czub et al. | |
| 7,493,264 B1 | 2/2009 | Kelly et al. | |
| 7,504,954 B2 | 3/2009 | Spaeder | |
| 7,505,916 B1 | 3/2009 | Adrian et al. | |
| 7,516,883 B2 | 4/2009 | Hardesty et al. | |
| 7,555,444 B1 | 6/2009 | Wilson et al. | |
| 7,624,051 B2 | 11/2009 | Gellman | |
| 7,653,594 B2 | 1/2010 | Davis | |
| 7,668,747 B2 | 2/2010 | Murphy et al. | |
| 7,672,857 B2 | 3/2010 | Padron et al. | |
| 7,739,115 B1 | 6/2010 | Pettay et al. | |
| 2002/0016535 A1 | 2/2002 | Martin et al. | |
| 2003/0050542 A1 | 3/2003 | Reihl et al. | |
| 2004/0030578 A1 | 2/2004 | Cross et al. | |
| 2005/0228692 A1 | 10/2005 | Hodgdon | |
| 2005/0234742 A1 | 10/2005 | Hodgdon | |
| 2005/0267382 A1 | 12/2005 | Church et al. | |
| 2005/0267784 A1 | 12/2005 | Slen et al. | |
| 2005/0273387 A1 | 12/2005 | Previdi | |
| 2006/0069619 A1 | 3/2006 | Walker et al. | |
| 2006/0095299 A1 | 5/2006 | Hilliard | |
| 2006/0218011 A1* | 9/2006 | Walker et al. | 705/3 |
| 2007/0015974 A1 | 1/2007 | Higgins et al. | |
| 2007/0039624 A1 | 2/2007 | Roberts et al. | |
| 2007/0067218 A1 | 3/2007 | Bingham | |
| 2007/0123772 A1 | 5/2007 | Euliano et al. | |
| 2007/0172424 A1* | 7/2007 | Roser | 424/9.1 |
| 2008/0033751 A1* | 2/2008 | Greene | 705/2 |
| 2008/0065413 A1 | 3/2008 | Taniike et al. | |
| 2008/0172337 A1 | 7/2008 | Banfield et al. | |
| 2008/0255409 A1 | 10/2008 | Graumann et al. | |
| 2009/0043609 A1 | 2/2009 | Nadas et al. | |
| 2010/0270257 A1 | 10/2010 | Wachman et al. | |

OTHER PUBLICATIONS

Guiffrida, Antonio et al.; "Should we pay the patient? Review of financial incentives to enhance patient compliance"; BMJ; Sep. 20, 1997; pp. 1-8; vol. 315, No. 703; downloaded from http://www.bmj.com/content/315/7110/703.full.

Singer, Emily; "Take TB Meds, Get Mobile Minutes: A program to boost TB drug compliance rewards patients with cell-phone minutes"; MIT, Technology Review; Jan. 12, 2009; 1 pg.; downloaded from http://www.technologyreview.com/printer_friendly_article.aspx?id=21945.

"Medication compliance improves with incentives, study finds"; Healthcare Finance News; Jan. 8, 2008; 2 pgs.; downloaded from http://www.healthcarefinancenews.com/print/9749.

"Behavioral Economics Emerge in Express Scripts Study on Medication Compliance"; Globe Newswire; Dec. 17, 2008; 2 pgs.; downloaded from http://www.globenewswire.com/newsroom/news_printer.html?d=156527&print=1.

"How the RxImpact structure works"; Humana RxImpact, Prescription Drug Coverage; Apr. 2007; 3 pgs.

Sutherland, Kim et al.; "Impact of Targeted Financial Incentives on Personal Health Behavior: A Review of the Literature"; Medical Care Research and Review; 2008; pp. 36S-78S; vol. 65.

"Pathology"; Merriam-Webster; accessed Jun. 9, 2013: pp. 1-4; located at http://www.merriam-webster.com/dictionary/pathology.

Benner et al.; "Association Between Short-Term Effectiveness of Statins and Long-Term Adherence to Lipid-Lowering Therapy"; American Journal of Health-System Pharmacy; Jul. 15, 2005; pp. 1468-1475; vol. 62, No. 14.

Halpern et al.; "Randomized trial of 5 dollars versus 10 dollars monetary incentives, envelope size, and candy to increase physician response rates to mailed questionaries."; located at http://www.ncbi.nlm.nih.gov/pubmed/12218773; Med Care; bearing a date of Sep. 2002; pp. 1-2; 40 (9); NCBI.

\* cited by examiner

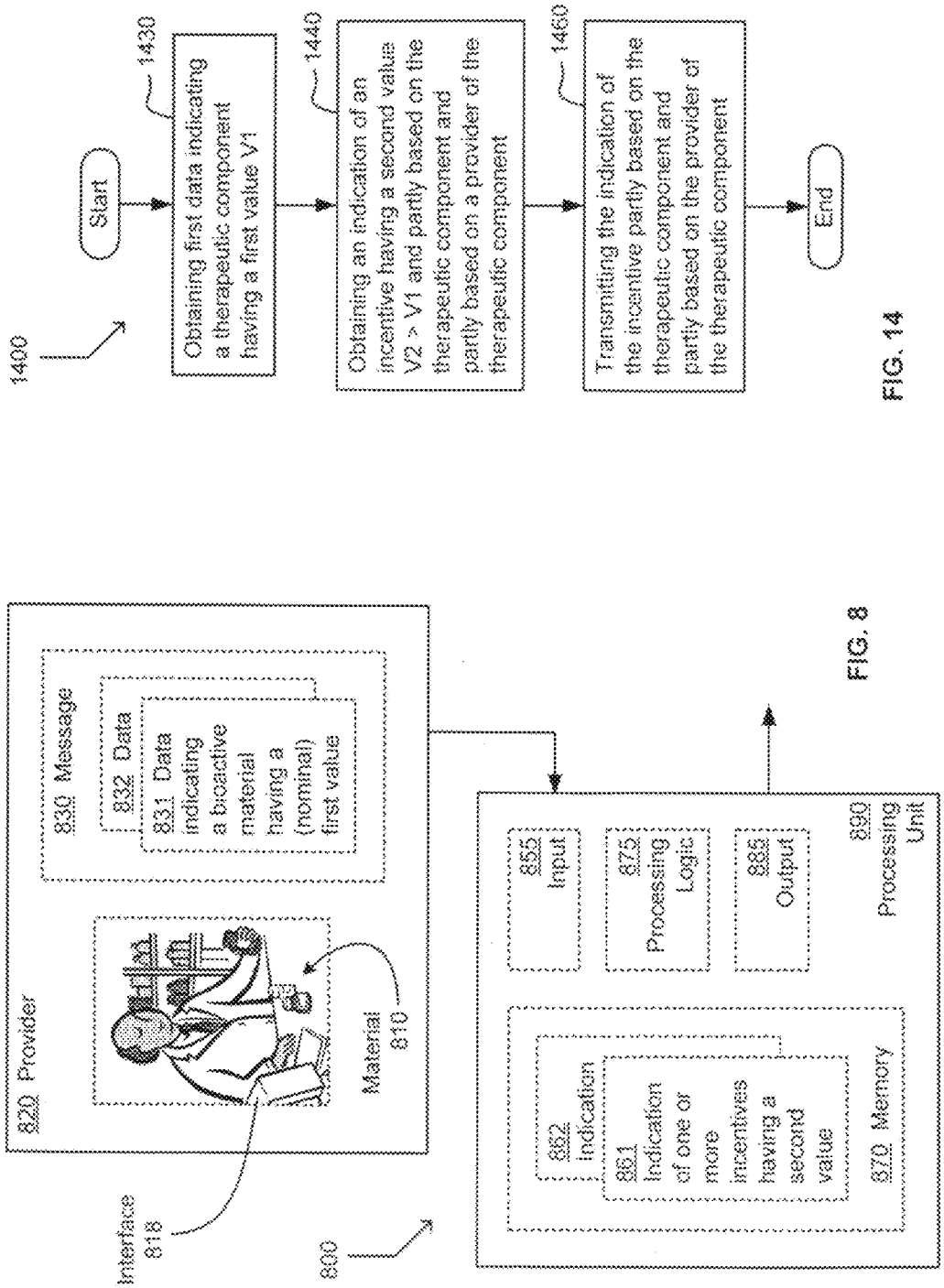

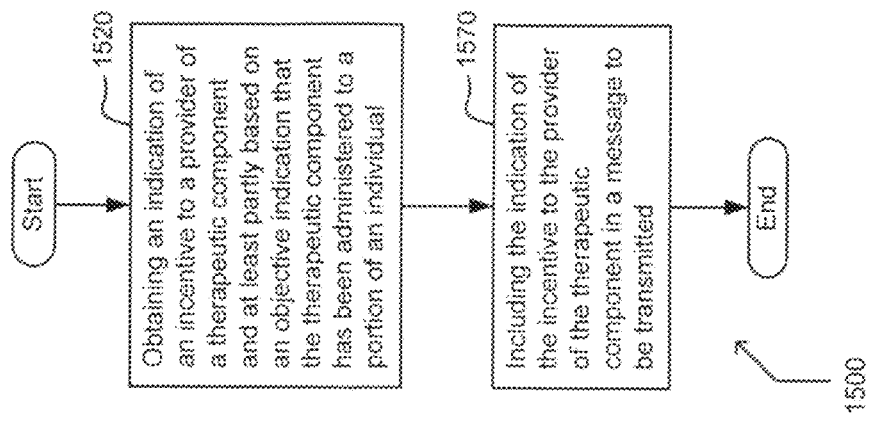
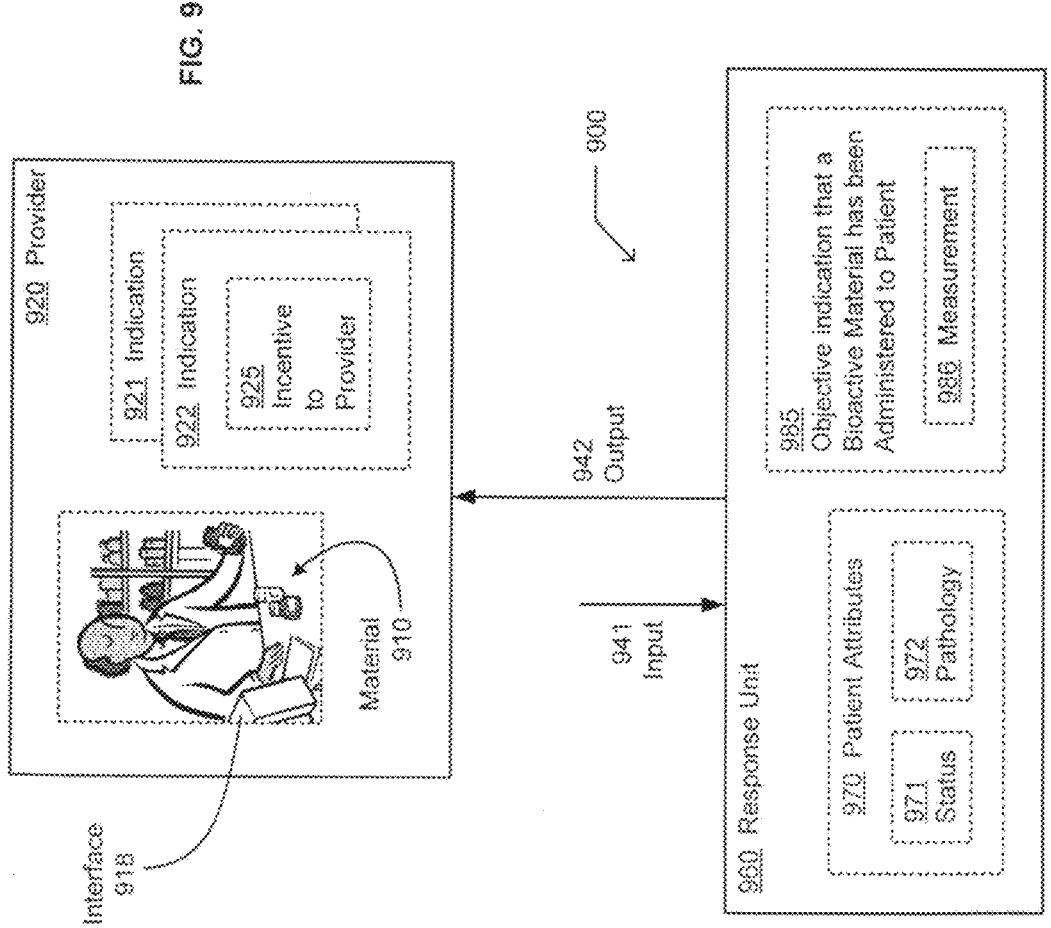

US 9,626,650 B2

COST-EFFECTIVE RESOURCE APPORTIONMENT TECHNOLOGIES SUITABLE FOR FACILITATING THERAPIES

TECHNICAL FIELD

Some variants relate to point-of-sale or monitoring systems that indicate or implement incentives based on therapeutic components or other records on data-bearing media (user cards or similar articles in local interfaces, e.g.) and which may be classified inter alia in U.S. Class 235, Subclass 379 or 494.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of application Ser. Nos. 13/066,444, 13/066,441, 13/066,454, 13/066,445, and 13/066,443, each entitled COST-EFFECTIVE RESOURCE APPORTIONMENT TECHNOLOGIES SUITABLE FOR FACILITATING THERAPIES, naming Rebeca Hwang, Roderick A. Hyde, Muriel Y. Ishikawa, Jordin T. Kare, Dennis J, Rivet, Elizabeth A. Sweeney, Clarence T. Tegreene, Victoria Y. H. Wood, and Lowell L. Wood, Jr., as inventors, filed on even date herewith, each of which is currently co-pending or is an application of which a currently co-pending application is entitled to the benefit of the filing date.

For purposes of the USPTO extra-statutory requirements, the present application claims benefit of priority of application Ser. Nos. 13/066,444, 13/066,441, 13/066,454, 13/066,445, and 13/066,443, each entitled COST-EFFECTIVE RESOURCE APPORTIONMENT TECHNOLOGIES SUITABLE FOR FACILITATING THERAPIES, naming Rebeca Hwang, Roderick A. Hyde, Muriel Y. Ishikawa, Jordin T. Kare, Dennis J, Rivet, Elizabeth A. Sweeney, Clarence T. Tegreene, Victoria Y. H. Wood, and Lowell L. Wood, Jr., as inventors, filed on even date herewith, each of which was filed within the twelve months preceding the filing date of the present application or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

An embodiment provides a method. In one implementation, the method includes but is not limited to obtaining an indication of an incentive partly based on a physical attribute of an individual and partly based on an indication of a therapeutic component available to the individual, a component of the incentive being an incentive to the individual, and transmitting the indication of the incentive partly based on the physical attribute of the individual and partly based on the indication of the therapeutic component available to the individual to a putative provider of the therapeutic component. In addition to the foregoing, other method aspects are described in the claims, drawings, and text forming a part of the present disclosure.

In one or more various aspects, related machines, compositions of matter, or manufactures of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for obtaining an indication of an incentive partly based on a physical attribute of an individual and partly based on an indication of a therapeutic component available to the individual, a component of the incentive being an incentive to the individual, and circuitry for transmitting the indication of the incentive partly based on the physical attribute of the individual and partly based on the indication of the therapeutic component available to the individual to a putative provider of the therapeutic component. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of an incentive partly based on a physical attribute of an individual and partly based on an indication of a therapeutic component available to the individual, a component of the incentive being an incentive to the individual, and transmitting the indication of the incentive partly based on the physical attribute of the individual and partly based on the indication of the therapeutic component available to the individual to a putative provider of the therapeutic component. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device (a) to obtain an indication of an incentive partly based on a physical attribute of an individual and partly based on an indication of a therapeutic component available to the individual, a component of the incentive being an incentive to the individual, and (b) to transmit the indication of the incentive partly based on the physical attribute of the individual and partly based on the indication of the therapeutic component available to the individual to a putative provider of the therapeutic component. In addition to the foregoing, other system aspects are described in the claims, drawings, and text forming a part of the present disclosure.

An embodiment provides a method. In one implementation, the method includes but is not limited to assigning a component of an incentive partly based on an indication of a therapeutic component administered to a portion of an individual and partly based on a profile of the individual and transmitting a result of assigning the component of the incentive. In addition to the foregoing, other method aspects are described in the claims, drawings, and text forming a part of the present disclosure.

In one or more various aspects, related machines, compositions of matter, or manufactures of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for assigning a component of an incentive partly based on an indication of a therapeutic component administered to a portion of an individual and partly based on a profile of the individual and circuitry for transmitting a result of assigning the component of the incentive. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to assigning a component of an incentive partly based on an indication of a therapeutic component administered to a portion of an individual and partly based on a profile of the individual and transmitting a result of assigning the component of the incentive. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device (a) to assign a component of an incentive partly based on an indication of a therapeutic component administered to a portion of an individual and partly based on a profile of the individual and (b) to transmit a result of assigning the component of the incentive. In addition to the foregoing, other system aspects are described in the claims, drawings, and text forming a part of the present disclosure.

An embodiment provides a method. In one implementation, the method includes but is not limited to obtaining an indication of an incentive partly based on an indication of a health status apparently resulting from a bioactive material administered to an individual and partly based on a profile of the individual and including the indication of the incentive in or with a (draft or transmitted signal or other) message. In addition to the foregoing, other method aspects are described in the claims, drawings, and text forming a part of the present disclosure.

In one or more various aspects, related machines, compositions of matter, or manufactures of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for obtaining an indication of an incentive partly based on an indication of a health status apparently resulting from a bioactive material administered to an individual and partly based on a profile of the individual and circuitry for including the indication of the incentive in or with a message. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of an incentive partly based on an indication of a health status apparently resulting from a bioactive material administered to an individual and partly based on a profile of the individual and including the indication of the incentive in or with a message. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device (a) to obtain an indication of an incentive partly based on an indication of a health status apparently resulting from a bioactive material administered to an individual and partly based on a profile of the individual and (b) to include the indication of the incentive in or with a message. In addition to the foregoing, other system aspects are described in the claims, drawings, and text forming a part of the present disclosure.

An embodiment provides a method. In one implementation, the method includes but is not limited to obtaining first data indicating a therapeutic component having a first value V1, obtaining an indication of an incentive having a second value V2>V1 and partly based on the therapeutic component and partly based on a provider of the therapeutic component and including the indication of the incentive in or with a (draft or transmitted signal or other) message. In addition to the foregoing, other method aspects are described in the claims, drawings, and text forming a part of the present disclosure.

In one or more various aspects, related machines, compositions of matter, or manufactures of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for obtaining first data indicating a therapeutic component having a first value V1, obtaining an indication of an incentive having a second value V2>V1 and partly based on the therapeutic component and partly based on a provider of the therapeutic component and circuitry for including the indication of the incentive in or with a message. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining first data indicating a therapeutic component having a first value V1, obtaining an indication of an incentive having a second value V2>V1 and partly based on the therapeutic component and partly based on a provider of the therapeutic component and including the indication of the incentive in or with a message. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device (a) to obtain data indicating a therapeutic component having a first value V1, (b) to obtain an indication of an incentive having a second value V2>V1 and partly based on the therapeutic component and partly based on a provider of the therapeutic component and (c) to include the indication of the incentive in or with a message. In addition to the foregoing, other system aspects are described in the claims, drawings, and text forming a part of the present disclosure.

An embodiment provides a method. In one implementation, the method includes but is not limited to obtaining an indication of an incentive at least partly based on an objective indication that a therapeutic component has been administered to a portion of an individual and including the indication of the incentive in or with a (draft or transmitted signal or other) message. In addition to the foregoing, other method aspects are described in the claims, drawings, and text forming a part of the present disclosure.

In one or more various aspects, related machines, compositions of matter, or manufactures of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for obtaining an indication of an incentive at least partly based on an objective indication that a therapeutic component has been administered to a portion of an individual and circuitry for including the indication of the incentive in or with a message. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of an incentive at least partly based on an objective indication that a therapeutic component has been administered to a portion of an individual and including the indication of the incentive in or with a message. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device (a) to obtain an indication of an incentive at least partly based on an objective indication that a therapeutic component has been administered to a portion of an individual and (b) to include the indication of the incentive in or with a message. In addition to the foregoing, other system aspects are described in the claims, drawings, and text forming a part of the present disclosure.

An embodiment provides a method. In one implementation, the method includes but is not limited to selecting an indication of an incentive partly based on a category of a therapeutic material and partly based on an indication of a dispensing device administering the therapeutic material to an individual and including the indication of the incentive in or with a (draft or transmitted signal or other) message. In addition to the foregoing, other method aspects are described in the claims, drawings, and text forming a part of the present disclosure.

In one or more various aspects, related machines, compositions of matter, or manufactures of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for selecting an indication of an incentive partly based on a category of a therapeutic material and partly based on an indication of a dispensing device administering the therapeutic material to an individual and circuitry for including the indication of the incentive in or with a message. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to selecting an indication of an incentive partly based on a category of a therapeutic material and partly based on an indication of a dispensing device administering the therapeutic material to an individual and including the indication of the incentive in or with a message. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device (a) to select an indication of an incentive partly based on a category of a therapeutic material and partly based on an indication of a dispensing device administering the therapeutic material to an individual and (b) to include the indication of the incentive in or with a message. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure. The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth below.

BRIEF DESCRIPTION OF THE FIGURES

FIGS. 3-10 respectively depict other exemplary environments in which one or more technologies may be implemented.

FIG. 14 depicts a high-level logic flow of an operational process described with reference to FIG. 8.

FIG. 15 depicts a high-level logic flow of an operational process described with reference to FIG. 9.

DETAILED DESCRIPTION

Figure 1:
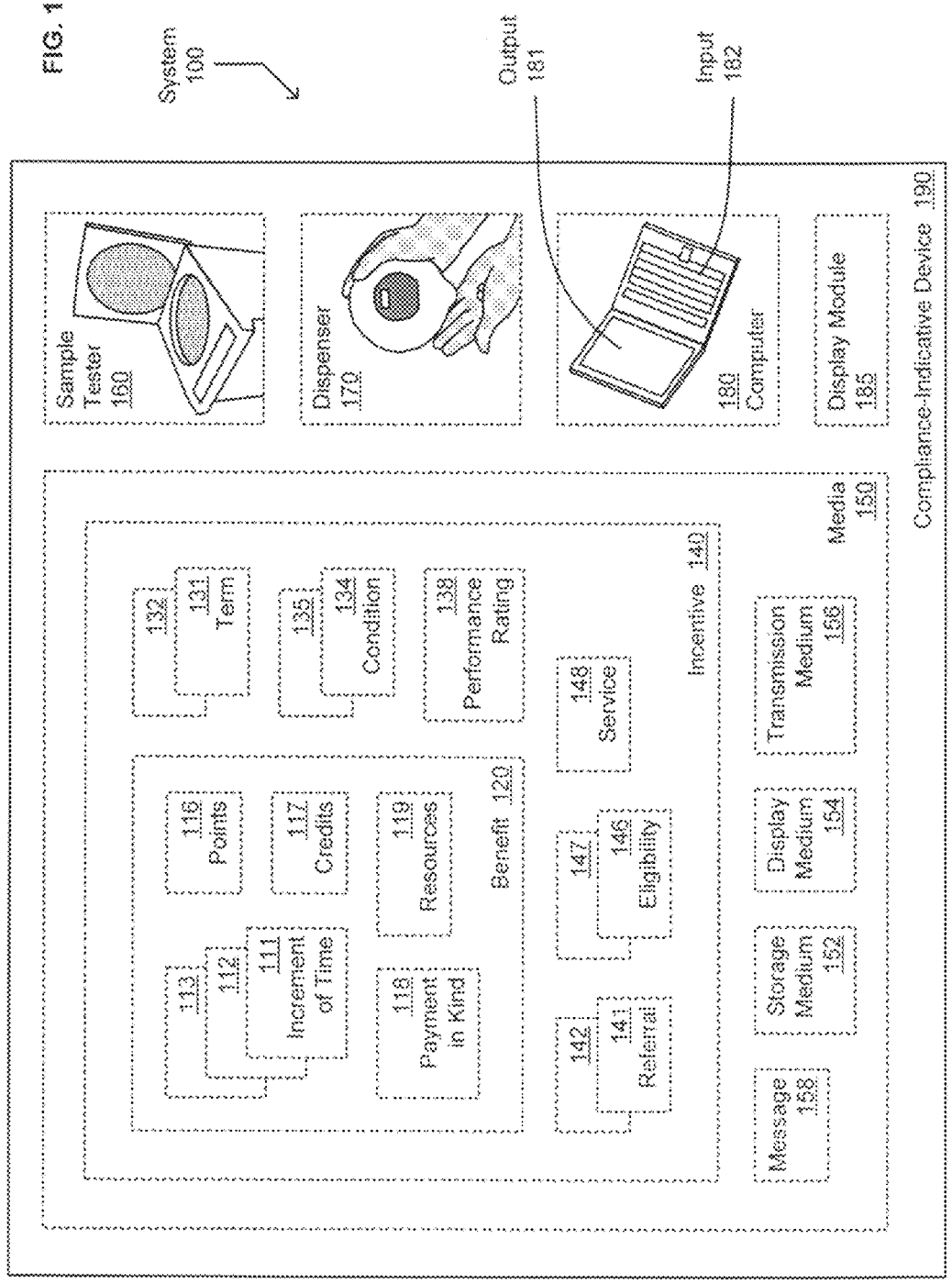
FIG. 1 depicts an exemplary environment in which one or more technologies may be implemented in a compliance-indicative device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art, has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

With reference now to FIG. 1, shown is a system 100 in which one or more technologies may be implemented. System 100 may include one or more sample testers 160, dispensers 170, computers 180, or portable display modules 185 implementing a compliance-indicative device 190. In some variants, such devices may include one or more inputs 182, outputs 181, magnetic or other storage media 152, display media 154, transmission media 156, or other media 150 for handing messages 158 indicative of compliance (or noncompliance) with a therapeutic regimen. In some contexts, such messages or other records may explicitly associate an actual (accomplished) or prospective incentive 140 that is physical and tangible: a card or other device-readable medium granting a membership or other temporary access for one or more increments 111, 112, 113 of time; cash or other certificates indicative of points 116, credits 117 or other physical media of exchange; medications, nutritional supplements, exercise equipment, or other goods transferred as payments in kind 118; or other such resources 119 directly manifesting a physical, tangible benefit 120 as (at least part of) the incentive. Alternatively or additionally, such incentives can include one or more discounts or other terms 131, 132 or conditions 134, 135; performance ratings 138 or favorable referrals 141, 142; policies, rebates, or other eligibilities 146, 147; or supplemental therapies or other such services 148. In some contexts, as exemplified below, a combination of such incentives may be necessary or helpful for motivating qualified patients to comply with a testing or treatment regimen or for motivating others to explain or otherwise facilitate an individual's participation or enrollment in a testing or treatment program.

In light of teachings herein, numerous existing techniques may be applied for identifying and administering tangible or other incentives effectively to motivate individuals to suggest or elect products or programs as described herein without undue experimentation. See, e.g., U.S. Pat. No. 7,739,115 ("Script compliance and agent feedback"); U.S. Pat. No. 7,668,747 ("System and method for providing incentives to purchasers"); U.S. Pat. No. 7,653,594 ("Targeted incentives based upon predicted behavior"); U.S. Pat. No. 7,624,051 ("Method and system for forming a list-based value discovery network"); U.S. Pat. No. 7,555,444 ("Dynamic time-of-purchasing-decision incentive system and method"); U.S. Pat. No. 7,433,834 ("Apparatus and method for facilitating transactions"); U.S. Pat. No. 7,389,245 ("Method and apparatus for providing incentives to physicians"); U.S. Pat. No. 7,376,700 ("Personal coaching system for clients with ongoing concerns such as weight loss"); U.S. Pat. No. 7,373,318 ("Information recommendation apparatus and information recommendation system"); U.S. Pat. No. 7,016,854 ("Loyalty link method and apparatus with audio performance for integrating customer information with dealer management information"); U.S. Pat. No. 6,988,132 ("System and method for identifying and establishing preferred modalities or channels for communications based on participants' preferences and contexts"); U.S. Pat. No. 6,952,678 ("Method, apparatus, and manufacture for facilitating a self-organizing workforce"); U.S. Pat. No. 6,901,347 ("Availability, reliability or maintainability index including outage characterization"); U.S. Pat. No. 6,739,508 ("Evaluation apparatus with voting system, evaluation method with voting system, and a computer product"); U.S. Pat. No. 6,699,124 ("Amusement game incentive points system"); U.S. Pat. No. 6,561,811 ("Drug abuse prevention computer game"); and U.S. Pat. No. 5,537,314 ("Referral recognition system for an incentive award program").

Figure 2:
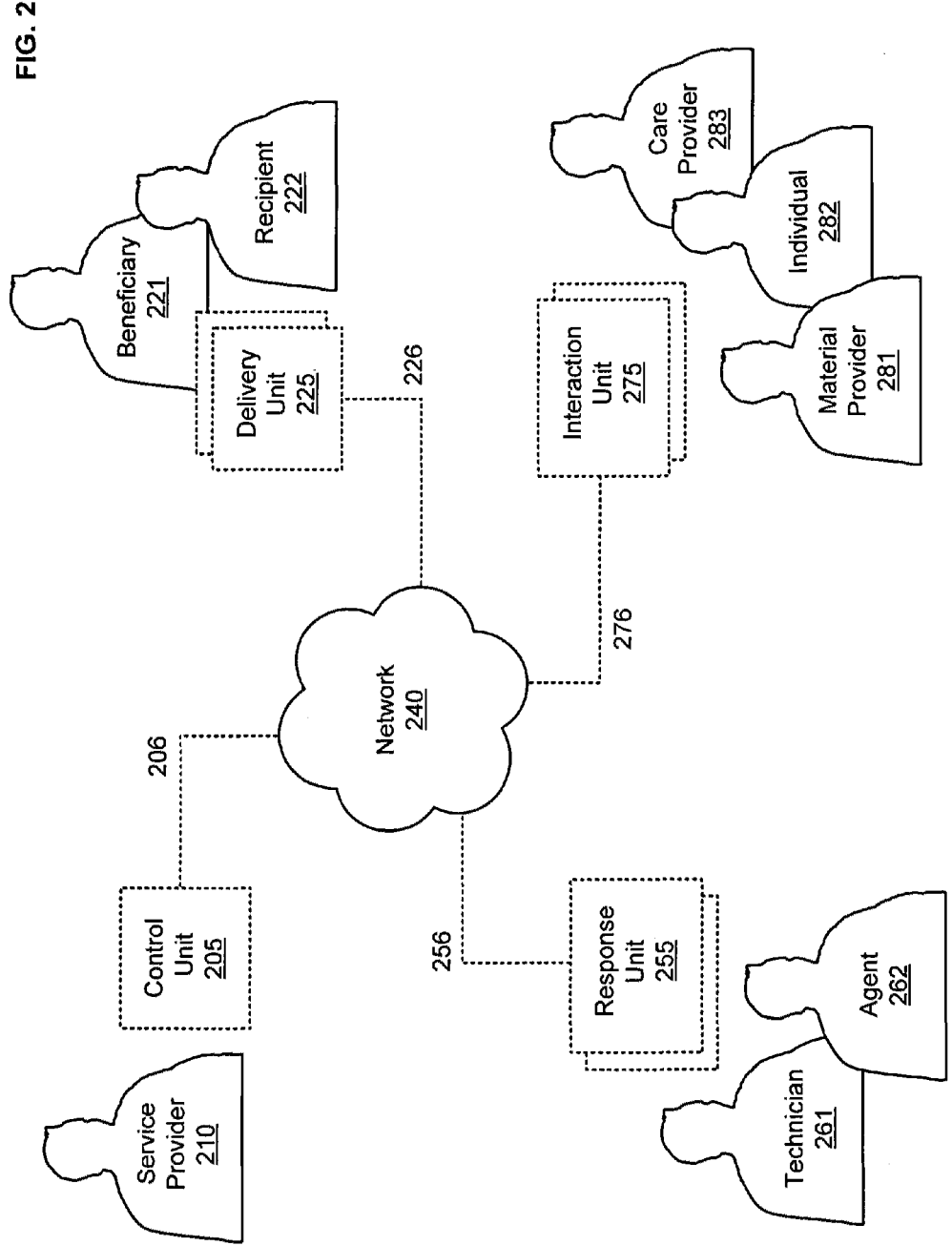
FIG. 2 depicts a network having wireless signal paths or other suitable linkages providing access among several parties.

With reference now to FIG. 2, shown is a network 240 having wireless signal paths or other suitable linkages 206, 226, 256, 276 providing access among several parties. An insurer, policymaker, program enrollment coordinator, or similar service provider 210 may have access through a control unit 205, for example, implementing a local display module 185 or other media 150 as described herein. One or more support technicians 261, program enrollment coordinators, or other such agents 262 may similarly access or provide data through network 240 via servers or other response units 255 implementing media 150. Individuals 282 prospectively or actually participating in a therapeutic or monitoring regimen as described herein may similarly communicate with others on network 240 via a portable or other local interaction unit 275. Material providers 281 or care providers 283 having regular opportunities to interact personally with such individuals 282 may likewise have local interaction units 276 operable for indicating compliance, enrollment, or similar events to be tracked pursuant to therapeutic components (products or other requirements of a prescribed regimen, e.g.) or artificial incentives 140 as described herein. Alternatively or additionally, correspondence or incentive deliveries to one or more beneficiaries 221 or other recipients 222 may occur automatically via one or more delivery units 225 as described herein. Any such control units 205, delivery units 225, response units 255, or interaction units 275 may (optionally) include one or more storage media 152, display media 154, transmission media 156 or other modules indicating, delivering, or otherwise manifesting one or more (artificial) incentives 140 as described herein.

Figure 3:
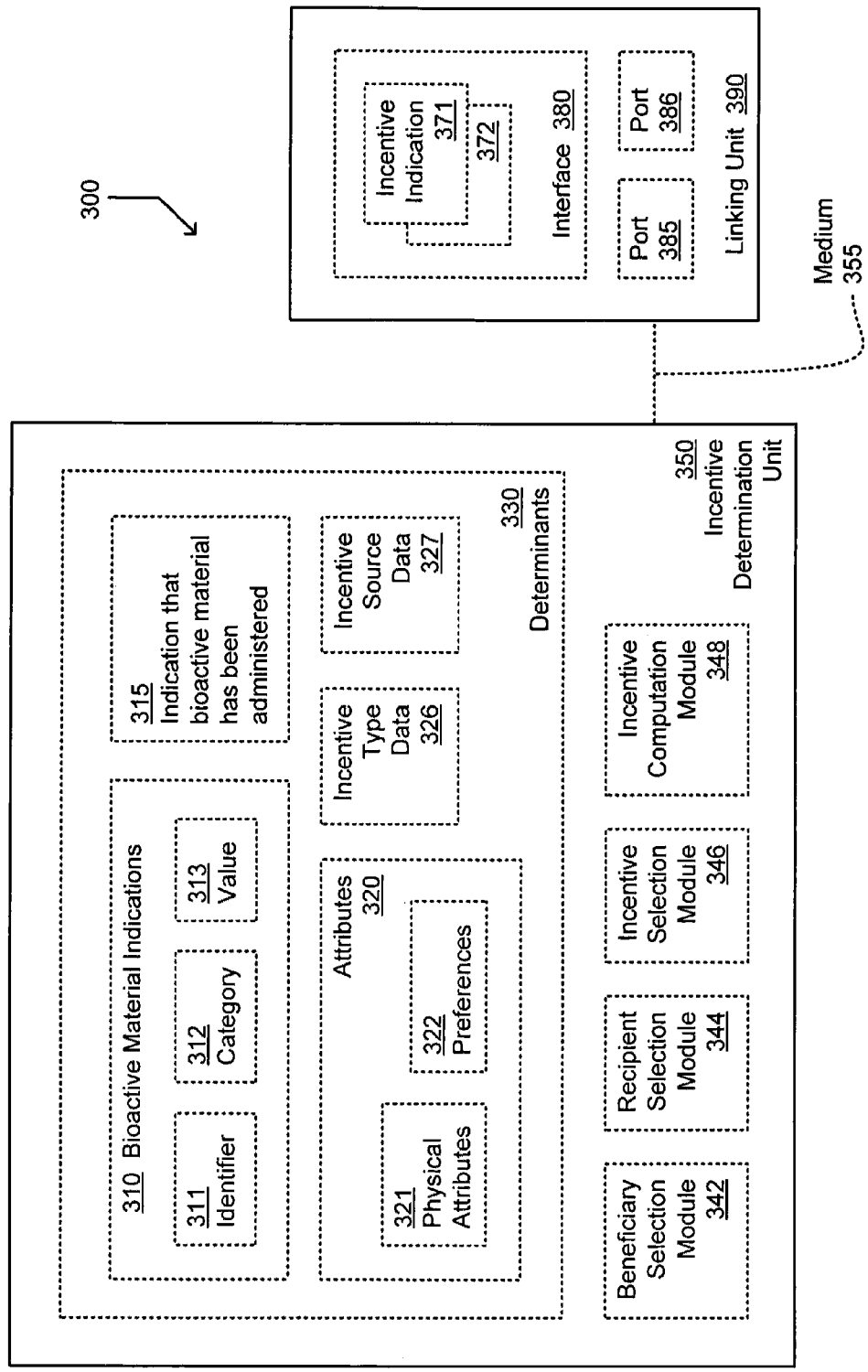

With reference now to FIG. 3, shown is a system 300 in which one or more technologies may be implemented. In some variants, units as described above may collectively or individually comprise system 300 such that one or more transmission media 355 operably couples an incentive determination unit 350 through one or more linking units 390 (via network 240 or with a local party, e.g.). Such incentive determination units 350 may include media bearing material identifiers 311, material categories 312, material values 313; or other such bioactive material indications 310; indications 315 that bioactive material has been administered; a patient's physical attributes 321, preferences 322, enrollment status, or other attributes 320 as described herein; and suitable incentive type data 326, inventory and other incentive source data 327, and other such determinants 330 useful for selecting, adapting, redirecting, or otherwise modulating an incentive for target individuals 282 to receive or accept a message about a therapeutic program or to enroll (as desired and identified by a study sponsor or other service provider 210, e.g.). In some variants, for example, a service provider 210 or technician 261 may automate an incentive determination module 350 by configuring one or more beneficiary selection modules 342, recipient selection modules 344, incentive selection modules 346, or incentive computation modules 348 therein. Such modules may include computer-executable code executable by one or more processors or other circuitry for conditioning the incentive upon various criteria (a result of comparing an identified provider with a preferred provider list, for example, or of comparing a preferred incentive type with an inventory of currently available incentives 140), for example, as described in detail below. Outputs from an incentive determination unit 350 may include one or more incentive indications 371, 372 (components of incentives indicated locally to a party via interface 380 or remotely as messages 158 via network 240, e.g.) or other components of messages 158 as described herein.

Figure 4:
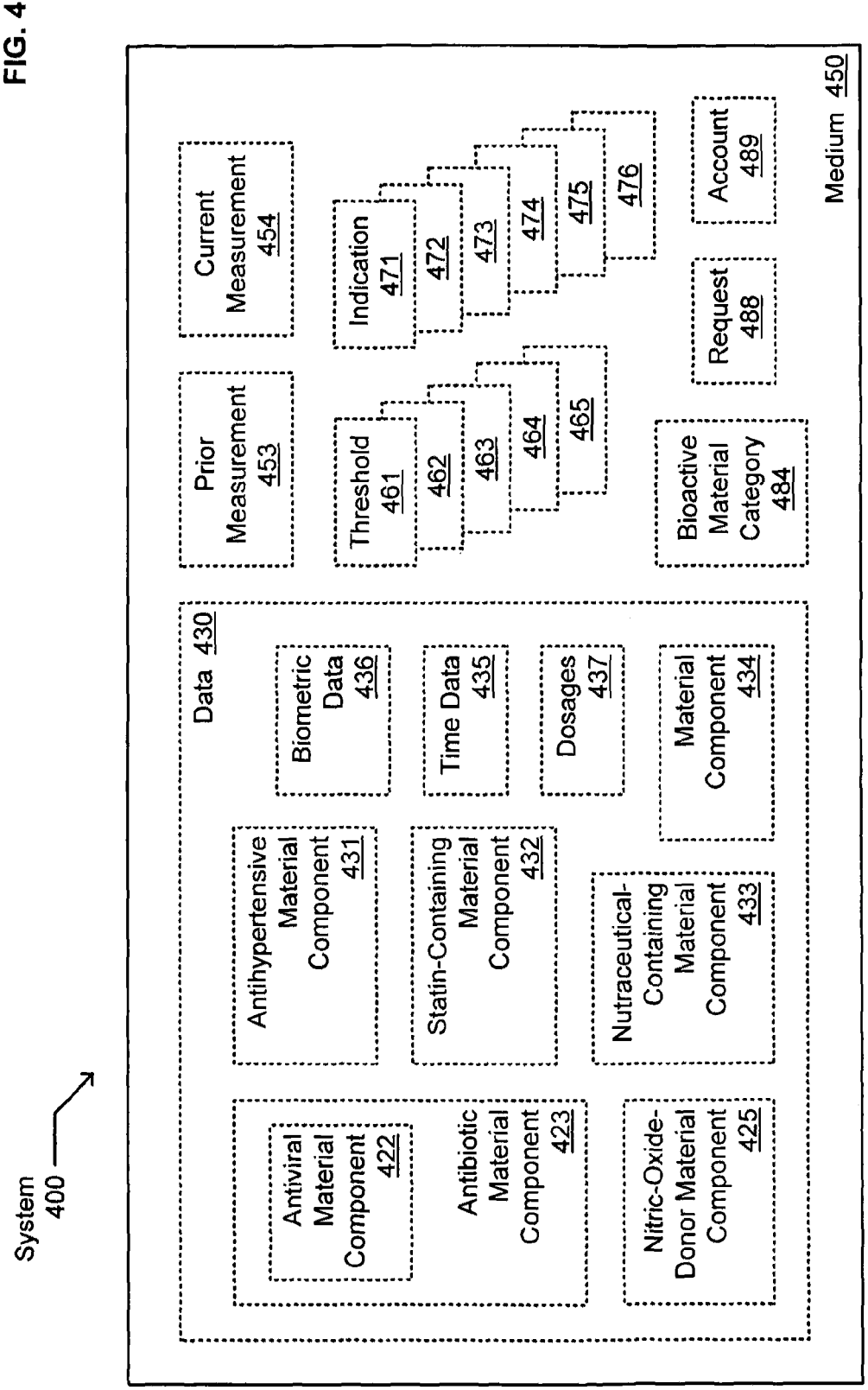

With reference now to FIG. 4, shown is a system 400 in which one or more technologies may be implemented. System 400 includes one or more physical, tangible media 450 (configured for data storage, display, or computation, e.g.) configured to bear various data 430 usable as determinants 330 affecting an incentive as described herein. Such data may include one or more antiviral material components 422 or other antibiotic material components 423 or other anti-infective material components, nitric-oxide-donor material components 425, antihypertensive material components 431, statin-containing material components 432 or other plasma-lipid modifying material components, nutraceutical-containing material components 433, biometric data 436 pertaining to one or more parties (as identified above, e.g.), event times or other time data 435, dosages 437, or other informational material components 434 as described below. Such media may likewise handle one or more prior measurements 453; current measurements 454; thresholds 461, 462, 463, 464, 465; bioactive material categories 484; requests 488; accounts 489; or other indications 471, 472, 473, 474, 475, 476 or results as described below. In some contexts, one or more determinants of an incentive may include an indication of whether a therapeutic component was administered within a prescribed interval—relative to a time of day, a meal, bedtime, or a prior administration of the same or another therapeutic component, for example. This can occur, for example, in a context in which the data indicates substantial or sufficient compliance: a measurement falling within a prescribed range, a success rate over 90%, a fixed number of successful or timely administrations, or some combination of such determinants designated by a physician or policy administrator.

Several of the above-described media 355, 450 or systems 100, 300 manifest respective embodiments configured to allocate informational or other resources in a sequence and manner that is sufficient to obtain one or more requisite indications of measurement, therapy, compliance, consent, apparent pathology, or other such events or conditions relating directly to an identifiable subpopulation. (Descriptive terms like "apparent" or "local" are used herein normally, except as otherwise dictated by context, to refer to a binary or absolute categorization of events or conditions and not as terms of degree.) This can occur, for example, in a context in which no available digital record identifies a group of individuals with the subpopulation or in which one or more demographic, psychological, genetic, or other attributes of specific interest are missing from a locally available record. In some variants, for example, the most useful data available on the medium or system may describe an intermediary (system, institution, or agent) having a restricted or other controlled relationship with several potential patients, research subjects, or other individuals 282 of potential interest. As described below, for example, such intermediaries may include one or more delivery units 225, interaction units 275, hospitals, clinics, material providers 281, care providers 283, or other entities (in a respective proximity to a beneficiary 221, recipient 222, or other individual 282, e.g.). In some variants, such monitoring units or interfaces may include one or more dispensing or record-update mechanisms configured to deliver a therapeutic or incentive component locally (in or on a user card, printed prescription, voucher, or vessel label accessible to a recipient 222 or other party, e.g.). Alternatively or additionally, some embodiments (of flows exemplified in FIGS. 11-16 and related systems, e.g.) may be configured to allocate such resources in a context in which a conventional apportionment is probably going to be insufficient (as designated by a researcher or other service provider 210 via control unit 205, e.g.) to cause a requisite level of enrollment or compliance.

Figure 5:
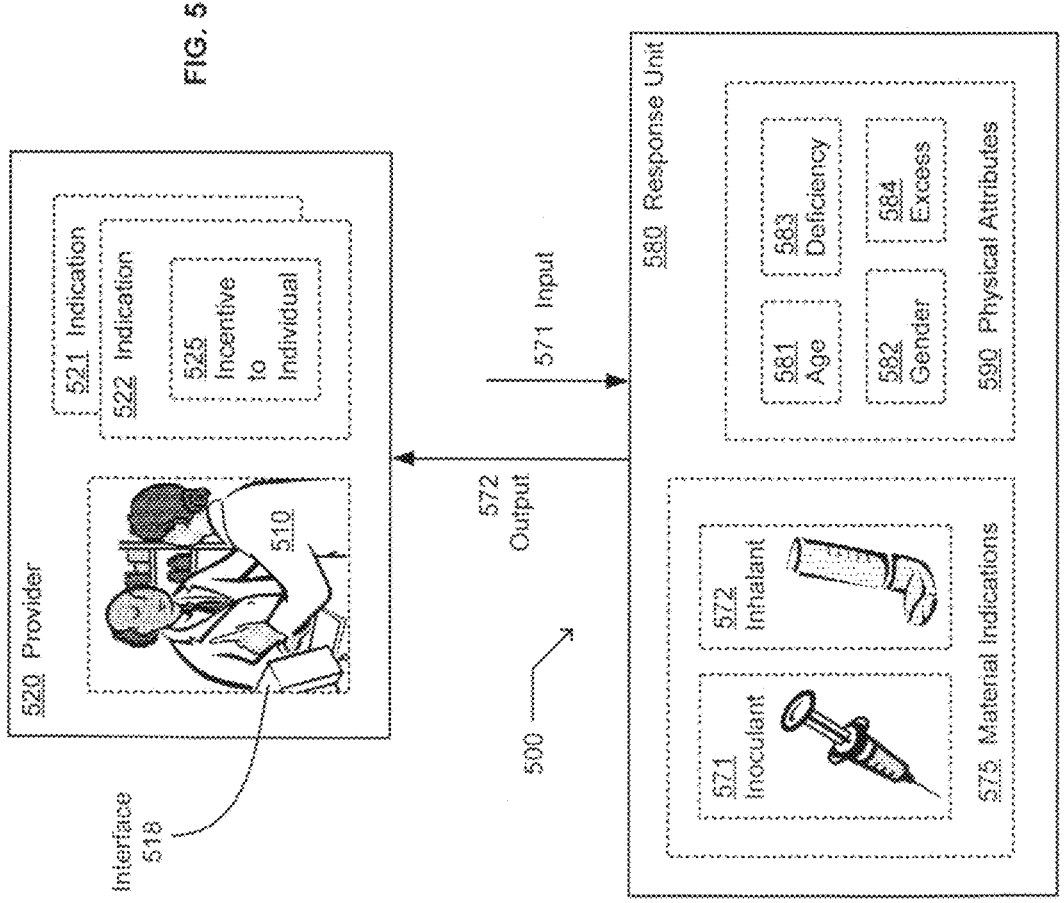

With reference now to FIG. 5, shown is a system 500 in which one or more technologies may be implemented. In response to input 571 (from material or service providers, e.g.), response unit 580 may provide output 572 to one or more providers 520 (via interfaces 518, e.g.) that includes one or more indications 521, 522 of incentives to individuals 525. Such indications may take into account material indications 575 of an inoculant 571, inhalant 572, or other therapeutic component available to the individual 510 to which the incentive may draw attention. In some variants, the incentive to be indicated may depend upon the age 581, gender 582, deficiencies 583 (of one or more measurements indicative of organ performance or nutrient concentration in blood, e.g.), excesses 584 (of blood pressure, body weight, or other such measurements, e.g.), or other demographic and/or physical attributes of the individual that become known to provider 520. This can occur, for example, in a context in which notifying qualifying individuals 282 indirectly (via putative material or service providers who may have access to such individuals) about such incentives available to the individual relating to a therapeutic component available to the individual, is expected to result in faster recruitment even in light of patient privacy considerations.

In some contexts, for example, a "therapeutic component" may include an antibiotic or other bioactive material, a physical therapy or other sequence of operations, an administration of one or more such materials or operations, a regimen calling for such material or operations, or informational data characterizing such therapeutic treatments (such as a dosage or duration, e.g.).

Figure 11:
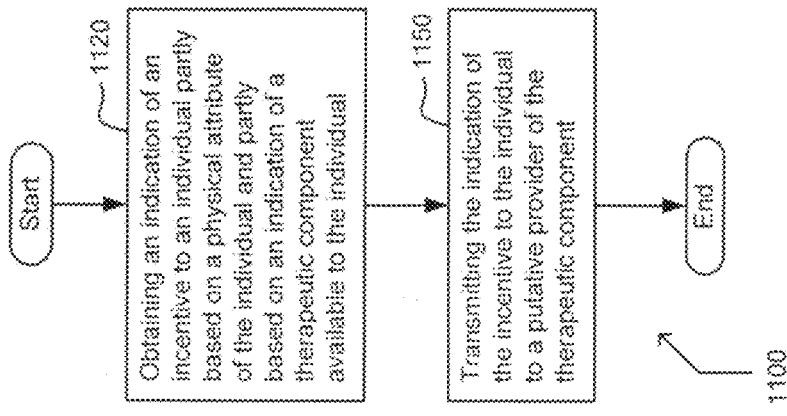
FIG. 11 depicts a high-level logic flow of an operational process described with reference to FIG. 5.

With reference now to FIG. 11, shown is a high-level logic flow 1100 of an operational process. Operation 1120 describes obtaining an indication of an incentive to an individual partly based on a physical attribute of the individual and partly based on an indication of a therapeutic component available to the individual (e.g. a public kiosk, handheld device, or other interface 518 receiving one or more indications 521, 522 of an offer or other incentive to an individual 525 based on a body weight, gender 582, or other such physical attributes 590 of the individual 510). This can occur, for example, in a context in which interface 518 uses such physical attribute(s) 590 to look up such an indication 521 (in a remote database via network 240, e.g.) or in which provider 520 enters local user data associating one or more physical attributes with one or more incentives to an individual 510. In some contexts, for example, information such as disease state, an eye color or other genetic indicator, a body mass index (BMI), a measurement or other objectively-manifested symptom, or other such attributes are received as input 571 and used to determine one or more incentives 140 suitable for a clinical trial subject, market demographic survey participant, or other member of a target subpopulation. Alternatively or additionally, in some variants, an attribute location and/or severity may be used to differentiate among two or more classes of incentive. For example, in some embodiments, looking up an injury or disease of the head or neck would yield a first indication 521 of an incentive to an individual 510 where a disorder of the legs or feet would yield a different indication 522 of another incentive to the individual 525.

In some variants, such interface units may contain one or more modules configured to perform operation 1120. Such modules may, for example, include incentive determination unit 350 or other circuitry configured to invoke incentive selection module 346 responsive to physical attributes 321 (and, optionally, other attributes 320) to obtain an indication 521 of an incentive to an individual 525. This can occur, for example, in a context in which interface unit 518 invokes incentive determination unit 350 to use indications of heart disease, diabetes, or other subject disorders to obtain one or more indications 521, 522 of incentive to an individual 525 and in which age or other physical attributes 590 are also used as determinant(s) in obtaining an indication 521 of incentive to an individual 525.

In some contexts, a result is "partly based on" a determinant if the result depends on the determinant conditionally (in combination with one or more other determinants, for example, by an AND or OR function). Whether a performance result is "noncompliant" can depend upon both (1) a program regimen indicating that a measurement is required and (2) an absence of the required measurement, for example, in which case the result is partly based on the requirement and partly based on the absence. A component of an incentive (to a specific individual 282 participating in a program, e.g.) that depends on a combination of current measurements 454, biometric data 436, bioactive material indications 310, or other such determinants 330 as exemplified herein, moreover, is "partly based on" each such value.

Moreover an incentive is "partly based" on a determinant (a preference or consent of the individual, e.g.) if it is also partly based on at least one other determinant (a category or cost of a therapeutic component, e.g.) such that the incentive depends on each of the determinants. As exemplified and described herein, such jointly-dependent determinations may depend upon some combination of two or more of (1) a category or provider of a therapeutic component, (2) a physical attribute or profile of the individual, (3) an indication of a health status of the individual, (4) an indication of a dispensing device administering a therapeutic material, (5) whether a component is in stock or otherwise "available to" an individual, or (6) other such indicia described herein. In some contexts, a bioactive material or other therapeutic component is "available to" an individual if a physician has prescribed the component or if the individual can obtain the component without a prescription. Also a material is "available to" an individual if it has been injected into the individual's tissue or vasculature, spread onto the individual's skin or mucous membrane, or otherwise "administered to a portion" of the individual.

Operation 1150 describes transmitting the indication of the incentive to the individual to a putative provider of the therapeutic component (e.g. a response unit 580 operatively coupled to the interface relaying output 572 containing one or more indications 521 of the incentive to provider 520). This can occur, for example, in a context in which response unit 580 packages at least an incentive to an individual 521 into a message 158 to a care provider 283, optionally with one or more (indications of) physical attributes 590. Alternatively or additionally, information pertaining to influenza, HIV, or other infectious diseases may be packaged with monetary, service or other incentives into message 158 sent to material provider 281 (via linking unit 390, e.g.).

In some variants, such a response unit may contain one or more modules configured to perform operation 1150. Such modules may, for example, include (one or more implementations of) linking unit 390 or other circuitry configured to transmit one or more messages 158 across network 240 to respective providers. This can occur, for example, in a context in which an injury type or location, a disease state, or some other physical attribute 590 coupled with a selected indication 521 of an incentive to individual 525 is compatible with a pharmaceutical or other material indication 575 for treatment and in which the message recipient is a material provider 281. Alternatively or additionally, physical therapists, psychologists, or other service providers 210 may be recipients of notification when a physical attribute 590 and a selected indication 525 of an incentive to individual 521 provide evidence that such attributes may qualify the individual for an opportunity.

In light of teachings herein, numerous existing techniques may be applied for transmitting age, disability status, or other qualifying attributes to a local or remote entity as described herein without undue experimentation. See, e.g., U.S. Pat. No. 7,416,544 ("Nursing pad"); U.S. Pat. No. 7,412,396 ("Virtual clinic for medical practice"); U.S. Pat. No. 7,399,276 ("Remote health monitoring system"); U.S. Pat. No. 7,264,591 ("System and method for monitoring air flow from a person"); U.S. Pat. No. 7,258,666 ("System and methods for monitoring a patient's heart condition"); U.S. Pat. No. 7,041,468 ("Blood glucose tracking apparatus and methods"); U.S. Pat. No. 6,968,375 ("Networked system for interactive communication and remote monitoring of individuals"); U.S. Pat. No. 6,942,616 ("System and method for collecting and transmitting medical data").

In some network contexts, more than one entity may perform instances of operation 1120. Operation 1120 may be performed by a service provider 210 who has a control unit 205 configured for receiving or otherwise obtaining an indication of an incentive to an individual partly based on a physical attribute of the individual and partly based on an indication of a therapeutic component available to the individual. Such an interface may generate or otherwise provide such indications to service provider 210 as computational output, in some embodiments, after obtaining such operands directly via network 240. In other contexts, however, a server or other circuitry for generating the indication of the incentive(s) (within network 240 or at a remote location, for example) may permit control unit 205 to perform operation 1120 merely by relaying such indication(s). More than one entity may likewise perform instances of operation 1150 in a sequential flow or by similar concurrent, overlapping, or other variant logical arrangement. In some contexts, for example, a person may perform operation 1150 by transmitting the indication via network 240, which remotely relays the indication to the individual 282 or other appropriate parties (via linkage 276, e.g.).

Figure 6:
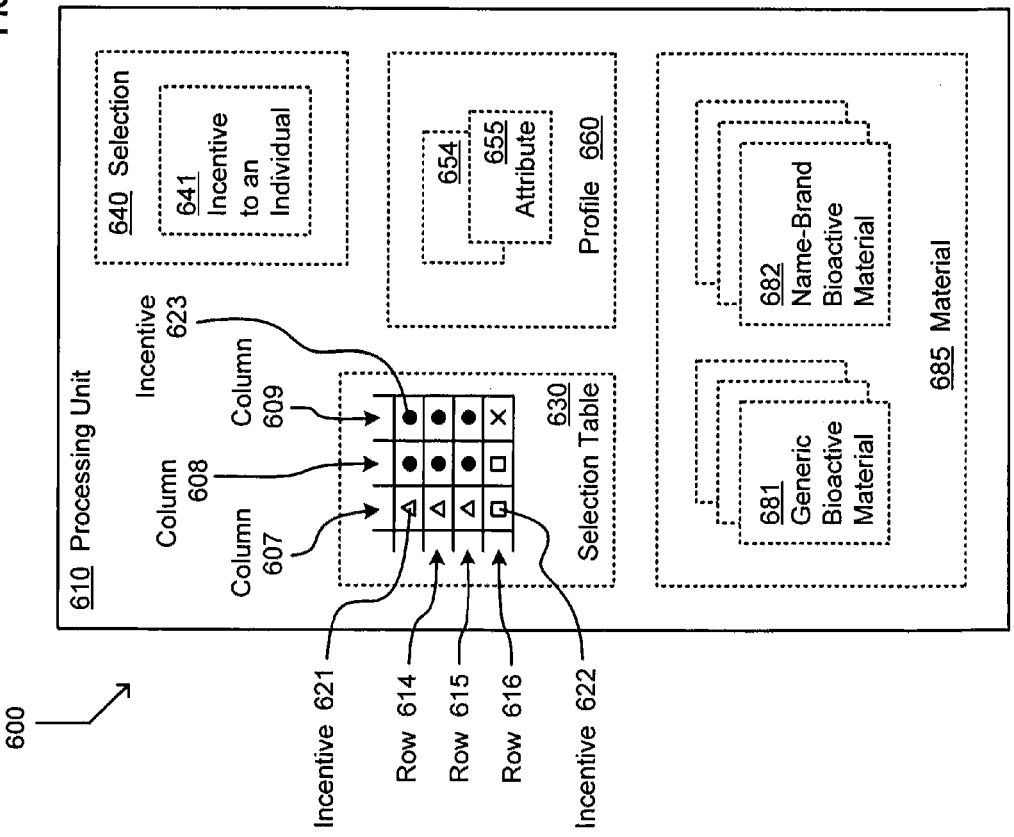

With reference now to FIG. 6, shown is a system 600 in which one or more technologies may be implemented. Processing unit 610 may be implemented as a standalone device installed at a kiosk or clinic, for example, or may be implemented in an incentive determination unit 350 (server, e.g.) remote from the target individual(s) 282 and their providers. Processing unit 610 includes one or more selection tables 630 artificially defining incentives 621, 622, 623 that depend on a combination of two or more determinants (depicted respectively as "rows" 614, 615, 616 and "columns" 607, 608, 609 in the example of FIG. 6). In some contexts, processing unit 610 responds to a combination of determinants (respectively identifying row 614 and column 609, e.g.) by generating a selection 640 of specific incentive 623 as a result. Alternatively or additionally, the resulting selection 640 may define an incentive to an individual 641 who is to receive or has received a therapeutic component described herein. In some variants, a profile 660 of such an individual defines a combination of attributes 654, 655 of specific interest to an agent 262 who configures the selection table(s) or equivalent control circuitry. For example, agent 262 can configure column 607 to define a first incentive 621 (represented as a triangle, e.g.) for otherwise-healthy obese individuals (represented as row 614, e.g.) or for healthy children (represented as row 615, e.g.) but to define a second incentive 622 (represented as, a square, e.g.) for individuals with significant infections or other major health problems (represented as row 616, e.g.). This can occur, for example, in a context in which the first incentive 621 includes at least an eligibility 147 (for prize drawings as an incentive component, for example) and the second incentive 622 includes at test a discount or cash rebate for pharmaceuticals or other conventional medical treatment (as another incentive component, e.g.). Alternatively or additionally, a second incentive may include different component incentives depending on a bioactive material category 484 ("generic" bioactive material 681 or "name-brand" bioactive material, e.g.) designated or used for the treatment.

Figure 12:
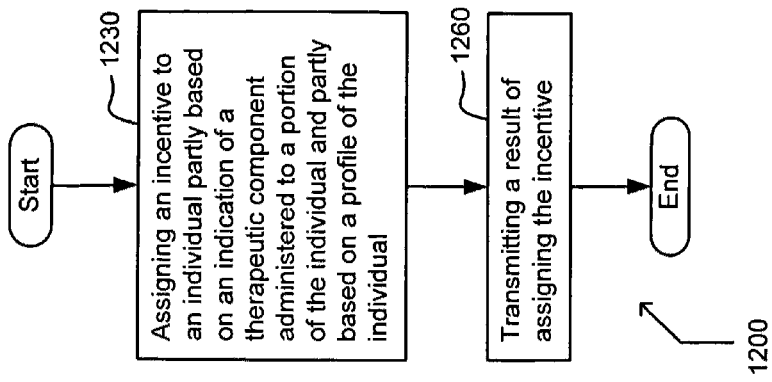
FIG. 12 depicts a high-level logic flow of an operational process described with reference to FIG. 6.

With reference now to FIG. 12, shown is a high-level logic flow 1200 of an operational process. Operation 1230 describes assigning an incentive to an individual partly based on an indication of a therapeutic component administered to a portion of the individual and partly based on a profile of the individual (e.g. a database or other processing unit 610 looking up a selection 640 of an incentive to an individual 641 from a selection table 630 responsive to an indication of administration of a bioactive material 685 onto or into the individual). This can occur, for example, in a context in which incentive to an individual 641 is selected from table 630 responsive to a current measurement 454 indicating application of bioactive material 685 locally to a portion of a patient (a targeted drug, topical creme, or other therapy that is not primarily systemic, e.g.) and in which two or more attributes 654, 655 of the patient's profile 660 define the respective row and column that pertains. In some contexts, for example, measurement 654 may be a direct measurement of a physical property of material 685 indicating presence of the material (or a metabolite thereof) in a region of interest. Alternatively or additionally, in some variants, measurement value 654 may be an indirect measurement of an apparent effect material 685 has on a body part of interest (such as changes in heart rate, intraocular pressure, or other physical attributes, e.g.).

In some variants, processing unit 610 may contain an incentive determination unit 350 or other circuitry for assigning an incentive to an individual partly based on an indication of a therapeutic component administered to a portion of the individual and partly based on a profile of the individual. This can occur, for example, in a context in which the profile includes the individual's (or a care provider's) preferences or other selections as determinant attributes 654, 655 at least sometimes affecting the result of the assignment and in which optical, chemical, and/or other measurement data 430 obtained in-vivo or in-vitro may be used to indicate a presence and/or quantity of bioactive material 685 in one or more subject regions of the individual. Using measurement data 654 as the indication of the therapeutic component administered to the portion of the individual, for example, incentive selection module 346 may select an incentive to an individual 641 from a selection table or equivalent logic, optionally implemented in software. In some contexts, for example, measurement values which exceed a threshold 461 indicating compliance by the individual will result in an assignment of name-brand bioactive material 682 to the individual, or some other such tangible incentive. In the example of selection table 630, for example, each row 614, 615, 616 and column 607, 608, 609 pairing provide a mechanism in which a particular incentive (including a component incentive to the individual) may be selected. For example, in one embodiment, each row in table 630 relates to a respective profile 660 of an individual 282 and each column corresponds to a respective indication of the therapeutic component administered to the portion of the individual. In some contexts, several stepwise thresholds 461, 462, 463 may be used in a context in which an additional or more desirable alternate incentive 622 is selected with exceeding each successive threshold reached. In some contexts, moreover, a selection of incentive 621 may depend upon the detection of one or more bioactive materials 685 and also upon the count, identity 311, category 312 (or combination thereof) of the materials 685 detected.

In light of teachings herein, numerous existing techniques may be applied for using physiological or other measurement values as one or more decision-making criteria in rebate, reward, or other program selections as described herein without undue experimentation. See, e.g., U.S. Pat. No. 7,493,264 ("Method of care assessment and health management"); U.S. Pat. No. 7,447,643 ("Systems and methods for communicating between a decision-support system and one or more mobile information devices"); U.S. Pat. No. 7,248,171 ("RFID systems for automatically triggering and delivering stimuli"); U.S. Pat. No. 7,184,963 ("Method for determining care and prevention pathways for clinical management of wounds"); U.S. Pat. No. 7,127,253 ("Penalty of cell reselection for a wireless device"); U.S. Pat. No. 6,699,188 ("Interactive reward devices and methods"); U.S. Pat. No. 6,366,848 (Engine control system for providing incentives to drivers"); U.S. Pat. No. 6,352,053 ("Apparatus and method for animal testing and training"); U.S. Pat. No. 5,394,136 ("Satellite communication and truck driver bonus notification and awards system").

In some contexts, a medical policy provider or similar service provider 210 may program a control unit or other processing unit 610 to perform operation 1230. The incentive selection 640 may be partly based on a material name, a prescription number, a therapy type, a body part, or some other such indication of the therapeutic component(s) represented within a finite list of allowable values (e.g., as schematically depicted in FIG. 6 as respective columns). The incentive selection 640 may likewise be based on one or more of an age, pathological condition, or other physical attribute of the individual 282 represented within a finite list of allowable values (e.g., as schematically depicted in FIG. 6 as respective rows). A corresponding incentive to the individual 282 may be an indirect or intangible component such as a lower policy premium or enhanced coverage. Another corresponding incentive to the individual 282 may be an immediate and tangible item such as cash or goods dispensed to the individual 282 via interaction unit 275. In some variants, service provider 210 may select different incentives 622, 623 for different individuals 282 who subscribe, based on their preferences or other attributes 655 of their respective profiles 660. Alternatively or additionally, although selection table 1230 is depicted in two dimensions, those skilled in the art will recognize that other variables may also affect the selection 640, readily implemented in tables of three or more dimensions or in functionally equivalent logic. In some variants, for example, an expert service provider or technician 261 may design a selection table that prioritizes subscribers and conditions based on the financial importance of having a treatment performed promptly or on the nature (severity or risk, e.g.) of a subscriber's condition. Alternatively or additionally, processing unit 610 may cause control unit 205 simply to display the indication of the therapeutic component administered to the portion of the individual and the physical attribute of the individual to an authorized service provider 210 and to receive the selection of the incentive(s) to the individual 282 received in response.

Operation 1260 describes transmitting a result of assigning the incentive (e.g. router or other linking unit 390 invoking TCP/IP or other interfaces 380 to transmit one or more components of the incentive selection to the individual 282 or his material provider 281). This can occur, for example, in a context in which a control unit 205 or other processing unit 610 has selected one or more incentives 641, triggering a notification of the selection to linking unit 390. Linking unit 390 invokes transmission circuitry including one or more interfaces 380 to transmit message 158 configured to contain at least a selection 640 of an incentive to an individual 282 to one or more of care provider 283, service provider 210, material provider 281, or other such party through network 240. In some contexts, for example, the individual 282, another message recipient 222, and a service provider 210 are notified of a selection of incentive(s) to process and deliver the incentive(s) to the individual 282 and to other beneficiaries 221. Alternatively or additionally, in some variants, a notification of an incentive to an individual 282 may be transmitted to a care provider 283 or service provider 210 as evidence of patient compliance.

In some variants, linking unit 390 may contain one or more modules configured to perform operation 1260. Such modules may, for example, include control unit 205 or other circuitry for the assembly of one or more messages 158 from a selected incentive to an individual 641. Alternatively or additionally, such modules may include one or more ports 386 configured to connect to network 240 for transmission of message 158 to one or more remote parties (a care provider 283, service provider 210, material provider 281, or beneficiary 221, e.g.). This can occur, for example, in a context in which interface 380 of linking unit 390 selects one or more ports 385, 386 for transmission of message 158 based upon a subscriber list or other predetermined distribution list of intended recipients of message 158. Alternatively or additionally, linking unit 390 may (optionally) contain an output 181 or other interface 380 configured to display message 158 on one or more local media devices such as a printer, PDA, mobile phone, or other display module 185.

In light of teachings herein, numerous existing techniques may be applied for transmitting incentive selections across a communication medium for appropriately disseminating requests or other notifications as described herein without undue experimentation. See, e.g., U.S. Pat. No. 7,483,670 ("Method and apparatus for educational testing"); U.S. Pat. No. 7,359,866 ("Systems and methods for promoting customer loyalty on the Internet"); U.S. Pat. No. 7,334,541 ("Animal behavior shaping device"); U.S. Pat. No. 6,699,188 ("Interactive reward devices and methods"); U.S. Pat. No. 6,651,592 ("Automatic positive behavior reinforcement trainer"); U.S. Pat. No. 6,434,534 ("Method and system for processing customized reward offers"); U.S. Pat. No. 6,151,586 ("Computerized reward system for encouraging participation in a health management program").

In some network contexts, more than one entity may perform instances of operation 1230. Operation 1230 may be performed by a recipient 222 who has a delivery unit 255 configured for computing (or remotely invoking an incentive determination unit 350 or other circuitry for assigning) an incentive to an individual partly based on an indication of a therapeutic component administered to a portion of the individual and partly based on a profile of the individual. Such an interface may generate or otherwise provide such indication(s) to recipient 222 as computational output, in some embodiments, after obtaining such operands directly via network 240. In other contexts, however, a server or other circuitry for generating the indication of the incentive(s) (within network 240 or at a remote location, for example) may permit delivery unit 255 to perform operation 1230 merely by relaying such indication(s). More than one entity may likewise perform instances of operation 1260 in a sequential flow or by similar concurrent, overlapping, or other variant logical arrangement. In some contexts, for example, an initial recipient 222 may perform operation 1260 by transmitting a notification directly indicative of the incentive(s), a resource constituting the incentive, or some other useful result of the assignment of the incentive (in network 240, e.g.).

Figure 7:
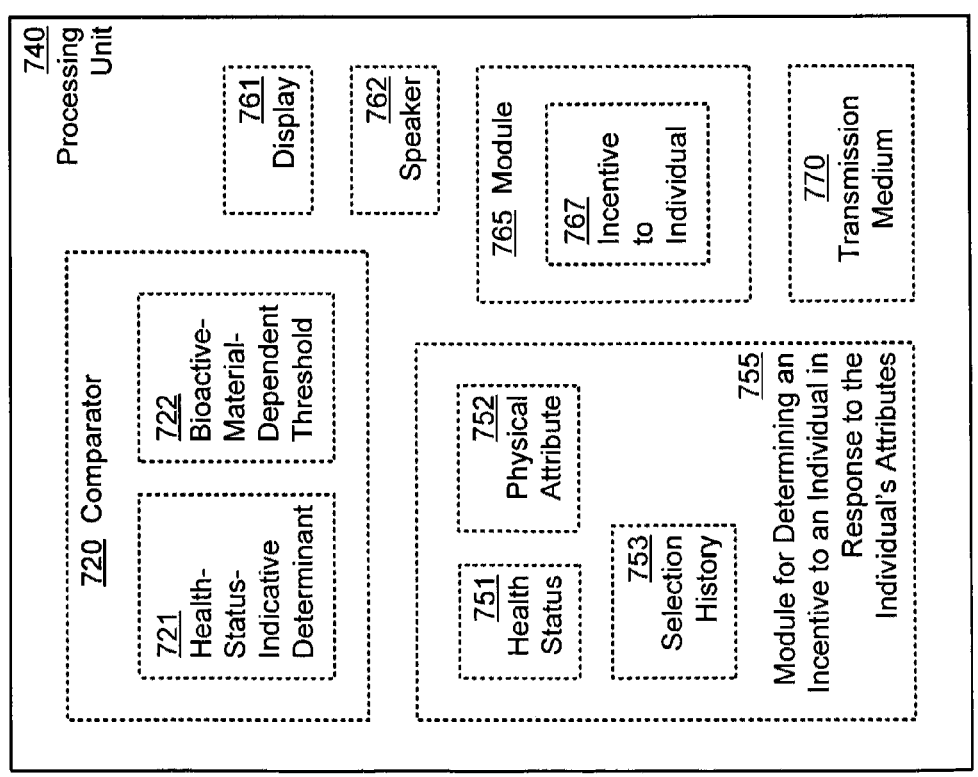

With reference now to FIG. 7, shown is a system 700 in which one or more technologies may be implemented. Processing unit 740 may include one or more instances of comparators 720, modules for determining an incentive to an individual in response to the individual's attributes 755, displays 761, speakers 762, modules 765 for handling incentives to individuals 767, and transmission media 770 as described herein. Comparator 720 may include circuitry for generating a Boolean or other digital output responsive to health-status-indicative determinants 721 or other scalar or natural language determinants as described herein. Such determinants may, for example, be compared (mathematically or textually, e.g.) against bioactive-material-dependent thresholds 722 or other comparands (associated with a trend or range of normalcy in or derived from a profile of an individual receiving a therapeutic component, e.g.) as described herein. In some variants comparison results from comparator 720 may be used to enable or otherwise modulate circuitry or other modules for determining an incentive to an individual in response to the individual's attributes 755 directly as determinants indicative of health status 751 (textually, numerically, or otherwise indicating "unimproved" during or after a therapeutic regimen targeting a measurable symptom or other device-detectable attribute, e.g.). During an interval in which a therapeutic objective (a specified weight loss or blood pressure reduction, e.g.) of a regimen was achieved, for example, a health status 751 may (conditionally and selectively) indicate an affirmative expression ("success," e.g.) or a quantity (computed as a difference, e.g.). In some variants, moreover, a "health status" may denote a normal state, a pathological state, a stage of a disease (a cancer stage, treatment stage, or remission stage, e.g.), a stage or state of pregnancy, or other such descriptors relating an individual to a disease, injury, symptom, or other variable health condition. Alternatively or additionally, the type and scale of the incentive may depend upon one or more physical attributes 752, a selection history 753 (potentially indicative of an incentive recipient's preferences, e.g.), or other components in a profile of the individual 282 or other party (provided by a therapist or other care provider 283, e.g.).

Figure 13:
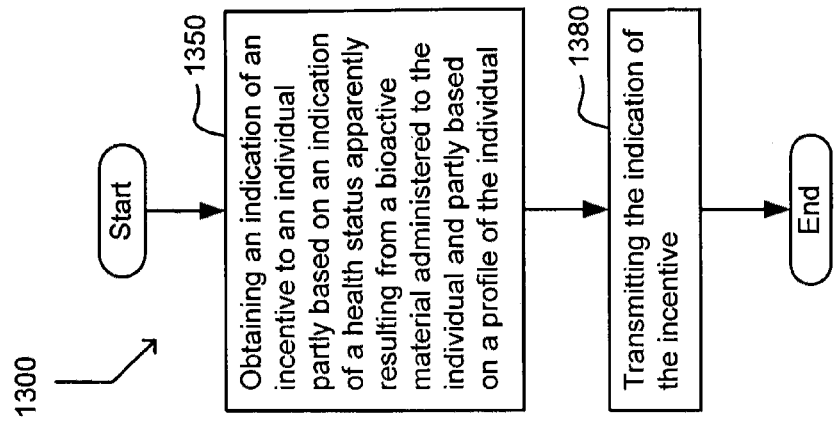
FIG. 13 depicts a high-level logic flow of an operational process described with reference to FIG. 7.

With reference now to FIG. 13, shown is a high-level logic flow 1300 of an operational process. Operation 1350 describes obtaining an indication of an incentive to an individual partly based on an indication of a health status apparently resulting from a bioactive material administered to the individual and partly based on a profile of the individual (e.g. a software-implemented or other module 755 for determining an incentive to individual 282 in response to the individual's attributes generating or otherwise obtaining an indication of an incentive 767 to an individual responsive to a topical treatment and to a weight, age, or other physical attribute 752 of the individual). This can occur, for example, in a context in which such a module receives a prompted menu selection or other indication of a patient reporting an unchanged health status 751 shortly after receiving an antibiotic or other bioactive material prescribed for a prior complaint or other symptom by the patient. In some contexts the circuitry may identify an incentive for a patient to cooperate with a nurse-assisted ingestion or injection of a material (by coming into a clinic, for example) in response to an indication (in profile 660, e.g.) that the therapy apparently failed because the patient was not following through with a prescribed dosage frequency (such indication having been selected by a clinician, e.g.). Alternatively or additionally, processing unit 740 may invoke one or more comparators 720 for the evaluation of one or more components of current health status 751 or other physical attributes 752 to obtain the indication of the incentive 767. In some contexts, for example, comparator 720 may be configured to apply band pass filters or other such computational operations to time data 435 or other such health-status-indicative determinants 721. Alternatively or additionally, in some embodiments, sensors placed on an individual may measure physical activity, temperature, or other physical attributes 752 of the individual as determinants of (i.e., affecting at least some indications of) incentives to individuals 767 or may be implemented as an automated telephonic inquiry to such patients, providers, or others identified herein.

In some variants, processing unit 740 may contain one or more modules configured to perform operation 1350. Such modules may, for example, include an incentive selection module 346 or other circuitry configured to invoke one or more comparators 720 to perform evaluation of one or more patient attributes 320. This can occur, for example, in a context in which a personal digital assistant (PDA) or other determinant module obtains indications of an incentive to individual 767 responsive to the comparison of a physical attribute 321 to a bioactive-material-dependant threshold 722 or other such comparison criteria. Alternatively or additionally, incentive selection module 346 may use other selection criteria such as patient preferences 322 in addition to a health status 751 or other value apparently resulting from a (successful or other) bioactive material 810 in determining the indication of incentive 767.

In light of teachings herein, numerous existing techniques may be applied for using physiological or other measurement data as decision criteria for assessing whether a reward, rebate, or other incentive is warranted as described herein without undue experimentation. See, e.g., U.S. Pat. No. 7,483,670 ("Method and apparatus for educational testing"); U.S. Pat. No. 7,434,541 ("Training guidance system for canines, felines, or other animals"); U.S. Pat. No. 7,375,640 ("System, method and implementation for increasing a likelihood of improved hand hygiene in a desirably sanitary environment"); U.S. Pat. No. 7,334,541 ("Animal behavior shaping device"); U.S. Pat. No. 6,699,188 ("Interactive reward devices and methods"); U.S. Pat. No. 6,651,592 ("Automatic positive behavior reinforcement trainer"); U.S. Pat. No. 6,585,518 ("Adaptive motivation for computer-assisted training system"); U.S. Pat. No. 6,305,943 ("Respiratory sinus arrhythmia training system"); U.S. Pat. No. 6,261,101 ("Method and apparatus for cognitive training of humans using adaptive timing of exercises"); U.S. Pat. No. 6,041,737 ("Litter box trainer").

Operation 1380 describes transmitting the indication of the incentive (e.g. cellular phone or other linking unit 390 invoking an antenna or other transmission medium 770 to transmit the indication of the incentive to the individual to a service provider). This can occur, for example, in a context in which system 300 implements processing unit 740 and in which an interface 380 receives a notification of an incentive to an individual 767 (as incentive indication 371, e.g.), packages it into one or more messages 158, and invokes linking unit 390 to transmit each such message 158 via a respective transmission medium 770. In some contexts, for example, linking unit 390 may transmit a message 158 indicating an available service 148 or other incentive 140 (tangible or otherwise) for which the individual qualifies to a party, a recipient selection module 344, or other such message recipients.

In some variants, transmission medium 770 may contain one or more modules configured to perform operation 1380. Such modules may, for example, include a linking unit 390 or other circuitry configured to invoke one or more ports 385, 386 linked to communication network 240 for the transmission of message 158 which includes a digitally-certified invitation (an attached coupon, e.g.) or other incentive to individual 767. This can occur, for example, in a context in which incentive determination unit 350 or other processing unit 740 invokes transmission medium 770 to configure message 158 to contain at least the incentive to individual 767. Transmission medium 770 may then invoke linking unit 390 to transmit message 158 to handheld devices or other suitable delivery units 225. Alternatively or additionally, other recipients such as service provider 210 or other providers may be the recipient of a message 158 about an incentive to an individual 282 who may be a client or customer of the provider(s).

In light of teachings herein, numerous existing techniques may be applied for transmitting a determination of incentive, service, or other program eligibility across a communications medium as described herein without undue experimentation. See, e.g., U.S. Pat. No. 7,483,838 ("System and method for recruitment of candidates for clinical trials while maintaining security"); U.S. Pat. No. 7,458,889 ("Bonus round for multiple gaming machines where award is multiplied based on certain variables"); U.S. Pat. No. 7,406,480 ("Automated voter registration and tabulation system"); U.S. Pat. No. 7,380,707 ("Method and system for credit card reimbursements for health care transactions"); U.S. Pat. No. 7,194,416 ("Interactive creation and adjudication of health care insurance claims"); U.S. Pat. No. 7,174,302 ("System and method for processing flexible spending account transactions"); U.S. Pat. No. 7,072,842 ("Payment of health care insurance claims using short-term loans"); U.S. Pat. No. 6,839,678 ("Computerized system for conducting medical studies"); U.S. Pat. No. 6,151,586 ("Computerized reward system for encouraging participation in a health management program"); U.S. Pat. No. 6,011,835 ("Method and apparatus for determining a caller's eligibility for a lottery and advising lottery winner during a same call"); U.S. Pat. No. 5,991,731 ("Method and system for interactive prescription and distribution of prescriptions in conducting clinical studies").

In some contexts, an insurance company or similar service provider 210 may program a control unit or other processing unit 740 to signal incentives to a subscriber (to a prescribed regimen, e.g.) responsive to evidence of compliance (with the prescribed regimen, e.g.) by the subscriber. Such evidence may include an indication of a health status 751 that has been deemed (by an insurance provider or other service provider 210, e.g.) sufficient to infer that a given therapeutic component has been administered to the individual. Such health status may be established as "apparently resulting" by a care provider 283 stating that the individual has received such therapies. In some contexts, moreover, it may be established by indirect evidence (accepting an unchanging skin tone as evidence that sunscreen has been applied to a patient's face, e.g.). Alternatively or additionally, a dispenser 170 or similar device may record or transmit indications of dispensations consistent or inconsistent with a regimen, which indications may constitute such evidence. Additionally, such evidence may include one or more other physical attributes of the individual, such as in a case where a physician selects a dosage or other aspect of a regimen according to a patient's physical attributes 590. Alternatively or additionally, non-physical attributes (patient or provider preferences, e.g.) or pragmatic considerations (a treatment cost or a physician-predicted likelihood of success, e.g.) may affect the incentive to the individual indicated by operation 1350. In some variants, moreover, module 765 may implement circuitry for obtaining an indication of an incentive to an individual partly based on an indication of a health status apparently resulting from a bioactive material administered to the individual and partly based on a profile of the individual by retrieving various incentives to individual 767 by performing a search (across network 240, e.g.) of one or more remote sources using one or more search terms obtained from the individual's profile.

With reference now to FIG. 8, shown is a system 800 in which one or more technologies may be implemented. Processing unit 890 may receive one or more messages 830 from a provider 820 (via interface 818, e.g.) relating to a bioactive material 810 or other therapeutic component as input 855. Processing logic 875 may (optionally) respond to data 831 indicating a bioactive material having a (published or other nominal) first value by generating or selecting an indication 861 of one or more incentives having a second value independent of or in excess of the first value. Processing logic 875 may likewise be configured to respond to data 832 indicating another material or other therapeutic component having a first value V1 by generating or selecting an indication 862 of an incentive having a second value V2 to be transmitted via output 885.

With reference now to FIG. 14, shown is a high-level logic flow 1400 of an operational process. Operation 1430 describes obtaining first data indicating a therapeutic component having a first value V1 (e.g. an input 182, 855 or other interface 818 retrieving or otherwise obtaining data 831 for a bioactive material 810 having a list price or other specified value V1). This can occur, for example, in a context M which interface 818 triggers a lookup operation or otherwise obtains a value V1 for material 810 responsive to one or more categories 312 of drugs or other such bioactive material indications 310. In some contexts, for example, interface 818 may include a computer 180 or other interaction unit 275 configured to perform operation 1430. Material value V1 may be contained, for example, on interaction unit 275 in a database or other storage medium 152. Alternatively or additionally, in some variants, information including value V1 may be stored at a remote site and accessed by interaction unit 275 (on the internet or in or via any other available network 240, e.g.). In some contexts, for example, material 810 may include one or more medications, supplements or other nutraceuticals, or other such therapeutic materials described herein. Value V1 may be a material cost, a retail value, or another such quantitative expression of a currency or other resource descriptive (according to a catalog, seller, or purchasing agent 262, e.g.) of the therapeutic component (material 810, e.g.).

In some variants, an interface 818 may contain one or more modules configured to perform operation 1430. Such modules may, for example, include an incentive selection module 346 or other circuitry for associating a value V1 with a dietary supplement, ointment, or other such material. This can occur, for example, in a context in which a provider 820 or other user identifies bioactive material 810 to interface 818, which may assign a preliminary value V1 (for example, by looking up the identifier in a price list) of the material 810. Alternatively or additionally, value V1 may be assigned by material provider 281, care provider 283, service provider 210, or other such parties. In some contexts, moreover, such a value V1 may be determined by agreement of two or more members from the set of material provider 281, care provider 283, service provider 210, or other providers. Alternatively or additionally, in some variants, a value V1 may relate to combinations of therapeutic components of an individual's regimen.

In light of teachings herein, numerous existing techniques may be applied for assigning a value to a bioactive material or other therapeutic component as described herein without undue experimentation. See, e.g., U.S. Pat. No. 7,505,916 ("System and method for allocating home health services"); U.S. Pat. No. 7,478,061 ("Automated audit process"); U.S. Pat. No. 7,430,515 ("System and method for externalization of formulas for assessing damages"); U.S. Pat. No. 7,418,400 ("Internet-enabled system and method for assessing damages"); U.S. Pat. No. 7,346,522 ("Medical payment system"); U.S. Pat. No. 6,879,959 ("Method of adjudicating medical claims based on scores that determine medical procedure monetary values"); U.S. Pat. No. 6,393,404 ("System and method for optimizing medical diagnosis, procedures and claims using a structured search space"); U.S. Pat. No. 6,061,657 ("Techniques for estimating charges of delivering healthcare services that take complicating factors into account"); U.S. Pat. No. 5,915,241 ("Method and system encoding and processing alternative healthcare provider billing").

Operation 1440 describes obtaining an indication of an incentive having a second value V2>V1 and partly based on the therapeutic component and partly based on a provider of the therapeutic component (e.g. server or other processing logic 875 receiving message 830 and using lookup tables or equivalent logic 875 to select one or more incentives 862, 861 having value V2 which exceeds a wholesale or other nominal value V1 of a nutritional supplement or other material 810 to be administered to an individual 282). This can occur, for example, in a context in which a processing unit 890 (in a control unit of service provider 210, e.g.) selects one or more indications of one or more incentives 862 whose individual or cumulative value V2 exceeds value V1. In some contexts, for example, one or more cash or cash-equivalent incentives 140 may be combined such that the aggregated value V2 exceeds a nominal value V1 of administered material 810. Alternatively or additionally, in some variants, incentives 140 may consist of policy rate reductions, gift certificates, or other such benefits 120. Also in some variants, the therapeutic component may comprise an immunization or diagnostic test relating to disease prevention (or other such service) performed, for example, by a professional care provider 283.

In some variants, processing unit 890 may contain one or more modules configured to perform operation 1440. Such modules may, for example, include an incentive determination unit 350 or other circuitry for selecting one or more incentives 140 based upon material value V1. This can occur, for example, in a context in which processing logic 875 selects one or more incentives 140 such that V2>V1, optionally such that V2 is based on an additive, multiplicative, polynomial, or other readily-computed function of V1. Alternatively or additionally, one or more incentives 140 may (optionally) be incremented or otherwise determined by processing logic 875 responsive to one or more identifiers 311, categories 312 of materials ("preferred" or not, e.g.), dosages 437 or other values 313, subject physical attributes 321, subject preferences 322, prices or other inputs 855 from material providers 281 or service providers 283, or other such quantifiable or categorical determinants 330.

In light of teachings herein, numerous existing techniques may be applied for selecting a membership rate reduction, rebate, or other incentive value generally sufficient to entice one or more individuals to perform a notification, enrollment, explanation, or compliance task as indicated herein without undue experimentation. See, e.g., U.S. Pat. No. 7,516,883 ("Financial transaction system with consumer reward and net settlement"); U.S. Pat. No. 7,398,248 ("System and method for using cards for sponsored programs"); U.S. Pat. No. 7,233,913 ("System and method for providing shopping aids and incentives to customers through a computer network"); U.S. Pat. No. 7,120,592 ("Method, apparatus and processed for real time interactive online ordering and reordering and over the counter purchasing with rebate, saving, and investing processes"); U.S. Pat. No. 7,072,862 ("Spending vehicles for payments"); U.S. Pat. No. 7,058,591 ("Method and apparatus for generating purchase incentives based on price differentials"); U.S. Pat. No. 6,980,960 ("System and method for providing a fuel purchase incentive"); U.S. Pat. No. 6,658,323 ("Vending machine apparatus for encouraging participation in a marketing effort"); U.S. Pat. No. 6,282,516 ("Process, system and computer readable medium for in-store printing of discount coupons and/or other purchasing incentives in various departments within a retail store"); U.S. Pat. No. 6,208,974 ("Method and system for managing wellness plans for a medical care practice").

Operation 1460 describes transmitting the indication of the incentive partly based on the therapeutic component and partly based on the provider of the therapeutic component (e.g. output 885 transmitting one or more indications 862 of incentives 140, 621, 622 to one or more message recipients 222). This can occur, for example, in a context in which processing logic 875 performs operation 1440 by providing one or more such indications 862 (the second value V2, a beneficiary identifier, or other attributes of the incentive, e.g.) at a portion of memory 870 accessible to output 885. Alternatively or additionally, such indications 862 may notify one or more material providers 281, care providers 282, service providers 210, or other entities who access network 240 of a delivered or offered incentive. In some variants, moreover, instances of flow 1400 may be performed without determining these respective values V1, V2 and without any direct reference to them.

In some contexts, service provider 820 may transmit one or more messages 830 containing data 831 indicating a bioactive material having a (nominal) first value. Alternatively or additionally, such messages may contain data 832 indicating a specific respiratory or physical therapy session or other therapeutic component having a nominal value V1, such indication(s) 861 being received via interaction unit 275 into a first portion of memory 870. A second portion of memory 870 may receive one or more indication(s) 862 of an incentive having a second value V2 partly based on biometric data 436, time data 435, dosages 437, or other attributes of the therapeutic component. As operation 1440 indicates, such an indication of an incentive may also be partly based on an identifier of a care provider 283 or input 855 from other providers of therapeutic components. In some contexts, such an incentive may be earmarked for a category of individuals 282 who need a painful treatment or who otherwise may be reluctant to receive a physical therapy. Alternatively or additionally, such an incentive may be earmarked for a material provider 281 or care provider 283 who encourages individual 282 to accept a treatment component and who would otherwise typically not provide such encouragement. In either case, V2 may be determined (by service provider 210 or by empirical methods, e.g.) according to the importance of the therapeutic component, a typical reluctance of the putative incentive recipient, a physician or other expert's indication of therapeutic importance, and other such factors irrespective of V1. In some contexts, for example, an insured individual 282 may buy a drug for a (nominal) retail value from a material provider 281, who then receives a larger compensation (having a value V2>V1, e.g.) from the service provider 210 responsive to output 885. Alternatively or additionally, one or more such transmissions (instances of operation 1460, e.g.) may cause such individuals 282 to receive rebates, credits 117, or other tangible or intangible benefits 120 (from service provider 210, e.g.). Such incentive selection decisions can be implemented by querying service providers 210 or subject individuals 282 and assimilating their input, for example, into a table or other logic as described herein or as indicated in the art.

In some network contexts, more than one entity may perform (instances of) any of operations 1430, 1440, 1460. Operations 1430 and 1440 may be performed by a physician or other skilled service provider 210 who provides or otherwise obtains the information about the therapeutic component, the provider thereof, and the indication of the incentive(s). In some contexts operation 1440 may include some computed comparison or other verification that V2>V1. A control unit 205 configured by such a person may likewise provide a selection or other ranking among several suitable therapeutic components or several potential providers of the (actual or resulting) therapeutic component, for example, as additional instances of operations 1440 and 1430. This can occur, for example, in a context in which control unit 205 implements one or more processing units 890, incentive determination units 350, interfaces 818, or other suitable logic described herein for performing "obtaining" functions. Alternatively or additionally, linkage 205, media 355, interfaces 380, or other features (of network 240, e.g.) described herein may be configured to perform operation 1460. In some contexts, moreover, a linking unit 390 may initially perform operations 1430 and 1440 by aggregating and transmitting provider-selected determinants 330 or other useful data 430 (via one or more media 355, 450) to incentive determination unit 350, which determines and transmits the resulting incentive indication 372 back via interface 380 and thus performs all of operations 1430, 1440, 1460. Moreover an interface 380 that transmits the indication of the incentive (from the incentive determination unit 350 via port 385 or by a display to a user, e.g.) literally performs another instance of operation 1460. In some contexts, moreover, the same user may perform operation 1460 yet again by invoking circuitry for relaying or otherwise transmitting the indication (to recipient 222 via network 240, e.g.).

With reference now to FIG. 9, shown is a system 900 in which one or more technologies may be implemented. In response to input 941 (from a dispenser or other interaction unit 275 in a vicinity of a subject individual 282, e.g.), response unit 960 may provide output 942 to one or more providers 920 of material 910 or other parties. Such output may include one or more indications 921, 922 of an incentive to a provider 925 of a therapeutic component at least partly based on a measurement 986 or other objective indication that the therapeutic component has been administered to a patient 985. This can occur, for example, in a context in which the incentive to provider 925 or indication 922 depends upon one or more (indications) of status 971, (apparent, potential, or diagnosed) pathology 972, or other patient attributes 970 as described herein. Alternatively or additionally, the incentive to provider 925 or indication 922 thereof may depend upon one or more categorical attributes of a material 910 or other therapeutic component (obtained as input 941 via one or more interfaces 380, 918 described herein).

With reference now to FIG. 15, shown is a high-level logic flow 1500 of an operational process. Operation 1520 describes obtaining an indication of an incentive to a provider of a therapeutic component and at least partly based on an objective indication that the therapeutic component has been administered to a portion of an individual (e.g. a computer 180 or other interface 918 obtaining an indication 921 of an incentive to provider 925 (an in-kind incentive to a care provider 283, e.g.) in response to an objective indication that a bioactive material has been administered to a patient or other individual 282 pursuant to a therapy). This can occur, for example, in a context in which compliance-indicative device 190 or other response unit 960 includes circuitry or other media 450 configured to compare a measurement 986 (of a current weight of a patient or of a therapeutic-material-containing vessel via a scale, e.g.) with one or more thresholds 461, 462 (indicating a recurrent presence of the patient on the device or an appropriate schedule of dispensations from the therapeutic-material-containing vessel, e.g.). Alternatively or additionally, such an interface may apply other such criteria to detect a presence or absence of an objective indication that a bioactive material has administered into or onto a patient (transmitted in response to an actuation or apparent manual movement of a vessel containing the bioactive material or similar event, e.g.). Those skilled in the art will recognize metabolite concentrations in bodily fluids or many other measurements 986 suitable for providing the objective indication that the therapeutic component has been administered to a portion of the individual in light of teachings herein. In some contexts, for example, a rise in skin temperature may signal an exposure of the portion of the individual to infrared radiation or other therapeutic warming.

In light of teachings herein, numerous existing techniques may be applied for requesting, receiving, or otherwise interacting with numerical thresholds and related criteria as described herein without undue experimentation. See, e.g., U.S. Pat. No. 7,250,855 ("False alarm mitigation using a sensor network"); U.S. Pat. No. 7,079,035 ("Method and apparatus for controlling an alarm while monitoring"); U.S. Pat. No. 7,037,273 ("Core body temperature monitoring in heart failure patients"); U.S. Pat. No. 6,942,626 ("Apparatus and method for identifying sleep disordered breathing"); U.S. Pat. No. 6,569,095 ("Adaptive selection of a warning limit in patient monitoring"); U.S. Pat. No. 6,552,531 ("Method and circuit for processing signals for a motion sensor"); U.S. Pat. No. 6,263,243 ("Rate adaptive pacemaker").

In some variants, interface 918 may contain one or more modules configured to perform operation 1520. Such modules may, for example, include cross-correlators or other data processing units that examine combinations of measurements 986 to provide an objective indication whether, when, how, or where a local therapeutic component was administered. This can occur, for example, in a context in which measurement data such as an electrocardiogram (ECG) trace may be processed using peak detection techniques to obtain a subject's heart rate over a period of time as evidence of performance of cardiovascular exercise or other cardiac treatment regimens. Alternatively or additionally, measurement of a bioactive material 910 (or a metabolyte thereof) in an individual 282 (or in samples acquired from the individual) may be used to verify compliance with a prescribed therapeutic regimen. In some contexts, moreover, long term trends in subject status information such as a rise or fall in weight may give an indication of diet or exercise compliance (in cases of obesity, anorexia, or other eating disorders, e.g.) useful as an incentive modulation index or other determinant as described herein.

In light of teachings herein, numerous existing techniques may be applied for using measurement data to determine compliance with medicinal or other programs targeting "a portion of" an individual as described herein without undue experimentation. See, e.g., U.S. Pat. No. 7,504,954 ("Radio frequency identification pharmaceutical tracking system and method"); U.S. Pat. No. 7,395,214 ("Apparatus, device and method for prescribing, administering and monitoring a treatment regimen for a patient"); U.S. Pat. No. 7,375,640 ("System, method and implementation for increasing a likelihood of improved hand hygiene in a desirably sanitary environment"); U.S. Pat. No. 7,369,919 ("Medication adherence system"); U.S. Pat. No. 7,295,890 ("Prescription drug compliance monitoring system"); U.S. Pat. No. 7,166,063 ("Brace compliance monitor"); U.S. Pat. No. 7,086,399 ("Apparatus for delivery of humidified gases therapy, associated methods and analysis tools"); U.S. Pat. No. 6,980,958 ("Apparatus and methods for monitoring and modifying anticoagulation therapy of remotely located patients"); U.S. Pat. No. 6,973,371 ("Unit dose compliance monitoring and reporting device and system"); U.S. Pat. No. 6,926,667 ("Patient compliance monitor"); U.S. Pat. No. 6,645,142 ("Glucose monitoring instrument having network connectivity"); U.S. Pat. No. 6,494,579 ("Eye self-test device"); U.S. Pat. No. 6,151,586 ("Computerized reward system for encouraging participation in a health management program").

Operation 1570 describes including the indication of the incentive to the provider of the therapeutic component in a message to be transmitted (e.g. a subject monitor or other response unit 255, 960 invoking a satellite communication circuit or other output 942 to transmit one or more such indications 921 in a message 158 about the subject's therapeutic regimen to a service or material provider 920). This can occur, for example, in a context in which response unit 960 contains or is otherwise in communication with a compliance-indicative device 190, in which output 942 is routed through network 240, and in which response unit 960 packages at least an incentive to provider 925 and optionally one or more measurements 986 or other objective indicia that a bioactive material has been administered to a patient 985 into a message 158 to be transmitted to provider 920. In some contexts, for example, information pertaining to temperature, absorbance or other measurement data may be packaged with trend values or other objective indications that a bioactive material has been administered in one or more messages 158 and transmitted (via linking unit 390, e.g.).

In some variants, such response units may contain one or more modules configured to perform operation 1570. Such modules may, for example, include linking unit 390 or other circuitry configured to invoke one or more ports 385 to transmit an incentive-indicative message 158 across network 240. This can occur, for example, in a context in which measurement data 430 from blood samples taken from an individual 282 show the presence of bioactive material 910 at a concentration appropriate for the clinical protocol in which the individual 282 is enrolled. Linking unit 390 may then invoke one or more ports 385, 386 to transmit such messages across network 240, optionally containing compliance-indicative or other useful data 430 as described herein. Alternatively or additionally, coloration, image processing results, or other processed information giving an indication of the effectiveness of treatment for liver disease, lesions, or other pathologies may be transmitted to expert consultants or other service providers 210 remotely.

In light of teachings herein, numerous existing techniques may be applied for transmitting therapeutic compliance information remotely across a communication medium as described herein without undue experimentation. See, e.g., U.S. Pat. No. 7,504,954 ("Radio frequency identification pharmaceutical tracking system and method"); U.S. Pat. No. 7,486,040 ("Circuit to momentarily increase the peak torque of a DC motor"); U.S. Pat. No. 7,395,214 ("Apparatus, device and method for prescribing, administering and monitoring a treatment regimen for a patient"); U.S. Pat. No. 7,375,640 ("System, method and implementation for increasing a likelihood of improved hand hygiene in a desirably sanitary environment"); U.S. Pat. No. 7,369,919 ("Medication adherence system"); U.S. Pat. No. 7,295,890 ("Prescription drug compliance monitoring system"); U.S. Pat. No. 7,166,063 ("Brace compliance monitor"); U.S. Pat. No. 7,086,399 ("Apparatus for delivery of humidified gases therapy, associated methods and analysis tools"); U.S. Pat. No. 6,980,958 ("Apparatus and methods for monitoring and modifying anticoagulation therapy of remotely located patients"); U.S. Pat. No. 6,973,371 ("Unit dose compliance monitoring and reporting device and system"); U.S. Pat. No. 6,926,667 ("Patient compliance monitor"); U.S. Pat. No. 6,645,142 ("Glucose monitoring instrument having network connectivity"); U.S. Pat. No. 6,494,579 ("Eye self-test device"); U.S. Pat. No. 6,151,586 ("Computerized reward system for encouraging participation in a health management program").

In some network contexts, more than one entity may perform operations 1350 and 1380. Operation 1350 may be performed by a technician 261 or other user as described herein, such as by invoking local circuitry (implemented in a response unit 255 or otherwise in an immediate vicinity of the user) for obtaining the indication of incentive 140 to an individual 282 in response to an indication that a therapeutic material was apparently effective. In a context in which the profile of individual 282 indicates a medication component or other data 430 related to a therapy for improving or maintaining a blood pressure, temperature, material concentration, or other such measurable biometric data 436, for example, technician 261 or incentive determination unit 350 may each respond by indicating the incentive 140 contingent upon whether the medication had the intended effect. This can occur, for example, in a context in which applying one or more thresholds 462 to the biometric data 436 readily indicates whether a chemotherapy, antibiotic, pain control, or other such predetermined regimen can indicate whether the regimen has been "apparently" effective according to a corresponding defined possible outcome set and in which an actuary or other analyst has indicated that an expected effect of the incentive 140 will be worth the corresponding expense. This can occur in a context in which a material provider 281 or care provider 283 has made such an indication based upon a personal familiarity with the individual 282, for example. Alternatively or additionally, such a configuration can become useful in a context in which service provider 210 has made such an indication based upon one or more demographic commonalities between the individual 282 and earlier program participants whose compliance patterns, therapeutic outcomes, and other relevant information were statistically aggregated. In some variants, moreover, interface 380 may perform operation 1380 (or one or more "transmitting" functions described herein) by transmitting the resulting incentive indication 371 (to or via a storage medium 152, display medium 154, or transmission medium 156, e.g.).

Figure 10:
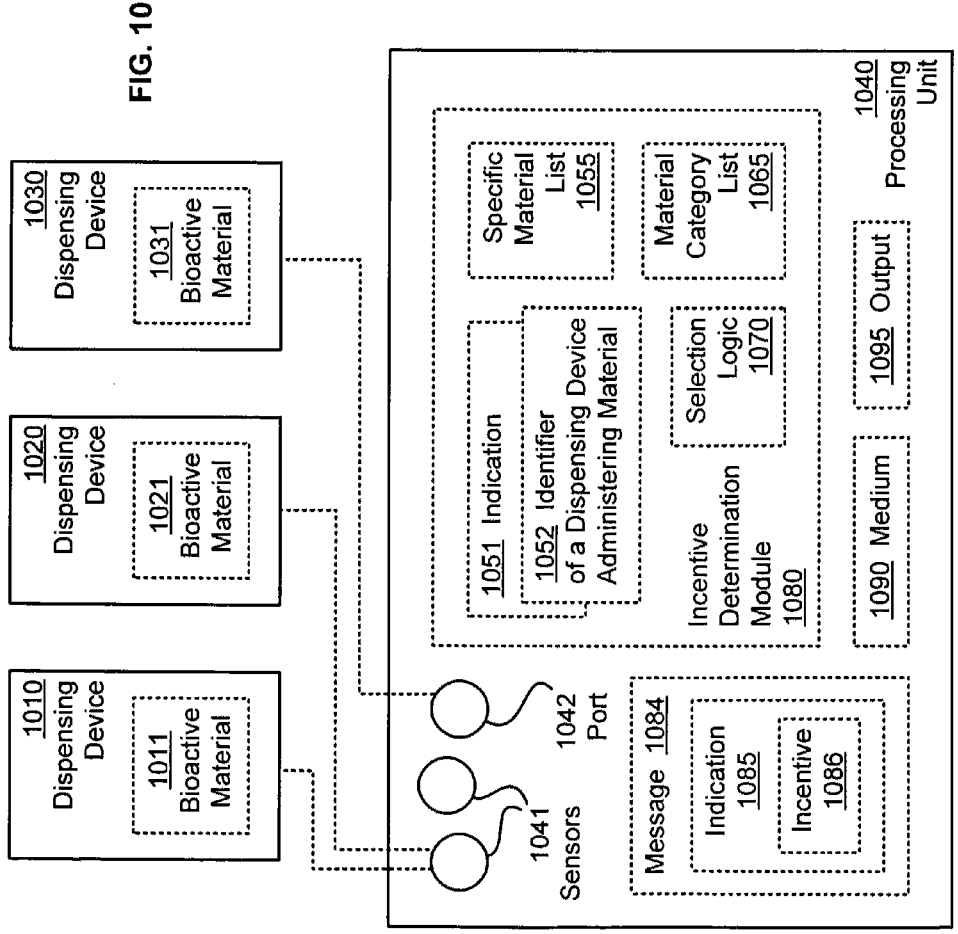

With reference now to FIG. 10, shown is a system 1000 in which one or more technologies may be implemented. One or more dispensing devices 1010, 1020, 1030 (configured to dispense bioactive materials 1011, 1021, 1031, for example) may be operatively coupled or otherwise monitored via one or more sensors 1041 or ports 1042 of a processing unit 1040. In some variants, processing unit 1040 includes or otherwise invokes an incentive determination module 1080 (implemented as selection logic 1070, e.g.) responsive to one or more indications 1051 from or identifiers 1052 of a dispensing device administering material on a specific material list 1055 or indicated by a material category list 1065. In some variants, such software-controlled or other special-purpose circuitry can generate a message 1084 manifesting a selection of an incentive 1086 or an indication 1085 of an incentive transmitted via a display or transmission medium 1090 or other output 1095 as described herein.

Figure 16:
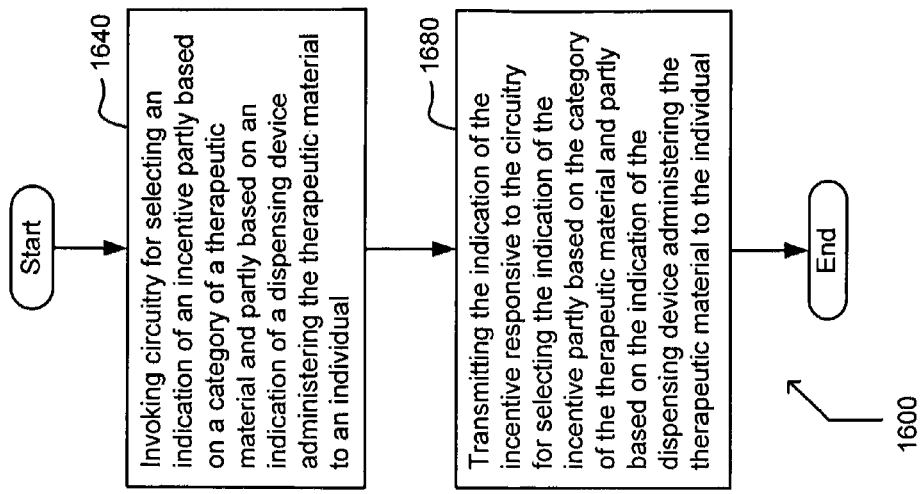
FIG. 16 depicts a high-level logic flow of an operational process described with reference to FIG. 10.

With reference now to FIG. 16, shown is a high-level logic flow 1600 of an operational process. Operation 1640 describes selecting an indication of an incentive partly based on a category of a therapeutic material and partly based on an indication of a dispensing device administering the therapeutic material to an individual (e.g. incentive determination module 1080 selecting at least one incentive 1086 in response to comparing one or more identifiers 1051 of bioactive material 1021, 1031 with one or more matches thereof in a material category list 1065 and in response to one or more dispensing devices 1010, 1020, 1030). This can occur, for example, in a context in which a dispensing device 1020, 1030 indicates a dispensation of a bioactive material 1021, 1031 and in which incentive determination module 1080 selects a default incentive in response to determining that the material is not on specific material list 1055 or that its category is not on material category list 1065. Alternatively or additionally, processing unit 1040 may receive an identifier of the bioactive material or an identifier of itself in a context in which incentive determination module 1080 has access to some indication of a material or incentive corresponding thereto. In some contexts, for example, such a determination may be triggered by one or more sensors 1041 or ports 1042 receiving one or more indications 1051 of a dispensing device administering such material. Alternatively or additionally, material category list 1055 may comprise a table or other records 1985 associating each category with a specific incentive so that incentive determination module 1080 can specify incentives in response to such categories or other indications. This can occur, for example, in a context in which incentive determination module 350 and port 385 each perform an instance of operation 1640 that causes port 385 or interface 380 to display or otherwise transmit the indication of the incentive 140 (to providers or other individuals 282 who subscribe to a program, e.g.) pursuant to "transmitting" operations described herein.

In some variants, a linking unit 390 or other such module (in control unit 205 or network 240, e.g.) may include one or more modules configured to perform operation 1640. Such modules may, for example, comprise circuitry for computing an incentive 140 partly based on a category 312 of a bioactive material and partly based on one or more other determinants 330 (an indication 474 of a handheld dispenser 170 or other dispensing device 1020 administering the bioactive material 1021, e.g.). This can occur, for example, in a context in which incentive determination unit 350 performs operation 1640 by indicating at least one incentive 140 and in which the individual or other beneficiary may accept the incentive. Alternatively or additionally, such a control unit 205 may present incentive indications 371, 372 to a service provider 210 for approval before triggering operation 1680. In some contexts, moreover, service provider 210 may be authorized to validate or modify one or more incentives 140, messages 150 or other indications by which the incentives are presented, or protocols by which the incentives are determined.

In light of teachings herein, numerous existing techniques may be applied for facilitating a service provider in managing automatic message generation as described herein without undue experimentation. See, e.g., U.S. Pat. No. 7,490,086 ("Apparatus and method for providing job searching services recruitment services and/or recruitment-related services"); U.S. Pat. No. 7,490,048 ("Apparatus and method for processing and/or for providing healthcare information and/or healthcare-related information"); U.S. Pat. No. 7,430,554 ("Method and system for telephonically selecting, addressing, and distributing messages"); U.S. Pat. No. 7,386,595 ("System for remote configuration of automatic reply message settings using an email message sent from a second email address to a first email address allocated to a user"); U.S. Pat. No. 7,272,212 ("System and method for the creation and automatic deployment of personalized, dynamic and interactive voice services"); U.S. Pat. No. 7,254,563 ("Method and arrangement for automatically ordering supplies which are consumed during usage of a device"); U.S. Pat. No. 7,242,308 ("Bed status information system for hospital beds"); U.S. Pat. No. 7,200,652 ("Method and system for providing automatic notification of end of lease of computers and their locations"); U.S. Pat. No. 7,103,154 ("Automatic transmission of voice-to-text converted voice message"); U.S. Pat. No. 6,975,231 ("Systems and methods for improving hand hygiene compliance"); U.S. Pat. No. 6,941,466 ("Method and apparatus for providing automatic e-mail filtering based on message semantics, sender's e-mail ID, and user's identity"); U.S. Pat. No. 6,505,051 ("System for real time notification of subscriber service changes using messaging systems"); U.S. Pat. No. 6,324,393 ("Auto locating emergency rescue transmitter (ALERT)"); U.S. Pat. No. 6,240,394 ("Method and apparatus for automatically generating advisory information for pharmacy patients"); U.S. Pat. No. 6,216,104 ("Computer-based patient record and message delivery system"); U.S. Pat. No. 6,064,318 ("Automated data acquisition and processing of traffic information in real-time system and method for same").

Operation 1680 describes transmitting the indication of the incentive responsive to the circuitry for selecting the indication of the incentive partly based on the category of the therapeutic material and partly based on the indication of the dispensing device administering the therapeutic material to the individual (e.g. output 1095 triggering a message 158 of congratulations as an indication 1085 of the incentive 1086 via a medium 1090 of display or wireless transmission). This can occur, for example in a context in which one or more dispensing devices 1010 mechanically support processing unit 1040, in which the message includes a description of a regimen 1747 associated with the dispensing device (vessel 1790, e.g.) and an attachment (a pleasing app, desktop image, or eligibility 147, e.g.) as a component of the incentive, e.g.), and in which output 1095 comprises software-controlled or other circuitry for transmitting indication 1085. See FIG. 17. In some contexts, for example, a service provider 210 (wholesaler or importer, e.g.) may assign such attachments each to a respective category of therapeutic materials in the provider's inventory. Alternatively or additionally, one or more components of the incentive (eligibilities 147 or terms 131 or conditions 134, e.g.) may be incrementally adjusted (by adjusting and transmitting a "current odds of winning" a prize as a quantified "indication of an incentive" or other readily-scalable control variable, e.g.) as a function of a frequency or other indication of a degree of apparent compliance with a regimen.

Each instance of operation 1690 may cause a respective transmission of such indications 1085, in some implementations, optionally as a succession of messages sent at programmatic intervals or to distinct recipients. If a care provider 283 does not accept an incentive within a given interval, for example, a processing unit 1040 or other response unit 255 may conditionally respond with an incentive to material provider 281 or other potential beneficiary 221 of such incentive(s). In some variants, each such instance may indicate a respective incentive 1086 available to a program participant or other party as described herein.

Alternatively or additionally, such units may likewise be configured to perform operation 1680 by invoking an interface 380 or port 386 (as an application-specific module or other circuitry for transmitting the indication of the incentive, e.g.). This can occur, for example, in a context in which such content is transmitted (via one or more physical, tangible media 355 in network 240, e.g.) to a beneficiary 221 or other party as exemplified herein. Alternatively or additionally, such an interface 380 may be used (in delivery unit 225 by a beneficiary 221 or other recipient 222, e.g.) to respond to the indication of the incentive, such as by manifesting a consent to be monitored or otherwise subscribe to a program as described herein. In some variants, moreover, one or more compliance-indicative devices 190 or other interfaces 518, 818, 918 may include one or more instances of a processing unit 610, 890, 740, 1040 or response unit 255, 580, 960 defining incentives to one or more parties as described above.

Figure 17:
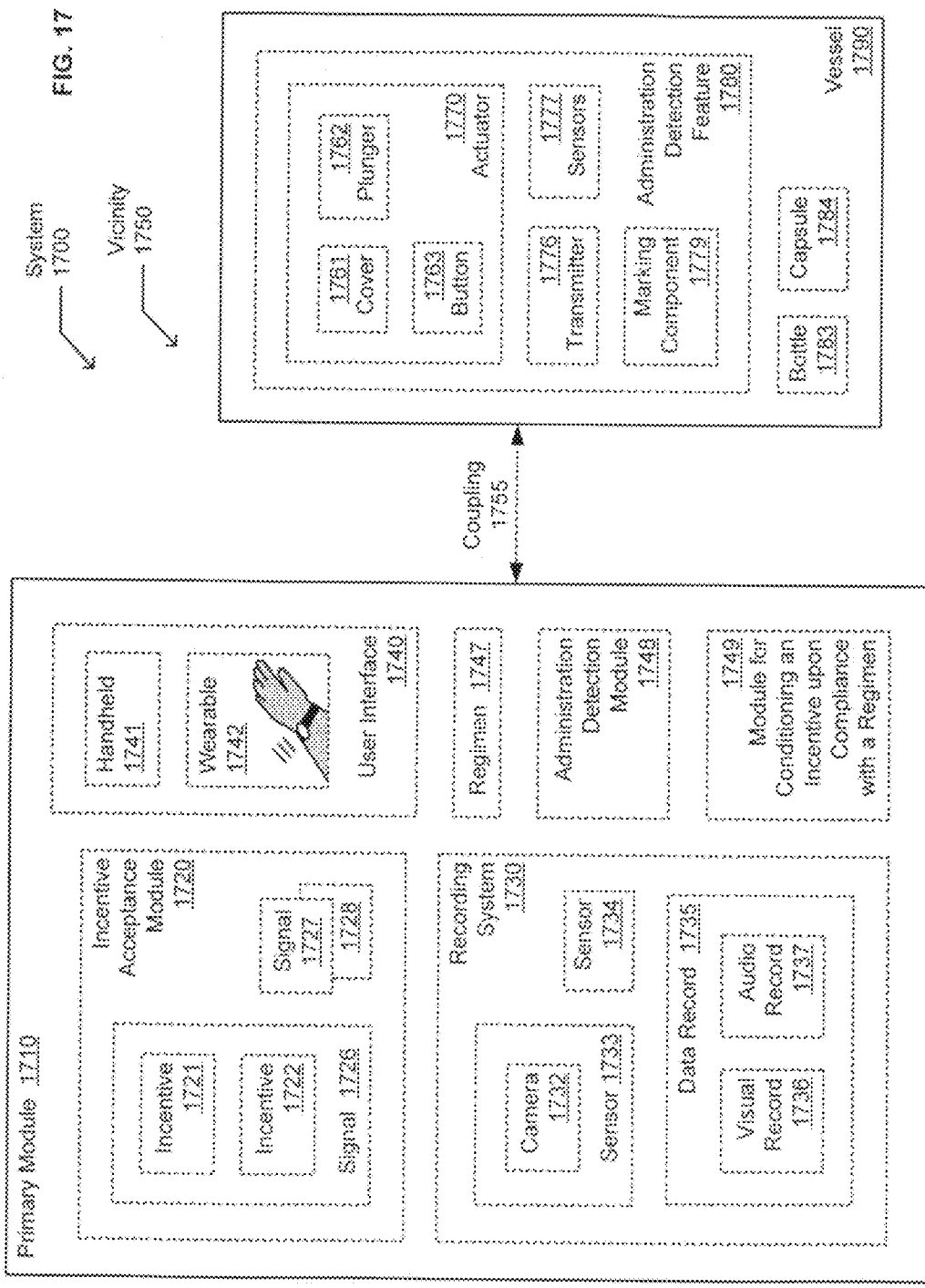
FIG. 17 depicts an exemplary environment facilitating interaction with or observation of a vessel.

With reference now to FIG. 17, shown is a system 1700 in which one or more technologies may be implemented. A bottle 1783, capsule 1784, or other vessel 1790 may include one or more plungers 1762, slidable or other covers 1761, buttons 1763, removable caps, or other actuators 1770. Such administration detection features 1780 may be configured effectively to permit one or more primary modules 1710 to monitor administrations (of a therapy, e.g.) within a vicinity of a vessel 1790, transdermal delivery device, iontophoretic device, patch with microprotrusions, or other dispenser. In some variants, for example, one or more transmitters 1776 on such dispensers permit periodic or occasional notifications (via a wireless or other coupling 1755 with a primary module 1710, e.g.) of such administrations (detected via one or more sensors 1777 of the vessel 1790, e.g.) or a remaining quantity of material (nominally or actually) available for dispensation. Alternatively or additionally, a colorant or other marking component 1779 permits direct optical or auditory monitoring (of a vessel or material, e.g.) within a vicinity 1750 of the dispenser or of a recipient 222 of the therapy. Such systems may likewise include or otherwise interact with a vessel 1790 or other object containing one or more bioactive materials 685, 1021 or other therapeutic components: medications, nutraceuticals, placebos, inhalants, inoculants or other such materials.

In some variants, delivery unit 225 may include one or more primary modules 1710 having one or more incentive instances of acceptance modules 1720, recording systems 1730, user interfaces 1740, regimens 1747, administration detection modules 1748, modules for conditioning an incentive upon compliance with a regimen 1749, or administration detection features 1780 as described herein. In some contexts, for example, incentive acceptance module 1720 may handle one or more instances of signals 1726 indicative of one or more incentives 1721, 1722 as described herein. Alternatively or additionally, such a module may handle one or more signals 1727 indicative of enrollment certification or signals 1728 indicative of informed consent (from a program participant or legal guardian, e.g.). Recording system 1730 may include a camera 1732 or other sensor 1733 (capable of capturing a visual record 1736 or other data record 1735 confirming an administration or other relevant event as described herein, e.g.). An auditory sensor 1734 may likewise capture an audio record 1737 or other data record 1735 confirming a notification, enrollment, acceptance, transfer, or other relevant event as described herein.

Figure 18:
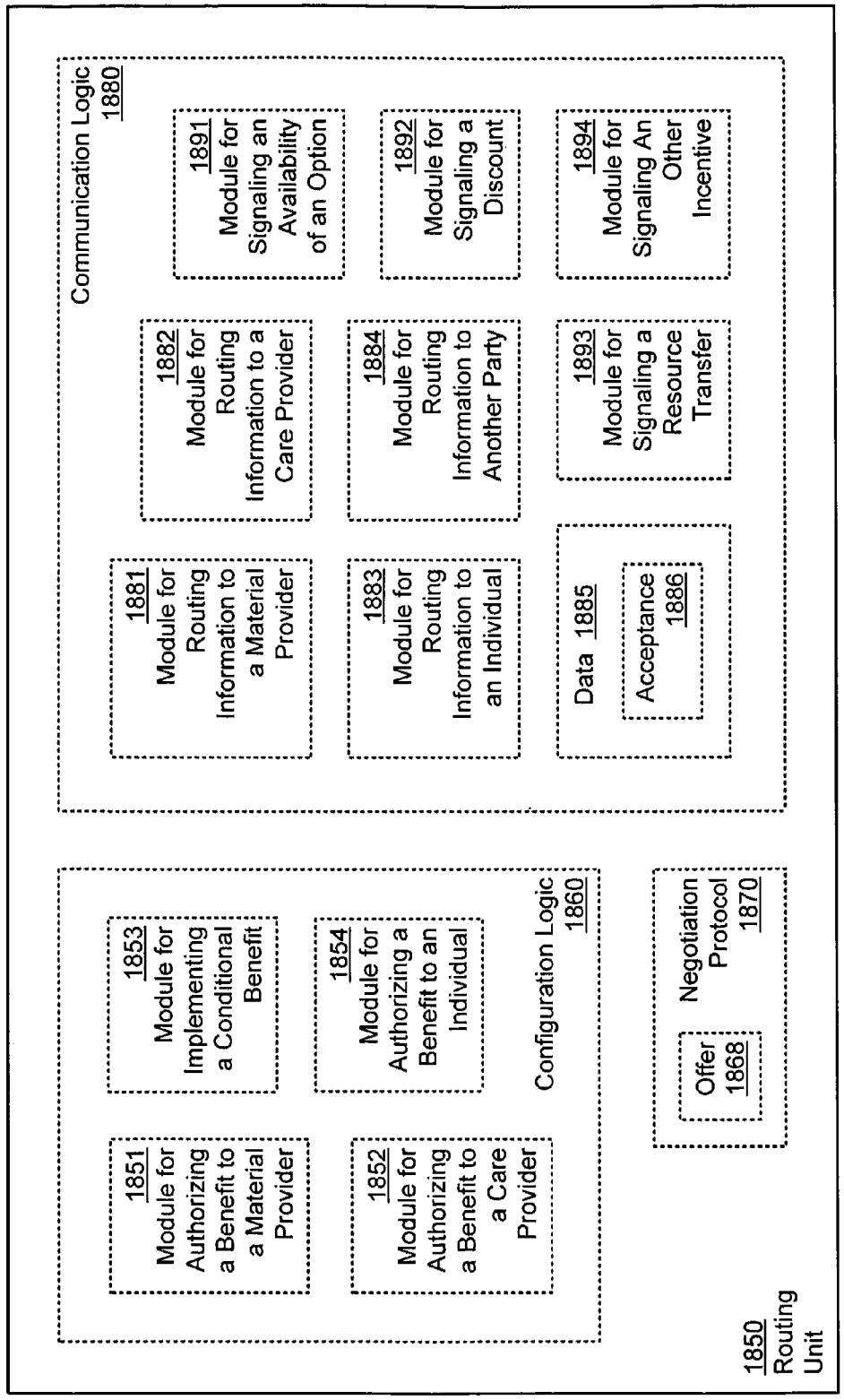
FIG. 18 depicts an exemplary environment featuring a routing unit.

With reference now to FIG. 18, shown is a system 1800 in which one or more technologies may be implemented. In some variants, a response unit or processing unit as described above may include one or more implementations (software, hardware, or other operable representations, e.g.) of configuration logic 1860, negotiation protocols 1870 (for handling offers 1868 or other incentives 140, e.g.), or communication logic 1880 as described herein. Configuration logic 1860 may include, for example, one or more instances of modules for authorizing a benefit to a material provide 1851, modules for authorizing a benefit to a care provider 1852, modules for implementing a conditional benefit 1853, or other modules for authorizing a benefit to an individual 1854 such as circuitry or device-executable instructions as described herein. Such modules may, for example, comprise circuitry for conditioning the benefit upon obtaining data 1885 indicative of an acceptance 1886 of an incentive or compliance with a regimen pursuant to one or more negotiation protocols 1870.

In some variants, for example, incentive determination module 350 may include or otherwise communicate with a module for authorizing a benefit to a material provider 1851 such as circuitry for manifesting an improvement in a reputation of material provider 281. This may be implemented, for example, by adjusting a personal, organizational, or other aggregate performance rating 138. This can occur, for example, in a context in which configuration logic 1860 resides in interaction unit 275 or other subsystems adjoining network 240, in which service provider 210 maintains such ratings on many such providers or other message recipients 222, in which the cumulative effect of such adjustments permit such recipients 222 to gain or retain an eligibility 146, and in which such eligibilities are valued by at least some such recipients 222. Alternatively or additionally, such a module for authorizing a benefit to a material provider 1852 may include or otherwise operate in conjunction with a module for implementing a conditional benefit 1853 (to the material provider or to another party identified herein, e.g.). As described further below, moreover, such a module may likewise be configured to transmit other incentive-indicative data, such as by including one or more of (a) circuitry for directly transferring one or more resources 119 to a provider, (b) other circuitry for authorizing a benefit to a material provider, or (c) circuitry for implementing a conditional or other benefit to another party.

In some variants, incentive determination module 350 may likewise (optionally) include or otherwise communicate with a module for authorizing a benefit to a care provider 1852 such as circuitry for transferring one or more credits 117 to a care provider 283 in response to one or more indications 472, 473 that a bioactive material 1021, 1031 was administered to a specific patient (to a portion of individual 282, e.g.). In some variants, for example, such credits may be an appropriate method for tracking and rewarding institutional care providers for encouraging the patient to take a nutraceutical or other regimen component. This can occur, for example, in a context in which configuration logic 1860 resides in interaction unit 275 or other subsystems adjoining network 240, in which individual 282 is unable or reluctant to follow a regimen with sufficient discipline, and in which one or more professional care providers 283 are routinely in a vicinity of individual 282. Alternatively or additionally, such a module may include or otherwise operate in conjunction with a module for routing information to a care provider 1882 as described below, such as circuitry for transmitting a message 158 to the care provider. In some variants, for example, such a message may be configured either to provide notice of a benefit in advance or to provide a care provider with other data about the benefit (such as one or more terms 131 or conditions 134 of the authorization, e.g.). As described further below, moreover, such a module may transmit incentive-indicative data, such as by including one or more of (a) circuitry for transferring one or more credits to a care provider in response to an indication that the bioactive material was administered, (b) other circuitry for authorizing a conditional or other benefit to a care provider, or (c) circuitry for providing a benefit to another party.

In some variants, incentive determination module 350 may include or otherwise communicate with a module for implementing a conditional benefit 1853 such as circuitry for conditioning a benefit upon an acceptance of an incentive. In some variants, such a module will not actualize a benefit until a beneficiary 221 or other authorized party transmits an acceptance 1886 (via a delivery unit 225 or other interface 380, e.g.). Alternatively or additionally, such a module may invoke a negotiation protocol 1870 in which an offer 1868 indicates a policy premium discount or other specific benefit 120 that will take effect after an offer 1868 is accepted. In some contexts, moreover, such a response may be conditioned upon a compliance monitoring program enrollment certification or other such condition-indicative signals 1726 as described herein. As described further below, moreover, such a module may transmit incentive-indicative data, such as by including one or more instances of (a) circuitry for conditioning a benefit upon an acceptance of an incentive or (b) circuitry for implementing another conditional benefit as (being) a component of the incentive 140.

In some contexts, incentive determination module 350 may include or otherwise communicate with a module for authorizing a benefit to an individual 1854 such as circuitry for assigning one or more increments of time 111 or other such resources 119 between accounts 489 (from service provider 210 to individual 282, e.g.). In some variants, such configuration logic 1860 may likewise trigger a benefit to another beneficiary 221, such as a party who referred the individual to service provider 210. This can occur, for example, in a context in which service provider 210 might not otherwise be able to find or enroll a desired number of qualified participants, in which the service provider 210 accordingly offered the other beneficiary 221 a referral reward having at least one condition 134 (conditional upon the individual 282 enrolling or complying, e.g.), and in which the condition was at least sometimes met. As described further below, moreover, such a module may include or otherwise operate in conjunction with a module for transmitting incentive-indicative data comprising one or more of (a) circuitry for transferring one or more resources into an account of a referring individual, (b) other circuitry for authorizing a benefit to a referred individual, (c) or circuitry for implementing a benefit to another party facilitating such enrollment.

Communication logic 1880 may likewise (optionally) include one or more instances of modules for routing information to a material provider 1881, modules for routing information to a care provider 1882, modules for routing information to an individual 1883 (patient, subject, or participant, e.g.), modules for routing information to another party 1884 (depicted in FIG. 2, e.g.), modules for signaling an availability of an option 1891, modules for signaling a discount 1892, modules for signaling a resource transfer 1893, or modules for signaling another such incentive 1894. Such components of configuration logic 1880 may (optionally) be configured to invoke or be invoked by configuration logic 1860 or hardware-implemented negotiation protocols 1870, for example, or other modules described herein.

In some variants, incentive determination module 350 may include or otherwise communicate with a module for routing information to a material provider 1881 such as circuitry for routing a message, 830 to provider 820 containing one or more indications 862 (relating one or more incentives 140 to a regimen, bioactive material 1011, dispensing device 1010, or bioactive material category 484, e.g.). In some variants, such a module may further implement one or more negotiation protocols 1870 by which such a provider may fulfill a condition 135 (for a unilateral offer, e.g.) or convey a binding acceptance 1886 (via network 240 to a service provider 210 or agent 262, e.g.). Alternatively or additionally, such a module may further facilitate such negotiations by conveying a material provider's preferences, policies, or other such data 1885 (so that service provider 210 may rapidly identify material providers willing to participate in such a program, e.g.). As described further below, moreover, a module for obtaining or transmitting an indication of an incentive to an individual may include or otherwise operate in conjunction with one or more of (a) circuitry for routing a message relating a physical product to the incentive to a material provider, (b) circuitry for routing a message relating the incentive to a bioactive material component, or (c) other circuitry for routing the indication of the incentive (to a material provider, e.g.).

In some variants, incentive determination module 350 may include or otherwise communicate with a module for routing information to a care provider 1882 such as circuitry for routing an offer 1868 that includes at least an indication of one or more benefits 120 that would accrue at least partly to care provider 283. A component of such incentives 140 may likewise accrue to another care provider or a care recipient, in some variants, optionally by invoking one or more negotiation protocols 1870 by which one or more indications of the incentive are disseminated to another party indirectly (effectively notifying beneficiary 221 via message recipient 222, e.g.). In some variants, such a module may indicate a first incentive component available to a first individual (to a patient for enrolling in a program, e.g.) and a second incentive component available to a second individual (to a care or material provider who suggests or explains the program to the patient, e.g.). In some contexts, moreover, such a composite incentive (of several such component incentives, e.g.) may have an aggregate value that exceeds a list price (or other nominal value) of the bioactive material to be used for the program. As described further below, moreover, a module for obtaining or transmitting an indication of an incentive to an individual may include or otherwise operate in conjunction with one or more of (a) circuitry for offering the incentive to a care provider, (b) circuitry for routing an offer that includes at least the indication of the incentive to a care provider, (c) circuitry for routing the indication of the incentive indirectly to a putative beneficiary of the incentive, (d) circuitry for routing the indication of the incentive to a material provider and to another party, (e) circuitry for routing the indication of the incentive to a care provider and to another party, (f) circuitry for notifying a first party of a first component incentive of the incentive and for notifying a second party of a second component incentive, (g) circuitry for routing the indication of the incentive indirectly to a patient via a care provider, (h) circuitry for routing the indication of the incentive indirectly to a recipient of the bioactive material via a provider of the bioactive material, (i) other circuitry for routing a message containing the indication of the incentive to a care provider, or (j) other circuitry for routing a message containing the indication of the incentive to a material provider.

In some variants, incentive determination module 350 may include or otherwise communicate with a module for routing information to an individual 1883 such as circuitry for identifying a nutraceutical-containing component 433 or other payment in kind 118 offered as a reward to an individual 282 for adopting a regimen that includes a smart dispenser 170 or other specific pharmaceutical product. In some variants, such a module may notify the individual 282 of a first benefit 120 responsive to the individual's acceptance 1886, for example, and notify the individual 282 of a second benefit 120 responsive to data 1885 (from a sample tester 160 or other compliance-indicative device 190, e.g.) objectively indicative of compliance with the regimen. Alternatively or additionally, one or more such benefits or notifications may be routed to another party (beneficiary 221 or message recipient 222, e.g.) as described below. As described further below, moreover, a module for obtaining or transmitting an indication of an incentive to an individual may include or otherwise operate in conjunction with one or more of (a) circuitry for routing the indication of the incentive to the individual, (b) circuitry for indicating a reward to an individual for adopting a regimen, (c) circuitry for indicating a reward to an individual for compliance with a regimen in response to data objectively indicative of compliance with the regimen, (d) circuitry for indicating a reward to an individual in response to data objectively indicative of the bioactive material having been administered to the individual, (e) circuitry for indicating a first benefit responsive to an acceptance of a regimen and a second benefit responsive to data objectively indicative of compliance with the regimen, or (f) other circuitry for indicating a first benefit responsive to an acceptance of a product and a second benefit responsive to data objectively indicative of use of the product.

In some variants, incentive determination module 350 may include or otherwise invoke a module for routing information to another party 1884 such as circuitry for notifying agent 262 of one or more offers 1868 sent (or to be sent) to other parties. In some variants, such a module may trigger negotiation protocol 1870 to transmit two or more respective offers 1868 such as (a) to an individual 282 for a discount (of an insurance premium or deductible, e.g.) in exchange for enrolling in a program that penalizes noncompliance and (b) to a material provider 281 for a monetary or other resource transfer in response to an acceptance 1886 from one or more such individuals (of an offer to enroll in such a program, e.g.). This can occur, for example, in a context in which such offers 1868 are transmitted in sequence; in which only one such party is eligible for such an incentive at any one time; in which at least one such offer indicates one or more conditions 134 as described herein, and in which such non-overlapping offers may indicate an incentive (for a single beneficiary, e.g.) larger than would be feasible for a distributed incentive. Alternatively or additionally, such a module may be configured to respond to or otherwise operate in conjunction with one or more other modules of configuration logic 1860 or communication logic 1880 as shown in FIG. 18. As described further below, moreover, a module for obtaining or transmitting an indication of an incentive to an individual may include or otherwise operate in conjunction with one or more of (a) circuitry for routing an offer to another party including at least the indication of the incentive, (b) circuitry for notifying a first party of a first offer indicating a first component of the incentive and for notifying a second party of a second offer indicating a second component of the incentive, or (c) other circuitry for notifying another party of one or more conditions 135 of the incentive 140.

In some variants, incentive determination module 350 may include or otherwise communicate with a module for signaling an availability of an option 1891 (such as circuitry for selecting an option as the incentive to an individual, e.g.) or a module for signaling an other incentive 1894 (such as a module for signaling a discount 1892, e.g.). In some contexts, for example, such a module may have selected the option as a function of one or more expressed or implied preferences 322 (lowest cost, earliest availability, smallest size, greatest safety, e.g.) of a patient or other interested party. Alternatively or additionally, such a module may invoke or respond to other configuration logic 1860 or communication logic 1880 as described herein, for example, with reference to FIG. 18. As described further below, moreover, a module for obtaining or transmitting an indication of an incentive to an individual may include or otherwise operate in conjunction with one or more of (a) circuitry for selecting an option as the incentive to the individual, (b) circuitry for signaling an availability of an option as the incentive to the individual, (c) circuitry for notifying a care provider about option as a component of the incentive to the individual, (d) circuitry for generating the incentive partly based on a physical attribute of the individual or (e) circuitry for generating the incentive partly based on an indication of a bioactive material available to the individual.

Figure 19:
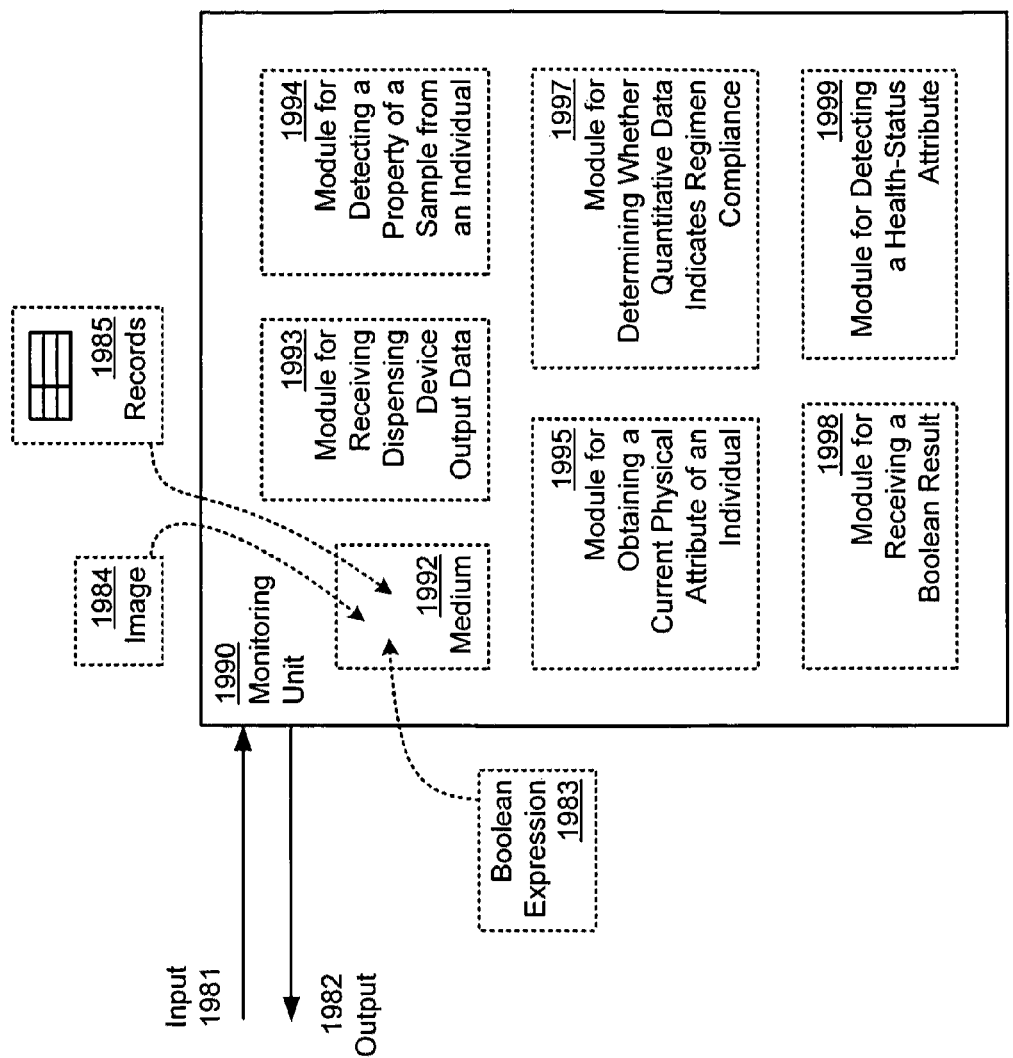
FIG. 19 depicts an exemplary environment featuring a monitoring unit.

With reference now to FIG. 19, shown is a context in which one or more technologies may be implemented. In some variants the above-described circuitry or other media may include or otherwise interact (via network 240, e.g.) with one or more monitoring units 1990 configured to receive input 1981 or transmit output 1982 as described below. Monitoring unit 1990 may include one or more media 1992 configured to store data, for example, or to display it to one or more of parties depicted in FIG. 2.

In some variants, vessel 1790 may communicate with a module for receiving dispensing device output data 1993, for example, such as circuitry for detecting when input 1981 from one or more sensors 1777 indicate that a vessel 1790 configured for the bioactive material was moved or used. In some variants, such a module may trigger (a) a protocol for inferring that an individual complied with a regimen or (b) a protocol for inferring that an individual did not comply with a regimen. This can occur, for example, in a context in which such sensor data effectively indicates whether and when vessel 1790 administers the bioactive material, in which monitoring unit 1990 facilitates operation 1640 by transmitting such inferences (as output 1982, e.g.), in which such determinants are used (by incentive determination unit 350, e.g.) in deciding whether the individual or another party receives an incentive, and in which such objective determinants would otherwise not be practical. Alternatively or additionally, such a monitoring unit 1990 may communicate wirelessly with portable circuitry (implementing an administration detection feature 1780 on a dispenser 170 or other vessel 1790, e.g.) containing one or more records 1985 indicating past actuations or other movements. In some contexts, moreover, monitoring unit 1990 may be configured to monitor one or more individuals 282, vessels 1790, or other entities of interest by capturing optical or auditory data relevant to regimen compliance as input 1981.

In light of teachings herein, numerous existing techniques may be applied for detecting when an object was moved or actuated as described herein without undue experimentation. See, e.g., U.S. Pat. No. 7,489,458 ("Piezoelectricity-driving optical lens module"); U.S. Pat. No. 7,489,143 ("Nanogripper device and method for detecting that a sample is gripped by nanogripper device"); U.S. Pat. No. 7,483,253 ("Systems and methods for detecting solenoid armature movement"); U.S. Pat. No. 7,477,147 ("System and method for actuating a remote control access system"); U.S. Pat. No. 7,477,051 ("Position sensor and position sensing method"); U.S. Pat. No. 7,469,679 ("Method for detecting and controlling movement of an actuated component"); U.S. Pat. No. 7,467,842 ("Ink jet nozzle assembly with over-actuation detection"); U.S. Pat. No. 7,453,982 ("System and method to acquire radiological images of an imaged subject"); U.S. Pat. No. 7,451,648 ("Internal sensor with disturbing current reduced by compensation branches"); U.S. Pat. No. 7,448,249 ("Clutch actuation control system with adjustable position encoder assembly"); U.S. Pat. No. 7,258,534 ("Fluid delivery device identification and loading system"); U.S. Pat. No. 6,752,145 ("Medication dispenser"); U.S. Pat. No. 6,379,393 ("Prosthetic, orthotic, and other rehabilitative robotic assistive devices actuated by smart materials"). In various implementations as described herein, for example, such logic may include one or more instances of (a) circuitry for detecting whether data from one or more sensors indicate a movement of a dispensing device, (b) circuitry for detecting whether data from one or more sensors indicate an actuation of a portion of a dispensing device, (c) a physical medium 1992 bearing sensor data indicating whether a specific or other portion of the dispensing device has moved.

In some variants, incentive determination unit 350 may include or otherwise interact with a module for detecting a property of a sample from an individual 1994 such as circuitry for detecting whether a fluor or other marking component 1779 is distributed uniformly along a length of hair from the individual. In some contexts, such a "detection" may include capturing an image 1984 (stored or displayed on medium 1992, e.g.) of the sample in which the marking component is readily or automatically detectable. This can occur, for example, in a context in which each of several capsules 1784 contain marking component 1779 and a bioactive material administered to the individual (over a course of days or months, e.g.), in which monitoring unit 1990 and incentive determination unit 350 perform operation 1640 jointly, in which the sample contains the fluor (or a relevant analyte to which the fluor may bond, e.g.), and in which monitoring unit 1990 includes or interacts with a fluorescence microscope (operated by technician 261, e.g.). Alternatively or additionally, such data may be distilled (by technician 261, e.g.) so that the "detection" comprises computing a percentage of apparently successful administrations or other such objective measures of compliance relating to a specific time interval of interest.

In some variants, another module for detecting a property of a sample from the individual 1994 may comprise circuitry for detecting a concentration, color, viscosity, density, or other intrinsic property of a bodily fluid or other sample from the individual. This can occur, for example, in a context in which technician 261 places blood or mucous from the sample into sample tester 160 and in which technician 261 enters an observation or other result into a computer 180 configured to receive data about an analyte of interest to be used for determining an eligibility or other incentive. Such analytes may indicate a health status of or an apparent regimen compliance of the individual, for example, or an unusual genetic or pathological property of special interest to a researcher. Alternatively or additionally, some such modules may detect one or more non-physical properties of the sample such as a time of extraction, place of extraction, or handling protocol (as indicated on a label of a vessel containing the sample, e.g.).

In light of teachings herein, numerous existing techniques may be applied for measuring health-indicative or other relevant physical properties from a sample extracted from an individual as described herein without undue experimentation. See, e.g., U.S. patent application Ser. No. 11/343,944 ("Establishing a Biological Recording Timeline by Artificial Marking") and U.S. patent application Ser. No. 11/343,966 ("Using a Biological Recording to Obtain Time Values"). See also U.S. Pat. No. 7,485,472 ("Simple method for quantitative measuring the adhesion of platelets ex vivo"); U.S. Pat. No. 7,480,032 ("Device and method for in vitro determination of analyte concentrations within body fluids"); U.S. Pat. No. 7,473,534 ("Assays for cancer patient monitoring based on levels of epidermal growth factor receptor (EGFR) extracellular domain (ECD) analyte, alone or in combination with other analytes, in body fluid samples"); U.S. Pat. No. 7,470,508 ("Method of screening for melanoma by detecting an increase in cyclin D1"); U.S. Pat. No. 7,459,286 ("Assessing the risk of a major adverse cardiac event in patients with chest pain"); U.S. Pat. No. 7,435,225 ("Method and arrangement for measuring breath gases of a patient"); U.S. Pat. No. 7,407,762 ("Diagnosis of gynecological neoplasms by detecting the levels of oviduct-specific glycoprotein"); U.S. Pat. No. 7,395,103 ("Surface plasmon resonance based nanoliter tear osmometer"); U.S. Pat. No. 7,361,306 ("Device and method for measuring coagulation time and platelet activity"); U.S. Pat. No. 7,335,166 ("System and method for the extraction and monitoring of a biological fluid"); U.S. Pat. No. 7,271,896 ("Detection of biomolecules using porous biosensors and raman spectroscopy"); U.S. Pat. No. 7,257,365 ("Serum biomarkers of Hepatitis B Virus infected liver and methods for detection thereof"); U.S. Pat. No. 7,252,959 ("Assays for diagnosis of thrombophilic disease"); U.S. Pat. No. 7,211,397 ("Method of analyzing non-complexed forms of prostate specific antigen in a sample to improve prostate cancer detection"); U.S. Pat. No. 7,179,612 ("Method for detecting a lipoprotein-acute phase protein complex and predicting an increased risk of system failure or mortality"); U.S. Pat. No. 7,128,877 ("Methods and devices for obtaining and assaying mammary fluid samples for evaluating breast diseases, including cancer"); U.S. Pat. No. 7,125,681 ("Methods for detection of disease-associated antibodies in urine"); U.S. Pat. No. 7,122,322 ("Endometriosis-specific secretory protein").

In various implementations as described herein, for example, such logic may include one or more instances of (a) circuitry for receiving an indication from a test of a bodily fluid of an individual after a dispensing device administers a bioactive material to the individual, (b) circuitry for detecting an intrinsic or other property of a sample from the individual, or (c) circuitry for detecting a concentration of a metabolite (of a bioactive material in a sample, e.g.) from the individual.

In some variants, incentive determination module 1080 may interact (within or via network 240, e.g.) with a module for obtaining a current physical attribute of the individual 1995 such as circuitry for detecting a health status change apparently resulting from a vessel 1790 or other dispensing device administering the bioactive material to the individual 282. In some variants, such a module may record a measurement, computed result, image, or other useful diagnostic attribute as the current physical attribute. This can occur, for example, in a context in which incentive determination module 1080 performs operation 1640 using output 1982 from monitoring unit 1990, in which the current physical attribute of the individual comprises a current measurement 454 (of a local dilation or blood pressure, e.g.) or a result of comparing the current measurement 454 with a prior measurement 453 or other threshold 461 suitable for detecting a trend toward normalcy, and in which such administrations may avoid a hospitalization. Alternatively or additionally, such circuitry may record new or worsening symptoms, in some contexts, or other relevant indications 471 (on medium 1992, e.g.) of a changing pathological state. In some variants, moreover, such circuitry may likewise be configured to notify the individual 282 or a care provider 283 of the new or worsening symptom.

In light of teachings herein, numerous existing techniques may be applied for measuring or otherwise documenting an onset, an abatement, or other such events reflecting symptoms of hypertension, diabetes, or many other such (generally treatable) pathologies. See, e.g., U.S. Pat. No. 7,468,040 ("Methods and systems for implantably monitoring external breathing therapy"); U.S. Pat. No. 7,465,273 ("Method for monitoring pre-eclamptic patients"); U.S. Pat. No. 7,404,796 ("System for determining insulin dose using carbohydrate to insulin ratio and insulin sensitivity factor"); U.S. Pat. No. 7,400,257 ("Vital signals and glucose monitoring personal wireless system"); U.S. Pat. No. 7,397,380 ("Device and method for monitoring state of thermal comfort of a baby at sleep or a partially disabled patient"); U.S. Pat. No. 7,395,216 ("Using predictive models to continuously update a treatment plan for a patient in a health care location"); U.S. Pat. No. 7,379,885 ("System and method for obtaining, processing and evaluating patient information for diagnosing disease and selecting treatment"); U.S. Pat. No. 7,356,364 ("Device for optical monitoring of constituent in tissue or body fluid sample using wavelength modulation spectroscopy, such as for blood glucose levels"); U.S. Pat. No. 7,340,296 ("Detection of pleural effusion using transthoracic impedance"); U.S. Pat. No. 7,297,108 ("Disease management system and method including analysis of disease specific changes"); U.S. Pat. No. 7,223,237 ("Implantable biosensor and methods for monitoring cardiac health"); U.S. Pat. No. 7,177,686 ("Using photo-plethysmography to monitor autonomic tone and performing pacing optimization based on monitored autonomic tone"); U.S. Pat. No. 7,035, 684 ("Method and apparatus for monitoring heart function in a subcutaneously implanted device"); U.S. Pat. No. 6,817,980 ("Automated diagnostic system and method including disease timeline"); U.S. Pat. No. 6,770,029 ("Disease management system and method including correlation assessment"); U.S. Pat. No. 6,383,135 ("System and method for providing self-screening of patient symptoms"); U.S. Pat. No. 6,234,964 ("Disease management system and method").

In various implementations as described herein, for example, such logic may include one or more instances of (a) circuitry for obtaining a current physical attribute of the individual, (b) circuitry for recording a diagnostic attribute as a current physical attribute of the individual, (c) circuitry for transmitting a notification of a health status change to the individual, (d) circuitry for transmitting a notification of the health status change to a care provider, (e) circuitry for detecting a health status change apparently resulting from the dispensing device administering the bioactive material to the individual, or (f) circuitry for comparing a current measurement of a physical attribute of the individual with a threshold suitable for detecting a trend toward normalcy (indicative of recovery or treatment efficacy, e.g.).

In some variants, a sample tester 160, computer 180, or other compliance-indicative device 190 may include a module for determining whether quantitative data indicates regimen compliance 1997, for example, such as circuitry for comparing one or more scalar indications 462, 463 of failure (rates, e.g.) each against a respective threshold 472, 473 (a minimum or maximum, e.g.). In some variants, such a module may apply a first threshold 472 or other criterion to determine a first aspect of compliance (indicative of a statin-containing component 432 or other material component 434, e.g.) and a second threshold 465 or other criterion to determine a second aspect of compliance (relating to time data 435 or proper dosages 437, e.g.). Such thresholds may pertain to measurements or other biometric data 436 manifesting a symptom or its absence, for example. Alternatively or additionally, some such thresholds may relate to time data 435 (manifesting how close each administration of the bioactive material was to an ideal time, e.g.) or to other such data 430 expressing quantitative aspects of a regimen or health status. This can occur, for example, in a context in which compliance-indicative device 190 includes at least a monitoring unit 1990 that generates records 1985 (each few hours or days, e.g.) indicating a degree of compliance. Alternatively or additionally, such a monitoring unit 1990 may trigger a presentation of one or more incentives 140 to the individual 282 under various conditions as described herein.

In light of teachings herein, numerous existing techniques may be applied for applying various provider-specified criteria (relating to counts or dosages provided by a physician or other service provider, e.g.) to device-detectable health-indicative data (for determining success, eligibility, or some other threshold event, e.g.) as described herein without undue experimentation. See, e.g., U.S. Pat. No. 7,488,291 ("Methods for detecting and monitoring sleep disordered breathing using an implantable medical device"); U.S. Pat. No. 7,487,774 ("Adaptive patient trigger threshold detection"); U.S. Pat. No. 7,465,551 ("Method of determining cytokine dosage for improving myelosuppressive state"); U.S. Pat. No. 7,366,571 ("Neurostimulator with activation based on changes in body temperature"); U.S. Pat. No. 7,246,619 ("Snore detecting method and apparatus"); U.S. Pat. No. 7,223,246 ("Diagnosis of the presence of cochlear hydrops using observed auditory brainstem responses"); U.S. Pat. No. 7,177,684 ("Activity monitor and six-minute walk test for depression and CHF patients"); U.S. Pat. No. 7,132,238 ("Method of determining a chemotherapeutic regimen based on ERCC1 expression"); U.S. Pat. No. 7,107,095 ("Device for and method of rapid noninvasive measurement of parameters of diastolic function of left ventricle and automated evaluation of the measured profile of left ventricular function at rest and with exercise"); U.S. Pat. No. 7,054,688 ("Heart stimulator with evoked response detector and an arrangement for determining the stimulation threshold"); U.S. Pat. No. 7,047,083 ("Method and apparatus for identifying lead-related conditions using lead impedance measurements"); U.S. Pat. No. 6,988,498 ("Administration of CPAP treatment pressure in presence of apnea"); U.S. Pat. No. 6,978,177 ("Method and apparatus for using atrial discrimination algorithms to determine optimal pacing therapy and therapy timing"); U.S. Pat. No. 6,671,548 ("Implantable stimulation device and method for discrimination atrial and ventricular arrhythmias"); U.S. Pat. No. 6,336,048 ("Implantable active medical device enslaved to at least one physiological parameter").

In various implementations as described herein, for example, such logic may include one or more instances of (a) circuitry for determining whether quantitative data indicates regimen compliance, (b) circuitry for comparing a scalar indication of failure against a threshold, (c) circuitry for comparing a computed rate against an allowable maximum, (d) a display medium presenting a component of a regimen of an individual, or (e) a display medium 154 presenting a Boolean expression 1983 of apparent compliance or of apparent noncompliance.

In some variants, monitoring unit 1990 may distill data from a module for receiving a Boolean result from a compliance detection device 1998, for example, such as circuitry for recognizing an indication 476 of past or current noncompliance from compliance-indicative device 190. This can occur, for example, in a context in which monitoring unit 1990 and incentive determination unit 350 jointly perform operation 1640, in which monitoring unit 1990 periodically requests such data from compliance detection device 1998 and reports the result, and in which incentive determination unit 350 receives the result as one of the individual's physical attributes 321. In one protocol, incentive determination unit 350 responds to a patient's first (apparent) failure to comply by using a larger-than-nominal incentive or a different message recipient, as compared with a prior incentive (a "nominal" incentive, e.g.). Incentive determination unit 350 may later respond to the patient's second apparent failure to comply by using another beneficiary 221 or message recipient 222, optionally with a smaller incentive (compared to a nominal or other prior incentive). Alternatively or additionally, such a monitoring unit 1990 may take no action until several (N) consecutive indications of apparent noncompliance are received, where N is an integer (selected by service provider 210, e.g.). In some variants, moreover, such a protocol may trigger a personal communication with the individual before proceeding to such an incentive modification (by generating an e-mail message or other request 488 that a human agent 262 contact individual 282, for example, by telephone or e-mail). In various implementations as described herein, for example, such logic may include one or more instances of (a) circuitry for recognizing an indication of apparent noncompliance from a compliance-indicative device, (b) circuitry for triggering a direct communication with the individual via an interaction unit 275 in response to a negative indication of compliance, or (c) a storage medium containing at least a Boolean expression 1983 indicative of input 1981 from an administration detection module 1748.

In some variants, control unit 205 may include or otherwise communicate with a module for detecting a health-status attribute apparently resulting from the bioactive material 1999, for example, such as circuitry for detecting a lower-than-previous arterial blood pressure measurement within a given time interval of a dispensation of an antihypertensive material. In some variants, such a module may detect measurement changes selectively, such as by ignoring those of less than 1% (or 3% or 10%, e.g.). This can occur, for example, in a context in which monitoring unit 1990 performs operation 1640 and triggers operation 1690 by invoking delivery unit 225 via linkage 226. Alternatively or additionally, such a monitoring unit 1990 may likewise detect such a (physical) health-status attribute or change for most bioactive materials having a predictable effect upon a measurable attribute of an individual to whom they are administered. See, e.g., Physicians' Desk Reference 2009 (PDR, 63rd Edition). In some variants, for example, such a module may detect a given physiological change within a time interval T (of a few minutes, hours, or days relative to a regimen inception, e.g.) of a transmucosal, transdermal, or other administration of the bioactive material, wherein T is a threshold specified by a technician 261, material provider 281, physician, or other appropriate entity. In some contexts, moreover, such a module may be configured to monitor sensor data for indicia of allergic or other side effects of the bioactive material.

As one example, such a module may be implemented for detecting whether or when a statin-containing product has apparently caused a desired effect, such as determining whether a decrease in an individual's LDL cholesterol level has exceeded 1 mg/dL (relative to an initial value) within a physician-specified time interval (of a few days or more of a regimen inception, e.g.). In a context in which data 430 indicates a recently prescribed or adopted regimen having a statin-containing material component 432 or other material component 434 tailored toward such improvement, for example, such a measurable change may objectively indicate either (a) significant compliance with the regimen or (b) at least some use of the plasma lipid-modifying material.

As another example, such a module may be implemented for detecting whether or when an appetite suppressant or weight loss regimen has apparently caused a given effect, such as determining whether an individual's average weight loss rate has exceeded a given threshold over a prescribed time interval. In a context in which data 430 indicates a recently prescribed or adopted regimen having a nutraceutical-containing component 433 tailored toward such improvement, for example, such a measurement may objectively indicate either (a) significant compliance with the regimen or (b) at least some use of the appetite suppressant or other bioactive material of the regimen.

As another example, such a module may be implemented for detecting whether or when a calcium supplement or other calcium-rich dietary component has apparently caused a desired effect, such as determining whether an increase in an individual's Z-score or T-score has exceeded 0.1 (relative to an initial value) within a given time interval (of up to several months, e.g.). In a context in which data 430 indicates a recently prescribed or adopted regimen having a nutraceutical-containing component 433 tailored toward such improvement, for example, such a measurement may objectively indicate either (a) significant compliance with the regimen or (b) at least some use of the calcium supplement or other bioactive material.

As another example, such a module may be implemented for detecting whether or when a decongestant has apparently caused a desired effect, such as determining whether an auditory indication of congestion (wheezing, sniffling, or nose-blowing, e.g.) or other measure of respiratory health has improved by more than a threshold (of 1% or 5%, for example, relative to an initial value) within a nominal therapeutic time interval (of up to a few weeks, e.g.). In a context in which data 430 indicates a recently prescribed or adopted regimen having a nutraceutical-containing component 433 or other material component 434 tailored toward such improvement, for example, such a measurement may objectively indicate either (a) significant compliance with the regimen or (b) at least some use of the bioactive material in the regimen.

As another example, such a module may be implemented for detecting whether or when a hormone regimen has apparently caused a given effect, such as determining whether an increase in an individual's concentration of a hormone has exceeded 1% (relative to an initial value) within a physician-specified time interval (of a few hours, days, or weeks, e.g.). In a context in which data 430 indicates a recently prescribed or adopted regimen having an "other material component" 434 tailored toward such improvement, for example, such a measurable change may objectively indicate either (a) significant compliance with the regimen or (b) at least some use of the hormone or other bioactive material.

As another example, such a module may be implemented for detecting whether or when a psychoactive material has apparently caused a given effect, such as determining whether an individual manifests any too-numerous or too-large (measurable) indications of agitation within a nominal therapeutic time interval (of up to a few hours after administration, e.g.). In a context in which data 430 indicates a recently prescribed or adopted regimen having a nutraceutical-containing component 433 or other material component 434 tailored toward such improvement, for example, such a measurement may objectively indicate either (a) significant compliance with the regimen or (b) at least some use of the material.

In light of teachings herein, many other existing techniques may be applied for implementing a measurement or other determination indicative of whether a bioactive material or other therapy is apparently having any effect. See, e.g., U.S. Pat. No. 7,185,650 ("Systems and methods for determining a minimum effective dose of an inhaled drug for an individual patient at a given time"); U.S. Pat. No. 7,138,240 ("Methods of assaying receptor activity"); U.S. Pat. No. 7,003,346 ("Method for illness and disease determination and management"); U.S. Pat. No. 6,942,619 ("Ultrasound radiation device"); U.S. Pat. No. 6,881,192 ("Measurement of sleep apnea duration and evaluation of response therapies using duration metrics"); U.S. Pat. No. 6,659,959 ("Catheter with physiological sensor"); U.S. Pat. No. 6,613,573 ("Method and apparatus for monitoring anti-platelet agents"); U.S. Pat. No. 6,581,607 ("Method and system for use in treating a patient with a biological substance to optimize therapy and prevent an adverse response"); U.S. Pat. No. 6,581,606 ("Method, apparatus and system for use in treating patient with a drug having an antineoplastic effect to optimize therapy and prevent an adverse drug response"); U.S. Pat. No. 6,575,169 ("Method and apparatus for use in treating a patient with any drug to optimize therapy and prevent an adverse drug"); U.S. Pat. No. 6,347,239 ("Method of evaluating the efficacy of drug on brain nerve cells"); U.S. Pat. No. 6,329,153 ("Method for evaluating immunosuppressive regimens"); U.S. Pat. No. 6,007,986 ("Methods for anti-addictive narcotic analgesic activity screening").

In various implementations as described herein, for example, such logic may include one or more instances of (a) circuitry for detecting a health-status attribute apparently resulting from a bioactive material, (b) circuitry for detecting an arterial blood pressure reduction of at least X, where X is a threshold of at least 1%, (c) circuitry for detecting a given physiological change within a time interval T of a transmucosal administration of a bioactive material, wherein T is a threshold of at least a few minutes, (d) circuitry for detecting a given physiological change within a time interval T of a transdermal administration of the bioactive material, wherein T is a threshold of at most a few months, (e) circuitry for detecting a given physiological change within a time interval T of an ingestion of a bioactive material, wherein T is a threshold of at least an hour, (f) circuitry for detecting a given physiological change within a time interval T of an ingestion of the bioactive material, wherein T is a threshold of at most a few weeks, (g) circuitry for detecting a given physiological change within a time interval T of first administration of a bioactive material to a portion of the individual, wherein T is a threshold of at least a few minutes, (h) circuitry for detecting a given physiological change within a time interval T of an injection of a bioactive material, wherein T is a threshold of at least a few seconds, (i) circuitry for detecting a physiological measurement change larger than X within a time interval T of an administration of the bioactive material, wherein T is a threshold of at most a few days and X is a threshold of at most 20%, or (j) circuitry for detecting a physiological measurement change larger than X within a time interval T of an administration of the bioactive material, wherein T is a threshold of at least a few seconds and X is a threshold of at least 1% of a previous measurement.

In some variants, a component of monitoring unit 1990 may likewise include or otherwise interact with configuration logic 1860 or communication logic 1880 as described above. A module for determining whether quantitative data indicates regimen compliance 1997, for example, may invoke or otherwise operate in conjunction with a module for signaling an availability of an option 1891. This can occur, for example, in a context in which configuration logic 1860 performs operation 1640, in which recent data from sample tester 160 contains one or more objective indicia of regimen compliance, and in which incentive selection logic 344, 1070 accordingly responds by offering one or more parties an option to receive a number of credits 117 or other resources 119 as a reward for the compliance. Alternatively or additionally, such a module may invoke a module for routing information to a material provider 1881 or a module for routing information to another party 1884 in response to an indication that such party suggested the regimen to the individual 282 (via an audible remark in person or a motivational message 158 borne on print or other media 150 as described herein, e.g.).

Figure 20:
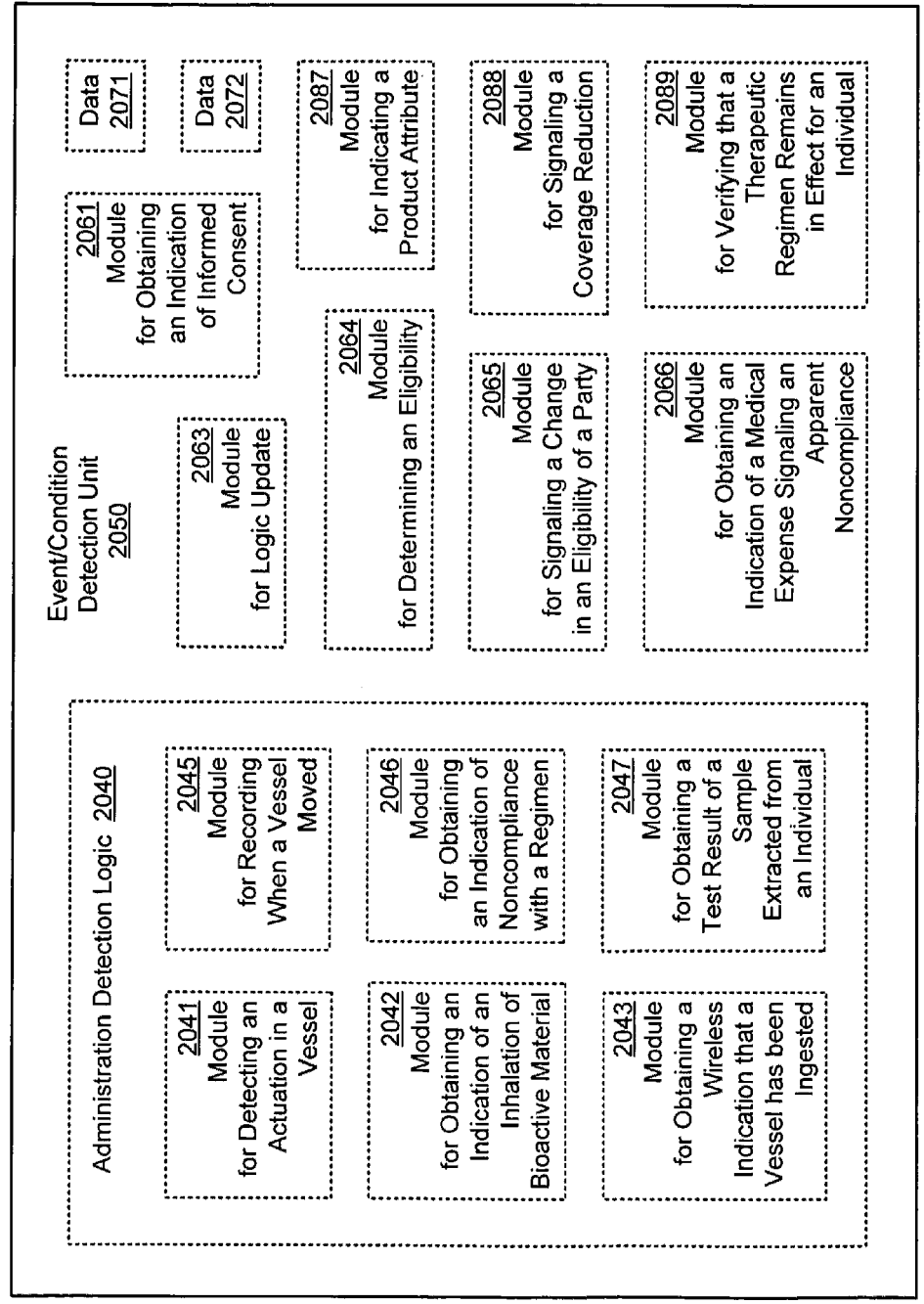
FIG. 20 depicts an exemplary environment featuring an event/condition detection unit.

Turning now to FIG. 20, there is shown a system 2000 in which one or more technologies may be implemented. An event/condition detection unit 2050 (in control unit 205 or coupled remotely via network 240, e.g.) may include one or more instances of administration detection logic 2040 or other modules for handling data 2071, 2072 as described below. Administration detection logic 2040 may include one or more instances of modules for detecting an actuation in a vessel 2041, modules for obtaining an indication of an inhalation of bioactive material 2042, modules for obtaining a wireless indication that a vessel has been ingested 2043, modules for recording when a vessel moved 2045, modules for obtaining an indication of noncompliance with a regimen 2046, or modules for obtaining a test result of a sample extracted from individual 2047.

Event/condition detection unit 2050 may likewise (optionally) include one or more instances of modules for obtaining an indication of informed consent 2061 (from a parent or other responsible party or from a program participant eligible to receive a therapeutic component, e.g.), modules for determining an eligibility 2064, modules for signaling a change in an eligibility of a party 2065, modules for obtaining an indication of a medical expense signaling an apparent noncompliance 2066, modules for indicating a product attribute 2087, modules for signaling a coverage reduction 2088, or modules for verifying that a therapeutic regimen remains in effect for an individual 2089. In some contexts, event/condition detection unit 2050 may also include one or more modules for logic update 2063 configured to invoke one or more modules (described with reference to FIGS. 17-20, e.g.) within another, so as to combine two or more modules described above. This can occur, for example, in a context in which the incentive includes a continuation of eligibility (for a discount or program participation, e.g.) and in which hardware or firmware implementing the combined modules physically overlaps (on a common ASIC, e.g.) and also in which software implementing the respective modules of the combination is executed sequentially, simultaneously, or otherwise in a mutually related manner. In some implementations, as exemplified below, such logic may be configured to invoke or be invoked by configuration logic 1860 or communication logic 1880.

In light of teachings herein, numerous existing techniques may be applied for implementing and interacting with decision logic, data capture or transformation configurations, or other components within or for use with condition or event detection as described herein without undue experimentation. See, e.g., U.S. Pat. No. 7,304,580 ("Intelligent medical vigilance system"); U.S. Pat. No. 7,261,690 ("Apparatus for monitoring health, wellness and fitness"); U.S. Pat. No. 7,155,281 ("Complimentary activity sensor network for disease monitoring and therapy modulation in an implantable device"); U.S. Pat. No. 7,024,234 ("Method and apparatus for monitoring the autonomic nervous system"); U.S. Pat. No. 6,984,207 ("Passive physiological monitoring (P2M) system"); U.S. Pat. No. 6,980,851 ("Method and apparatus for determining changes in heart failure status"); U.S. Pat. No. 6,689,069 ("Apparatus and method for blood pressure pulse waveform contour analysis"); U.S. Pat. No. 6,600,949 ("Method for monitoring heart failure via respiratory patterns"); U.S. Pat. No. 6,358,201 ("Method and apparatus for facilitating physiological coherence and autonomic balance"); U.S. Pat. No. 6,312,378 ("System and method for automated collection and analysis of patient information retrieved from an implantable medical device for remote patient care"); U.S. Pat. No. 6,179,793 ("Cardiac assist method using an inflatable vest"); U.S. Pat. No. 5,978,693 ("Apparatus and method for reduction of motion artifact"); U.S. Pat. No. 4,860,751 ("Activity sensor for pacemaker control").

In some variants, administration detection logic 2040 may include a module for obtaining an indication of an inhalation of the bioactive material 2042, for example, such as circuitry for recognizing an inhaler usage (by auditory pattern recognition, e.g.). This can occur, for example, in a context in which such a module obtains data 2071 indicative of a patient or device administering an inhalant 572 (as digitized auditory data from one or more sensors 1041, e.g.), optionally by receiving such data as a wireless or other signal transmitted from such a dispensing device 1020. Alternatively or additionally, such indications may be detected by a module for detecting an actuation in a vessel 2041 or other logic described herein.

In some variants, for example, incentive determination module 350 may include or otherwise communicate with a module for signaling an availability of an option 1891. Such a hybrid or other combined module may include circuitry for notifying a material provider 281 of an eligibility of a customer or other individual 282 to participate in a clinical trial, for example, invoked by a module for determining the eligibility 2064. This can occur, for example, in a context in which the customer expresses one or more physical attributes 321, preferences 322, or other patient attributes 320 that confer the eligibility; in which the clinical trial or other program offers payments in kind 118 or other incentives 140 to those who elect to participate; and in which the material provider 281 will receive points 116 or other benefits 120 if the customer participates (by a module for authorizing a benefit to a material provider 1852, e.g.). Alternatively or additionally, in some implementations, the module for determining the eligibility 2064 may invoke a negotiation protocol 1870 by which the individual 282 may participate in the program only after the participant (a) confirms such determinants 330 relating to eligibility and (b) acknowledges any terms 131 and conditions 135 of the incentive 140, such as by a software-controlled enrollment protocol (via an interaction unit 275, e.g.).

In light of teachings herein, numerous existing techniques may be applied for using physical conditioning, injury, or other subject status information as an indication of qualification for or enrollment in an incentive or other program as described herein without undue experimentation. See, e.g., U.S. Pat. No. 7,672,857 ("Health services delivery system with incentives"); U.S. Pat. No. 7,415,447 ("Apparatus and method for prediction and management of participant compliance in clinical research"); U.S. Pat. No. 7,273,277 ("Advanced vision intervention algorithm"); U.S. Pat. No. 7,255,987 ("Selecting animals for parentally imprinted traits"); U.S. Pat. No. 7,226,792 ("Method for selecting an optimal diet and exercise regimen based on LDL and HDL subclass determination"); U.S. Pat. No. 7,194,301 ("Method for screening and treating patients at risk of medical disorders"); U.S. Pat. No. 6,566,064 ("Method for anticipating sensitivity to medicine for osteoporosis"); U.S. Pat. No. 6,473,646 ("Method and apparatus for assessing cardiac functional status"); U.S. Pat. No. 6,268,145 ("Screening test for the lethal genetic trait of recurrent spontaneous pregnancy loss").

In some variants, an implementation may include or otherwise communicate with a vessel (1) being an inhaler or syringe, (2) being a bottle or capsule, (3) containing a bioactive or other therapeutic material in liquid or solid form, (4) having an administration detection feature, or (5) more than one of the above. Alternatively or additionally, administration detection logic 2040 may include a module for recording when a vessel moved 2045, for example, such as circuitry for comparing serial images of a visual field. This can occur, for example, in a context in which a vessel 1790 contains a first supply of the bioactive material, in which the module receives such data 2072 from one or more sensors 1041, in which an early image indicates a first position of the vessel, in which a later image indicates whether the vessel is still substantially (approximately) in the first position, and in which such images are acquired frequently enough to indicate whether the vessel was moved within an acceptable window of time (of an ideal dispensation time, e.g.). Alternatively or additionally, such a vessel 1777 may likewise contain auditory or other sensors 1777 effective for detecting such vessel movement. In some contexts, moreover, administration detection logic 2040 or other special-purpose hardware (on vessel 1790, e.g.) may be configured to include storage or other media 400 containing time data 435 indicative of when such dispensation have occurred. In some contexts, moreover, administration detection logic 2040 may be configured to monitor another bioactive material supply, optionally including a quantity of the same bioactive material.

In light of teachings herein, numerous existing techniques may be applied for determining and recording whether scheduled events are happening within a given interval of time as described herein without undue experimentation. See, e.g., U.S. Pat. No. 7,369,476 ("Device for reading from or writing to optical recording media having a control unit for a data slicer"); U.S. Pat. No. 7,335,106 ("Closed-loop system for displaying promotional events and granting awards for electronic video games"); U.S. Pat. No. 7,330,101 ("Prescription compliance device and method of using device"); U.S. Pat. No. 7,293,645 ("Method for monitoring hand hygiene compliance"); U.S. Pat. No. 7,287,031 ("Computer system and method for increasing patients compliance to medical care instructions"); U.S. Pat. No. 7,271,728 ("Method for assessing improvement in hand hygiene practices"); U.S. Pat. No. 7,170,823 ("Medical dispenser, a blister card for use in the dispenser and a method of dispensing medical doses"); U.S. Pat. No. 6,973,371 ("Unit dose compliance monitoring and reporting device and system"); U.S. Pat. No. 6,882,278 ("Apparatus and methods for monitoring compliance with recommended hand-washing practices"); U.S. Pat. No. 6,655,583 ("Medical billing method and system"); U.S. Pat. No. 6,514,200 ("Patient compliance monitor"); U.S. Pat. No. 6,375,038 ("Dispenser having timing means, multisensory output and means of tracking usage number"); U.S. Pat. No. 6,371,931 ("Reflex tester and method for measurement of range of motion and peripheral vision"); U.S. Pat. No. 6,198,695 ("Event monitoring device"); U.S. Pat. No. 6,198,383 ("Prescription compliance device and method of using device").

Figure 21:
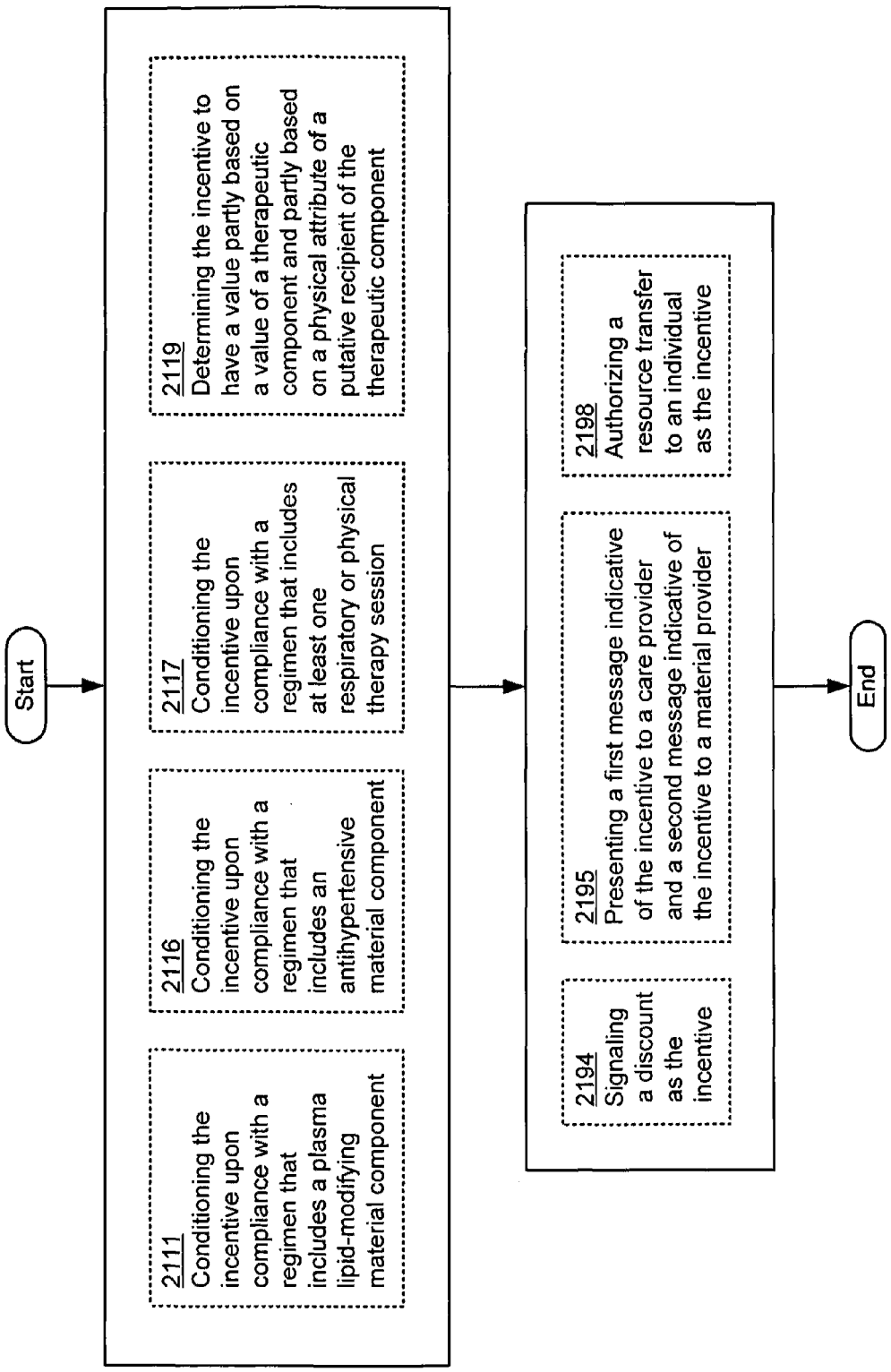
FIG. 21 depicts variants of flows shown in one or more of FIGS. 11-16.

With reference now to FIG. 21 and to other flows described above, one or more instances of operation 1120, 1230, 1350, 1440, 1520, or 1640 may each (optionally) include one or more instances of operation 2111, operation 2116, or operation 2117 as shown. Also one or more instances of operation 1150, 1260, 1380, 1460, 1570, or 1680 may likewise include one or more instances of operation 2194, operation 2195, or operation 2198 as described below.

Operation 2111 describes conditioning the incentive upon compliance with a regimen that includes a plasma lipid-modifying material component (e.g. one or more modules 2064 for determining an eligibility designating a regimen or individual 282 as "eligible" for payment in kind 118 or other tangible resources 119 as an incentive 140 if data 430 relating to the individual's regimen includes a statin-containing material component 432 prescribed for or otherwise provided to the individual). Alternatively or additionally, the material component may include (a) niacin gemfibrozil or other bioactive materials therapeutically effective for increasing an individual's HDL level or (b) agents therapeutically effective for lowering lipid, cholesterol, or triglycerides—fenofibrate or other peroxisome proliferator-activated receptor alpha (PPARα) activators, 3-hydroxy-3- methylglutaryl-coenzyme A (HMG CoA) inhibitors, statins, or the like. This can occur, for example, in a context in which (each) module 2064 is implemented in application-specific circuitry or in software (in response unit 255 or interaction unit 275, e.g.) and in which the regimen or individual would otherwise generally not be eligible. Alternatively or additionally, the incentive can accrue (conditionally upon compliance of a care provider 283 or the individual 282, e.g.) to the benefit of an authorized agent 262 who registers the individual 282 or of other parties as described herein.

Alternatively or additionally, a routing unit 1850 that contains one or more other modules of event/condition detection unit 2050 may perform operation 2111 by transmitting an offer 1868 to the individual 282 or other party that identifies one or more incentives 140 that are conditioned upon compliance with a regimen that includes statin-containing material component 432. This can occur, for example, in a context in which an inoculant 571 or other dispensed material contains the statin(s), in which the event/ condition detection unit 2050 includes a module 2045 for recording when a vessel 1790 containing a bioactive material moved (or other administration detection logic 2040), in which sensed data 2071 indicates when the vessel containing the material has moved as an indication 315 that bioactive material has been administered, and in which a physician or other service provider 210 defines a regimen that infers compliance from such indications being received daily. In some variants, module 2064 may implement one or more determinants 330 to select an incentive 140 (giving a performance rating 138 or tangible benefit 120 dependent upon a material category 312 or other bioactive material indications 310, e.g.) for which the beneficiary 221 of the incentive may be eligible.

Operation 2116 describes conditioning the incentive upon compliance with a regimen that includes an antihypertensive material as a bioactive material (e.g. one or more modules 2088 for signaling a coverage reduction warning an individual 282 or care provider 283 that the individual will lose some aspect of medical insurance coverage if a blood pressure medication is not administered to the individual for more than a number of hours defined by service provider 210). This can occur, for example, in a context in which service provider 210 represents a medical insurance provider, in which the regimen includes an antihypertensive material component 431 and several other material components 434 in competition for the attention of the individual 282 or care provider 283, and in which service provider 210 makes an actuarial determination that noncompliance with most of such "other" aspects of the regimen would probably not have such costly consequences as with that of the antihypertensive material component 431.

In some variants, operation 2116 may be performed by one or more modules 2043 for obtaining a wireless indication that a vessel has been ingested responding to a wireless pulse from an antenna (a transmitter 1776 or other administration feature 1780 in or near a containing vessel 1790, e.g.) by signaling one or more components of the incentive 140 as described herein. This can occur, for example, in a context in which a bottle 1783 or capsule 1784 contains an antihypertensive material, in which one or more flows (of FIGS. 11-16, e.g.) relate to the material (as a therapeutic component, e.g.), and in which the wireless pulse signifies the ingestion (inferred from a temperature rise or movement detected by one or more sensors 1777, e.g.) Alternatively or additionally, one or more such flows may be triggered in response to a consent, benefit 120, or other incentive 140 as described herein being indicated (via one or more media 150 of a compliance-indicative device 190, e.g.).

Operation 2117 describes conditioning the incentive upon compliance with a regimen that includes at least one respiratory or physical therapy session (e.g. one or more modules 2046 for obtaining an indication of noncompliance with a regimen signaling a loss of service 148 or other benefits 120 to a patient in response to an indication 475 from a care provider 283 that the patient failed to appear for a mandatory respiratory or physical therapy). This can occur, for example, in a context in which a service provider 210 is obliged to compensate the care provider 283 for the missed appointment and for the task of providing massage, electrotherapeutic or mechanical agents, or other physical therapeutic components in such a session, in which at least one such module 2064 (in a handheld 1741 or other portable digital device, e.g.) warns the patient of an incremental or other imminent lost benefit 120, and in which a service provider 210 has determined that such prompt notifications (within a few hours before or after the appointment via a wireless message, e.g.) are effective for deterring costly no-shows. Alternatively or additionally, a service provider 210 may configure module 2046 or other components of event/condition detection unit 2050 to add points 116 to an account in response to each compliance and to subtract points 116 from the account in response to each noncompliance and to condition a reward (to a patient or care provider 283, e.g.) upon the account exceeding an upper limit (indicative of general compliance) and to condition a penalty or warning upon the account traversing a lower limit (indicative of a cumulative noncompliance). In some variants, service provider 210 may effectively determine such limits by applying a simple formula ("three strikes and you're out," e.g.) defining an acceptable count for each type of compliance-indicative event (success or failure, e.g.).

More generally, administration detection logic 2040 or other event/condition detection units 2050 as described herein can perform such operations by implementing both a conditional benefit 120 for an incremental compliance (rewarding a timely dose or therapy with a higher performance rating 138 or other positive incentive 140, e.g.) and a conditional penalty for an incremental noncompliance (penalizing a missed dose or therapy with a lower performance rating 138, reward reduction, or other negative incentive 140, e.g.). This can occur, for example, in a context in which a material provider 281 or care provider 283 administers the therapeutic component to an individual 282; in which interaction unit 275 includes one or more components capable of performing one or more of operations 1350, 1520, or 1640 as described herein; and in which such component(s) are operably coupled with event/condition detection unit 2050.

Operation 2119 describes determining the incentive to have a value partly based on a value of a therapeutic component and partly based on a physical attribute of a putative recipient of the therapeutic component (e.g. one or more modules 2046 for obtaining an indication of noncompliance with a regimen signaling a loss of service 148 or other benefits 120 to a patient in response to an indication 475 from a care provider 283 that the patient failed to appear for a mandatory physical therapy). This can occur, for example, in a context in which a service provider 210 is obliged to compensate the care provider 283 for the missed appointment and for the task of providing massage, electrotherapeutic or mechanical agents, or other physical therapeutic components in such a session, in which at least one such module 2064 (a handheld device, e.g.) warns the patient of an incremental or other imminent lost benefit 120, and in which a service provider 210 has determined that such prompt notifications (within a few hours before or after the appointment via a wireless message, e.g.) are effective for deterring costly no-shows. Alternatively or additionally, a service provider 210 may configure module 2046 or other components of event/condition detection unit 2050 to add points 116 to an account in response to each compliance and to subtract points 116 from the account in response to each noncompliance and to condition a reward (to a patient or care provider 283, e.g.) upon the account exceeding an upper limit (indicative of general compliance) and to condition a penalty or warning upon the account traversing a lower limit (indicative of a cumulative noncompliance). In some variants, service provider 210 may effectively determine such limits by applying a simple formula ("three strikes and you're out," e.g.) defining an acceptable count for each type of compliance-indicative event (success or failure, e.g.).

More generally, administration detection logic 2040 or other event/condition detection units 2050 as described herein can perform such operations by implementing both a conditional benefit 120 for an incremental compliance (rewarding a timely dose or therapy with a higher performance rating 138 or other positive incentive 140, e.g.) and a conditional penalty for an incremental noncompliance (penalizing a missed dose or therapy with a lower performance rating 138, reward reduction, or other negative incentive 140, e.g.). This can occur, for example, in a context in which a material provider 281 or care provider 283 administers the therapeutic component to an individual 282; in which interaction unit 275 includes one or more components capable of performing one or more of operations 1230, 1350, or 1640 as described herein; and in which such component(s) are operably coupled with event/condition detection unit 2050.

Operation 2194 describes signaling a discount as the incentive (e.g. one or more modules 1892 for signaling a discount generating a message 158 suitable for transmission to a point of sale authorizing a retailer to discount a purchase, e.g., via an interaction unit 275). In some contexts, for example, processing unit 890 and module 1892 jointly perform operation 1440—transmitting [an] indication of [an] incentive partly based on [a] therapeutic component and partly based on [a] provider of the therapeutic component. Module 1892 may respond to data comprising a therapeutic component ("immersion therapy," e.g.) and a provider of the therapeutic component ("XYZ Clinic," e.g.) and other such inputs, for example, by generating one or more messages for notifying a provider or patient of a discount. In some contexts, such a discount may have a value (V2) that exceeds a nominal value (V1) of the service or other therapeutic component. Such discounts may apply to the therapeutic component or to concurrent or other purchases (of topical pain relievers or shiatsu services, e.g.). Alternatively or additionally, the generated message may be broadcast to the provider(s) or other message recipients 222. This can occur, for example, in a context in which routing unit 1850 implements processing unit 890 and in which a service provider 210 funding the discount has determined that the therapeutic component is (apparently) likely enough to prevent a need for a surgical procedure or other more-costly treatment so that the value of the discount is justified.

In some variants, computer 180 and module 1892 are configured jointly to perform operation 1520 (obtaining an indication of an incentive to a provider of a therapeutic component at least partly based on an objective indication that the therapeutic component has been administered to a portion of an individual) and operation 1570 (including the indication of the incentive to the provider of the therapeutic component in a message). Module 1892 may signal an incentive to a provider (a wholesale food discount accruing to a restaurant, e.g.), for example, directly responsive to each indication that hand sanitizer has been dispensed (from sensors 1777 or other administration detection features 1780 in a dispensing device in the restaurant's entryway, e.g.). This can occur, for example, in a context in which computer 180 implements a response unit 960 in communication with routing unit 1850 via network 240 and in which a material provider 281 advertises on the dispensing device. Alternatively or additionally, each such message may be configured to include time data 435, digital photographs, or other such objective data effective for deterring fraudulent access to the incentive.

Operation 2195 describes presenting a first message indicative of the incentive to a care provider and a second message indicative of the incentive to a material provider (e.g. one or more instances of a module for conditioning an incentive 1722 upon compliance with a regimen 1749 transmitting a first message notifying care provider 283 of a first part of the incentive 1722 and also transmitting a second message notifying material provider 281 of at least a second part of the incentive 1722 so that both providers are motivated to encourage compliance with regimen 1747). This can occur, for example, in a context in which a primary module 1710 contains or can otherwise present the first message via (an instance of) a user interface 1740 identified with the care provider 283, in which a wearable 1742 or other interaction unit 275 associated with the material provider 281 can present the second message, and in which agent 262 programs (at least) these two notifications in response to an association between these providers and an individual 282 who is (apparently) at risk for noncompliance. Alternatively or additionally, agent 262 may identify such individuals based on one or more of their selection histories 753, a diagnosed cognitive or other noted deficiency 583 of the individual, financial importance of having a treatment performed, on the nature (e.g., severity) of the individual's status 971 or pathology 972, or other such actuarial determinants 330. This can occur, for example, in a context in which response unit 255 implements a primary module 1710 that transmits a common signal 1726 containing distinct incentives 1721, 1722 or a composite incentive 1722 (one configured to benefit two or more different parties, for example, or to combine distinct types of incentive 140, as exemplified in FIG. 1) to two or more interaction units 275. One such interaction unit 275 may implement a handheld 1741 associated with the material provider 281, for example, and others may implement user interfaces 1740 associated with other providers (worn or carried by them, for example, and listed in an ordinary distribution list or similar records 1985 accessible by response unit 255).

In light of teachings herein, numerous existing techniques may be applied for the display of sensor data and/or derived information as described herein without undue experimentation. See, e.g., U.S. Pat. No. 7,321,862 ("System and method for patient-worn monitoring of patients in geographically dispersed health care locations"); U.S. Pat. No. 7,319,386 ("Configurable system for alerting caregivers"); U.S. Pat. No. 7,285,090 ("Apparatus for detecting, receiving, deriving and displaying human physiological and contextual information"); U.S. Pat. No. 6,731,976 ("Device and method to measure and communicate body parameters"); U.S. Pat. No. 6,246,992 ("Multiple patient monitoring system for proactive health management"); U.S. Pat. No. 5,576,952 ("Medical alert distribution system with selective filtering of medical information"); U.S. Publication No.

20040030578 ("Automated clinical system to facilitate secondary review and authentication of clinical laboratory result values"); U.S. Pat. No. 6,332,502 ("Pipe loading device for a directional drilling apparatus"); U.S. Pat. No. 6,893,396 ("Wireless internet bio-telemetry monitoring system and interface"); U.S. Pat. No. 7,304,580 ("Intelligent medical vigilance system"); U.S. Pat. No. 6,694,177 ("Control of data transmission between a remote monitoring unit and a central unit"); U.S. Pat. No. 6,035,230 ("Real-time biological signal monitoring system using radio communication network").

Operation 2198 describes authorizing a resource transfer to an individual as the incentive (e.g. one or more modules 1893 for signaling a resource transfer allocating increments of time 111, points 116, payments in kind 118, or other such resources 119 to the individual 282). This can occur, for example, in a context in which the transfer is implemented at a point of sale (in an interaction unit 275 accessed by a material provider 281, e.g.) and in which the individual receives the goods or other resource(s) merely by stating that a generic bioactive material 681 will be used as recommended. Alternatively or additionally, other configuration logic 1860 may indicate one or more favorable terms 131, payments in kind 118, or other such benefits 120 to the individual or to other parties, as a further incentive.

Alternatively or additionally, in some contexts, a module 1998 for receiving a Boolean result from a compliance detection device or other components in a monitoring unit 1990 can perform operation 2198 by authorizing the transfer (in a screen display or other output 1982, e.g.) conditionally in response to input 1981 (individually or cumulatively) indicative of compliance with a regimen. This can occur, for example in a context in which such input is received from an actuator 1770 (a plunger 1762, e.g.) or other administrative detection feature 1780 of a vessel 1790 (containing a liquid or other therapeutic material, e.g.).

Figure 22:
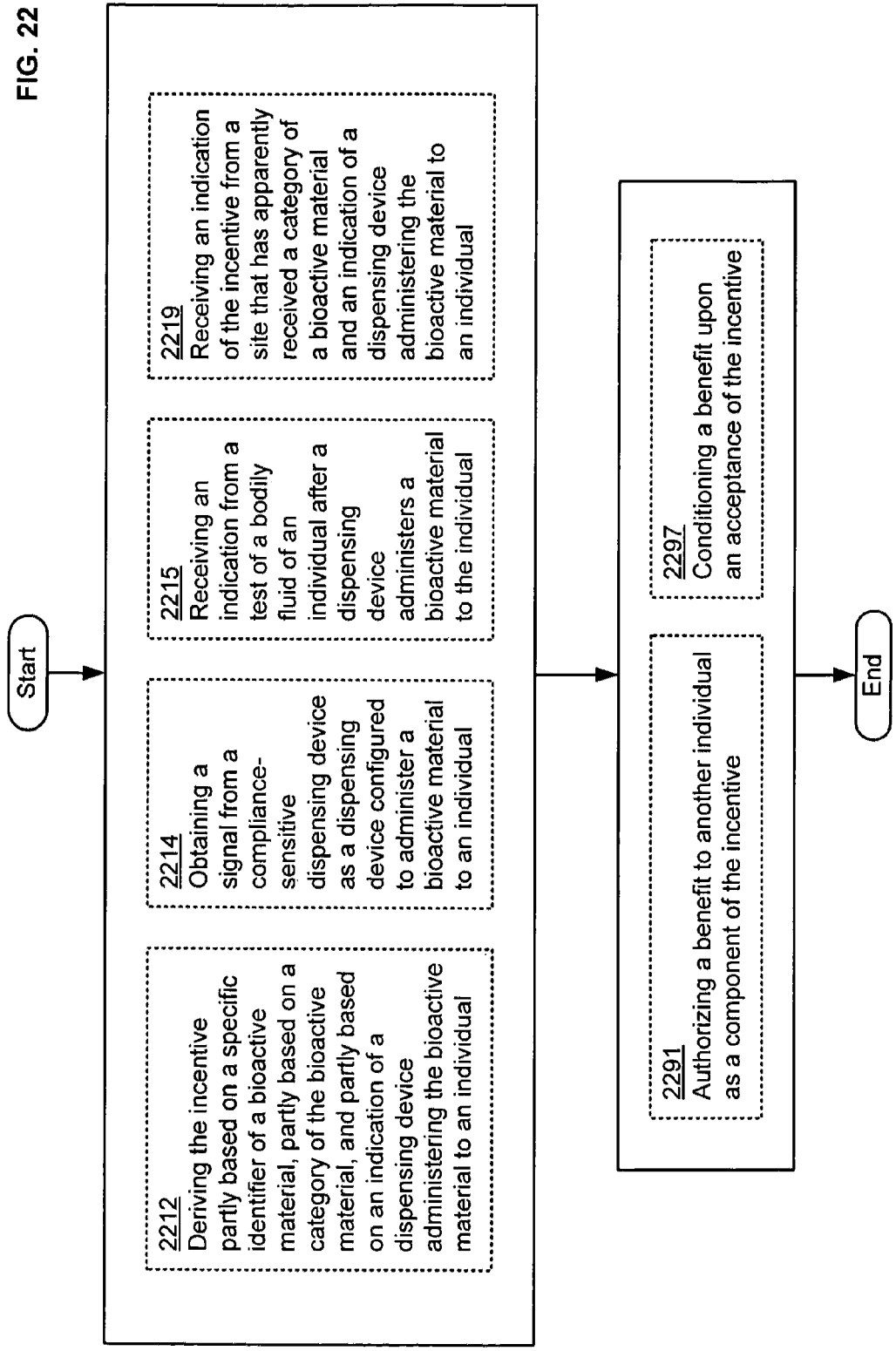
FIG. 22 depicts variants of flows shown in one or more of FIG. 11-16 or 21.

With reference now to FIG. 22 and to other flows described above, one or more instances of operation 1120, 1230, 1350, 1440, 1520, or 1640 may (optionally, each) include one or more instances of operation 2212, operation 2214, operation 2215, or operation 2219 as shown. One or more instances of operation 1150, 1260, 1380, 1460, 1570, or 1680 may likewise include one or more instances of operation 2291 or operation 2297.

Operation 2212 describes deriving the incentive partly based on a specific identifier of a bioactive material, partly based on a category of the bioactive material, and partly based on an indication of a dispensing device administering the bioactive material to an individual (e.g. one or more modules 1894 for signaling an other incentive designating food stamps or other tangible items as an incentive in response to an indication that dispensing device 1020 has dispensed an antibiotic or other bioactive material 1021 categorized as "time-critical" to the individual). This can occur, for example, in a vending machine implements system 1000 in which communication logic 1880 and incentive determination module 1080 jointly perform operation 1640, in which an (earlier-mentioned) incentive 140 accrues to the benefit of an entity that services the vending machine (material provider 281, e.g.), and in which timely regimen compliance by patients (indigent individuals taking an antibiotic for treating tuberculosis, e.g.) would otherwise occur less often. In some contexts many specific identifiers (drug or other chemical names, e.g.) may each map across several such categories ("daily injection," "dietary supplement," or "placebo component," e.g.), depending upon how the bioactive material is (apparently) to be administered, regimen timing, terms of use of the material, or other designations of service provider 210. In a context in which data is needed for regulatory or other quality control compliance concerning the specified bioactive material administered as a "daily injection," for example (but not for other materials or modes of administration), one or more modules of communication logic 1880 may selectively respond by identifying another incentive and transmitting a new offer 1868 indicating the incentive to interaction unit 275. Alternatively or additionally, operation 2212 may be performed by a compliance-indicative device 190 that modifies the terms 131 or conditions 134 of future transactions in response to an indication that physician-prescribed materials 685 dispensed by a processing unit 610 (incentive determination unit 350 containing module 1894, e.g.) are of a name-brand (non-generic) category.

Alternatively or additionally, operation 2212 may be performed by a processing unit 610 (a nursing station, e.g.) configured to contain a dispensing device (a smart syringe or pill dispenser, e.g.) that contains a generic bioactive material 681 or a name-brand bioactive material 682 and to generate the signal when it dispenses a bioactive material (an inoculant 571, e.g.). In some variants, computer 180 may be configured to contain a processing unit 610 and module 1993 configured jointly to perform one or more of the above-described flows. This can occur, for example, in a context in which processing unit 610 interacts with routing unit 1850 via network 240 and in which routing unit 1850 is configured to aggregate occurrences of noncompliance and to notify one or more service providers 210 or care providers 283 conditionally (of a noncompliance count or rate exceeding a threshold 465 defined by such provider, e.g.).

Operation 2214 describes obtaining a signal from a compliance-sensitive dispensing device as a dispensing device configured to administer a bioactive material to an individual (e.g. one or more modules 1993 for receiving dispensing device output data receiving input 1981 from a compliance-indicative device 190 that includes a dispenser 170 configured to administer a bioactive material). This can occur, for example, in a context in which the dispensing device is expected to transmit biometric data 436, one or more photographic images 1984, medical records, or other data 430 relating the individual. Alternatively or additionally, monitoring unit 1990 may have one or more records 1985 associating a dispensing device identifier with one or more other identifiers (of the individual or a bioactive material, e.g.) so that the data 430 may include the device identifier or omit an identifier of the bioactive material. This can occur, for example, in a context in which routing unit 1850 interacts with processing unit 610 or interface 518 via network 240.

Alternatively or additionally, operation 2214 may be performed by a processing unit 610 (a nursing station, e.g.) that is configured to contain a dispensing device (a smart syringe or pill dispenser, e.g.) that contains a generic bioactive material 681 or a name-brand bioactive material 682 and to generate the signal when it dispenses a bioactive material (an inoculant 571, e.g.). In some variants, computer 180 is configured to contain processing unit 610 and module 1993, which are configured jointly to perform operation 1640 (obtaining an indication of an incentive partly based on a category of a bioactive material and partly based on an indication of a dispensing device administering the bioactive material, to an individual) and operation 1680 (transmitting the indication of the incentive). This can occur, for example, in a context in which computer 180 implements processing unit 610 in communication with routing unit 1850 via network 240 and in which routing unit 1850 is configured to aggregate occurrences of noncompliance and to recognize trends therein (as a determinant in deciding whether to signal a care provider 283 that a patient needs to improve compliance, for example, by a message 158 suggesting training or reminding the patient transmitted to the provider's compliance-indicative device 190).

Operation 2215 describes receiving an indication from a test of a bodily fluid of an individual after a dispensing device administers a bioactive material to the individual (e.g. one or more modules 1994 for detecting a property of a sample from an individual receiving input 1981 from a sample tester 160 or other compliance-indicative device 190). This can occur, for example, in a context in which monitoring unit 1990 has received an indication (as input 281, e.g.) that the bioactive material was administered to the individual (from an interaction unit 275 operated by a material provider 281 or other individual 282 authorized to transmit such indications 4U4, e.g.) before a sample of bodily fluid (urine or blood, e.g.) is received and tested. Alternatively or additionally, the indication of the test of the bodily fluid may include one or more scalar measurements (one or more prior measurements 453 or current measurements 454, e.g.) to facilitate an expert monitoring such data 430 for trends or other correlations. This can occur, for example, in a context in which monitoring unit 1990 is configured to include one or more response units 580 (configured to monitor data 430, for example, by applying to a material indication 575 one or more thresholds 462 or other criteria that depend on physical attributes 590 of the individual).

Alternatively or additionally, operation 2215 may be performed by a processing unit 890 (implemented in a response unit 255 that is remote from individual 282, e.g.) that uses such dispensation-indicative data as objective indicia of compliance or noncompliance. In some variants, for example, response unit 255 may be configured to indicate noncompliance on any day that data indicating compliance is not received (in which interaction unit 275 includes a sample tester 160 configured to indicate compliance upon detecting the absence of a metabolite of an illegal drug, e.g.). This can occur, for example, in a context in which processing logic 875 and module 1994 jointly perform operation 1440 and in which the indication of the incentive (or absence thereof) is transmitted daily to service provider 210 and individual 282.

Operation 2219 describes receiving an indication of the incentive from a site that has apparently received a category of a bioactive material and an indication of a dispensing device administering the bioactive material to an individual (e.g. one or more interfaces 380 receiving a notice of credits 117 earned from an incentive determination unit 350 that can access a bioactive material identifier 311 or category 312 in response to the bioactive material being administered by a dispenser 170 to an individual 282). This can occur, for example, in a context in which the dispensing device is in a vicinity of the individual, in which a response unit 255 implements the incentive determination unit 350 remotely from the dispensing device, and in which a control unit 205 remote from the incentive determination unit 350 and from the dispensing device receives the indication of the incentive. In some variants, for example, the dispensing device may include a vending machine, kiosk, or other such interaction unit 275 configured to dispense an inoculant 571 or inhalant 572. Alternatively or additionally, incentive determination unit 350 may determine one or more incentives 140, potential or actual beneficiaries of the incentive, or message recipients 222 to be notified of the incentive partly based upon the identifier 311 or category 312 and partly based upon attributes of the individual as described herein.

In some variants, operation 2219 may be performed by an event/condition detection unit 2050 that includes a module 2065 for signaling a change in an eligibility of a party (responding conditionally to a patient's compliance by making the patient eligible for additional benefits 120, e.g.). This can occur, for example, in a context in which module 2065 determines compliance (positively or negatively) from one or more "first" indications (that a dispensing device given to the individual has or has not administered the bioactive material, e.g.). Alternatively or additionally, this can occur in a context in which the dispensing device includes a delivery unit 225 in a vicinity of the beneficiary 221 of the incentive that can transmit or otherwise give the incentive to the beneficiary 221 (via a printer or other display medium 156, e.g.).

Operation 2291 describes authorizing a benefit to another individual as a component of the incentive (e.g. one or more modules 1854 for authorizing a benefit to an individual delivering or otherwise allocating some combination of referrals 141, eligibilities 146, services 148, payments in kind 118, or other benefits 120 to one or more material providers 281 or care providers 283). This can occur, for example, in a context in which module 1854 resides in or communicates with an interaction unit 275 in a vicinity of such "other" individual(s), in which a first or primary beneficiary 221 has a mental disorder or other disability that might preclude that individual from using a bioactive material or other therapy on his or her own initiative, and in which the participation of such a material provider 281 or care provider 283 (in the form of a suggestion or other message indicating a regimen, for example, or a direct administration of a therapeutic component) would sometimes facilitate the enrollment of such individuals in a program or policy that requires a therapeutic regimen. Alternatively or additionally, module 1854 may perform operation 2291 by invoking a module 1881 for routing information to a material provider or other communication logic 1880 as described herein and by determining whether a response to that communication constituted an acceptance 1886 of the incentive.

Operation 2297 describes conditioning a benefit upon an acceptance of the incentive (e.g. one or more modules 1853 for implementing a conditional benefit generating an authorization signal conditionally upon receiving data 1885 signifying a recipient's acceptance 1886 of a benefit 120). This can occur, for example, in response to an instance of operation 1350—obtaining an indication of an incentive to an individual partly based on an indication of a health status apparently resulting from a therapeutic component administered to a portion of the individual and partly based on another physical attribute of the individual. In response to an abatement of a symptom (indicating an apparently improved health status, e.g.), for example, module 1853 and module 765 can jointly perform operation 1380—transmitting the indication of the incentive. Module 1853 may respond to data comprising a therapeutic component ("immersion therapy," e.g.) and a provider of the therapeutic component ("XYZ Clinic," e.g.) and other such inputs by generating one or more messages for notifying a provider or patient of a discount. In some contexts, such a discount may have a value (V2) that exceeds a nominal value (V1) of the service or other therapy. Such discounts may apply to the therapeutic component or to concurrent or other purchases (of topical pain relievers or shiatsu services, e.g.). Alternatively or additionally, the generated message may be broadcast to the provider(s) or other message recipients 222. This can occur, for example, in a context in which routing unit 1850 implements processing unit 890 and in which a service provider 210 authorizing the discount has determined that the therapeutic component is likely to prevent the need for a surgery or other more-costly treatment.

In some variants, processing unit 610, linking unit 390, and module 1853 are configured jointly to perform operation 1230 (obtaining a selection of an incentive to an individual partly based on an indication of a therapeutic component administered to a portion of the individual and partly based on a physical attribute of the individual) and operation 1260 (transmitting the selection of the incentive). Module 1853 may implement operation 2297 (conditioning a benefit upon an acceptance of at least a portion of the incentive), for example, in a context in which module 1853 awards points 116, miles, or other such quantifiable benefits expressed as a scalar value in response to an indication that a patient with an identified physical attribute ("fair complexion" or "on corticosteroids," e.g.) manifests an indication of a willingness to have the therapeutic component administered to a portion of the patient (sunscreen being applied to the patient's skin or a portion thereof, e.g.). Such an award of benefits may trigger a communication to the individual (via a display medium 154 or otherwise as an instance of operation 1260, e.g.) or to a dispenser 170 (of candy, tickets or other tangible items as the incentive, e.g.). This can occur, for example, in a context in which a child or other difficult-to-motivate patient might otherwise not use sufficient diligence in accepting or otherwise obtaining the therapeutic component. In some cases, a dispenser 170 may include one or more keys by which an individual may manifest the acceptance or lack thereof (as "Y" and "N" keys, e.g.). Alternatively or additionally, each such acceptance of an incentive may be manifested as a verbal input (e.g., a "yes" in response to a question of "will you apply sunscreen if I give you a nickel?") detectable by an incentive acceptance module 1720 (implementing a microphone/speech recognition module analyzing signal 1727, e.g.).

Figure 23:
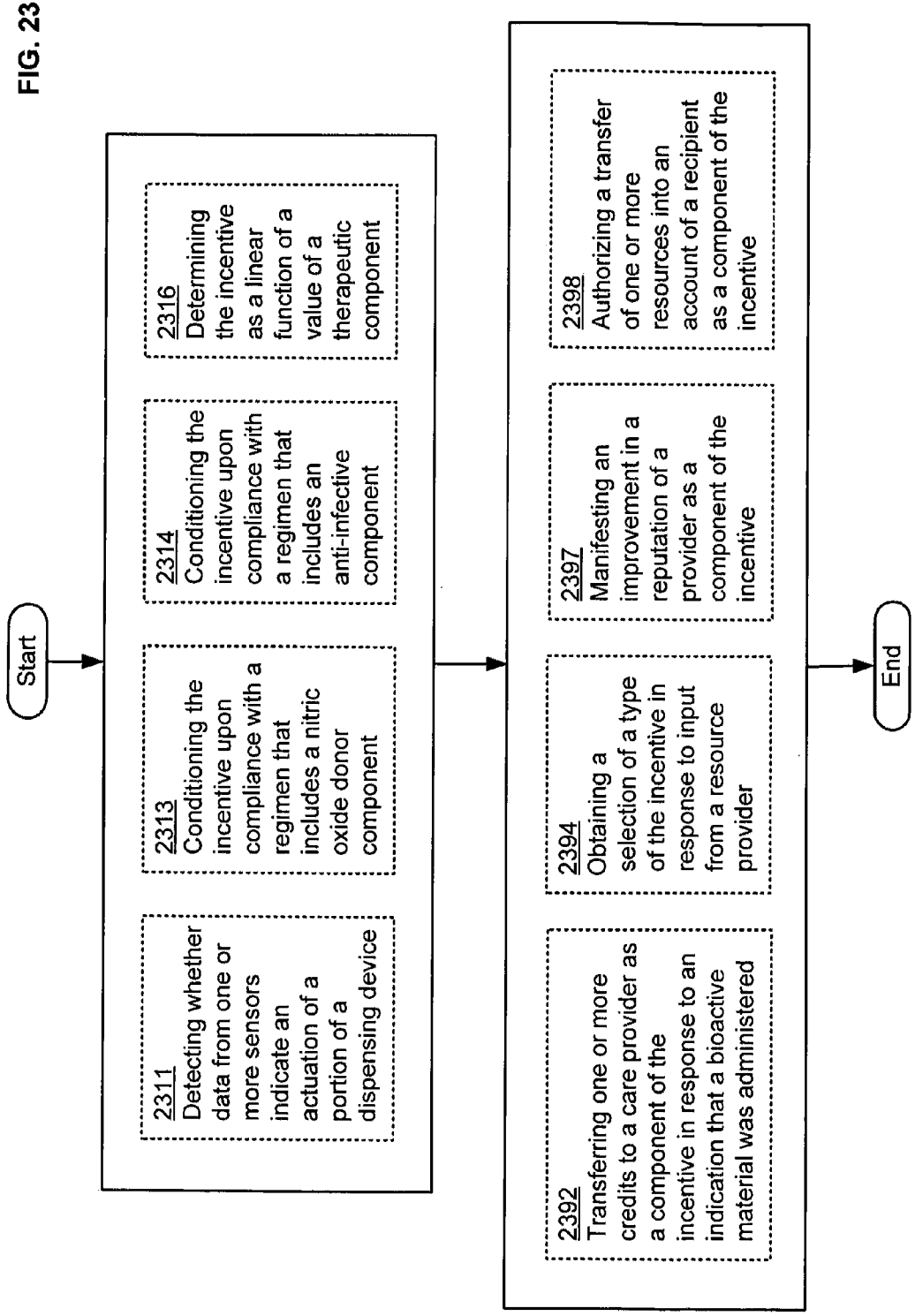
FIG. 23 likewise depicts variants of earlier-presented flows.

FIG. 23 depicts flow 2300 in relation to other flows described above in FIGS. 5-11. One or more instances of operation 1120, 1230, 1350, 1440, 1520, or 1640 may (each, optionally) include one or more instances of operation 2311, operation 2313, operation 2314, or operation 2316 as exemplified below. Also one or more instances of operation 1150, 1260, 1380, 1460, 1570, or 1680 may likewise. (each, optionally) include one or more instances of operation 2392, operation 2394, operation 2397, or operation 2398.

Operation 2311 describes detecting whether data from one or more sensors indicate an actuation of a portion of a dispensing device (e.g. administration detection module 1748 or event/condition detection unit 2050 selectively recognizing the sound of a cover 1761, plunger 1762, button 1763, or other actuator 1770 of the dispensing device in operation). This can occur, for example, in a context in which vessel 1790 is configured as the dispensing device and in which data from one or more sensors 1734, 1777 is of sufficient resolution to permit auditory pattern recognition. Alternatively or additionally, event/condition detection unit 2050 may be configured to use visual or other sensor data (on medium 450, e.g.) to detect one or more events in sequence as an objective indication that a therapeutic component is being administered.

Operation 2313 describes conditioning the incentive upon compliance with a regimen that includes a nitric oxide donor component (e.g. a primary module 1710 or module 2064 for determining an eligibility selecting an eligibility 147 for additional increments 112, 113 of days or months of close monitoring in response to indications of noncompliance exceeding a threshold 465, and otherwise selecting a more favorable eligibility 146). This can occur, for example, in a context in which such modules include media 450 bearing a nitric-oxide-donor material component 425 and in which a researcher or other service provider 210 wants to ensure that a dispersed group of care providers 283 are effectively and sufficiently motivated to follow a specific study protocol of topical organic nitrate administration to patients who have a pathology of interest for product development. Alternatively or additionally, operation 2313 may be performed by other modules of incentive determination unit 350 or event/condition detection unit 2050 as described above.

Operation 2314 describes conditioning the incentive upon compliance with a regimen that includes an anti-infective component (e.g. beneficiary selection module 342 awarding services 148, certificates, or other benefits 120 selectively to motivate a population of parents to immunize their children according to a prescribed antiviral regimen). Alternatively or additionally, in some contexts, operation 2314 can include a sample tester 160 transmitting one or more current measurements 454 (indicating a concentration of the antiviral component or a metabolite thereof, e.g.) to a module 1997 for determining whether quantitative data indicates regimen compliance on the part of an individual 282 having an infection-indicative pathology 972. In some variants, for example, such material components 434 may include one or more protease inhibitors, cellular transport/efflux inhibitors, neuraminidase inhibitors, monoclonal or polyclonal antibiotics, immune serums, antimicrobials, antimycobacterials (such as isoniazid, rifampicin, or other antituberculosis drugs, e.g.), anti-fungals, antivirals, antiretrovirals (ARVs), or other such bioactive materials 1031. Alternatively or additionally, operation 2314 may be performed by other modules of incentive determination unit 350 or event/condition detection unit 2050 that include one or more media 450 bearing an antiviral material component 422 as described above.

Operation 2316 describes determining the incentive as a linear function of a value of a therapeutic component (e.g. one or more incentive computation modules 348 setting V2=k×V1, k being a multiplier between 1 and 3, V1 being a value of a therapeutic component, and V2 being a value of one or more components of the incentive). In some variants, such multipliers may have dimensional transfer units (like "points per milligram" or "candies per session," e.g.) and may be vector-valued or matrix-valued (for implementing composite incentives or in relation to composite indicators of regimen compliance, e.g.). Alternatively or additionally, incentive selection module 346 may be used to select among several incentive computation modules 348 as a function of one or more patient attributes 320, contemporaneous measurements 654, or other such determinants 330. This can occur, for example, in a context in which an individual 282 has an age 581 of less than a threshold 464 (of ten years, e.g.) and in which incentive selection module 346 responds to this condition by selecting one or more incentive computation modules 348 dealing in highly tangible incentives 140 (coins or coupons, e.g.) instead of those dealing in less tangible incentives 140 (referrals 142, e.g.). Alternatively or additionally, incentive selection module 346 may select an incentive component in response to an inventory that is local to the individual 282 (in a compliance-indicative device 190 or other interaction unit 275 available to the individual 282, e.g.), held by a material provider 281 available to the individual 282, or otherwise known to incentive selection module 346.

In some variants, the incentive can be determined as a nonlinear function of a value of a therapeutic component (e.g. one or more incentive computation modules 348 using a logarithmic or other common monotonic function of V1 to obtain V2). In some contexts, for example, a service provider 210 may implement such a function for systematically defining incentives for thousands of material components 434 (within a given category of material 685, e.g.) each having a known wholesale value.

Operation 2392 describes transferring one or more credits to a care provider in response to an indication that a bioactive material was administered (e.g. a module for authorizing a benefit to a care provider 1852 signaling a transfer of currency or other credits 117 into a nurse's account 489 conditionally in response to the nurse reporting the administration via a specific transmission medium 156). In some contexts, for example, administration detection logic 2040 reporting (apparent) compliance with a medication regimen may directly invoke interaction unit 275 (in a kiosk, e.g.) to signal material provider 281 to (send or otherwise) transfer tangible resources 119 to the care provider. Alternatively or additionally, a care provider may obtain an eligibility 146 (to enter a club or a website, for example, operated by the material provider) by such an account growing sufficiently large or in exchange for such credits. Alternatively or additionally, operation 2392 may be performed by other modules of routing unit 1850 or event/condition detection unit 2050 as described above.

Operation 2394 describes obtaining a selection of a type of the incentive in response to input from a resource provider (e.g. one or more ports 385 receiving from incentive selection modules 346 incentive type data 326 that is responsive to data from a service provider 210 who allocates resources to serve as enrollment or compliance incentives). This can occur, for example, in a context in which service provider 210 sponsors an enrollment by providing or promising credits 117, payments in kind 118, discounts, referrals 141, or services 148 of various types, some of which may be effective for enticing material providers 281 or other individuals 282 to facilitate enrollment or compliance as described herein.

Operation 2397 describes manifesting an improvement in a reputation of a provider (e.g. interaction unit 275 transmitting an award notification or other laudatory message 158 about a material provider 281 to various other message recipients by invoking one or more modules 1884 for routing information to another party). This can occur, for example, in a context in which an agent 262 configures such modules in response unit 255 to broadcast the message across multiple linkages 206, 226, 276 as an automatic response to an indication (from interaction unit 275, e.g.) of the provider reaching a defined goal. A program manager or technician 261 may implement such goals, for example, by causing one or modules for authorizing a benefit to an individual 1854 to increase a success ratio or other performance rating 138 of the provider (as the individual, e.g.) responsive to instances of successful delivery of services or materials (or vice versa). Alternatively or additionally, operation 2397 may be performed by other modules of routing unit 1850 and event/condition detection unit 2050 as described above.

Operation 2398 describes authorizing a transfer of one or more resources into an account of a recipient of the incentive (e.g. one or more modules for signaling a resource transfer 1893 causing an account 489 belonging to one or more beneficiaries 221 to reflect one or more credits 117 or other quantifiable resources 119 of an incentive 140). Alternatively or additionally, incentive determination units 350 as described herein can perform operation 2398 by transmitting such an authorization as an incentive indication 372 to an agent 262 or other individual (at an interface 380 or other response unit 255, e.g.) who can perform the transfer.

Figure 24:
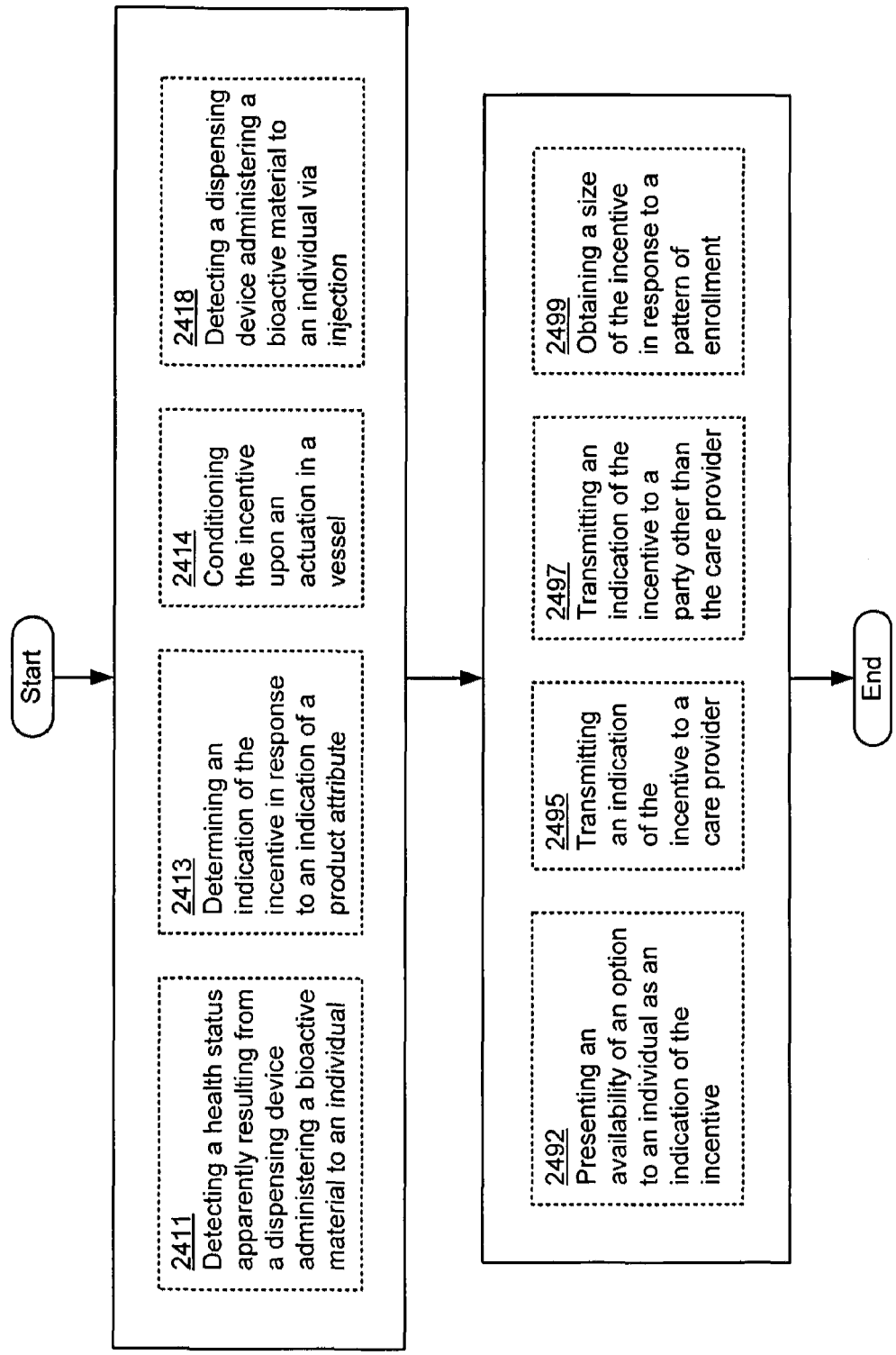
FIG. 24 likewise depicts variants of earlier-presented flows.

With reference now to FIG. 24 and to other flows described above in relation to FIGS. 5-11, one or more instances of operation 1120, 1230, 1350, 1440, 1520, or 1640 may (each, optionally) include one or more instances of operation 2411, operation 2413, operation 2414, or operation 2418 as exemplified below. Also one or more instances of operation 1150, 1260, 1380, 1460, 1570, or 1680 may likewise include one or more instances of operation 2492, operation 2495, operation 2497, or operation 2499.

Operation 2411 describes detecting a health status apparently resulting from a dispensing device administering a bioactive material to an individual (e.g. one or more modules 1999 for detecting a health-status attribute, such as circuitry for recognizing a current measurement 454 that is closer to normal than a prior measurement 453 after recognizing one or more indications 473-475 that care provider 283 has administered the bioactive material to a patient or other individual 282). This can occur, for example, in a context in which one or more records 1985 associate the bioactive material with an anticipated improvement in such measurements, in which interaction unit 275 includes the dispensing device or other vessel 1790 as described herein, in which response unit 255 implements monitoring unit 1990, and in which care provider 283 signals the administration and the health status via interaction unit 275. In some variants, for example, response unit 255 queries interaction unit 275 for such data items in sequence via interaction unit 275.

Operation 2413 describes determining the indication of the incentive in response to an indication of a product attribute (e.g. one or more modules 2087 for indicating a product attribute signaling one or more material identifiers 311, categories 312, values 313, or other bioactive material indications 310; an expiration date; or a dosage capacity, an indication of whether a vessel 1790 has an administration detection feature 1780, or other such vessel attribute). Alternatively or additionally, such a module may obtain such indications from a material provider 281 (via interaction unit 275, e.g.).

Operation 2414 describes conditioning the incentive upon an actuation in a vessel (e.g. one or more modules 2041 for detecting and responding to an actuation in a vessel, such as circuitry for responding to an ejection of pills from a dispenser by transmitting data 2072 effective for identifying the incentive 140). In some variants, such a module may reside in an interaction unit 275 physically separate from the vessel. This can occur, for example, in a context in which a care provider 283 or other individual 282 triggers the actuation, in which at least one module 2041 includes circuitry for detecting an ejection of one or more pills from a dispenser 170 or circuitry for detecting a component actuation in a syringe or other dispensing device, and in which administration detection unit 2040 is configured to detect one or more of a timely dispensation of the bioactive material, an image of the individual pushing a button 1763 or otherwise triggering the actuation, or some other objective indication of compliance as described herein. Alternatively or additionally, such modules may detect an actuation that signifies a systemic or other direct administration (into the individual's mouth or vein, e.g.) of a bioactive material configured to provide a systemic treatment. In some contexts, moreover, an event/condition detection unit 2050 may include such administration detection logic 2040 configured to transmit (across a network 240 or other transmission media 355, e.g.) an indication of the actuation in real time (wirelessly via a network linkage 276, e.g.) or after storing a series of such indications of a sufficient number of actuations (as data 2071 on a storage medium 152 indicating an actuation count that exceeds a threshold value, e.g.).

In light of teachings herein, numerous existing techniques may be applied for detecting actuations in a portion of a vessel as described herein without undue experimentation. See, e.g., U.S. Pat. No. 7,480,543 ("Ultrasonic sensor for detecting the dispensing of a product"); U.S. Pat. No. 7,442,180 ("Apparatus and methods for administering bioactive compositions"); U.S. Pat. No. 7,396,511 ("Dispensing device, dispensing method and method of detecting defective discharge of solution containing biological sample"); U.S. Pat. No. 7,347,200 ("Medicament dispenser"); U.S. Pat. No. 7,299,944 ("Fluid dispenser calibration system and method"); U.S. Pat. No. 7,269,476 ("Smart medicine container"); U.S. Pat. No. 7,233,015 ("System and method for detecting liquid flow from a nozzle in a semiconductor processing device"); U.S. Pat. No. 7,170,823 ("Medical dispenser, a blister card for use in the dispenser and a method of dispensing medical doses"); U.S. Pat. No. 7,117,653 ("Flavoring system and method"); U.S. Pat. No. 7,086,269 ("Apparatus and method for testing seed singulation of a seed meter"); U.S. Pat. No. 7,027,935 ("Sample dispensing apparatus and automatic analyzer using the same"); U.S. Pat. No. 6,998,230 ("Array fabrication with drop detection"); U.S. Pat. No. 6,920,372 ("Audit monitoring and product drop system for retrofitting vending machines"); U.S. Pat. No. 6,895,307 ("Data processing system for managing chemical product usage").

Bioactive agents are dosed by a jet dispenser using inkjet technology, such as that used in printing devices. The jet dispenser dispenses precise amounts of bioactive agent into a fluid manifold, in which the bioactive agent can be mixed with an infusion liquid for infusing into a patient. A controller may control delivery of one or more drugs, timing of drug administration, or change drug regimens in response to a changing medical condition of a patient. A drop detector can be used to detect various characteristics of the droplets of the bioactive agent dispensed by the jet dispenser and provide a feedback signal to the controller to determine whether a detected characteristic satisfies a predetermined condition. In particular embodiments, one or more drop detectors are employed to detect a characteristic of the droplets of fluid dispensed from a jet dispenser. For example, a drop detector may determine whether any droplets are being dispensed from a particular jet dispenser. Other droplet characteristics that can be detected by a drop detector include the volume and velocity of the droplets. The drop detector sends this information to a controller, which can be used to activate an alarm, such as an audio and/or visual alarm, if the detected characteristic does not satisfy a predetermined condition or requirement. In one specific implementation, for example, an alarm is activated if a drop detector determines that a jet dispenser is not dispensing any drops.

Operation 2418 describes detecting a dispensing device administering a bioactive material to an individual via injection (e.g. one or more modules 1998 for receiving a Boolean result indicating a plunger 1762 or other administration detection feature 1780 of a syringe having injected an inoculant 571). This can occur, for example, in a context in which such a module 1998 receives material indications 575 signifying the inoculant or other indications 1051 signaling the dispensing device 1030 injecting the bioactive material 1031. Alternatively or additionally, processing unit 1040 may be configured to perform one or more flows as described above.

Operation 2492 describes presenting an availability of an option to an individual as an indication of the incentive (e.g. one or more modules 1883 for routing information to an individual and modules 1891 for signaling an availability of an option jointly displaying a message 158 expressing the option to individual 282 via interaction unit 275). This can occur, for example, in a context in which the individual receives eligibilities 146, discounts, or other such options as benefits 120 that may entice the individual to subscribe to a policy or adopt a regimen. Alternatively or additionally, communication logic 1880 may include one or more modules 1884 for routing information to another party (a material provider 281, e.g.) who can, in turn, explain the option to the individual or entice the individual to obtain or exercise the option.

Operation 2495 describes transmitting an indication of the incentive to a care provider (e.g. one or more modules for routing information to a care provider 1882 transmitting data 1885 indicative of an actual or potential incentive to care provider 283). This can occur, for example, in a context in which routing unit 1850 performs one or more instances of operation 1150, 1260, 1380, 1460, 1570, or 1680; and in which care provider 283 explains and potentially administers such incentive(s) in conjunction with any related terms and conditions; and in which care provider 283 can thereafter transmit any such parties' acceptance 1886 of such terms, conditions, or incentives.

Operation 2497 describes transmitting an indication of the incentive to a party other than the care provider (e.g. one or more modules for signaling an other incentive 1894 transmitting data 1885 indicative of a component of an incentive 140 to a material provider, beneficiary 221, another recipient 222, or an individual 282 receiving therapy). This can occur, for example, in a context in which said component of the incentive 140 is not conditional upon any indication of an acceptance 1886; in which other communication logic 1880 notifies other parties of one or more other components of the incentive; in which routing unit 1850 performs one or more instances of operation 1150, 1260, 1380, 1460, 1570, or 1680; and in which a desirable administration of a therapeutic component would often not occur in the absence of cooperation between two or more parties. Alternatively or additionally, said component of the incentive 140 may include one or more physical, tangible resources 119, certificates, or other manifestations of benefits 140 concurrently shipped to one or more recipients 222.

Operation 2499 describes obtaining a size of the incentive in response to a pattern of enrollment (e.g. one or more ports 385, 386 receiving from incentive computation modules 348 quantitative incentive indications 372 that are responsive to whether prior offers 1868 resulted in a higher-than-needed or lower-than-needed rate of acceptance 1886). This can occur, for example, in a context in which an incentive computation module 348 will designate (1) a 10% incentive increase each time a given offer 1868 of incentive is not accepted X1 consecutive times and (2) a 10% incentive decrease each time a given offer 1868 of incentive is accepted X2 consecutive times. Alternatively or additionally, service provider 210 may designate other incentive type, beneficiary, or size adjustments responsive to patterns of program enrollment or regimen compliance as described herein.

Figure 25:
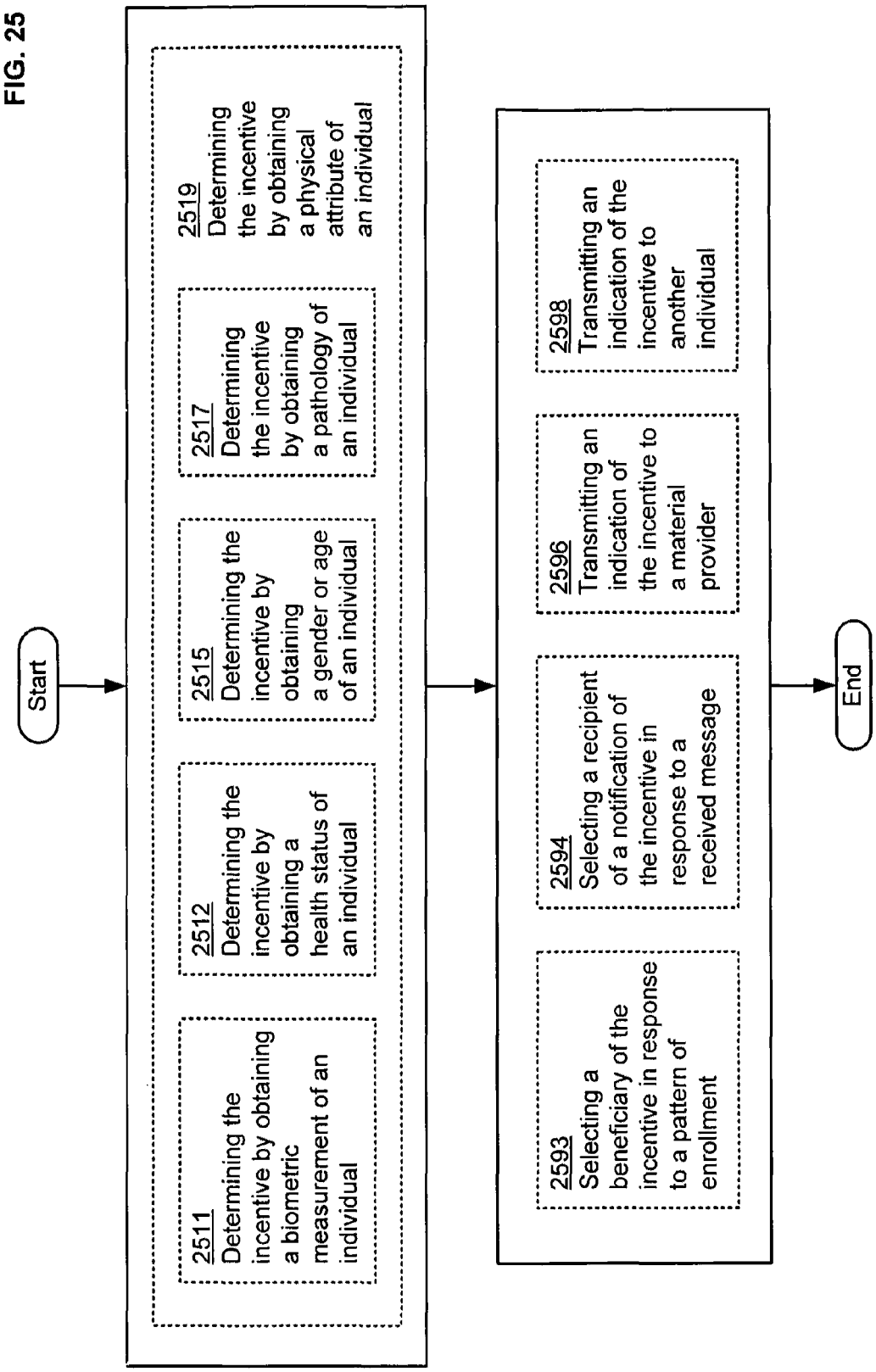
FIG. 25 likewise depicts variants of earlier-presented flows.

FIG. 25 depicts flow 2500 in relation to other flows described above in FIGS. 5-11, one or more instances of operation 1120, 1230, 1350, 1440, 1520, or 1640 may include one or more instances of operation 2511, operation 2512, operation 2515, operation 2517, or other implementations of operation 2519 as exemplified below. Also one or more instances of operation 1150, 1260, 1380, 1460, 1570, or 1680 may likewise include one or more instances of operation 2593, operation 2594, operation 2596, or operation 2598.

Operation 2511 describes determining the incentive by obtaining a biometric measurement of an individual (e.g. incentive determination unit 350 obtaining one or more determinants 330 by invoking one or more modules for obtaining a current physical attribute of an individual 1995 such as a current measurement 454 of a temperature, concentration, optical parameter, feature size, or other current physical attribute of the individual for comparison with earlier measurement data or other data indicative of normality or change). This can occur, for example, in a context in which the biometric measurement indicates whether a treatment regimen has been successful or otherwise indicates a health status (feature) of the individual.

In light of teachings herein, numerous existing techniques may be applied for recording of event information resulting from the comparison of measured and/or derived information to other information as described herein without undue experimentation. See, e.g., U.S. Pat. No. 7,226,422 ("Detection of congestion from monitoring patient response to a recumbent position"); U.S. Pat. No. 7,127,370 ("Attitude indicator and activity monitoring device"); U.S. Pat. No. 6,980,851 ("Method and apparatus for determining changes in heart failure status"); U.S. Pat. No. 6,978,182 ("Advanced patient management system including interrogator/transceiver unit"); U.S. Pat. No. 6,881,192 ("Measurement of sleep apnea duration and evaluation of response therapies using duration metrics"); U.S. Pat. No. 6,336,903 ("Automated collection and analysis patient care system and method for diagnosing and monitoring congestive heart failure and outcomes thereof"); U.S. Pat. No. 6,035,230 ("Real-time biological signal monitoring system using radio communication network").

Operation 2512 describes determining the incentive by obtaining (an indication of) a health status of an individual (e.g. incentive determination unit 350 obtaining one or more determinants 330 by responding to one or more sensors 1734 that provide an audio record 1737 or other data 2071 signaling the individual reporting how he or she is feeling or has been feeling). In some variants, for example, incentive computation module 348 may (1) cause interaction unit 275 or other user interfaces to present one or more queries relating to the individual's health status or to a therapeutic component, (2) receiving one or more health status indications in response, and (3) designate a larger incentive for a patient who indicates a health status improvement (and perhaps for component providers as well). Alternatively or additionally, beneficiary selection module 342 may add an incentive component for another party (as a potential advocate, e.g.) responsive to an indication that a patient (a) apparently has a worsening symptom and (2) is apparently not complying with a diagnostic or other regimen related to the symptom. Alternatively or additionally, the health status 751 may depend on scalar or other biometric data 436 or other input 1981 constituting a past or present status of a normal or other aspect of the individual's physical health (as a baseline, e.g.). This can occur, for example, in a context in which a therapeutic material (a diuretic or other medication, e.g.) is associated with an indicator of the health status (a blood pressure or concentration-indicative measurement, e.g.) by virtue of its therapeutic application. More generally, the PDR Family Guide to Prescription Drugs (9th ed.) and PDR for Nonprescription Drugs, Dietary Supplements, and Herbs (32nd ed.) each identifies numerous bioactive materials in association with corresponding foreseeable health status indications (a current measurement 454 indicative of one or more therapeutic improvements or side effects or their absence relative to a prior measurement 453 or other norm, e.g.). Both are incorporated by reference to the extent not inconsistent herewith.

In light of teachings herein, numerous existing techniques may be applied for aggregating symptomatic or other structural data or implementing predictive or other expert systems as described herein without undue experimentation. See, e.g., U.S. Pat. No. 7,315,825 ("Rules-based patient care system for use in healthcare locations"); U.S. Pat. No. 7,272,435 ("System and method for sudden cardiac death prediction"); U.S. Pat. No. 7,225,013 ("Adaptive prediction of changes of physiological/pathological states using processing of biomedical signals"); U.S. Pat. No. 7,027,871 ("Aggregation of data from external data sources within an implantable medical device"); U.S. Pat. No. 6,988,088 ("Systems and methods for adaptive medical decision support"); U.S. Pat. No. 6,643,646 ("Analysis of massive data accumulations using patient rule induction method and on-line analytical processing"); U.S. Pat. No. 6,533,724 ("Decision analysis system and method for evaluating patient candidacy for a therapeutic procedure"); U.S. Pat. No. 6,442,421 ("Method for the medical monitoring in real time of a patient from the analysis of electroencephalograms to characterize and differentiate between physiological or pathological conditions, and a method for anticipating epileptic seizures"); U.S. Pat. No. 6,317,731 ("Method for predicting the therapeutic outcome of a treatment"); U.S. Pat. No. 6,025,128 ("Prediction of prostate cancer progression by analysis of selected predictive parameters").

Operation 2515 describes determining the incentive by obtaining a gender or age of an individual (e.g. one or more modules of incentive determination unit 350 obtaining one or more determinants 330 by invoking a user interface 518 or other interaction unit 275 receiving indications of physical attributes 590 that include an age 581 or gender 582 of a subject individual 282). This can occur, for example, in a context in which a care provider 283 provides such data to facilitate enrolling the individual in a treatment program or other regimen.

Operation 2517 describes determining the incentive by obtaining a pathology of an individual (e.g. incentive determination unit 350 obtaining one or more determinants 330 and interaction unit 275 jointly generating incentive type data 326 or incentive source data 327 responsive to indications of patient attributes 970 that include a disease state or other pathology 972 of an individual 282). This can occur, for example, in a context in which an uncommon pathology may qualify the individual for special incentives for enrollment in or compliance with a regimen as described herein and in which incentive determination unit 350 otherwise would not be able to obtain data about which individuals exhibit the pathology (because of patient confidentiality issues, e.g.). Alternatively or additionally, a provider may qualify for special incentives as described herein for referring participants having such pathologies (or other uncommon attributes) to a program as described herein.

Operation 2519 describes determining the incentive by obtaining a physical attribute of an individual (e.g. one or more modules of incentive determination unit 350 obtaining a biometric measurement, health status, gender, age, pathology, or other such physical attributes 321 of the individual 282 usable as described herein as determinants 330 affecting incentives 140 suggested or conferred as described herein). Service provider 210 may configure one or more beneficiary selection modules 342, message recipient selection modules 344, incentive selection modules 346, incentive computation modules 348 to depend upon such determinants 330 as described herein. In a context in which one or more current measurements 454 indicate that a measured weight of the individual 282 reflects a large-enough excess 584 (in view of a height or other physical attributes 590 of the individual 282, e.g.), for example, service provider 210 may include, enhance, or selectively indicate incentive components to an individual 282 who agrees to provide use an appetite suppressant, exercise regimen, healthy dietary regimen, or other such therapeutic component (suitable for helping the individual 282 lose weight, e.g.). Alternatively or additionally, the incentive may include one or more components for benefiting a care provider 283 (a physical trainer, e.g.) or a material provider 281 (grocer, e.g.) in response to an endorsement, reminder, or other message 148 about such regimen(s) forwarded to the individual 282 or to the individual subscribing to or complying with such regimen(s). This can occur, for example, in a context in which the excess 584 or other patient attributes 970 indicate that individual 282 suffers from diabetes, polycystic ovary syndrome (PCOS), obesity, or other pathologies or risks associated with excess weight.

In a context in which such measurement(s) indicate that that the measured weight signifies a large-enough deficiency 583, conversely, service provider 210 may include, enhance, or selectively indicate incentive components to a subscribing/compliant individual 282 and to a material provider 281 or care provider 283 in response to an endorsement, reminder, or other message 148 about a weight-enhancement regimen given to the subscribing/compliant individual 282. This can occur, for example, in a context in which (the deficiency 583 and other) patient attributes 970 indicate that individual 282 suffers from anorexia or is undergoing chemotherapy or other health conditions associated with underweight individuals.

Various context are described herein in which an incentive component may be created or enhanced in response (a) to measurements or other indications that a therapeutic component may be appropriate or necessary for the well-being of an individual 282 and (b) to indications that a rate of enrollment in a research study or other program will not achieve an adequate level of participation for a given subpopulation (defined by gender, age, weight, pathology, or other such attributes, for example). Some or all of such qualifications may be confidential and not directly available until such confidentiality is waived, in some contexts, such that service provider 210 might elect to create incentives for participation (and such waiver) that are highly generous. In response to one or more indications of overinclusive incentives/enrollment, however, a roll-back of such incentives may be warranted in response to an indication that a given individual 282 is not in a most-sought subclass of participants. In these and similar contexts in which a roll-back is warranted, service provider 210 may exclude, reduce, or selectively omit incentive components or notifications to the individual 282 or other parties in response to physical attributes 321 or other current measurements 454 indicating that one or more therapeutic components were successful or in which specific components of incentives 140 are longer needed. This can occur, for example, in a context in which the individual's weight, blood pressure, material concentration, thermal indications, or other biometric data 436 indicative of infection or other disease (have crossed one or more thresholds 464, 465 so that they now) fall within normal parameters. Alternatively or additionally, such reductions may be appropriate in relation to one or more beneficiaries 221 of incentives 140 whose primary role was to introduce or explain a program to the individual(s) 282 or to facilitate a setup or otherwise whose ongoing participation is not crucial.

In light of teachings herein, numerous existing techniques may be applied for monitoring apparent vascular changes or other such phenomena as described herein without undue experimentation. See, e.g., U.S. Pat. No. 7,331,928 ("Ultrasonic doppler bloodstream measurement device"); U.S. Pat. No. 7,297,280 ("Method and apparatus to measure blood flow in hemodialysis shunts"); U.S. Pat. No. 7,289,927 ("Method and apparatus for the monitoring of body temperature and/or blood flow"); U.S. Pat. No. 7,254,432 ("Method and device for non-invasive measurements of blood parameters"); U.S. Pat. No. 7,226,415 ("Microwave hemorrhagic stroke detector"); U.S. Pat. No. 7,200,431 ("Implantable blood flow monitoring system"); U.S. Pat. No. 7,195,598 ("Method for determining the effectiveness of a medical therapy by analysis of collateral vessels"); U.S. Pat. No. 7,171,251 ("Physiological stress detector device and system"); U.S. Pat. No. 7,128,713 ("Doppler ultrasound method and apparatus for monitoring blood flow and hemodynamics"); U.S. Pat. No. 6,740,042 ("Bilateral simultaneous doppler measurement of segmented sphygmomanometry"); U.S. Pat. No. 6,520,919 ("Inferior-and-superior-limb blood-pressure-index measuring apparatus"); U.S. Pat. No. 6,413,223 ("Cuffless continuous blood pressure monitor"); U.S. Pat. No. 6,117,087 ("Method and apparatus for noninvasive assessment of a subject's cardiovascular system"); U.S. Pat. No. 5,724,983 ("Continuous monitoring using a predictive instrument").

Also in light of teachings herein, numerous existing techniques may be applied for receiving, extracting, or otherwise obtaining thermal indications via sensors or other structures in, on, or near body parts as described herein without undue experimentation. See, e.g., U.S. Pat. No. 6,983,178 ("Probe for use in non-invasive measurements of blood related parameters"); U.S. Pat. No. 6,975,232 ("Apparatus and method for "seeing" foot inside of shoe to determine the proper fit of the shoe"); U.S. Pat. No. 7,340,293 ("Methods and apparatus for a remote, noninvasive technique to detect core body temperature in a subject via thermal imaging"); U.S. Pat. No. 7,275,867 ("Probe assembly of infrared thermometer"); U.S. Pat. No. 7,087,903 ("Gamma camera and CT system"); U.S. Pat. No. 6,979,293 ("Blood flow reestablishment determination"); U.S. Pat. No. 6,542,767 ("Method and system for controlling heat delivery to a target"); U.S. Pat. No. 6,402,371 ("Axillary infrared thermometer and method of use").

Operation 2593 describes selecting a beneficiary of the incentive in response to a pattern of enrollment (e.g. one or more beneficiary selection modules 342 responding to a pattern of individuals 282 enrolling in a research program by selecting one or more of a material provider 281, a care provider 283, or such individuals 282 to be the beneficiaries 221 of respective incentives. In some contexts, for example, a beneficiary selection module 342 may designate a material provider 281 and care provider 283 as beneficiaries of a very large benefit in response to a pattern of enrollment indicating that such incentives result in higher rates of acceptance 1886 than similar incentives offered directly to individuals 282 who enroll. Alternatively or additionally, service provider 210 may implement a composite system of incentives in response to a pattern of enrollment that indicates that enrollment efficiency is maximized by offering a first-type incentive to the individuals and a second-type incentive to the material or service provider(s).

Operation 2594 describes selecting a recipient of a notification of the incentive in response to a received message (e.g. one or more recipient selection modules 344 transmitting an offer 1868 or other incentive notification message 158 to a material provider 281 or other provider as a prompt conditional response to a message from the provider). This can occur, for example, in a context in which another party may be the message recipient 222 in the absence of such a message from the provider(s), in which a least subject or other individual 282 may qualify for another incentive for enrollment or regimen compliance as described herein, in which such provider(s) can relay or explain the availability of such other incentive to the (potentially) qualifying individual, and in which some such individuals may otherwise be less able to understand the incentive or regimen.

Operation 2596 describes transmitting an indication of the incentive to a material provider (e.g. one or more modules for routing information to a material provider 1881 or modules for authorizing a benefit to a material provider 1851 transmitting one or more such indications 471, 472 via interaction unit 275). This can occur, for example, in a context in which routing unit 1850 performs one or more instances of operation 1150, 1260, 1380, 1460, 1570, or 1680; and in which incentive determination unit 350 generates such indication(s) in response to one or more bioactive material indications 310, indications 315 that bioactive material has been administered, or other such determinants 330 as described herein.

Operation 2598 describes transmitting an indication of the incentive to another individual (e.g. one or more modules for routing information to another party 1884 transmitting an offer 1868 or other indication 471 of a putative incentive to a qualifying patient or service provider 210 in response to one or more physical attributes 321, emotions, preferences 322, or other such attributes 320 signifying that the patient qualifies for a study or other treatment regimen). This can occur, for example, in a context in which material providers 281 or care providers 283 are notified by other operations (operation 2495 or 2596, e.g.), in which service provider 210 wants to enroll as many qualifying patients as quickly as practicable without going over a set maximum, and in which service provider 210 would not otherwise be able to track how many potential participants (patients, e.g.) currently have a pending offer of enrollment.

In light of teachings herein, numerous existing techniques may be applied for using physiological and/or other measurement data to detect an emotional state of a patient or other individual as described herein without undue experimentation. U.S. Pat. No. 7,340,393 ("Emotion recognizing method, sensibility creating method, device, and software"); U.S. Pat. No. 7,298,256 ("Crisis monitoring system"); U.S. Pat. No. 7,289,949 ("Method for routing electronic correspondence based on the level and type of emotion contained therein"); U.S. Pat. No. 7,283,962 ("Methods and systems for detecting, measuring, and monitoring stress in speech"); U.S. Pat. No. 7,282,028 ("Method and apparatus for measuring animal's condition by acquiring and analyzing its biological signals"); U.S. Pat. No. 7,249,263 ("Method and system for user authentication and identification using behavioral and emotional association consistency"); U.S. Pat. No. 7,222,075 ("Detecting emotions using voice signal analysis"); U.S. Pat. No. 7,165,033 ("Apparatus and methods for detecting emotions in the human voice"); U.S. Pat. No. 6,852,086 ("Detection of signs of attempted deception and other emotional stresses by detecting changes in weight distribution of a standing or sitting person"); U.S. Pat. No. 6,656,116 ("Apparatus and method for perceiving physical and emotional state"); U.S. Pat. No. 6,638,217 ("Apparatus and methods for detecting emotions"); U.S. Pat. No. 6,292,688 ("Method and apparatus for analyzing neurological response to emotion-inducing stimuli"); U.S. Pat. No. 5,771,261 ("Telethermometric psychological evaluation by monitoring of changes in skin perfusion induced by the autonomic nervous system"); U.S. Pat. No. 5,676,138 ("Emotional response analyzer system with multimedia display").

Figure 26:
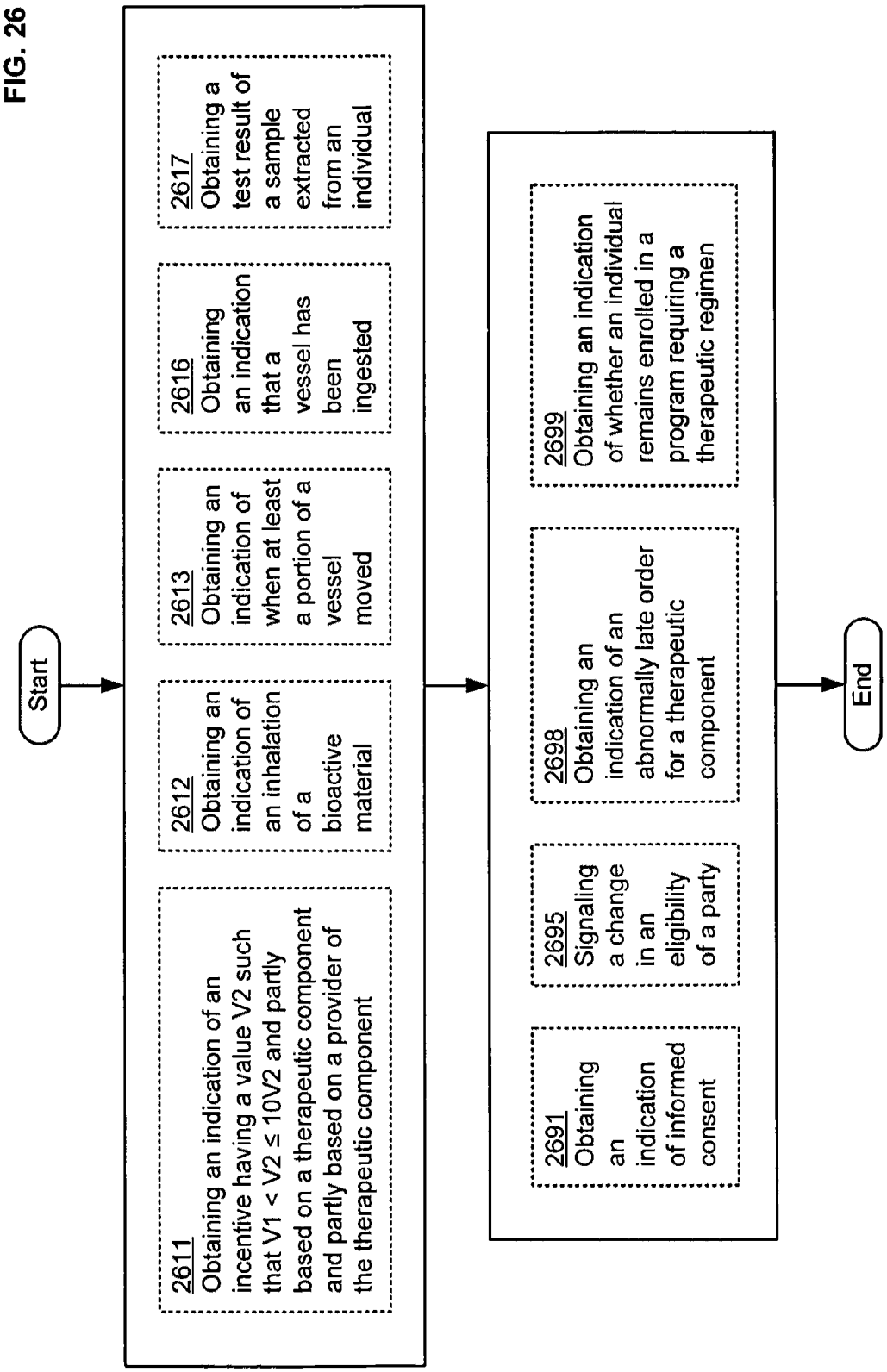
FIG. 26 likewise depicts variants of earlier-presented flows.

FIG. 26 depicts flow 2600 in relation to other flows described above in FIGS. 5-11, one or more instances of operation 1120, 1230, 1350, 1440, 1520, or 1640 may include one or more instances of operation 2611, operation 2612, operation 2613, operation 2616, or operation 2617. Also one or more instances of operation 1150, 1260, 1380, 1460, 1570, or 1680 may likewise include one or more instances of operation 2691, operation 2695, operation 2698, or operation 2699.

Operation 2611 describes obtaining an indication of an incentive having a value V2 such that V1<V2≤10×V2 and partly based on a therapeutic component and partly based on a provider of the therapeutic component, V1 being the value of the therapeutic component (e.g. implementation module 2718 or incentive selection module 346 selecting one or more qualifying incentives from incentive source data 327 or other records 1985 listing an inventory of items with prices). This can occur, for example, in a context in which medium 1992 contains current data (updated daily, e.g.) from the provider of the therapeutic component (amazon.com, e.g.) that includes a listed price assigned to V2, in which "qualifying" means at least that V1<V2≤10×V1, in which items priced below V1 or above 10×V1 are removed, in which a median price of remaining item(s) corresponds with the item to be indicated as the incentive. In some variants, "qualifying" may also depend on one or more attributes 320 of the individual 282 (such as stated preferences 322 or past incentive selections, e.g.) or other incentive type data 326 so that qualifying items (books describing the therapeutic component, promoted by the supplier, or identified by the individual, e.g.) are available only intermittently. Alternatively or additionally, a nearest-value (qualifying or other) item may be selected or offered (among qualifying selections, e.g.).

Operation 2612 describes obtaining an indication of an inhalation of a bioactive material (e.g. one or more modules for obtaining an indication of an inhalation of a bioactive material 2042 detecting an auditory or other direct indication of an actuation of an inhaler or similar dispensing device; a presence of an inhalant, metabolite, or other marker thereof in a subject's system; or other such indications of an inhalant 572 dispensed as described herein). This can occur, for example, in a context in which a provider or other beneficiary 221 is promised or receives tangible resources 119 or other incentive 140 in response to such indications via a compliance-indicative device 190 (of delivery unit 225, e.g.).

Operation 2613 describes obtaining an indication of when at least a portion of a vessel moved (e.g. one or more modules for recording when a vessel moved 2045 detecting or receiving time data 435 indicating a series of instances when a vessel 1790 containing a therapeutic material moved as an indication that the therapeutic material was or was not taken in compliance with a regimen). If the regimen required that the therapeutic material be taken with a frequency F but the time data 435 indicates that the vessel was moved less frequently than 0.9×F, for example, such a deviation may justify an inference of regimen noncompliance and/or a withholding of an incentive. Suitable implementations may include or be configured to respond to accelerometers or any of numerous other suitable implementation circuitry affixed to or otherwise supported by the vessel that can readily be implemented in light of teachings herein. Alternatively or additionally, such implementations may include or be configured to respond to circuitry for comparing a first image of a visual field with a second image of the visual field or any of numerous other suitable implementation circuitry that may be in view of the vessel or otherwise not mechanically supported by the vessel, also readily implemented in light of teachings herein. In some variants, moreover, operation 2613 may include or be configured to respond to circuitry for detecting an actuation (of a valve, cap, cover 1761, or other portion of the vessel, e.g.).

Operation 2616, describes obtaining an indication that a vessel has been ingested (e.g. one or more modules for obtaining a wireless indication that a vessel has been ingested 2043 detecting a current measurement 454 indicating that a capsule 1784 has been swallowed). This can occur, for example, in a context in which such a vessel 1790 has one or more sensors 1777 or other administration detection features 1780 configured to detect one or more of (a) a temperature about equal to that of a living body; (b) a pH about equal to that of stomach acid; (c) auditory or optical indicia of ingestion; or (d) an ambient pressure, electrical conductivity, or other device-detectable property consistent with immersion in a digestive fluid.

Operation 2617 describes obtaining a test result of a sample extracted from an individual (e.g. one or more modules for obtaining a test result of a sample extracted from an individual 2047 detecting an analyte of a therapeutic material or other regimen compliance indication in a bodily fluid, hair, or other sample extracted from individual 282). This can occur, for example, in a context in which such a module (within or in communication with a sample tester 160, e.g.) has one or more a priori thresholds 462, 465 indicative of a marker or other material component 434 of the therapeutic material in a concentration sufficient to indicate regimen compliance.

In light of teachings herein, numerous existing techniques may be applied for measuring a concentration or otherwise obtaining a result of a test of a sample extracted from a person as described herein without undue experimentation. See, e.g., U.S. Pat. No. 7,491,493 ("Method and kit for molecular identification of smallpox"); U.S. Pat. No. 7,480,032 ("Device and method for in vitro determination of analyte concentrations within body fluids"); U.S. Pat. No. 7,455,973 ("Methods and compositions for the detection of cervical disease"); U.S. Pat. No. 7,356,364 ("Device for optical monitoring of constituent in tissue or body fluid sample using wavelength modulation spectroscopy, such as for blood glucose levels"); U.S. Pat. No. 7,257,365 ("Serum biomarkers of Hepatitis B Virus infected liver and methods for detection thereof"); U.S. Pat. No. 7,063,782 ("Electrochemical detection of ischemia"); U.S. Pat. No. 6,989,891 ("Device and method for in vitro determination of analyte concentrations within body fluids"); U.S. Pat. No. 6,884,223 ("Method for detecting .alpha.-oxoaldehydes in the whole blood, blood plasma and/or serum of a patient"); U.S. Pat. No. 6,750,053 ("Apparatus and method for assaying coagulation in fluid samples"); U.S. Pat. No. 6,718,007 ("Using hair to screen for breast cancer"); U.S. Pat. No. 6,623,972 ("Automated method for detecting, quantifying and monitoring exogenous hemoglobin in whole blood, plasma and serum"); U.S. Pat. No. 6,461,830 ("Determining existence of preeclampsia in pregnancies by measuring levels of glycerophosphatidyl compounds, glycerophosphatidycholine, lysophospholipids and lysophosphatidylcholine"); U.S. Pat. No. 6,306,614 ("Measurement of analytes in whole blood"); U.S. Pat. No. 6,245,511 ("Method and apparatus for exponentially convergent therapy effectiveness monitoring using DNA microarray based viral load measurements").

Operation 2691 describes obtaining an indication of informed consent (e.g. one or more modules for obtaining an indication of informed consent 2061 generating one or more images 1984 or other records 1985 signaling that an individual 282 authorizes an incentive 140, a mode of tracking the individual's eligibility 147 for the incentive, and other terms 131 or conditions 135 that affect the incentive). This can occur, for example, in a context in which such terms and conditions are set forth in a shrink-wrap license or in which the individual provides an electronic signature, audio record 1737, or other data record 1735 manifesting a legally enforceable offer, acceptance, or partial performance.

Operation 2695 describes signaling a change in an eligibility of a party (e.g. one or more modules for signaling a change in an eligibility of a party 2065 conditioning one or more eligibilities 146, 147 upon some combination of conditions 134, 135 described herein). In some contexts, for example, a party may become eligible for an incentive in response to a request 488, data 1885 indicative of an acceptance 1886 of an offer 1868, or other manifestations of an informed consent. Alternatively or additionally, the party may become ineligible for the incentive 140 in response to an absence of an indication that a bioactive material has been administered 315 or to other conditions 134, 135 as described herein.

Operation 2698 describes obtaining an indication of an abnormally late order for a therapeutic component (e.g. one or more modules for obtaining an indication of a medical expense signaling an apparent noncompliance 2066 detecting that a material provider 281 or other individual has not been ordering a requisite quantity of a therapeutic component fast enough to permit compliance with a regimen). This can occur, for example, in a context in which such orders are nominally sufficient to provide P treatments for Q individuals for a given period of weeks but in which supplies for fewer than P×Q/2 treatments have been ordered before or during that period of weeks, warranting an inference that at least one such individual has apparently not received one or more requisite treatments of a prescribed regimen within one or more acceptable time intervals.

Operation 2699 describes obtaining an indication of whether an individual remains enrolled in a program requiring a therapeutic regimen (e.g. one or more modules for verifying that a therapeutic regimen remains in effect for an individual 2089 determining whether a provider has confirmed that an individual 282 remains enrolled in a program after having sent a request for such confirmation to the provider). This can occur, for example, in a context in which the provider has been given ample opportunity and incentive for replying (by following a "confirm enrollment" link in an electronic message identifying the program and the individual, for example, in a context in which affirmative and accurate responses are rewarded with an enhanced eligibility 146, e.g.). Alternatively or additionally, in some variants, one or more incentives 140 to the individual(s) may depend upon whether their continued enrollment is confirmed.

Substantially any of the above-described systems may further include one or more cameras 1732 configured to obtain video data or other visual records 1736. Such records may include an objective indication of a bioactive or other therapeutic material 685 administered to a portion of an individual 282, such as a video clip of a care provider 283 administering a topical treatment. This can occur, for example, in a context in which the therapeutic component comprises a targeted drug or other topical bioactive material that is not well suited for the individual to use as a systemic treatment, in which such data is consistently available for review (stored in an archive, e.g.) as an objective indication that the material has been administered to a specific portion of the individual, in which such records are not generally reviewed, and in which an underwriter or other service provider 210 can authorize a type of benefit 120, coverage, or other service 148 to a class of individuals conditionally in response to such records being generally available. Such classes may be defined by one or more physical attributes 321, preferences 322, or other patient attributes 320, for example. Such records may also include an indication of a health status apparently resulting from a bioactive material administered to the individual, such as a biometric measurement (indicating an increase in temperature, e.g.) or a comparative photo (indicating a skin color change or other expected improvement after a regimen that includes topical or systemic steroid treatments, e.g.).

Data records 1735 may likewise include a video clip of a patient's face during such administration, biometric data or other input 1981 from a patient or provider, or other such indications of physical attributes of a treatment recipient. In some variants, recording system 1730 may be configured to obtain a voice recording of individual 282 or other such auditory records 1737 indicating some or all of (a) a therapeutic component administered to a portion of the individual; (b) a unique vocal signature or other identifying attribute of the individual; (c) a report of nausea or other symptoms; (d) a pulse or other systemic attribute of the individual; or (e) other physical attributes pertaining to the individual. Alternatively or additionally, such recording systems may operate in conjunction with a sensor 1734 configured to generate an indication of a vessel 1790 or other local device administering a medication or other therapeutic component.

Substantially any of the above-described systems may (optionally) include printable labels or other display media 154 as well as storage media 152 other components of user interfaces 1740. In some contexts, such media 150 may bear one or more indications 474 of the incentive partly based on a provider of a therapeutic component (a drugstore identifier or clinic name, e.g.) and partly based on the therapeutic component (as a lookup function of a drug or a percentage of its price, e.g.). Alternatively or additionally, such indications may depend upon data 2072 received from a remote source (incentive determination unit 350, e.g.) via network 240. Interaction unit 275 may include a display medium 154, for example, configured to transmit to a material provider 281 the indication of the incentive partly based on the therapeutic component and partly based on the provider of the therapeutic component. Alternatively or additionally, a bottle 1783 or other vessel 1790 containing a therapeutic component may bear such display media 154 (as a printed label, e.g.).

Substantially any of the above-described systems may include a vessel 1790 (vending machine or other dispensing device, e.g.) containing a bioactive material in one or more bottles 1783, tubes, syringes, or other such forms suitable for handling. Such vessels may likewise include a retractable cover 1761 or other actuator 1770 facilitating administration or a response unit or static media 450 containing product numbers or other data 430 indicative of material components 434. Such material components may (optionally) include one or more antihypertensives, eyedrops or other liquids, nutraceuticals, statins, or other dosed bioactive materials or other therapeutic materials (placebos, e.g.). In some variants, for example, the bioactive material includes a coating or other material effective for delaying the release of another (component) bioactive material in which the vessel is a capsule 1784 within a bottle 1783 having an administration detection feature 1780 configured so that an administration is detectable by a radio frequency identification (RFID) unit or other administration detection module 1748 (via visual detection within a vicinity 1750 of vessel 1790, a wireless coupling 1755, a mechanical linkage, or other such administration detection features 1780 of vessel 1790 or primary module 1710 e.g.).

Some instances of vessel 1790 or similar devices may include a targeted drug or prescribed inoculant as a therapeutic component administered by a material provider 281 (a pharmacist or medical facility, e.g.). Vessel 1790 may likewise include one or more sensors 1777, administration detection logic 2040, or other administration detection features 1780 configured to detect and transmit (via transmitter 1776 to a handheld 1741 or other user interface 1740, e.g.) data 2071 indicating an administration of a bioactive material. Vessel 1790 may include one or more actuators 1770, recording systems 1730, or other response units containing digital data 832, 430 or other device-detectable manifestations of one or more bioactive material categories 484 (a narcotic, a controlled substance, an amino acid, an active ingredient, a generic product, a coating, an antibiotic, or a precursor, e.g.), dispensation time data 435, dosages 437, or other such indications 960 of a material component 434. This can occur, for example, in a context in which vessel 1790 is configured to signal (via transmitter 1776 to a wearable 1742 or other user interface 1740, e.g.) an indication of a marking component 1779 identifying or otherwise indicating the therapeutic component(s) in a vessel. Even in a context without any transmitter 1776 or other coupling 1755, moreover, an administration detection feature 1780 may manifest a device-detectable event or condition (a dispensation or material component 434, e.g.), such as by triggering a color change or other such physical phenomena detectable (visually or audibly within a vicinity 1750 of vessel 1790, for example) via a camera 1732 or other sensor 1733). Alternatively or additionally, a primary module 1710 or other dispenser having an incentive acceptance module 1720 a user interface 1740 may be configured to contain vessels 1790 or to administer a bioactive material directly to (into or onto, e.g.) a therapy recipient.

In some variants, such a device may contain or otherwise include an ingestible tablet or other capsule 1784 comprising the therapeutic component and having a label or other external marking indicating an ingestible or other therapeutic component available to the individual (a nutraceutical or over-the-counter drug, e.g.). Alternatively or additionally, the vessel 1790 may include a dye or other marking component 1779 or packaging identifying a product, a category of an ingredient material 685, a material provider 281, or other such indications of a systemic or other therapeutic component. A material-containing vessel may likewise include a syringe, inhaler, pump, or other dose-metering structure having an administration detection feature 1780 configured to detect an indication of the therapeutic component being (or to be or having been) administered to a portion of an individual. In some variants in which the vessel includes a dispenser 170 or other administration device (a bottle or tube configured to administer a steroid or other bioactive material into or onto a patient, e.g.), one or more sensors 1734, 1777 in, on, or in a vicinity 1750 of the vessel 1790 may be configured to obtain a temperature or other biometric measurement, image, or other physical attribute of (some or all of) the individual. Such variants may likewise have an administration detection module 1748 or other device configured to signal a presence of a marking component 1779 (a fluorescent dye or other human-detectable feature mixed with or applied to the therapeutic component before administration, e.g.) as an indication of the therapeutic component.

In some contexts a research protocol or other treatment regimen comprises several therapeutic components of which some are material components (relating to a timing, dosage, manner, tracking, expected or actual effect, or other aspect of an ingestion or other administration of a bioactive material or placebo, e.g.). Such regimens may be facilitated by various combinations of (a) therapeutic material to be administered into or onto a portion of an individual 282; (b) a primary module 1710 administering or facilitating an administration of a topical or other therapeutic component to an individual 282; (c) one or more media 150, 450 transmitting, displaying, storing, or otherwise bearing data 430 directly or indirectly indicating that the material has been administered; (d) an event/condition detection unit 2050 counting, qualifying, or otherwise tracking such indications in various contexts described herein; (e) a compliance-indicative device 190 or other monitoring unit 1990 indicating an aggregation of such indications manifesting compliance with a term 131 or condition 135 of a regimen or eligibility 147; or (f) an incentive determination unit 350 configured remotely via a control unit 205 defining a putative incentive type, source, beneficiary 221, and prospective or other notification mode as described herein. Substantially any such combination may (optionally) be implemented either within interaction unit 275 or via a routing unit 1850 within network 240. This can occur, for example, in a context in which interaction unit 275 may include a monitoring unit 1990, a vending or other dispensing device (implementing processing unit 610, e.g.), or a handheld or other interface 380, 518, 918 at a point of service or sale.

In some variants, as articulated above, operation 1350 can be performed by software-controlled or special-purpose circuitry for obtaining an indication of an incentive to an individual partly based on an indication of a health status apparently resulting from a therapeutic component administered to a portion of the individual and partly based on another physical attribute of the individual. In some contexts, such circuitry can include one or more media bearing data indicative of the therapeutic component including a bioactive material configured for topical application.

Alternatively or additionally, operation 1350 may include some or all of obtaining an indication of an inhalation of another bioactive material (by operation 2612, e.g.); conditioning the incentive upon compliance with a regimen that includes an antiviral component (by operation 2314, e.g.); deriving the incentive partly based on a specific identifier of the therapeutic component and partly based on an indication of a dispensing device administering the therapeutic component to the portion of the individual (by operation 2212, e.g.); obtaining a gender or age of the individual (as another physical attribute of the individual or as a determinant affecting the incentive or the indication of the incentive, e.g., such as by operation 2515); conditioning the incentive upon an actuation in a vessel (by operation 2414, e.g.); conditioning the incentive to the individual upon compliance with a regimen that includes a statin-containing material component (by operation 2111, e.g.); detecting whether data from one or more sensors indicate an actuation of a portion of a dispensing device (by operation 2311, e.g.); or detecting a health status apparently resulting from a dispensing device administering a bioactive material to the individual (a symptom alleviation or side effect of an administered steroid, e.g., such as by operation 2411).

Alternatively or additionally, operation 1350 may include some or all of obtaining a signal from a compliance-sensitive dispensing device as a dispensing device configured to administer a bioactive material to the individual (as the therapeutic component administered to the portion of the individual or as another physical attribute of the individual, e.g., such as by operation 2214); obtaining a pathology of the individual (as another physical attribute of the individual and as a determinant affecting the incentive or the indication of the incentive, e.g., such as by operation 2517); receiving an indication from a test of a bodily fluid of the individual (as another physical attribute of the individual or as an indication that a dispensing device administered a material to the individual, e.g.) after a dispensing device administers a bioactive material to the individual (by operation 2215, e.g.); obtaining an indication that a vessel has been ingested (by operation 2616, e.g.); or obtaining an indication of when a vessel moved (by operation 2613, e.g.).

Alternatively or additionally, operation 1350 may include some or all of obtaining a test result of a sample extracted from the individual (as another physical attribute of the individual, e.g., such as by operation 2617); receiving an indication of the incentive from a site that has apparently received a category of a bioactive material and an indication of a dispensing device administering the bioactive material to the individual (by operation 2219, e.g.); obtaining a health status of the individual (as another physical attribute of the individual, e.g., such as by operation 2512); determining the indication of the incentive in response to an indication of a product attribute (by operation 2413, e.g.); obtaining a biometric measurement of the individual (as another physical attribute of the individual, e.g., such as by operation 2511); determining the incentive to the individual to have a value partly based on a value of a therapeutic component and partly based on a physical attribute of the individual (by operation 2119, e.g.); detecting a dispensing device administering a bioactive material to the individual via injection (by operation 2418, e.g.); conditioning the incentive upon compliance with a regimen that includes a nitric oxide donor component (by operation 2313, e.g.); or conditioning the incentive to the individual upon compliance with a regimen that includes an antihypertensive material component (by operation 2116, e.g.) or that includes at least one respiratory or physical therapy session (by operation 2117, e.g.).

In some contexts, such systems may include circuitry for obtaining an indication of an incentive to an individual partly based on an indication of a health status apparently resulting from a therapeutic component administered to a portion of the individual and partly based on another physical attribute of the individual. Such circuitry or other modules may include or otherwise access media storing or otherwise bearing data indicative of the therapeutic component, for example, such as a bioactive material dosed or otherwise configured for topical application.

In some variants, such systems may likewise include one or more instances of (a) physical media bearing time data indicative of when one or more dispensations of the therapeutic component have occurred; (b) administration detection software or other logic configured to detect one or more optical indications of a movement of a vessel containing the therapeutic component; (c) a camera configured to obtain a visual record as the indication of the health status apparently resulting from the therapeutic component administered to the portion of the individual; (d) a sensor configured to obtain a biometric measurement as the indication of the health status apparently resulting from the therapeutic component administered to the portion of the individual; or (e) a vessel containing the therapeutic component or otherwise configured to facilitate a dispensation of the therapeutic component as described above. In some contexts, for example, such a vessel may include one or more instances of administration detection logic configured to detect one or more auditory indications of a movement of the vessel, a bottle containing the therapeutic component and having an administration detection feature configured to detect an indication of the therapeutic component being administered, a tube containing the therapeutic component and having an administration detection feature configured to detect an indication of the therapeutic component being administered, the vessel containing an inoculant as the therapeutic component, a response unit containing one or more material indications of the therapeutic component, the vessel containing the therapeutic component and having an actuator, or the vessel containing the therapeutic component and having a wireless communication coupling device.

Alternatively or additionally, such systems may further comprise one or more instances of a device configured to detect (by imaging or auditory analysis, e.g.) the indication of the therapeutic component being administered to the portion of the individual, a device including an administration detection feature and configured to administer the therapeutic component, a device including administration detection logic and containing the therapeutic component, a dispenser including an administration detection feature and configured to administer the therapeutic component to the portion of the individual, or a dispenser including administration detection logic and configured to administer the therapeutic component, in which the therapeutic component includes a bioactive material.

In some variants, as articulated above, operation 1430 can be performed by software-controlled or special-purpose circuitry for obtaining first data indicating a therapeutic component having a first value V1. In some contexts, such circuitry can include one or more media bearing data indicative of the first value V1. Operation 1440 may likewise be performed by software-controlled or special-purpose circuitry for obtaining an indication of an incentive having a second value V2 and partly based on the therapeutic component and partly based on a provider of the therapeutic component. In some contexts, such circuitry can include one or more media bearing data indicative of an informed consent of the individual (or other non-physical attribute of the individual affecting the incentive or the indication of the incentive, e.g.).

Alternatively or additionally, operation 1430/1340 may include one or more instances of receiving an indication of the incentive from a site that has apparently received a category of a bioactive material and an indication of a dispensing device administering the bioactive material to an individual as the therapeutic component (by operation 2219, e.g.); deriving the incentive partly based on a specific identifier of a bioactive material, partly based on a category of the bioactive material, and partly based on an indication of a dispensing device administering the bioactive material to an individual as the therapeutic component (by operation 2212, e.g.); or detecting a dispensing device administering a bioactive material to an individual via injection as the therapeutic component (by operation 2418, e.g.).

Alternatively or additionally, operation 1430/1340 may include some or all of conditioning the incentive upon an actuation in a vessel (by operation 2414, e.g.); receiving an indication from a test of a bodily fluid of an individual after a dispensing device administers a bioactive material to the individual as the therapeutic component (by operation 2215, e.g.); obtaining an indication of when a vessel moved (by operation 2613, e.g.); or determining the incentive so that V2>V1 (by operation 2119 or 2212, e.g.).

Alternatively or additionally, operation 1440 may include some or all of obtaining a health status of an individual (as a determinant of the incentive or the indication of the incentive, e.g., such as by operation 2512); determining the incentive to have the (second) value V2 partly based on the (first) value V1 of a therapeutic component and partly based on a physical attribute of a putative recipient of the therapeutic component (by operation 2119, e.g.); obtaining an indication that a vessel has been ingested (by operation 2616, e.g.); or determining the incentive as a linear function of a value of a therapeutic component (by operation 2316, e.g.).

Alternatively or additionally, operation 1430/1340 may include some or all of obtaining an age or a biometric measurement of an individual (as a determinant of the incentive or the indication of the incentive, e.g., such as by operation 2511 or 2515); detecting whether data from one or more sensors indicate an actuation of a portion of a dispensing device (by operation 2311, e.g.); conditioning the incentive upon compliance with a regimen that includes an antihypertensive material component as the therapeutic component (by operation 2116, e.g.); conditioning the incentive upon compliance with a regimen that includes a nitric oxide donor component as the therapeutic component (by operation 2313, e.g.); or conditioning the incentive upon compliance with a regimen that includes an antiviral component of the therapeutic component (by operation 2314, e.g.).

Alternatively or additionally, operation 1440 may include some or all of obtaining a pathology of an individual (as a determinant of the incentive or the indication of the incentive, e.g., such as by operation 2517, e.g.); obtaining a signal from a compliance-sensitive dispensing device as a dispensing device configured to administer a bioactive material to an individual as the therapeutic component (by operation 2214, e.g.); obtaining a physical attribute of an individual (as a determinant affecting the incentive or the indication of the incentive, e.g., such as by operation 2519); determining the incentive so that V2>V1 (by operation 2119 or 2212, e.g.); obtaining an indication of an inhalation of a bioactive material (by operation 2612, e.g.); obtaining a test result of a sample extracted from an individual (as a determinant affecting the incentive or the indication of the incentive, e.g., such as by operation 2617); or detecting a health status apparently resulting from a dispensing device administering a bioactive material to an individual as the therapeutic component (by operation 2411, e.g.).

In some variants, circuitry for obtaining first data indicating a therapeutic component having a first value V1 may include a medium bearing data indicative of the first value V1. Alternatively or additionally, circuitry for obtaining an indication of an incentive having a second value V2 and partly based on the therapeutic component and partly based on a provider of the therapeutic component may include one or more instances of media bearing data indicative of an informed consent of the individual (or other non-physical attribute of the individual affecting the incentive or the indication of the incentive, e.g.).

In some variants, as articulated above, operation 1520 can be performed by software-controlled or special-purpose circuitry for obtaining an indication of an incentive to a provider of a therapeutic component at least partly based on an objective indication that the therapeutic component has been administered to a portion of an individual. In some contexts, such circuitry can include one or more media bearing data indicative of the therapeutic component including a bioactive material configured for topical application.

Alternatively or additionally, operation 1520 may include some or all of receiving an indication of the incentive from a site that has apparently received a category of a bioactive material and an indication of a dispensing device administering the bioactive material to the individual (by operation 2219, e.g.); detecting whether data from one or more sensors indicate an actuation of a portion of a dispensing device or obtaining an indication of when a vessel moved (as the objective indication that the therapeutic component has been administered to the portion of the individual, e.g., such as by operation 2311 or 2613); determining the incentive to the provider of the therapeutic component to have a value partly based on a value of the therapeutic component and partly based on a physical attribute of the individual (by operation 2119, e.g.); conditioning the incentive to the provider of the therapeutic component upon compliance with a regimen that includes an antihypertensive material component (by operation 2116, e.g.); conditioning another incentive to the provider of the therapeutic component upon compliance with a regimen that includes a nitric oxide donor component (by operation 2313, e.g.); obtaining a signal from a compliance-sensitive dispensing device as a dispensing device configured to administer a bioactive material to the individual (by operation 2214, e.g.); or conditioning an incentive to the individual upon an actuation in a vessel (by operation 2414, e.g.).

Alternatively or additionally, operation 1520 may include one or more instances of obtaining an indication that a vessel has been ingested (as the objective indication that the therapeutic component has been administered to the portion of the individual, e.g., such as by operation 2616); obtaining a physical attribute of the individual (a pathology or the objective indication that the therapeutic component has been administered to the portion of the individual, e.g., such as by operation 2519); determining the incentive to the provider of the therapeutic component as a linear function of a value of the therapeutic component (by operation 2316, e.g.); deriving the incentive to the provider of the therapeutic component partly based on a specific identifier of the therapeutic component, partly based on a category of the therapeutic component, and partly based on an indication of a dispensing device administering the therapeutic component to the individual (by operation 2212, e.g.); conditioning the incentive to the provider of the therapeutic component upon compliance with a regimen that includes at least one physical therapy session (by operation 2117, e.g.); or conditioning another incentive upon compliance with a regimen that includes an antiviral component (by operation 2314, e.g.).

In light of teachings herein, numerous existing techniques may be applied for detecting that an object has apparently been ingested as described herein without undue experimentation. See, e.g., U.S. Pat. No. 7,504,954 ("Radio frequency identification pharmaceutical tracking system and method"); U.S. Pat. No. 7,437,195 ("Regulation of eating habits"); U.S. Pat. No. 7,427,266 ("Method and apparatus for verification of ingestion"); U.S. Pat. No. 7,414,534 ("Method and apparatus for monitoring ingestion of medications using an implantable medical device"); U.S. Pat. No. 7,382,263 ("Oral drug compliance monitoring using radio frequency identification tags"); U.S. Pat. No. 7,141,016 ("Systems and methods for monitoring gastrointestinal system"); U.S. Pat. No. 7,118,531 ("Ingestible medical payload carrying capsule with wireless communication"); U.S. Pat. No. 7,062,312 ("Combination and method including a visual marker for determining compliance with a medication regimen"); U.S. Pat. No. 6,663,846 ("Devices and methods for monitoring drug therapy compliance"); U.S. Pat. No. 6,136,801 ("Therapeutic agent with quantitative consumption marker").

Alternatively or additionally, operation 1520 may include some or all of obtaining an indication of an inhalation of a bioactive material (by operation 2612, e.g.); obtaining a test result of a sample extracted from the individual (as the objective indication that the therapeutic component has been administered to the portion of the individual, e.g., such as by operation 2617); obtaining a pathology of the individual (by operation 2517, e.g.); obtaining a gender or age of the individual (by operation 2515, e.g.); receiving an indication from a test of a bodily fluid of the individual or otherwise obtaining a biometric measurement of the individual (as the objective indication that the therapeutic component has been administered to the portion of the individual, e.g., such as by operation 2511 or 2215); detecting a health status apparently resulting from a dispensing device administering a bioactive material to the individual or otherwise obtaining a health status of the individual (by operation 2411 or 2512, e.g.); or detecting a dispensing device administering a bioactive material to the individual via injection (as the objective indication that the therapeutic component has been administered to the portion of the individual, e.g., such as by operation 2418).

In some variants, as articulated above, operation 1120 can be performed by software-controlled or special-purpose circuitry for obtaining a selection of an incentive to an individual partly based on an indication of a therapeutic component administered to a portion of the individual and partly based on a physical attribute of the individual.

Alternatively or additionally, operation 1230 may include some or all of obtaining a gender as a physical attribute of the individual (as a determinant affecting an eligibility, e.g., such as by operation 2515); conditioning the incentive upon compliance with a regimen that includes a statin-containing material component or an antihypertensive material component as another therapeutic component administered to the individual (by operation 2111 or 2116, e.g.); determining the indication of the incentive in response to an indication of a product attribute (using dosage, package type, cost, etc.) as a determinant for generating the indication of the therapeutic component (by operation 2413, e.g.); or deriving the incentive partly based on a specific identifier of a bioactive material (a prescription number or product name partly or fully identifying the therapeutic component, e.g.), partly based on a category of the bioactive material ("prescription drug" or "antibiotic," e.g.), and partly based on an indication of a dispensing device administering the bioactive material to the individual (by operation 2212, e.g.).

Alternatively or additionally, operation 1230 may include some or all of obtaining a biometric measurement as a physical attribute of the individual (by operation 2511, e.g.); detecting a dispensing device administering a bioactive material to the individual via injection (by operation 2418, e.g.); obtaining an indication of an inhalation of another bioactive material as the indication of the therapeutic component administered to the portion of the individual or as another indication of a therapeutic component administered to the individual (by operation 2612, e.g.); or obtaining a test result of a sample extracted from an individual as a physical attribute of the individual (by operation 2617, e.g.); obtaining an indication of when a vessel moved (by operation 2613, e.g.).

Alternatively or additionally, operation 1230 may include one or more instances of obtaining a signal from a compliance-sensitive dispensing device as a dispensing device configured to administer a bioactive material (of the therapeutic component, e.g.) to the individual (by operation 2214, e.g.); receiving an indication from a test of a bodily fluid of the individual after a dispensing device administers another bioactive material to the individual (identifying or indicating a presence or concentration of the other bioactive material or an analyte or other marker thereof, e.g., such as by operation 2215); conditioning the incentive upon an actuation in a vessel (by operation 2414, e.g.); determining the incentive as a linear function of a value of the therapeutic component administered to the portion of the individual (by operation 2316, e.g.); conditioning the incentive upon compliance with a regimen that includes an antiviral component or a nitric oxide donor component of the therapeutic component administered to the portion of the individual (by operation 2313 or 2314, e.g.); detecting whether data from one or more sensors indicate an actuation of a portion of a dispensing device (by operation 2311, e.g.); receiving an indication of the incentive from a site that has apparently received a category of a bioactive material ("topical" or "systemic" or "steroid," e.g.) and an indication of a dispensing device administering the bioactive material to the individual (by operation 2219, e.g.); or detecting a health status ("improved" or "inflamed," e.g.) apparently resulting from a dispensing device administering a bioactive material to the individual (by operation 2411, e.g.).

In some variants, as articulated above, operation 1120 can be performed by software-controlled or special-purpose circuitry for obtaining an indication of an incentive to an individual partly based on a physical attribute of the individual and partly based on an indication of a therapeutic component available to the individual. In some contexts, such circuitry can include one or more media bearing data indicative of the therapeutic component including a bioactive material configured for topical application.

Alternatively or additionally, operation 1120 may include some or all of conditioning the incentive upon compliance with a regimen that includes a statin-containing material component as the therapeutic component available to the individual (by operation 2111, e.g.); conditioning the incentive upon an actuation in a vessel (comprising the therapeutic component, e.g., such as by operation 2414); obtaining a biometric measurement of or a pathology of the individual (as a physical attribute of the individual, e.g., such as by operation 2511 or 2517); or obtaining an indication that a vessel has been ingested (as the therapeutic component, e.g., such as by operation 2616).

Alternatively or additionally, operation 1120 may include some or all of conditioning the incentive upon compliance with a regimen that includes an antihypertensive material component as the therapeutic component available to the individual (by operation 2116, e.g.); obtaining a test result of a sample extracted from the individual (as a physical attribute of the individual, e.g., such as by operation 2617); or determining the incentive to have a value partly based on a value of the therapeutic component and partly based on the physical attribute of the individual (by operation 2119, e.g.).

Alternatively or additionally, operation 1120 may include some or all of conditioning the incentive upon compliance with a regimen that includes at least one respiratory or physical therapy session as the therapeutic component available to the individual (by operation 2117, e.g.); or receiving an indication from a test of a bodily fluid of the individual after a dispensing device administers a bioactive material to the individual (as the therapeutic component, e.g., such as by operation 2215).

Alternatively or additionally, operation 1120 may include some or all of deriving the incentive partly based on a specific identifier of a bioactive material, partly based on a category of the bioactive material, and partly based on an indication of a dispensing device administering the bioactive material to the individual (by operation 2212, e.g.); obtaining a signal from a compliance-sensitive dispensing device as a dispensing device configured to administer a bioactive material to the individual (by operation 2214, e.g.); obtaining a health status of the individual (as a physical attribute of the individual, e.g., such as by operation 2512); obtaining a gender or age of the individual (as another physical attribute of the individual or as a determinant of the incentive, e.g., such as by operation 2515); or detecting a dispensing device administering a bioactive material to the individual via injection (as the therapeutic component, e.g., such as by operation 2418).

In some variants, as articulated above, operation 1640 can be performed by software-controlled or special-purpose circuitry for obtaining an indication of an incentive partly based on a category of a bioactive material and partly based on an indication of a dispensing device administering the bioactive material to an individual. In some contexts, such circuitry can include one or more media bearing data indicative of the bioactive material including an antihypertensive-material component (as the category of the bioactive material, e.g.) or data indicative of a preference of the individual (or other non-physical attribute of the individual affecting the incentive or the indication of the incentive, e.g.)

Alternatively or additionally, operation 1640 may include some or all of conditioning the incentive upon compliance with a regimen that includes a statin-containing material component or an antiviral component (as the category of the bioactive material, e.g., such as by operation 2111 or 2314); conditioning the incentive upon compliance with a regimen that includes a respiratory or physical therapy session and an administration of the bioactive material (by operation 2117, e.g.); conditioning the incentive upon compliance with a regimen that includes a nitric oxide donor component (as another bioactive material component, e.g., such as by operation 2313); conditioning the incentive upon an actuation in a vessel (containing one or more bioactive material components, e.g., such as by operation 2414); obtaining a pathology or other physical attribute of the individual (as a determinant affecting the incentive, e.g., such as by operation 2517 or 2519); detecting whether data from one or more sensors indicate an actuation of a portion of the dispensing device (as the indication of the dispensing device administering one or more bioactive materials to the individual, e.g., such as by operation 2311); receiving an indication from a test of a bodily fluid of the individual after the dispensing device administers the bioactive material to the individual (for tracking compliance with or results of a regimen, e.g., such as by operation 2215); or deriving the incentive partly based on a specific identifier of the bioactive material, partly based on a category of the bioactive material, and partly based on the indication of the dispensing device administering the bioactive material to the individual (by operation 2212, e.g.).

Alternatively or additionally, operation 1640 may include some or all of determining the indication of the incentive in response to an indication of a product attribute (as the category of the bioactive material, e.g., such as by operation 2413); obtaining an indication of an inhalation of the bioactive material (with "an inhalant" or a specific material configured to be inhaled as the category of the bioactive material, e.g., such as by operation 2612); receiving an indication of the incentive from a site that has apparently received a category of a bioactive material and an indication of a dispensing device administering the bioactive material to the individual (by operation 2219, e.g.); obtaining an indication of when a vessel moved (by operation 2613, e.g.); detecting a health status apparently resulting from the dispensing device (concurrently or otherwise) administering the bioactive material to the individual (by operation 2411, e.g.); determining the incentive to have a value partly based on a value of the bioactive material and partly based on a physical attribute of the individual (by operation 2119, e.g.); obtaining a biometric measurement of the individual (as a determinant of the incentive or the indication of the incentive, e.g., such as by operation 2511); or obtaining an age of the individual (or other physical or other attribute of the individual affecting the incentive or the indication of the incentive, e.g., such as by operation 2515).

Alternatively or additionally, operation 1640 may include some or all of obtaining an indication that a vessel has been ingested (by operation 2616, e.g.); detecting the dispensing device administering the bioactive material to the individual via injection (by operation 2418, e.g.); determining the incentive as a linear function of a value of the bioactive material (or of another therapeutic component described herein, e.g., such as by operation 2316); obtaining a health status of the individual (by operation 2512, e.g.); obtaining a signal from a compliance-sensitive dispensing device as the dispensing device (by operation 2214, e.g.); or obtaining a test result of a sample extracted from the individual (by operation 2617, e.g.).

In some variants, systems as describe above may include one or more instances of (a) circuitry for obtaining an indication of an incentive to a provider of a therapeutic component at least partly based on an objective indication that the therapeutic component has been administered to a portion of an individual; (b) circuitry for obtaining an indication of an incentive partly based on a category of a bioactive material and partly based on an indication of a dispensing device administering the bioactive material to an individual; (c) circuitry for obtaining an indication of an incentive to an individual partly based on a physical attribute of the individual and partly based on an indication of a therapeutic component available to the individual; (d) circuitry for transmitting the indication of the incentive to a putative provider of the therapeutic component; (e) circuitry for determining one or more components of the incentive in response to one or more prior responses from a recipient, such as by incrementing a quantitative attribute of the incentive; (f) circuitry for determining one or more components of the incentive in response to one or more prior responses from a recipient, such as by changing a type of the component of the incentive; (g) other such modules as described above, or combinations thereof. In some contexts, one or more such modules may include or otherwise be configured to access (via a remote network 240 or a local source, e.g.) one or more media 150, 450 bearing data indicative of the bioactive material including an antihypertensive-material component (as a category of the bioactive material, e.g.), media 150, 450 bearing data indicative of a preference of the individual (or other non-physical attribute of the individual affecting the incentive or the indication of the incentive, e.g.); media 150, 450 bearing data indicative of the therapeutic component including a bioactive material configured for topical application, media 150, 450 bearing data indicative of the therapeutic component including a bioactive material configured for topical application, or other media 150, 450 as described herein.

In some contexts, such systems may further include one or more instances of (1) a bottle containing the therapeutic component, the bottle having a retail price as the first value V1; (2) a capsule containing a targeted drug as the therapeutic component, the provider of the therapeutic component comprising a pharmacist; (3) a device configured to detect the therapeutic component being administered to a portion of an individual or to signal an indication of a marking component as the first data indicating the therapeutic component; (4) a device including administration detection logic or other administration detection features; (5) a device configured to administer the therapeutic component, such as a dispenser configured to administer the therapeutic component to a portion of an individual; (6) a dispenser including administration detection logic and configured to administer the therapeutic component, in which the therapeutic component includes a bioactive material; (7) a display configured to transmit to the provider of the therapeutic component the indication of the incentive partly based on the therapeutic component and partly based on the provider of the therapeutic component; (8) a printed medium bearing the indication of the incentive partly based on the therapeutic component and partly based on the provider of the therapeutic component; or (9) a vessel containing an inoculant or inhalant as the therapeutic component. In some contexts, moreover, such vessels may (a) have an actuator, (b) contain the therapeutic component and bear the indication of the incentive partly based on the therapeutic component and partly based on the provider of the therapeutic component; (c) include an administration detection feature configured to detect an indication of the therapeutic component administered to a portion of the individual; (d) contain the therapeutic component; (d) include a response unit containing one or more material indications of the therapeutic component, (e) include an administration device configured to administer a bioactive material, as the therapeutic component, onto a portion of an individual; (f) include an administration device configured to administer a bioactive material to an individual as the therapeutic component; or (g) a combination of (two or more of) the above.

In some variants, systems described herein may include or otherwise interact with a compliance-indicative device 190 that is (a) configured to administer a bioactive material to the individual as the therapeutic component; (b) configured to detect the indication of the therapeutic component being administered to the portion of the individual; (c) configured to detect the therapeutic component being administered to a portion of the individual; (d) configured to generate and store the objective indication that the therapeutic component has been administered to the portion of the individual; (e) configured to administer the therapeutic component; (f) configured to administer a therapeutic component, the therapeutic component including a bioactive material; or (g) two or more of these. For example, the device may be configured to signal a presence of a marking component (a dye that was mixed with a bioactive material before administration, e.g.) as an indication of a therapeutic component administered to a portion of the individual.

In some systems described herein, one or more compliance-indicative devices 190 may work in tandem with microphones or other sensors 1733, 1734 capable of detecting an apparent administration (to a portion of an individual, e.g.) of a therapeutic component (via recognizable attributes of a visual record 1736, an audio record 1737, or other data record 1735 from a sensor 1734 as an objective indication, e.g.) as described above. This can occur, for example, in a context in which the vessel or other dispensing device is not integrally constructed with administration detection features or in which such features are passive (labels, colorants, or other optically detectable features, e.g.). Some variants may include one or more recording systems (a) configured to obtain a first auditory record as the indication of the therapeutic component administered to the portion of the individual and a second auditory record as an indication of the physical attribute of the individual; (b) configured to obtain an auditory record as the objective indication that the therapeutic component has been administered to the portion of the individual; (c) configured to obtain an auditory record (a report of nausea from the individual or perhaps just a sample of the individual's voice, e.g.) representative of the physical attribute (a nauseated or hoarse condition, e.g.) of the individual; or (d) more than one of the above. Alternatively or additionally, such systems may include one or more cameras 1732 (a) configured to obtain a visual record as the indication of the dispensing device administering a bioactive material to the individual; (b) configured to obtain a visual record of a portion of the individual as a physical attribute of the individual; (c) configured to obtain a visual record as an objective indication that the therapeutic component has been administered (to the individual for later use or to a portion of an individual, e.g.); or (d) more than one of the above. Alternatively or additionally, such systems may likewise include one or more sensors 1734 (a) configured to obtain a biometric measurement as the objective indication that the therapeutic component has been administered to the portion of the individual; (b) configured to obtain a biometric measurement as a physical attribute of the individual; (c) configured to obtain a systemic measurement of the individual as a physical attribute of the individual; or (d) more than one of the above.

In some variants, systems described herein may include or otherwise interact with one or more dispensing devices (syringes, catheters, or other vessels 1790, e.g.) that may include one or more instances of administration detection logic (of a primary module 1710 or vessel 1790, e.g.) and may also be (1) configured to administer the therapeutic component to a portion of the individual; (2) configured to administer the therapeutic component, in which the therapeutic component includes a bioactive material; (3) configured to administer the therapeutic component, in which the therapeutic component includes a bioactive material; (4) configured to administer the therapeutic component, in which the therapeutic component includes a systemic antibiotic; (5) configured to administer the therapeutic component to the portion of the individual, in which the therapeutic component includes a bioactive material; (6) configured to administer the therapeutic component to the portion of the individual; (7) configured to administer the therapeutic component to the portion of the individual; (8) configured to obtain an indication of the dispensing device administering the therapeutic component to the individual as the objective indication that the therapeutic component has been administered to the portion of the individual; or (9) otherwise configured for use by a program participant (individual 282, e.g.) or a generally unsophisticated provider. A bottle 1783 or capsule 1784, for example, may contain a bioactive material that includes a liquid and also be configured to generate the objective indication that the therapeutic component has been administered to the portion of the individual. Alternatively or additionally, such dispensing devices may have a label as an indication of a therapeutic component suitable for administration by such less-sophisticated parties.

In light of teachings herein, numerous existing techniques may be applied for obtaining imaging or other measurement systems as described herein without undue experimentation. See, e.g., U.S. Pat. No. 7,308,292 ("Optical-based sensing devices"); U.S. Pat. No. 7,305,262 ("Apparatus and method for acquiring oximetry and electrocardiogram signals"); U.S. Pat. No. 7,280,858 ("Pulse oximetry sensor"); U.S. Pat. No. 7,004,907 ("Blood-pressure monitoring device featuring a calibration-based analysis"); U.S. Pat. No. 5,755,741 ("Body position and activity sensor"); U.S. Pat. No. 5,601,811 ("Substantive water-soluble cationic UV-absorbing compounds"); U.S. Publication No. 20030050542 ("Device for in-vivo measurement of the concentration of a substance contained in a body fluid"); U.S. Publication No. 20020016535 ("Subcutaneous glucose measurement device") or U.S. Pat. No. 7,181,054 ("System for processing image representative data").

In some contexts, moreover, method embodiments described above may include one or more instances of conditioning (some or all of) the incentive upon compliance with a regimen that includes a statin-containing material component as the therapeutic component (by operation 2111, e.g.); conditioning the incentive upon compliance with a regimen that includes an antihypertensive material component as the therapeutic component (by operation 2116, e.g.); conditioning the incentive upon compliance with a regimen that includes at least one respiratory or physical therapy session as the therapeutic component (by operation 2117, e.g.); determining the incentive to have the (second) value V2 partly based on the (first) value V1 of a therapeutic component and partly based on a physical attribute of a putative recipient of the therapeutic component (by operation 2119, e.g.); determining the incentive so that V2>V1; deriving the incentive partly based on a specific identifier of a bioactive material, partly based on a category of the bioactive material, and partly based on an indication of a dispensing device administering the bioactive material to an individual as the therapeutic component (by operation 2212, e.g.); obtaining a signal from a compliance-sensitive dispensing device as a dispensing device configured to administer a bioactive material to an individual as the therapeutic component (by operation 2214, e.g.); receiving an indication from a test of a bodily fluid of an individual after a dispensing device administers a bioactive material to the individual as the therapeutic component (by operation 2215, e.g.); receiving an indication of the incentive from a site that has apparently received a category of a bioactive material and an indication of a dispensing device administering the bioactive material to an individual as the therapeutic component (by operation 2219, e.g.); detecting whether data from one or more sensors indicate an actuation of a portion of a dispensing device (by operation 2311, e.g.); conditioning the incentive upon compliance with a regimen that includes a nitric oxide donor component as the therapeutic component (by operation 2313, e.g.); conditioning the incentive upon compliance with a regimen that includes an antiviral component of the therapeutic component (by operation 2314, e.g.); determining the incentive as a linear function of a value of a therapeutic component (by operation 2316, e.g.); detecting a health status apparently resulting from a dispensing device administering a bioactive material to an individual as the therapeutic component (by operation 2411, e.g.); conditioning the incentive upon an actuation in a vessel (by operation 2414, e.g.); detecting a dispensing device administering a bioactive material to an individual via injection as the therapeutic component (by operation 2418, e.g.); obtaining a biometric measurement of an individual (by operation 2511, e.g.); obtaining a health status of an individual (by operation 2512, e.g.); obtaining a gender of or age of an individual (by operation 2515, e.g.); obtaining an apparent pathology or other physical attribute of an individual (as a determinant affecting the incentive or the indication of the incentive, such as by operation 2519, e.g.); obtaining an indication of an inhalation of a bioactive material (by operation 2612, e.g.); obtaining an indication of when a vessel moved (by operation 2613, e.g.); obtaining an indication that a vessel has been ingested (by operation 2616, e.g.); or obtaining a test result of a sample extracted from an individual (as a determinant affecting the incentive or the indication of the incentive, e.g.); or in other combinations as described above.

Figure 27:
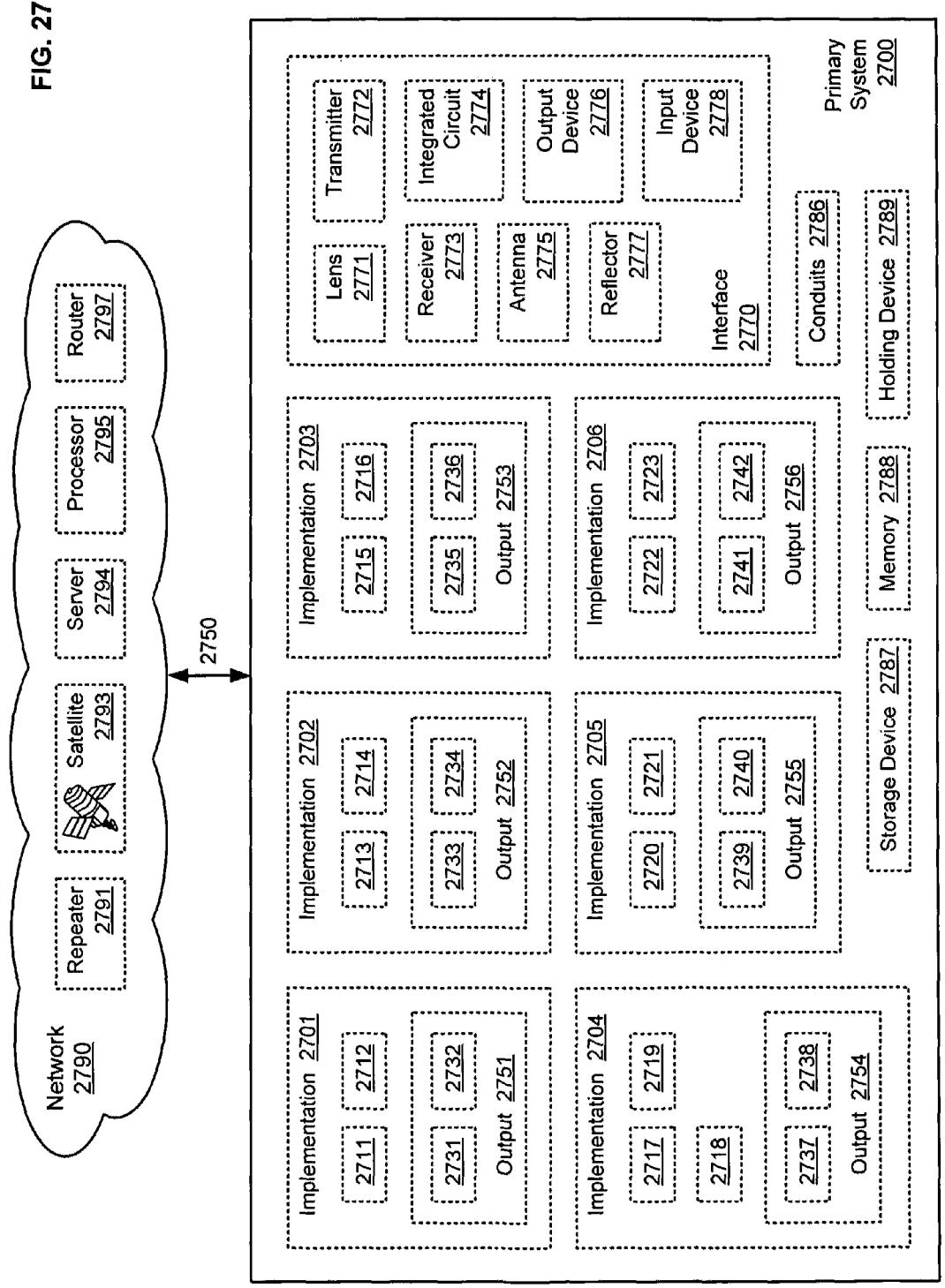
FIG. 27 depicts a context for introducing one or more processes, systems, or other articles described herein.

With reference now to FIG. 27, shown is an example of a system that may serve as a context for introducing one or more processes, systems or other articles described herein. Primary system 2700 may include one or more instances of data outputs 2751-2756 or other implementations 2701-2706 of machines, articles of manufacture, or compositions of matter that include circuitry or other logic as described herein. Implementations 2701-2706 may be held or transmitted by interfaces 2770, conduits 2786, storage devices 2787, memories 2788, other holding devices 2789, or other circuitry for handling data or software as described herein. In various embodiments as described herein, for example, one or more instances of implementation components 2711, 2712, 2713, 2714, 2715, 2716, 2717, 2718, 2719, 2720, 2721, 2722, 2723 or implementation output data 2731, 2732, 2733, 2734, 2735, 2736, 2737, 2738, 2739, 2740, 2741, 2742 may each be expressed within any aspect or combination of software, firmware, or hardware as signals, data, designs, logic, instructions, or the like. The interface(s) 2770 may include one or more instances of lenses 2771, transmitters 2772, receivers 2773, integrated circuits 2774, antennas 2775, output devices 2776, reflectors 2777, input devices 2778, or the like for handling data or communicating with local users or with network 2790 via linkage 2750, for example. Several variants of primary system 2700 are described below with reference to one or more instances of repeaters 2791, communication satellites 2793, servers 2794, processors 2795, routers 2797, or other elements of network 2790.

Those skilled in the art will recognize that some list items may also function as other list items. In the above-listed types of media, for example, some instances of interface(s) 2770 may include conduits 2786, or may also function as storage devices that are also holding devices 2789. One or more transmitters 2772 may likewise include input devices or bidirectional user interfaces, in many implementations of interface(s) 2770. Each such listed term should not be narrowed by any implication from other terms in the same list but should instead be understood in its broadest reasonable interpretation as understood by those skilled in the art.

Several variants described herein refer to device-detectable "implementations" such as one or more instances of computer-readable code, transistor or latch connectivity layouts or other geometric expressions of logical elements, firmware or software expressions of transfer functions implementing computational specifications, digital expressions of truth tables, or the like. Such instances can, in some implementations, include source code or other human-readable portions. Alternatively or additionally, functions of implementations described herein may constitute one or more device-detectable outputs such as decisions, manifestations, side effects, results, coding or other expressions, displayable images, data files, data associations, statistical correlations, streaming signals, intensity levels, frequencies or other measurable attributes, packets or other encoded expressions, or the like from invoking or monitoring the implementation as described herein.

Referring again to FIG. 11, flow 1100 may be performed by one or more instances of server 2794 remote from primary system 2700, for example, but operable to cause output device(s) 2776 to receive and to present results via linkage 2750. Alternatively or additionally, device-detectable data 2731 may be borne by one or more instances of integrated circuits 2774, signal-bearing conduits 2786, holding devices 2789, or the like as described herein. Such data may optionally be configured for transmission (in operation 1150, e.g.) by a semiconductor chip or other embodiment of integrated circuit 2774 that contains or is otherwise operatively coupled with antenna 2775 (in a radio-frequency identification tag, for example).

In some variants, one or more instances of flow 1100 may be implemented entirely within primary system 2700, optionally configured as a stand-alone system. Operation 1120 may be implemented by configuring component 2711 as logic for obtaining an indication of an incentive to an individual partly based on a physical attribute of the individual and partly based on an indication of a therapeutic component available to the individual, for example. This can be accomplished by including special-purpose instruction sequences or special-purpose-circuit designs for this function, for example, in optical or other known circuit fabrication operations, in programming by various known voltage modulation techniques, or otherwise as described herein or known by those skilled in the art. Output data 2731 from such a component in primary system 2700 or network 2790 may be recorded by writing to or otherwise configuring available portions of storage device(s) 2787.

Alternatively or additionally, such specific output data may be transmitted by configuring transistors, relays, or other drivers or conduits 2786 of primary system 2700 to transfer it to component 2712, for example. Component 2712 may perform operation 1150 via implementation as logic for transmitting the indication of the incentive to the individual to a putative provider of the therapeutic component. (In some contexts, a "putative provider of the therapeutic component" includes an entity who is, was, or will be providing the therapeutic component or who is indicated as possibly being able or authorized to provide the therapeutic component—optionally subject to confirmation or other further screening) Implementation output data 2732 from such a component in primary system 2700 or network 2790 may be recorded into available portions of storage device(s)

2787 or sent to processor 2795 for execution, for example. Each portion of implementation 2701 may likewise include one or more instances of software, hardware, or the like implementing logic that may be expressed in several respective forms as described herein or otherwise understood by those skilled in the art.

Referring again to FIG. 12, some instance of flow 1200 may likewise be implemented (optionally) entirely within primary system 2700. Operation 1230 may be implemented by configuring component 2713 as logic for assigning (a component of) an incentive to an individual partly based on an indication of a therapeutic component administered to a portion of the individual and partly based on a profile of the individual, for example, such as by including special-purpose instruction sequences or special-purpose-circuit designs for this function. This can occur, for example, in a context in which component 2713 implements response unit 580 and incentive determination unit 350; in which one or more of ages 581, genders 582, or other such demographic or other attributes 320 of the individual(s) or other recipient(s) are used as determinants 330 affecting which (incentive) component type is selected and what quantity of resources will be apportioned for use as the incentive. Output data 2733 from such a component in primary system 2700 or network 2790 may be recorded into available portions of storage device(s) 2787 or sent to component 2714, for example. Component 2714 may perform operation 1260 via implementation as logic for transmitting a result of assigning an incentive, for example. (In some contexts, for example, a "result" of such an assignment may include an acceptance, a transfer notification, an inventory adjustment, or other such manifestations of or relating to a resource transfer.) Implementation output data 2734 from such a component in primary system 2700 or network 2790 may be recorded into available portions of one or more memories 2788 or sent to processor 2795, for example. Each portion of implementation 2702 may likewise include one or more instances of software, hardware, or the like implementing logic that may be expressed in several respective forms as described herein or otherwise understood by those skilled in the art.

In light of teachings herein, numerous existing techniques may be applied for requesting or otherwise receiving demographic parameters, event data, or other data via an interface with subjects as described herein without undue experimentation. See, e.g., U.S. Pat. No. 7,258,666 ("System and methods for monitoring a patient's heart condition"); U.S. Pat. No. 6,968,375 ("Networked system for interactive communication and remote monitoring of individuals"); U.S. Pat. No. 6,926,668 ("System and method for analyzing normalized patient voice feedback in an automated collection and analysis patient care system"); U.S. Pat. No. 6,893,396 ("Wireless internet bio-telemetry monitoring system and interface"); U.S. Pat. No. 6,755,783 ("Apparatus and method for two-way communication in a device for monitoring and communicating wellness parameters of ambulatory patients"); U.S. Pat. No. 6,478,737 ("System and method for analyzing normalized patient voice feedback an automated collection and analysis patient care system"); U.S. Pat. No. 6,168,563 ("Remote health monitoring and maintenance system").

Referring again to FIG. 13, some instances of flow 1300 (optionally) may be implemented entirely within primary system 2700. Operation 1350 may be implemented by configuring component 2715 as logic for obtaining an indication of an incentive to an individual partly based on an indication of a health status apparently resulting from a bioactive material administered to the individual and partly based on a profile of the individual, for example, such as by including special-purpose instruction sequences or special-purpose-circuit designs for this function. Output data 2735 from such a component in primary system 2700 or network 2790 may be recorded into available portions of storage device(s) 2787 or sent to component 2716, for example. Component 2716 may perform operation 1380 via implementation as logic for transmitting an indication of the incentive, for example. Implementation output data 2736 from such a component in primary system 2700 or network 2790 may be recorded into available portions of storage device(s) 2787 or sent to an output device (a display 761 or speaker 762, e.g.), for example. Each portion of implementation 2703 may likewise include one or more instances of software, hardware, or the like implementing logic that may be expressed in several respective forms as described herein or otherwise understood by those skilled in the art.

Referring again to FIG. 14, some instances of flow 1400 (optionally) may be implemented entirely within primary system 2700. Operation 1430 may be implemented by configuring component 2717 as logic for obtaining first data indicating a therapeutic component having a first value V1, for example, such as by including special-purpose instruction sequences or special-purpose-circuit designs for this function. Operation 1440 may likewise be implemented by configuring component 2718 as logic for obtaining an indication of an incentive having a second value V2>V1 and partly based on the therapeutic component and partly based on a provider of the therapeutic component. Output data 2737 from (combined) components 2717, 2718 in primary system 2700 or network 2790 may be recorded into available portions of storage device(s) 2787 or sent to component 2719, for example. Component 2719 may perform operation 1460 via implementation as logic for transmitting the indication of the incentive partly based on the therapeutic component and partly based on the provider of the therapeutic component, for example. Implementation output data 2738 from such a component in primary system 2700 or network 2790 may be recorded into available portions of storage device(s) 2787 or sent to processor 2795, for example. Each portion of implementation 2704 may likewise include one or more instances of software, hardware, or the like implementing logic that may be expressed in several respective forms as described herein or otherwise understood by those skilled in the art.

Referring again to FIG. 15, some instances of flow 1500 (optionally) may be implemented entirely within primary system 2700. Operation 1520 may be implemented by configuring component 2720 as logic for obtaining an indication of an incentive to a provider of a therapeutic component and at least partly based on an objective indication that the therapeutic component has been administered to a portion of an individual, for example, such as by including special-purpose instruction sequences or special-purpose-circuit designs for this function. Output data 2739 from such a component in primary system 2700 or network 2790 may be recorded into available portions of holding device(s) 2789 or sent to component 2721, for example. Component 2721 may perform operation 1570 via implementation as logic for the indication of the incentive to the provider of the therapeutic component in a message to be transmitted, for example. Implementation output data 2740 from such a component in primary system 2700 or network 2790 may be recorded into available portions of storage device(s) 2787 or sent to an output device (a display 761 or speaker 762, e.g.), for example. Each portion of implementation 2705 may likewise include one or more instances of software, hardware, or the like implementing logic that may be expressed in several respective forms as described herein or otherwise understood by those skilled in the art.

Referring again to FIG. 16, some instances of flow 1600 (optionally) may be implemented entirely within primary system 2700. Operation 1640 may be implemented by configuring component 2722 as logic for selecting an indication of an incentive partly based on a category of a therapeutic material and partly based on an indication of a dispensing device administering the therapeutic material to an individual, for example, such as by including special-purpose instruction sequences or special-purpose-circuit designs for this function. Output data 2741 from such a component in primary system 2700 or network 2790 may be recorded into available portions of storage device(s) 2787 or sent to component 2723, for example. Component 2723 may perform operation 1680 via implementation as logic for transmitting the indication of the incentive responsive to the circuitry for selecting the indication of the incentive partly based on the category of the therapeutic material and partly based on the indication of the dispensing device administering the therapeutic material to the individual, for example. Implementation output data 2742 from such a component in primary system 2700 or network 2790 may be recorded into available portions of storage device(s) 2787 or sent to processor 2795, for example. Each portion of implementation 2706 may likewise include one or more instances of software, hardware, or the like implementing logic that may be expressed in several respective forms as described herein or otherwise understood by those skilled in the art.

In some embodiments, output device 2776 may indicate an occurrence of flow 1100 concisely as a decision, an evaluation, an effect, an hypothesis, a probability, a notification, or some other useful technical result. For example, such "indicating" may comprise such modes as showing, signifying, acknowledging, updating, explaining, associating, or the like in relation to any past or ongoing performance of such actions upon the common item(s) as recited. Such indicating may also provide one or more specifics about the occurrence: the parties or device(s) involved, a description of the method or performance modes used, any sequencing or other temporal aspects involved, indications of resources used, location(s) of the occurrence, implementation version indications or other update-indicative information, or any other such contextual information that may be worthwhile to provide at potential output destinations.

Concise indication may occur, for example, in a context in which at least some items of data 2731-2742 do not matter, or in which a recipient may understand or access portions of data 2731-2742 without receiving a preemptive explanation of how it was obtained. By distilling one or more outputs 2751, 2752, 2753, 2754, 2755, 2756 at an "upstream" stage (which may comprise integrated circuit 2774, for example, in some arrangements), downstream-stage media (such as other elements of network 2790, for example) may indicate occurrences of various methods described herein more effectively. Variants of flow 1100, for example, may be enhanced by distillations described herein, especially in bandwidth-limited transmissions, security-encoded messages, long-distance transmissions, complex images, or compositions of matter bearing other such expressions.

In some variants, a local implementation comprises a service operable for accessing a remote system running a remote implementation. In some embodiments, such "accessing" may include one or more instances of establishing or permitting an interaction between the server and a local embodiment such that the local embodiment causes or uses another implementation or output of one or more herein-described functions at the server. Functioning as a web browser, remote terminal session, or other remote activation or control device, for example, interface(s) 2770 may interact with one or more primary system users via input and output devices 2776, 2778 so as to manifest an implementation in primary system 2700 via an interaction with server 2794, for example, running a secondary implementation of flow 1100. Such local implementations may comprise a visual display supporting a local internet service to the remote server, for example. Such a remote server may control or otherwise enable one or more instances of hardware or software operating the secondary implementation outside a system, network, or physical proximity of primary system 2700. For a building implementing primary system 2700, for example, "remote" devices may include those in other countries, in orbit, or in adjacent buildings. In some embodiments, "running an implementation" may include invoking one or more instances of software, hardware, firmware, or the like atypically constituted or adapted to facilitate methods or functions as described herein. For example, primary system 2700 running an implementation of flow 1100 may be a remote activation of a special-purpose computer program resident on server 2794 via an internet browser session interaction through linkage 2750, mediated by input device 2778 and output device 2776.

In some variants, some or all of components 2711-2723 may be borne in various data-handling elements—e.g., in one or more instances of storage devices 2787, in memories 2788 or volatile media, passing through linkage 2750 with network 2790 or other conduits 2786, in one or more registers or data-holding devices 2789, or the like. For example, such processing or configuration may occur in response to user data or the like received at input device 2778 or may be presented at output device 2776. Instances of input devices 2778 may (optionally) include one or more instances of cameras or other optical devices, hand-held systems or other portable systems, keypads, sensors, or the like as described herein. Output device(s) 2776 may likewise include one or more instances of image projection modules, touch screens, wrist-wearable systems or the like adapted to be worn while in use, headphones and speakers, eyewear, liquid crystal displays (LCDs), actuators, lasers, organic or other light-emitting diodes, phosphorescent elements, portions of (hybrid) input devices 2778, or the like.

A device-detectable implementation of variants described herein with reference to flows depicted in FIGS. 11-16, for example, may be divided into several components 2711-2723 carried by one or more instances of active modules such as signal repeaters 2791, communication satellites 2793, servers 2794, processors 2795, routers 2797, or the like. For example, in some embodiments, component 2712 may be borne by an "upstream" module (e.g., repeater 2791 or the like) while or after component 2711 is borne in a "downstream" module (e.g., another instance of repeater 2791, communication satellite 2793, server 2794, or the like). Such downstream modules may "accept" such bits or other portions of implementation 2702 or implementation 2701 sequentially, for example, such as by amplifying, relaying, storing, checking, or otherwise processing what was received actively. Sensors and other "upstream" modules may likewise "accept" raw data, such as by measuring physical phenomena or accessing one or more databases.

In some embodiments, a medium bearing data (or other such event) may be "caused (directly or indirectly) by one or more instances of prior or contemporaneous measurements, decisions, transitions, circumstances, or other causal determinants. Any such event may likewise depend upon one or more other prior, contemporaneous, or potential determinants, in various implementations as taught herein. In other words, such events may occur "in response" to both preparatory (earlier) events and triggering (contemporaneous) events in some contexts.

In some embodiments, such integrated circuits 2774 may comprise transistors, capacitors, amplifiers, latches, converters, or the like on a common substrate of a semiconductor material, operable to perform computational tasks or other transformations. An integrated circuit may be application-specific ("ASIC") in that it is designed for a particular use rather than for general purpose use. An integrated circuit may likewise include one or more instances of memory circuits, processors, field-programmable gate arrays (FPGA's), antennas, or other components, and may be referred to as a system-on-a-chip ("SoC").

In some embodiments, one or more instances of integrated circuits or other processors may be configured to perform auditory pattern recognition. In FIG. 27, for example, instances of the one or more input devices 2778 may include a microphone or the like operable to provide auditory samples in data 2731-2742. Some form or portion of such output may be provided remotely, for example, to one or more instances of neural networks or other configurations of remote processors 2795 operable to perform automatic or supervised speech recognition, selective auditory data retention or transmission, or other auditory pattern recognition, upon the samples. Alternatively or additionally such sound-related data may include annotative information relating thereto such as a capture time or other temporal indications, capture location or other source information, language or other content indications, decibels or other measured quantities, pointers to related data items or other associative indications, or other data aggregations or distillations as described herein.

In some embodiments, one or more instances of integrated circuits or other processors may be configured for optical image pattern recognition. In FIG. 27, for example, instances of lenses 2771 or other input devices 2778 may include optical sensors or the like operable to provide one or more of geometric, hue, or optical intensity information in data 2731-2742. Some form or portion of such output may be provided locally, for example, to one or more instances of optical character recognition software, pattern recognition processing resources, or other configurations of integrated circuits 2774 operable to perform automatic or supervised image recognition, selective optical data retention or transmission, or the like. Alternatively or additionally such image-related data may include annotative information relating thereto such as a capture time or other temporal indications, capture location or other source information, language or other content indications, pointers to related data items or other associative indications, or other data aggregations or distillations as described herein.

Figure 28:
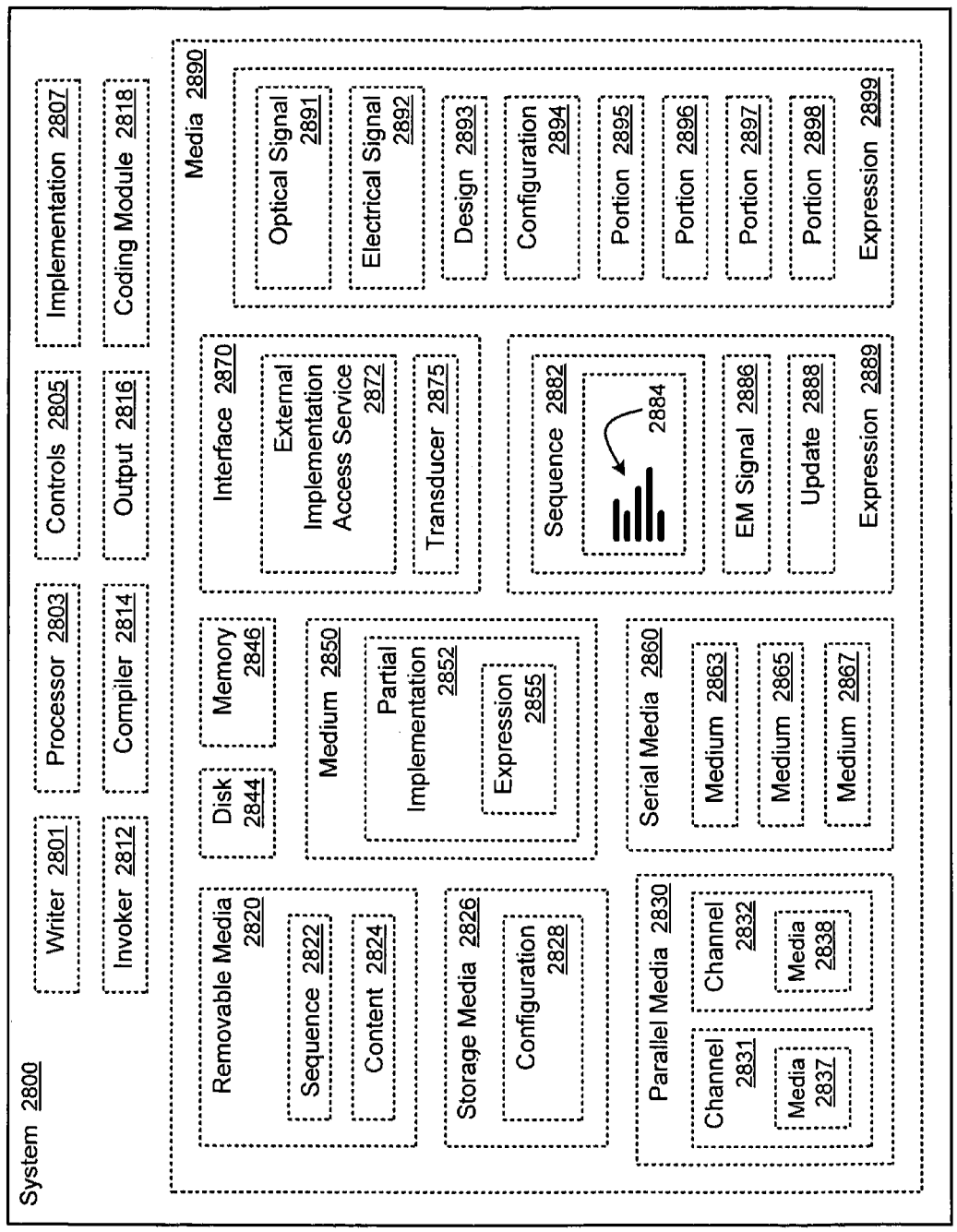
FIG. 28 depicts another context for introducing one or more processes, systems, or other articles described herein.

In some embodiments, one or more instances of integrated circuits or other processors may be configured to perform linguistic pattern recognition. In FIG. 28, for example, instances of input devices 2778 may include keys, pointing devices, microphones, sensors, reference data, or the like operable to provide spoken, written, or other symbolic expressions in data 2731-2742. Some form or portion of such output may be provided locally, for example, to one or more instances of translation utilities, compilers, or other configurations of integrated circuits 2774 operable to perform automatic or supervised programming or other language recognition, selective linguistic data retention or transmission, or the like. Alternatively or additionally such language-related data may include annotative information relating thereto such as a capture time or other temporal indications, capture location or other source information, language or other content indications, pointers to related data items or other associative indications, or other data classifications, aggregations, or distillations as described herein.

In some embodiments, one or more antennas 2775 or receivers 2773 may include a device that is the receiving end of a communication channel as described herein. For example, such a receiver may gather a signal from a dedicated conduit or from the environment for subsequent processing and/or retransmission. As a further example, such antennas or other receivers may include one or more instances of wireless antennas, radio antennas, satellite antennas, broadband receivers, digital subscriber line (DSL) receivers, modem receivers, transceivers, or configurations of two or more such devices for data reception as described herein or otherwise known.

In one variant, two or more respective portions of output data 2731-2742 may be sent from server 2794 through respective channels at various times, one portion passing through repeater 2791 and another through router 2797. Such channels may each bear a respective portion of a data aggregation or extraction, a publication, a comparative analysis or decision, a record selection, digital subscriber content, statistics or other research information, a resource status or potential allocation, an evaluation, an opportunity indication, a test or computational result, or some other output 2701-2706 of possible interest. Such distributed media may be implemented as an expedient or efficient mode of bearing such portions of output data to a common destination such as interface 2770 or holding device 2789. Alternatively or additionally, some such data may be transported by moving a medium (carried on storage device 2787, for example) so that only a small portion (a purchase or other access authorization, for example, or a contingent or supplemental module) is transferred via linkage 2750.

In some embodiments, one or more instances of signal repeaters 2791 may include a device or functional implementation that receives a signal and transmits some or all of the signal with one or more of an altered strength or frequency, or with other modulation (e.g., an optical-electrical-optical amplification device, a radio signal amplifier or format converter, a wireless signal amplifier, or the like). A repeater may convert analog to digital signals or digital to analog signals, for example, or perform no conversion. Alternatively or additionally, a repeater may reshape, retime or otherwise reorder an output for transmission. A repeater may likewise introduce a frequency offset to an output signal such that the received and transmitted frequencies are different. A repeater also may include one or more instances of a relay, a translator, a transponder, a transceiver, an active hub, a booster, a noise-attenuating filter, or the like.

In some embodiments, such communication satellite(s) 2793 may be configured to facilitate telecommunications while in a geosynchronous orbit, a Molniya orbit, a low earth orbit, or the like. Alternatively or additionally, a communication satellite may receive or transmit, for example, telephony signals, television signals, radio signals, broadband telecommunications signals, or the like.

In some variants, processor 2795 or any components 2711-2723 of implementations 2701-2706 may (optionally) be configured to perform flow variants as described herein with reference to FIGS. 11-16. An occurrence of such a variant can be expressed as a computation, a transition, or as one or more other items of data 2731-2742 described herein. Such output 2751-2756 can be generated, for example, by depicted components of primary system 2700 or network 2790 including one or more features as described with reference to FIGS. 5-10.

With reference now to FIG. 28, shown is an example of another system that may serve as a context for introducing one or more processes, systems or other articles described herein. As shown system 2800 comprises one or more instances of writers 2801, processors 2803, controls 2805, software or other implementations 2807, invokers 2812, compilers 2814, outputs 2816, coding modules 2818, or the like with one or more media 2890 bearing expressions or outputs thereof. In some embodiments, such media may include distributed media bearing a divided or otherwise distributed implementation or output. For example, in some embodiments, such media may include two or more physically distinct solid-state memories, two or more transmission media, a combination of such transmission media with one or more data-holding media configured as a data source or destination, or the like.

In some embodiments, transmission media may be "configured" to bear an output or implementation (a) by causing a channel in a medium to convey a portion thereof or (b) by constituting, adapting, addressing, or otherwise linking to such media in some other mode that depends upon one or more atypical traits of the partial or whole output or implementation. Data-holding elements of media may likewise be "configured" to bear an output or implementation portion (a) by holding the portion in a storage or memory location or (b) by constituting, adapting, addressing, or otherwise linking to such media in some other mode that depends upon one or more atypical traits of the partial or whole output or implementation. Such atypical traits may include a name, address, portion identifier, functional description, or the like sufficient to distinguish the output, implementation, or portion from a generic object.

In some embodiments described herein, "logic" and similar implementations can include software or other control structures operable to guide device operation. Electronic circuitry, for example, can manifest one or more paths of electrical current constructed and arranged to implement various logic functions as described herein. In some embodiments, one or more media are "configured to bear" a device-detectable implementation if such media hold or transmit a special-purpose device instruction set operable to perform a novel method as described herein. Alternatively or additionally, in some variants, an implementation may include special-purpose hardware or firmware components or general-purpose components executing or otherwise invoking special-purpose components. Specifications or other implementations may be transmitted by one or more instances of transmission media as described herein, optionally by packet transmission or otherwise by passing through distributed media at various times.

In some embodiments, one or more of the coding modules 2818 may be configured with circuitry for applying, imposing, or otherwise using a syntactic or other encoding constraint in forming, extracting, or otherwise handling respective portions of the device-detectable implementation or output. In encoding a software module or other message content, for example, compiler 2814 or coding module 2818 may implement one or more such constraints pursuant to public key or other encryption, applying error correction modes, certifying or otherwise annotating the message content, or implementing other security practices described herein or known by those skilled in the art. Alternatively or additionally, another instance of coding module 2818 may be configured to receive data (via receiver 2773, e.g.) and decode or otherwise distill the received data using one or more such encoding constraints. Compiler 2814 may, in some variants, convert one or more of components 2711-2723 from a corresponding source code form before the component(s) are transmitted across linkage 2750.

System 2800 may be implemented, for example, as one or more instances of stand-alone workstations, servers, vehicles, portable devices, removable media 2820, as components of primary system 2700 or network 2790 (of FIG. 27), or the like. Alternatively or additionally, media 2890 may include one or more instances of signal repeaters 2791, communication satellites 2793, servers 2794, processors 2795, routers 2797, portions of primary system 2700 as shown, or the like.

Media 2890 may include one or more instances of removable media 2820, tapes or other storage media 2826; parallel (transmission) media 2830; disks 2844; memories 2846; other data-handling media 2850; serial media 2860; interfaces 2870; or expressions 2889, 2899. Removable media 2820 can bear one or more device-detectable instances of instruction sequences 2822 or other implementations of flow 1100 or flow 1200, for example. Alternatively or additionally, in some embodiments, removable media 2820 can bear alphanumeric data, audio data, image data, structure-descriptive values, or other content 2824 in a context that indicates an occurrence of one or more flows shown in FIGS. 11-16. In some circumstances, transmission media may bear respective portions of implementations as described herein serially or otherwise non-simultaneously. In some variants in which two portions 2897, 2898 constitute a partial or complete software implementation or product of a novel method described herein, portion 2897 may follow portion 2898 successively through serial media 2863, 2865, 2867 (with transmission of portion 2897 partly overlapping in time with transmission of portion 2898 passing through medium 2863, for example). As shown, parallel channels 2831, 2832 are respectively implemented at least in media 2837, 2838 of a bus or otherwise effectively in isolation from one another. In some embodiments, a bus may be a system of two or more signal paths—not unified by a nominally ideal conduction path between them—configured to transfer data between or among internal or external computer components. For example, one data channel may include a power line (e.g., as medium 2865) operable for transmitting content of the device-detectable implementation as described herein between two taps or other terminals (e.g., as media 2863, 2867 comprising a source and destination). In another such configuration, one or more media 2837 of channel 2831 may bear portion 2897 before, while or after one or more other media 2838 of parallel channel 2832 bear portion 2898. In some embodiments, such a process may occur "while" another process occurs if they coincide or otherwise overlap in time substantially (by several clock cycles, for example). In some embodiments, such a process may occur "after" an event if any instance of the process begins after any instance of the event concludes, irrespective of other instances overlapping or the like.

In a variant in which a channel through medium 2850 bears an expression 2855 partially implementing an operational flow described herein, the remainder of the implementation may be borne (earlier or later, in some instances) by the same medium 2850 or by one or more other portions of media 2890 as shown. In some embodiments, moreover, one or more controls 2805 may configure at least some media 2890 by triggering transmissions as described above or transmissions of one or more outputs 2816 thereof.

In some embodiments, the one or more "physical media" may include one or more instances of conduits, layers, networks, static storage compositions, or other homogenous or polymorphic structures or compositions suitable for bearing signals. In some embodiments, such a "communication channel" in physical media may include a signal path between two transceivers or the like. A "remainder" of the media may include other signal paths intersecting the communication channel or other media as described herein. In some variants, another exemplary system comprises one or more physical media 2890 constructed and arranged to receive a special-purpose sequence 2882 of two or more device-detectable instructions 2884 for implementing a flow as described herein or to receive an output of executing such instructions. Physical media 2890 may (optionally) be configured by writer 2801, transmitter 2772, or the like.

In some embodiments, such a "special-purpose" instruction sequence may include any ordered set of two or more instructions directly or indirectly operable for causing multipurpose hardware or software to perform one or more methods or functions described herein: source code, macro code, controller or other machine code, or the like. In some embodiments, an implementation may include one or more instances of special-purpose sequences 2882 of instructions 2884, patches or other implementation updates 2888, configurations 2894, special-purpose circuit designs 2893, or the like. Such "designs," for example, may include one or more instances of a mask set definition, a connectivity layout of one or more gates or other logic elements, an application-specific integrated circuit (ASIC), a multivariate transfer function, or the like.

Segments of such implementations or their outputs may (optionally) be manifested one or more information-bearing static attributes comprising the device-detectable implementation. Such attributes may, in some embodiments, comprise a concentration or other layout attribute of magnetic or charge-bearing elements, visible or other optical elements, or other particles in or on a liquid crystal display or other solid-containing medium. Solid state data storage modules or other such static media may further comprise one or more instances of laser markings, barcodes, human-readable identifiers, or the like, such as to indicate one or more attributes of the device-detectable implementation. Alternatively or additionally such solid state or other solid-containing media may include one or more instances of semiconductor devices or other circuitry, magnetic or optical digital storage disks, dynamic or flash random access memories (RAMs), or the like. Magnetoresistive RAMs may bear larger implementation or output portions or aggregations safely and efficiently, moreover, and without any need for motors or the like for positioning the storage medium.

Segments of such implementations or their outputs may likewise be manifested in electromagnetic signals 2886, laser or other optical signals 2891, electrical signals 2892, or the like. In some embodiments, for example, such electrical or electromagnetic signals may include one or more instances of static or variable voltage levels or other analog values, radio frequency transmissions or the like. In some embodiments, the above-mentioned "optical" signals may likewise include one or more instances of time- or position-dependent, device-detectable variations in hue, intensity, or the like. Alternatively or additionally, portions of such implementations or their outputs may manifest as one or more instances of magnetic, magneto-optic, electrostatic, or other physical configurations 2828 of nonvolatile storage media 2826 or as external implementation access services 2872.

In some embodiments, physical media can be configured by being "operated to bear" or "operated upon to bear" a signal. For example, they may include physical media that generate, transmit, conduct, receive, or otherwise convey or store a device-detectable implementation or output as described herein. Such conveyance or storing of a device-detectable implementation or output may be carried out in a distributed fashion at various times or locations, or such conveyance or storing of a device-detectable implementation or output may be done at one location or time. As discussed above, such physical media "operated to bear" or "operated upon to bear" may include physical media that are atypically constituted or adapted to facilitate methods or functions as described herein.

In some configurations, one or more output devices 2776 may present one or more results of transmitting the indication of the incentive to the individual to a putative provider of the therapeutic component in response to interface(s) 2770 receiving one or more invocations or outputs of an implementation of this function via linkage 2750. Such an "invocation" may, in some embodiments, comprise one or more instances of requests, hardware or software activations, user actions, or other determinants as described herein. Alternatively or additionally, in some embodiments, one or more input devices 2778 may later receive one or more invocations or results of transmitting the indication of the incentive to the individual to a putative provider of the therapeutic component. In contexts like these, processor 2795 or other components of network 2790 may likewise constitute a secondary implementation having access to a primary instance of interface 2770 implementing methods like flow 1100 as described herein.

Serial media 2860 comprises a communication channel of two or more media configured to bear a transition or other output increment successively. In some embodiments, for example, serial media 2860 may include a communication line or wireless medium (e.g., as medium 2865) between two signal-bearing conduits (e.g., terminals or antennas as media 2863, 2867). Alternatively or additionally, one or more lenses 2771 or other light-transmissive media may comprise a serial medium between a light-transmissive medium and a sensor or other light receiver 2773 or transmitter 2772. In some embodiments, such "light-transmissive" media may (optionally) comprise metamaterials or other media operable for bearing one or more instances of microwave signals, radiowave signals, visible light signals, or the like.

In some embodiments, such a lens may be an optical element that causes light to converge or diverge along one or more signal paths. Such a light-transmissive medium may include a signal-bearing conduit, glass, or other physical medium through which an optical signal may travel. More generally, a signal-bearing conduit may be an electrical wire, a telecommunications cable, a fiber-optic cable, or a mechanical coupling or other path for the conveyance of analog or digital signals.

Alternatively or additionally, system 2800 may likewise include one or more instances of media for handling implementations or their outputs: satellite dishes or other reflectors 2777, antennas 2775 or other transducers 2875, arrays of two or more such devices configured to detect or redirect one or more incoming signals, caching elements or other data-holding elements (e.g., disks 2844, memories 2846, or other media 2890), integrated circuits 2774, or the like. In some variants, one or more media may be "configured" to bear a device-detectable implementation as described herein by being constituted or otherwise specially adapted for that type of implementation at one or more respective times, overlapping or otherwise. Such "signal-bearing" media may include those configured to bear one or more such signals at various times as well as those currently bearing them.

In some embodiments, such caching elements may comprise a circuit or device configured to store data that duplicates original values stored elsewhere or computed earlier in time. For example, a caching element may be a temporary storage area where frequently-accessed data may be held for rapid access by a computing system. A caching element likewise may be machine-readable memory (including computer-readable media such as random access memory or data disks). In some embodiments, such caching elements may likewise comprise a latching circuit or device configured to store data that has been modified from original values associated with the data (held elsewhere or computed earlier in time, for example).

In one variant, respective portions 2895, 2896 of an expression 2899 of implementation 2807 may be sent through respective channels at various times. Invoker 2812 may request or otherwise attempt to activate a computer program or streaming media overseas via a telephone cable or other channel 2831. Meanwhile, output 2816 may attempt to trigger a session or other partial implementation 2852, success in which may be indicated by receiving expression 2855 into a visual display or other medium 2850. Such a program or other implementation may be made complete, for example, once both of these attempts succeed.

In some embodiments, transducer(s) 2875 may comprise one or more devices that convert a signal from one form to another form. For example, a transducer may be a cathode ray tube that transforms electrical signals into visual signals. Another example of a transducer comprises a microelectromechanical systems ("MEMS") device, which may be configured to convert mechanical signals into electrical signals (or vice versa).

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

CLAUSES 1. (Independent) A resource apportionment system comprising:
circuitry for obtaining an indication of an incentive partly based on a physical attribute of an individual and partly based on an indication of a therapeutic component available to the individual, a component of the incentive being an incentive to the individual; and circuitry for transmitting the indication of the incentive partly based on the physical attribute of the individual and partly based on the indication of the therapeutic component available to the individual to a putative provider of the therapeutic component.
2. The resource apportionment system of CLAUSE 1, in which the circuitry for obtaining an indication of an incentive partly based on a physical attribute of an individual and partly based on an indication of a therapeutic component available to the individual comprises:
circuitry for conditioning (some or all of) the incentive partly based on the physical attribute of the individual and partly based on the indication of the therapeutic component available to the individual upon compliance with a regimen that includes a statin-containing material component as the therapeutic component.
3. The resource apportionment system of either CLAUSE 1 or CLAUSE 2, in which the circuitry for obtaining an indication of an incentive partly based on a physical attribute of an individual and partly based on an indication of a therapeutic component available to the individual comprises:
circuitry for conditioning the incentive partly based on the physical attribute of the individual and partly based on the indication of the therapeutic component available to the individual upon compliance with a regimen that includes an antihypertensive material component as the therapeutic component.
4. The resource apportionment system of any one of the above CLAUSES, in which the circuitry for obtaining an indication of an incentive partly based on a physical attribute of an individual and partly based on an indication of a therapeutic component available to the individual comprises:
circuitry for conditioning the incentive partly based on the physical attribute of the individual and partly based on the indication of the therapeutic component available to the individual upon compliance with a regimen that includes at least one respiratory or physical therapy session.
5. The resource apportionment system of any one of the above CLAUSES, in which the circuitry for obtaining an indication of an incentive partly based on a physical attribute of an individual and partly based on an indication of a therapeutic component available to the individual comprises:
circuitry for determining (some or all of) the incentive partly based on the physical attribute of the individual and partly based on the indication of the therapeutic component available to the individual to have a value partly based on a value of the therapeutic component and partly based on a physical attribute of another individual, the other individual being a putative recipient of the therapeutic component.
6. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for signaling a discount as a component of the incentive partly based on the physical attribute of the individual and partly based on the indication of the therapeutic component available to the individual.
7. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for authorizing a resource transfer to the individual as a component of the incentive partly based on the physical attribute of the individual and partly based on the indication of the therapeutic component available to the individual.
8. The resource apportionment system of either of the consecutively-preceding CLAUSES, in which the circuitry for transmitting the indication of the incentive partly based on the physical attribute of the individual and partly based on the indication of the therapeutic component available to the individual to a putative provider of the therapeutic component comprises:
circuitry for authorizing a benefit to another individual as another component of the incentive partly based on the physical attribute of the individual and partly based on the indication of the therapeutic component available to the individual.
9. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for presenting a first message indicative of the incentive partly based on the physical attribute of the individual and partly based on the indication of the therapeutic component available to the individual to a care provider and a second message indicative of the incentive partly based on the physical attribute of the individual and partly based on the indication of the therapeutic component available to the individual to the putative provider, the putative provider being a material provider.
10. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for conditioning a benefit upon an acceptance of at least a portion of the incentive from the individual.
11. The resource apportionment system of any one of the above CLAUSES, in which the circuitry for obtaining an indication of an incentive partly based on a physical attribute of an individual and partly based on an indication of a therapeutic component available to the individual comprises:
circuitry for conditioning (some or all of) the incentive partly based on the physical attribute of the individual and partly based on the indication of the therapeutic component available to the individual upon compliance with a regimen that includes a nitric oxide donor component.

12. The resource apportionment system of any one of the above CLAUSES, in which the circuitry for obtaining an indication of an incentive partly based on a physical attribute of an individual and partly based on an indication of a therapeutic component available to the individual comprises:
circuitry for conditioning the incentive partly based on the physical attribute of the individual and partly based on the indication of the therapeutic component available to the individual upon compliance with a regimen that includes an antiviral component.

13. The resource apportionment system of any one of the above CLAUSES, in which the circuitry for obtaining an indication of an incentive partly based on a physical attribute of an individual and partly based on an indication of a therapeutic component available to the individual comprises:
circuitry for determining the incentive partly based on the physical attribute of the individual and partly based on the indication of the therapeutic component available to the individual as a linear function of a value of the therapeutic component.

14. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for transferring one or more credits to a care provider as a component of the incentive partly based on the physical attribute of the individual and partly based on the indication of the therapeutic component available to the individual in response to an indication that the therapeutic component was administered, the therapeutic component being a bioactive material.

15. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for obtaining a selection of a type of the incentive partly based on the physical attribute of the individual and partly based on the indication of the therapeutic component available to the individual in response to input from a resource provider who is not the putative provider of the therapeutic component.

16. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for manifesting an improvement in a reputation of a provider as a component of the incentive partly based on the physical attribute of the individual and partly based on the indication of the therapeutic component available to the individual.

17. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for authorizing a transfer of one or more resources into an account of a recipient as a component of the incentive partly based on the physical attribute of the individual and partly based on the indication of the therapeutic component available to the individual.

18. The resource apportionment system of any one of the above CLAUSES, in which the circuitry for obtaining an indication of an incentive partly based on a physical attribute of an individual and partly based on an indication of a therapeutic component available to the individual comprises:
circuitry for determining the indication of the incentive in response to an indication of a product attribute.

19. The resource apportionment system of any one of the above CLAUSES, in which the circuitry for obtaining an indication of an incentive partly based on a physical attribute of an individual and partly based on an indication of a therapeutic component available to the individual comprises:
circuitry for conditioning the incentive partly based on the physical attribute of the individual and partly based on the indication of the therapeutic component available to the individual upon an actuation in a vessel.

20. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for presenting an availability of an option to the individual as the indication of the incentive.

21. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for transmitting the indication of the incentive to a care provider as the putative provider of the therapeutic component.

22. The resource apportionment system of CLAUSE 21, in which the circuitry for transmitting the indication of the incentive partly based on the physical attribute of the individual and partly based on the indication of the therapeutic component available to the individual to a putative provider of the therapeutic component comprises:
circuitry for transmitting the indication of the incentive to another putative provider of the therapeutic component, the therapeutic component being a therapeutic material.

23. The resource apportionment system of CLAUSE 21, in which the circuitry for transmitting the indication of the incentive partly based on the physical attribute of the individual and partly based on the indication of the therapeutic component available to the individual to a putative provider of the therapeutic component comprises:
circuitry for transmitting the indication of the incentive to the individual.

24. The resource apportionment system of CLAUSE 21, in which the circuitry for transmitting the indication of the incentive partly based on the physical attribute of the individual and partly based on the indication of the therapeutic component available to the individual to a putative provider of the therapeutic component comprises:
circuitry for transmitting the indication of the incentive to a party other than the putative provider of the therapeutic component.

25. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for obtaining a size of the incentive partly based on the physical attribute of the individual and partly based on the indication of the therapeutic component available to the individual in response to a pattern of enrollment.

26. The resource apportionment system of any one of the above CLAUSES, in which the circuitry for obtaining an indication of an incentive partly based on a physical attribute of an individual and partly based on an indication of a therapeutic component available to the individual comprises:
circuitry for determining the incentive partly based on the physical attribute of the individual and partly based on the indication of the therapeutic component available to the individual by obtaining a physical attribute of the individual.

27. The resource apportionment system of CLAUSE 26, in which the circuitry for determining the incentive partly based on the physical attribute of the individual and partly based on the indication of the therapeutic component available to the individual by obtaining a physical attribute of the individual comprises:
circuitry for determining the incentive partly based on the physical attribute of the individual and partly based on the indication of the therapeutic component available to the individual by obtaining a biometric measurement as the physical attribute of the individual.

28. The resource apportionment system of CLAUSE 26, in which the circuitry for determining the incentive partly based on the physical attribute of the individual and partly based on the indication of the therapeutic component available to the individual by obtaining a physical attribute of the individual comprises:
circuitry for determining the incentive partly based on the physical attribute of the individual and partly based on the indication of the therapeutic component available to the individual by obtaining a health status as the physical attribute of the individual.

29. The resource apportionment system of CLAUSE 26, in which the circuitry for determining the incentive partly based on the physical attribute of the individual and partly based on the indication of the therapeutic component available to the individual by obtaining a physical attribute of the individual comprises:
circuitry for determining the incentive partly based on the physical attribute of the individual and partly based on the indication of the therapeutic component available to the individual by obtaining a gender of or an age of the individual as the physical attribute of the individual.

30. The resource apportionment system of CLAUSE 26, in which the circuitry for determining the incentive partly based on the physical attribute of the individual and partly based on the indication of the therapeutic component available to the individual by obtaining a physical attribute of the individual comprises:
circuitry for determining the incentive partly based on the physical attribute of the individual and partly based on the indication of the therapeutic component available to the individual by obtaining a pathology as the physical attribute of the individual.

31. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for selecting a beneficiary of the incentive partly based on the physical attribute of the individual and partly based on the indication of the therapeutic component available to the individual in response to a pattern of enrollment.

32. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for selecting a recipient of a notification of the incentive partly based on the physical attribute of the individual and partly based on the indication of the therapeutic component available to the individual in response to a received message.

33. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for transmitting the indication of the incentive to a material provider.

34. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for transmitting the indication of the incentive to another individual.

35. The resource apportionment system of any one of the above CLAUSES, in which the circuitry for obtaining an indication of an incentive partly based on a physical attribute of an individual and partly based on an indication of a therapeutic component available to the individual comprises:
circuitry for obtaining an indication of an inhalation of the therapeutic component as an objective indication that the therapeutic component has been administered to the portion of the individual, the therapeutic component being a bioactive material.

36. The resource apportionment system of any one of the above CLAUSES, in which the circuitry for obtaining an indication of an incentive partly based on a physical attribute of an individual and partly based on an indication of a therapeutic component available to the individual comprises:
circuitry for obtaining an indication of when at least a portion of a vessel moved as an objective indication that the therapeutic component has been administered to the portion of the individual.

37. The resource apportionment system of any one of the above CLAUSES, in which the circuitry for obtaining an indication, of an incentive partly based on a physical attribute of an individual and partly based on an indication of a therapeutic component available to the individual comprises:
circuitry for obtaining an indication that a vessel has been ingested as an objective indication that the therapeutic component has been administered to the portion of the individual.

38. The resource apportionment system of any one of the above CLAUSES, in which the circuitry for obtaining an indication of an incentive partly based on a physical attribute of an individual and partly based on an indication of a therapeutic component available to the individual comprises:
circuitry for obtaining a test result of a sample extracted from the individual as an objective indication that the therapeutic component has been administered to the portion of the individual.

39. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for obtaining an indication of informed consent.

40. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for signaling a change in an eligibility of the provider of the therapeutic component as the indication of the incentive to the provider of the therapeutic component.

41. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for obtaining an indication of an abnormally late order for the therapeutic component.

42. The resource apportionment system of any one of the above CLAUSES, in which the circuitry for transmitting the indication of the incentive partly based on the physical attribute of the individual and partly based on the indication of the therapeutic component available to the individual to a putative provider of the therapeutic component comprises:
circuitry for obtaining an indication of whether the individual remains enrolled in a program requiring a therapeutic regimen that includes the therapeutic component.

43. The resource apportionment system of any one of the above CLAUSES, further comprising:
a vessel containing an inhalant and having an administration detection feature configured to generate a device-detectable indication that the therapeutic component has been administered to the portion of the individual, the therapeutic component including the inhalant.

44. The resource apportionment system of any one of CLAUSES 1 through 42, further comprising:
a vessel containing an inoculant and having an administration detection feature configured to generate a device-detectable indication that the therapeutic component has been administered to the portion of the individual, the therapeutic component being the inoculant.

45. The resource apportionment system of any one of CLAUSES 1 through 42, further comprising:
a vessel containing the therapeutic component; and administration detection logic configured to detect one or more device-detectable auditory indications of a movement of the vessel containing the therapeutic component.

46. The resource apportionment system of any one of CLAUSES 1 through 42, in which the circuitry for obtaining an indication of an incentive partly based on a physical attribute of an individual and partly based on an indication of a therapeutic component available to the individual comprises:
circuitry for deriving (some or all of) the incentive partly based on the physical attribute of the individual and partly based on the indication of the therapeutic component available to the individual partly based on a specific identifier of the therapeutic component, partly based on a category of the therapeutic component, and partly based on an indication of a dispensing device administering the therapeutic component to the individual, the therapeutic component being a bioactive material.

47. The resource apportionment system of any one of CLAUSES 1 through 42, in which the circuitry for obtaining an indication of an incentive partly based on a physical attribute of an individual and partly based on an indication of a therapeutic component available to the individual comprises:
circuitry for obtaining a signal from a compliance-sensitive dispensing device.

48. The resource apportionment system of any one of CLAUSES 1 through 42, in which the circuitry for obtaining an indication of an incentive partly based on a physical attribute of an individual and partly based on an indication of a therapeutic component available to the individual comprises:
circuitry for receiving an indication from a test of a bodily fluid of the individual after a dispensing device administers the therapeutic component to the individual, the therapeutic component being a bioactive material.

49. The resource apportionment system of any one of CLAUSES 1 through 42, in which the circuitry for obtaining an indication of an incentive partly based on a physical attribute of an individual and partly based on an indication of a therapeutic component available to the individual comprises:
circuitry for receiving the indication of the incentive from a site that has apparently received a category of the therapeutic component and an indication of a dispensing device administering the therapeutic component to the individual, the therapeutic component being a bioactive material.

50. The resource apportionment system of any one of CLAUSES 1 through 42, in which the circuitry for obtaining an indication of an incentive partly based on a physical attribute of an individual and partly based on an indication of a therapeutic component available to the individual comprises:
circuitry for detecting whether data from one or more sensors indicate an actuation of a portion of a dispensing device.

51. The resource apportionment system of any one of CLAUSES 1 through 42, in which the circuitry for obtaining an indication of an incentive partly based on a physical attribute of an individual and partly based on an indication of a therapeutic component available to the individual comprises:
circuitry for detecting a health status apparently resulting from a dispensing device administering the therapeutic component to the individual, the therapeutic component being a bioactive material.

52. The resource apportionment system of any one of CLAUSES 1 through 42, in which the circuitry for obtaining an indication of an incentive partly based on a physical attribute of an individual and partly based on an indication of a therapeutic component available to the individual comprises:

circuitry for detecting a dispensing device administering the therapeutic component to the individual via injection, the therapeutic component being a bioactive material.

53. The resource apportionment system of any one of CLAUSES 1 through 42, further comprising:

a dispensing device, including administration detection logic and configured to administer the therapeutic component, in which the therapeutic component includes a topical treatment.

54. The resource apportionment system of any one of CLAUSES 1 through 42, further comprising:

a dispensing device, including administration detection logic and configured to administer the therapeutic component, in which the therapeutic component includes an antibiotic.

55. The resource apportionment system of any one of CLAUSES 1 through 42, further comprising:

a dispensing device, including an administration detection feature and configured to administer the therapeutic component to the portion of the individual, the therapeutic component being a bioactive material.

56. The resource apportionment system of any one of CLAUSES 1 through 42, further comprising:

a vessel containing the therapeutic component and having an actuator.

57. The resource apportionment system of any one of the above CLAUSES, further comprising:

one or more physical media bearing time data indicative of when one or more dispensations of the therapeutic component have occurred as an objective indication that the therapeutic component has been administered to the portion of the individual.

58. (Independent) A resource apportionment method comprising:

invoking circuitry for obtaining an indication of an incentive partly based on a physical attribute of an individual and partly based on an indication of a therapeutic component available to the individual, a component of the incentive being an incentive to the individual; and transmitting the indication of the incentive partly based on the physical attribute of the individual and partly based on the indication of the therapeutic component available to the individual to a putative provider of the therapeutic component.

59. The resource apportionment method of METHOD CLAUSE 58, in which the invoking circuitry for obtaining an indication of an incentive partly based on a physical attribute of an individual and partly based on an indication of a therapeutic component available to the individual comprises:

conditioning the incentive partly based on the physical attribute of the individual and partly based on the indication of the therapeutic component available to the individual upon compliance with a regimen that includes a statin-containing material component as the therapeutic component.

60. The resource apportionment method of either METHOD CLAUSE 58 or 59, in which the invoking circuitry, for obtaining an indication of an incentive partly based on a physical attribute of an individual and partly based on an indication of a therapeutic component available to the individual comprises:

conditioning (some or all of) the incentive partly based on the physical attribute of the individual and partly based on the indication of the therapeutic component available to the individual upon compliance with a regimen that includes an antihypertensive material component as the therapeutic component.

61. The resource apportionment method of any one of the METHOD CLAUSES above, in which the invoking circuitry for obtaining an indication of an incentive partly based on a physical attribute of an individual and partly based on an indication of a therapeutic component available to the individual comprises:

conditioning the incentive partly based on the physical attribute of the individual and partly based on the indication of the therapeutic component available to the individual upon compliance with a regimen that includes at least one respiratory or physical therapy session.

62. The resource apportionment method of any one of the METHOD CLAUSES above, in which the invoking circuitry for obtaining an indication of an incentive partly based on a physical attribute of an individual and partly based on an indication of a therapeutic component available to the individual comprises:

determining (some or all of) the incentive partly based on the physical attribute of the individual and partly based on the indication of the therapeutic component available to the individual to have a value partly based on a value of the therapeutic component and partly based on a physical attribute of another individual, the other individual being a putative recipient of the therapeutic component.

63. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

signaling a discount as a component of the incentive partly based on the physical attribute of the individual and partly based on the indication of the therapeutic component available to the individual.

64. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

authorizing a resource transfer to the individual as a component of the incentive partly based on the physical attribute of the individual and partly based on the indication of the therapeutic component available to the individual.

65. The resource apportionment method of either of the consecutively-preceding CLAUSES, in which the transmitting the indication of the incentive partly based on the physical attribute of the individual and partly based on the indication of the therapeutic component available to the individual to a putative provider of the therapeutic component comprises:

authorizing a benefit to another individual as another component of the incentive partly based on the physical attribute of the individual and partly based on the indication of the therapeutic component available to the individual.

66. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

presenting a first message indicative of the incentive partly based on the physical attribute of the individual and partly based on the indication of the therapeutic component available to the individual to a care provider and a second message indicative of the incentive partly based on the physical attribute of the individual and partly based on the indication of the therapeutic component available to the individual to the putative provider, the putative provider being a material provider.

67. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: conditioning a benefit upon an acceptance of at least a portion of the incentive partly based on the physical attribute of the individual and partly based on the indication of the therapeutic component available to the individual.

68. The resource apportionment method of any one of the METHOD CLAUSES above, in which the invoking circuitry for obtaining an indication of an incentive partly based on a physical attribute of an individual and partly based on an indication of a therapeutic component available to the individual comprises: conditioning the incentive partly based on the physical attribute of the individual and partly based on the indication of the therapeutic component available to the individual upon compliance with a regimen that includes a nitric oxide donor component.

69. The resource apportionment method of any one of the METHOD CLAUSES above, in which the invoking circuitry for obtaining an indication of an incentive partly based on a physical attribute of an individual and partly based on an indication of a therapeutic component available to the individual comprises: conditioning (some or all of) the incentive partly based on the physical attribute of the individual and partly based on the indication of the therapeutic component available to the individual upon compliance with a regimen that includes an antiviral component.

70. The resource apportionment method of any one of the METHOD CLAUSES above, in which the invoking circuitry for obtaining an indication of an incentive partly based on a physical attribute of an individual and partly based on an indication of a therapeutic component available to the individual comprises: determining the incentive partly based on the physical attribute of the individual and partly based on the indication of the therapeutic component available to the individual as a linear function of a value of the therapeutic component.

71. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: transferring one or more credits to a care provider as a component of the incentive partly based on the physical attribute of the individual and partly based on the indication of the therapeutic component available to the individual in response to an indication that the therapeutic component was administered.

72. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: obtaining a selection of a type of the incentive partly based on the physical attribute of the individual and partly based on the indication of the therapeutic component available to the individual in response to input from a resource provider.

73. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: manifesting an improvement in a reputation of a provider as a component of the incentive partly based on the physical attribute of the individual and partly based on the indication of the therapeutic component available to the individual.

74. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: authorizing a transfer of one or more resources into an account of a recipient as a component of the incentive partly based on the physical attribute of the individual and partly based on the indication of the therapeutic component available to the individual.

75. The resource apportionment method of any one of the METHOD CLAUSES above, in which the invoking circuitry for obtaining an indication of an incentive partly based on a physical attribute of an individual and partly based on an indication of a therapeutic component available to the individual comprises: determining the indication of the incentive in response to an indication of a product attribute.

76. The resource apportionment method of any one of the METHOD CLAUSES above, in which the invoking circuitry for obtaining an indication of an incentive partly based on a physical attribute of an individual and partly based on an indication of a therapeutic component available to the individual comprises: conditioning the incentive partly based on the physical attribute of the individual and partly based on the indication of the therapeutic component available to the individual upon an actuation in a vessel as an objective indication that the therapeutic component has been administered to a portion of the individual.

77. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: presenting an availability of an option to the individual as the indication of the incentive.

78. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises: transmitting the indication of the incentive to a care provider as the putative provider of the therapeutic component.

79. The resource apportionment method of METHOD CLAUSE 78, in which the transmitting the indication of the incentive partly based on the physical attribute of the individual and partly based on the indication of the therapeutic component available to the individual to a putative provider of the therapeutic component comprises:

transmitting the indication of the incentive to another putative provider of the therapeutic component, the therapeutic component being a therapeutic material.

80. The resource apportionment method of METHOD CLAUSE 78, in which the transmitting the indication of the incentive partly based on the physical attribute of the individual and partly based on the indication of the therapeutic component available to the individual to a putative provider of the therapeutic component comprises:
transmitting the indication of the incentive to the individual.

81. The resource apportionment method of METHOD CLAUSE 78, in which the transmitting the indication of the incentive partly based on the physical attribute of the individual and partly based on the indication of the therapeutic component available to the individual to a putative provider of the therapeutic component comprises:
transmitting the indication of the incentive to a party other than the putative provider of the therapeutic component.

82. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:
obtaining a size of the incentive partly based on the physical attribute of the individual and partly based on the indication of the therapeutic component available to the individual in response to a pattern of enrollment.

83. The resource apportionment method of any one of the METHOD CLAUSES above, in which the invoking circuitry for obtaining an indication of an incentive partly based on a physical attribute of an individual and partly based on an indication of a therapeutic component available to the individual comprises:
determining the incentive partly based on the physical attribute of the individual and partly based on the indication of the therapeutic component available to the individual by obtaining a physical attribute of the individual.

84. The resource apportionment method of METHOD CLAUSE 83, in which the determining the incentive partly based on the physical attribute of the individual and partly based on the indication of the therapeutic component available to the individual by obtaining a physical attribute of the individual comprises:
determining the incentive partly based on the physical attribute of the individual and partly based on the indication of the therapeutic component available to the individual by obtaining a biometric measurement as the physical attribute of the individual.

85. The resource apportionment method of METHOD CLAUSE 83, in which the determining the incentive partly based on the physical attribute of the individual and partly based on the indication of the therapeutic component available to the individual by obtaining a physical attribute of the individual comprises:
determining the incentive partly based on the physical attribute of the individual and partly based on the indication of the therapeutic component available to the individual by obtaining a health status as the physical attribute of the individual.

86. The resource apportionment method of METHOD CLAUSE 83, in which the determining the incentive partly based on the physical attribute of the individual and partly based on the indication of the therapeutic component avail-able to the individual by obtaining a physical attribute of the individual comprises:
determining the incentive partly based on the physical attribute of the individual and partly based on the indication of the therapeutic component available to the individual by obtaining a gender of or an age of the individual as the physical attribute of the individual.

87. The resource apportionment method of METHOD CLAUSE 83, in which the determining the incentive partly based on the physical attribute of the individual and partly based on the indication of the therapeutic component available to the individual by obtaining a physical attribute of the individual comprises:
determining the incentive partly based on the physical attribute of the individual and partly based on the indication of the therapeutic component available to the individual by obtaining a pathology as the physical attribute of the individual.

88. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:
selecting (at least) a beneficiary of the incentive partly based on the physical attribute of the individual and partly based on the indication of the therapeutic component available to the individual in response to a pattern of enrollment.

89. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:
selecting a recipient of a notification of the incentive partly based on the physical attribute of the individual and partly based on the indication of the therapeutic component available to the individual in response to a received message.

90. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:
transmitting the indication of the incentive to a material provider.

91. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:
transmitting the indication of the incentive to another individual.

92. The resource apportionment method of any one of the METHOD CLAUSES above, in which the invoking circuitry for obtaining an indication of an incentive partly based on a physical attribute of an individual and partly based on an indication of a therapeutic component available to the individual comprises:
obtaining an indication of an inhalation of the therapeutic component as an objective indication that the therapeutic component has been administered to the portion of the individual, the therapeutic component being a bioactive material.

93. The resource apportionment method of any one of the METHOD CLAUSES above, in which the invoking circuitry for obtaining an indication of an incentive partly based on a physical attribute of an individual and partly based on an indication of a therapeutic component available to the individual comprises:

obtaining an indication of when at least a portion of a vessel moved as an objective indication that the therapeutic component has been administered to the portion of the individual.

94. The resource apportionment method of any one of the METHOD CLAUSES above, in which the invoking circuitry for obtaining an indication of an incentive partly based on a physical attribute of an individual and partly based on an indication of a therapeutic component available to the individual comprises:

obtaining an indication that a vessel has been ingested as an objective indication that the therapeutic component has been administered to the portion of the individual.

95. The resource apportionment method of any one of the METHOD CLAUSES above, in which the invoking circuitry for obtaining an indication of an incentive partly based on a physical attribute of an individual and partly based on an indication of a therapeutic component available to the individual comprises:

obtaining a test result of a sample extracted from the individual as an objective indication that the therapeutic component has been administered to the portion of the individual.

96. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

obtaining an indication of informed consent.

97. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

signaling a change in an eligibility of the putative provider of the therapeutic component as the indication of the incentive to the putative provider of the therapeutic component.

98. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

obtaining an indication of an abnormally late order for the therapeutic component.

99. The resource apportionment method of any one of the METHOD CLAUSES above, in which the transmitting the indication of the incentive partly based on the physical attribute of the individual and partly based on the indication of the therapeutic component available to the individual to a putative provider of the therapeutic component comprises:

obtaining an indication of whether the individual remains enrolled in a program requiring a therapeutic regimen that includes the therapeutic component.

100. The resource apportionment method of any one of the METHOD CLAUSES above, in which the invoking circuitry for obtaining an indication of an incentive partly based on a physical attribute of an individual and partly based on an indication of a therapeutic component available to the individual comprises:

deriving (some or all of) the incentive partly based on the physical attribute of the individual and partly based on the indication of the therapeutic component available to the individual partly based on a specific identifier of the therapeutic component, partly based on a category of the therapeutic component, and partly based on an indication of a dispensing device administering the therapeutic component to the individual, the therapeutic component being a bioactive material.

101. The resource apportionment method of any one of METHOD CLAUSES 58-99, in which the invoking circuitry for obtaining an indication of an incentive partly based on a physical attribute of an individual and partly based on an indication of a therapeutic component available to the individual comprises:

invoking circuitry for obtaining a signal from a compliance-sensitive dispensing device.

102. The resource apportionment method of any one of METHOD CLAUSES 58-99, in which the invoking circuitry for obtaining an indication of an incentive partly based on a physical attribute of an individual and partly based on an indication of a therapeutic component available to the individual comprises:

invoking circuitry for receiving an indication from a test of a bodily fluid of the individual after a dispensing device administers the therapeutic component to the individual.

103. The resource apportionment method of any one, of METHOD CLAUSES 58-99, in which the invoking circuitry for obtaining an indication of an incentive partly based on a physical attribute of an individual and partly based on an indication of a therapeutic component available to the individual comprises:

invoking circuitry for receiving the indication of the incentive from a site that has apparently received a category of the therapeutic component and an indication of a dispensing device administering the therapeutic component to the individual.

104. The resource apportionment method of any one of METHOD CLAUSES 58-99, in which the invoking circuitry for obtaining an indication of an incentive partly based on a physical attribute of an individual and partly based on an indication of a therapeutic component available to the individual comprises:

invoking circuitry for detecting whether data from one or more sensors indicate an actuation of a portion of a dispensing device.

105. The resource apportionment method of any one of METHOD CLAUSES 58-99, in which the invoking circuitry for obtaining an indication of an incentive partly based on a physical attribute of an individual and partly based on an indication of a therapeutic component available to the individual comprises:

invoking circuitry for detecting a health status (of or relating to the individual) apparently resulting from a dispensing device administering the therapeutic component to the individual, the therapeutic component being a bioactive material.

106. The resource apportionment method of any one of METHOD CLAUSES 58-99, in which the invoking circuitry for obtaining an indication of an incentive partly based on a physical attribute of an individual and partly based on an indication of a therapeutic component available to the individual comprises:

invoking circuitry for detecting a dispensing device administering the therapeutic component to the individual via injection.

107. (Independent) A first method comprising:
invoking circuitry for performing a reception of or a transmission of one or more instructions in relation to a second method that includes at least:
invoking circuitry for selecting an indication of an incentive partly based on a category of a therapeutic material and partly based on an indication of a dispensing device administering the therapeutic material to an individual; and
transmitting the indication of the incentive responsive to the circuitry for selecting the indication of the incentive partly based on the category of the therapeutic material and partly based on the indication of the dispensing device administering the therapeutic material to the individual.

108. The first method of METHOD CLAUSE 107, wherein said second method comprises:
the resource apportionment method of any one of the above CLAUSES that depend from CLAUSE 58, the therapeutic component being the therapeutic material.

109. (Independent) A resource apportionment method comprising:
invoking circuitry for assigning a component of an incentive to an individual partly based on an indication of a therapeutic component administered to a portion of the individual and partly based on a profile of the individual; and
transmitting a result of assigning the component of the incentive to the individual.

110. The resource apportionment method of METHOD CLAUSE 109, further comprising:
performing the resource apportionment operation(s) of any one or more of the above CLAUSES that depend from CLAUSE 58.

111. (Independent) A resource apportionment method comprising:
invoking circuitry for obtaining an indication of an incentive to an individual partly based on an indication of a health status apparently resulting from a bioactive material administered to the individual and partly based on a profile of the individual; and transmitting the indication of the incentive.

112. The resource apportionment method of METHOD CLAUSE 111, further comprising:
performing the resource apportionment operation(s) of any one or more of the above CLAUSES that depend from CLAUSE 58, the therapeutic component being the bioactive material.

113. (Independent) A resource apportionment method comprising:
obtaining first data indicating a therapeutic component having a first value V1; invoking circuitry for obtaining an indication of an incentive having a second value V2>V1 and partly based on the therapeutic component and partly based on a provider of the therapeutic component; and
transmitting the indication of the incentive partly based on the therapeutic component and partly based on the provider of the therapeutic component.

114. The resource apportionment method of METHOD CLAUSE 113, further comprising:
performing the resource apportionment operation(s) of any one or more of the above CLAUSES that depend from CLAUSE 58.

115. (Independent) A resource apportionment method comprising:
invoking circuitry for obtaining an indication of an incentive to a provider of a therapeutic component and at least partly based on an objective indication that the therapeutic component has been administered to a portion of an individual; and
including the indication of the incentive to the provider of the therapeutic component in or with a message.

116. The resource apportionment method of METHOD CLAUSE 115, further comprising:
performing the resource apportionment operation(s) of any one or more of the above CLAUSES that depend from CLAUSE 58.

117. (Independent) A resource apportionment method comprising:
invoking circuitry for selecting an indication of an incentive partly based on a category of a therapeutic material and partly based on an indication of a dispensing device administering the therapeutic material to an individual; and
transmitting the indication of the incentive responsive to the circuitry for selecting the indication of the incentive partly based on the category of the therapeutic material and partly based on the indication of the dispensing device administering the therapeutic material to the individual.

118. The resource apportionment method of METHOD CLAUSE 117, further comprising:
performing the resource apportionment operation(s) of any one or more of the above METHOD CLAUSES that depend from METHOD CLAUSE 58, the therapeutic component being the therapeutic material.

119. (Independent) A resource apportionment system comprising:
means for performing the resource apportionment operation(s) of any one or more of METHOD CLAUSES 58-118.

120. (Independent) An article of manufacture comprising:
one or more physical media configured to bear a device-detectable implementation of a method including at least
obtaining an indication of an incentive partly based on a physical attribute of an individual and partly based on an indication of a therapeutic component available to the individual, a component of the incentive being an incentive to the individual; and
transmitting the indication of the incentive partly based on the physical attribute of the individual and partly based on the indication of the therapeutic component available to the individual to a putative provider of the therapeutic component.

121. The article of manufacture of CLAUSE 120, in which a portion of the one or more physical media comprises:
one or more signal-bearing media configured to transmit one or more instructions for performing the resource apportionment operation(s) of any one or more of METHOD CLAUSES 59-118.

122. (Independent) An article of manufacture comprising:
one or more physical media bearing a device-detectable output indicating an occurrence of obtaining an indication of an incentive partly based on a physical attribute of an individual and partly based on an indication of a therapeutic component available to the individual, a component of the incentive being an incentive to the individual; and
transmitting the indication of the incentive partly based on the physical attribute of the individual and partly based on the indication of the therapeutic component available to the individual to a putative provider of the therapeutic component.

123. The article of manufacture of CLAUSE 122, in which a portion of the one or more physical media comprises:
one or more signal-bearing media configured to transmit one or more instructions for performing the resource apportionment operation(s) of any one or more of METHOD CLAUSES 59-118.

124. The article of manufacture of CLAUSE 122, in which at least one of the one or more physical media comprises:

one or more signal-bearing media transmitting a portion of the device-detectable output at least partly responsive to circuitry for obtaining the indication of the incentive partly based on the physical attribute of the individual and partly based on the indication of the therapeutic component available to the individual.

125. The article of manufacture of CLAUSE 122, in which at least one of the one or more physical media comprises: one or more signal-bearing media bearing at least one signal from an implementation having at least circuitry for obtaining the indication of the incentive partly based on the physical attribute of the individual and partly based on the indication of the therapeutic component available to the individual and circuitry for transmitting the indication of the incentive partly based on the physical attribute of the individual and partly based on the indication of the therapeutic component available to the individual to a putative provider of the therapeutic component.

All of the patents and other publications referred to above are incorporated herein by reference generally—including those identified in relation to particular new applications of existing techniques—to the extent not inconsistent herewith. While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A health status improvement incentive method, comprising:
   obtaining, using a first sensor disposed at least one of in a vessel, on the vessel, or in a vicinity of the vessel, a first measurement of a physical attribute of an individual and an indication of a therapeutic component available to the individual;
   receiving an auditory indication that the indicated therapeutic component has been administered to the individual, the auditory indication obtained via at least one microphone configured as an administration-detection feature on the vessel;
   receiving an identifier of an administerer of the indicated therapeutic component to the individual;
   obtaining a second measurement of the physical attribute of the individual;
   determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual; and
   transmitting an indication of the incentive,
   wherein at least one of the obtaining, receiving, determining, or transmitting is at least partly implemented using at least one processing device.

2. A health status improvement incentive system, comprising:
   circuitry for obtaining, using a first sensor disposed at least one of in a vessel, on the vessel, or in a vicinity of the vessel, a first measurement of a physical attribute of an individual and an indication of a therapeutic component available to the individual;
   circuitry for receiving an auditory indication that the indicated therapeutic component has been administered to the individual, the auditory indication obtained via at least one microphone configured as an administration-detection feature on the vessel;
   circuitry for receiving an identifier of an administerer of the indicated therapeutic component to the individual;
   circuitry for obtaining a second measurement of the physical attribute of the individual;
   circuitry for determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual; and
   circuitry for transmitting an indication of the incentive.

3. The system of claim 2, wherein circuitry for obtaining, using a first sensor disposed at least one of in a vessel, on the vessel, or in a vicinity of the vessel, a first measurement of a physical attribute of an individual and an indication of a therapeutic component available to the individual comprises:
   circuitry for identifying at least one abnormal health status at least partly based on a particular pathology indicated by the first measurement of the physical attribute of the individual, the particular pathology treatable via the indicated therapeutic component.

4. The system of claim 2, wherein circuitry for receiving an identifier of an administerer of the indicated therapeutic component to the individual comprises:
   circuitry for receiving at least one verbal communication from the administerer of the indicated therapeutic component at least partly via the microphone of the vessel;
   circuitry for determining, at least partly via speech recognition, a unique vocal signature from the at least one verbal communication; and
   circuitry for identifying the administerer of the indicated therapeutic component at least partly based on the unique vocal signature.

5. The system of claim 2, wherein circuitry for determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual comprises:
   circuitry for determining the incentive for the administerer of the indicated therapeutic component as a linear function of at least a value of the therapeutic component.

6. The system of claim 2, wherein circuitry for determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual comprises:
   circuitry for obtaining a selection of a type of the incentive in response to input from a resource provider who is not the administerer of the therapeutic component.

7. The system of claim 3, wherein circuitry for identifying at least one abnormal health status at least partly based on a particular pathology indicated by the first measurement of the physical attribute of the individual, the particular pathology treatable via the therapeutic component comprises:
  circuitry for assigning a provider as the administerer of the therapeutic component, including at least selecting the provider at least partly based on at least one profile of the provider associated with an ability to administer the therapeutic component.

8. The system of claim 2, wherein circuitry for receiving an auditory indication that the indicated therapeutic component has been administered to the individual, the auditory indication obtained via at least one microphone configured as an administration-detection feature on the vessel comprises:
  circuitry for obtaining an indication of an inhalation of the therapeutic component as an objective indication that the therapeutic component has been administered to the individual, the therapeutic component being a bioactive material, including at least circuitry for recognizing, at least partly based on auditory pattern recognition of digitized auditory data from the microphone, inhaler usage.

9. The system of claim 2, wherein circuitry for receiving an auditory indication that the indicated therapeutic component has been administered to the individual, the auditory indication obtained via at least one microphone configured as an administration-detection feature on the vessel comprises:
  circuitry for storing a representation of the auditory indication.

10. A health status improvement incentive system, comprising:
  circuitry for obtaining, using a first sensor disposed at least one of in a bottle, on the bottle, or in a vicinity of the bottle, a first measurement of a physical attribute of an individual and an indication of a therapeutic component available to the individual;
  circuitry for receiving an indication of liquid flow from the bottle indicating that the indicated therapeutic component has been administered to the individual, the indication of liquid flow obtained via at least one transducer configured as an administration-detection feature on the bottle;
  circuitry for receiving an identifier of an administerer of the indicated therapeutic component to the individual;
  circuitry for obtaining a second measurement of the physical attribute of the individual;
  circuitry for determining an incentive, including at least one performance rating, at least partly based on an improved health status of the individual indicated by the second measurement being closer to normal than the first measurement after receiving the indication of liquid flow from the bottle indicating that the indicated therapeutic component has been administered to the individual and at least partly based on the identifier of the administerer of the indicated therapeutic component to the individual; and
  circuitry for transmitting an indication of the incentive including the at least one performance rating.

11. A health status improvement incentive computer program product, comprising:
  at least one non-transitory computer-readable medium bearing one or more instructions which, when executed by at least one processing device, cause the at least one processing device to perform one or more operations including at least:
    obtaining, using a first sensor disposed at least one of in a vessel, on the vessel, or in a vicinity of the vessel, a first measurement of a physical attribute of an individual and an indication of a therapeutic component available to the individual;
    receiving an auditory indication that the indicated therapeutic component has been administered to the individual, the auditory indication obtained via at least one microphone configured as an administration-detection feature on the vessel;
    receiving an identifier of an administerer of the indicated therapeutic component to the individual;
    obtaining a second measurement of the physical attribute of the individual;
    determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual; and
    transmitting an indication of the incentive.

12. The system of claim 2, wherein circuitry for obtaining a second measurement of the physical attribute of the individual comprises:
  circuitry for obtaining a second measurement of the physical attribute of the individual indicative of an apparent effect of the indicated therapeutic component on the individual, the apparent effect of the indicated therapeutic component on the individual associated with compliance with a therapeutic regimen including at least the indicated therapeutic component for treating at least one pathology indicated by the first measurement of the physical attribute of the individual.

13. The system of claim 2, wherein circuitry for determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual comprises:
  circuitry for determining the incentive in response to an indication of a selection of an administration-detection-featured vessel for dispensing of the indicated therapeutic component instead of a vessel without an administration detection feature.

14. The system of claim 2, wherein circuitry for receiving an auditory indication that the indicated therapeutic component has been administered to the individual, the auditory indication obtained via at least one microphone configured as an administration-detection feature on the vessel comprises:
  circuitry for receiving the indication that the indicated therapeutic component has been administered to the individual at least partly based on the microphone and at least partly based on a sensor of the administration-detection-featured vessel indicating change in a weight of a content of the administration-detection-featured vessel.

15. The system of claim 2, wherein circuitry for receiving an auditory indication that the indicated therapeutic component has been administered to the individual, the auditory indication obtained via at least one microphone configured as an administration-detection feature on the vessel comprises:
   circuitry for receiving the indication that the indicated therapeutic component has been administered to the individual at least partly based on the microphone of the vessel detecting one or more auditory indications of a movement of the vessel.

16. The system of claim 2, wherein circuitry for receiving an auditory indication that the indicated therapeutic component has been administered to the individual, the auditory indication obtained via at least one microphone configured as an administration-detection feature on the vessel comprises:
   circuitry for receiving an indication of time data associated with movement of the vessel; and
   circuitry for transmitting an indication to the administerer of the indicated therapeutic component of a time for subsequent administration of the indicated therapeutic component at least partly based on the indication of time data associated with movement of the vessel.

17. The system of claim 2, wherein circuitry for receiving an identifier of an administerer of the indicated therapeutic component to the individual comprises:
   circuitry for receiving one or more photographic images from at least one image sensor of the vessel; and
   circuitry for recognizing the identity of the administerer of the indicated therapeutic component at least partly based on image recognition of at least a portion of the received one or more photographic images.

18. The system of claim 2, wherein circuitry for receiving an auditory indication that the indicated therapeutic component has been administered to the individual, the auditory indication obtained via at least one microphone configured as an administration-detection feature on the vessel comprises:
   circuitry for receiving digitized auditory data from the microphone of the vessel; and
   circuitry for recognizing, at least partly via auditory pattern recognition of at least a portion of the received digitized auditory data, administration of the indicated therapeutic component to a portion of an individual.

19. The system of claim 2, wherein circuitry for receiving an auditory indication that the indicated therapeutic component has been administered to the individual, the auditory indication obtained via at least one microphone configured as an administration-detection feature on the vessel comprises:
   circuitry for receiving digitized auditory data from one or more sensors of a wearable device associated with the administerer and transmitted via the vessel; and
   circuitry for recognizing, at least partly via auditory pattern recognition of at least a portion of the received digitized auditory data, administration of the indicated therapeutic component to a portion of an individual.

20. The system of claim 7, wherein circuitry for assigning a provider as the administerer of the therapeutic component, including at least selecting the provider at least partly based on at least one profile of the provider associated with an ability to administer the therapeutic component comprises:
   circuitry for assigning a provider as the administerer of the therapeutic component at least partly based on an identification of the individual as at risk for noncompliance with a treatment regimen associated with treatment of the particular pathology at least partly based on at least one severity level of the particular pathology of the individual for which the therapeutic component is to be administered, the at least one severity level determined at least partly via the first measurement.

21. The system of claim 7, wherein circuitry for assigning a provider as the administerer of the therapeutic component, including at least selecting the provider at least partly based on at least one profile of the provider associated with an ability to administer the therapeutic component comprises:
   circuitry for assigning a provider as the administerer of the therapeutic component at least partly based on identifying the individual as apparently at risk for noncompliance with a treatment regimen associated with treatment of the particular pathology at least partly based on a diagnosed cognitive deficiency indicated at least partly by the first measurement of the physical attribute of the individual.

22. The system of claim 2, wherein circuitry for receiving an auditory indication that the indicated therapeutic component has been administered to the individual, the auditory indication obtained via at least one microphone configured as an administration-detection feature on the vessel comprises:
   circuitry for receiving the indication originating from at least one of one or more bottles, one or more tubes, or one or more syringes suitable for handling the therapeutic component.

23. The system of claim 2, wherein circuitry for determining an incentive at least partly based on an improved health status of the individual indicated by the second measurement being closer to normal than the first measurement after receiving the auditory indication that the indicated therapeutic component has been administered to the individual and at least partly based on the identifier of the administerer of the indicated therapeutic component to the individual comprises:
   circuitry for determining the incentive for the administerer of the indicated therapeutic component at least partly based on at least one of a financial importance of having a treatment indicated by the first measurement of the individual performed promptly or a severity of a condition indicated by the first measurement of the individual.

24. The system of claim 10, wherein circuitry for receiving an indication of liquid flow from the bottle indicating that the indicated therapeutic component has been administered to the individual, the indication of liquid flow obtained via at least one transducer configured as an administration-detection feature on the bottle comprises:
   circuitry for receiving an indication of liquid flow from the bottle indicating that the indicated therapeutic component has been administered to the individual, the indication of liquid flow obtained via at least one transducer configured to detect pressure on at least one of a valve, cap, or cover of the bottle.

25. The system of claim 10, wherein circuitry for receiving an indication of liquid flow from the bottle indicating that the indicated therapeutic component has been administered to the individual, the indication of liquid flow obtained via at least one transducer configured as an administration-detection feature on the bottle comprises:
   circuitry for receiving an indication of nutraceutical liquid flow from the bottle indicating that the indicated therapeutic component has been administered to the individual, the indication of liquid flow obtained via at least one transducer configured to detect mouth pressure in association with direct administration of the nutraceutical liquid into a mouth of the individual.

26. The system of claim 10, wherein circuitry for obtaining, using a first sensor disposed at least one of in a bottle, on the bottle, or in a vicinity of the bottle, a first measurement of a physical attribute of an individual and an indication of a therapeutic component available to the individual comprises:
- circuitry for obtaining, using a first sensor disposed at least one of in a bottle, on the bottle, or in a vicinity of the bottle, a first measurement of a physical attribute of a child and an indication of a therapeutic component available to the child.

27. The system of claim 10, wherein circuitry for transmitting an indication of the incentive including the at least one performance rating comprises:
- circuitry for transmitting an indication of the incentive including at least one of a policy rate reduction, a discount on the therapeutic component, or a rebate in association with the at least one performance rating.

* * * * *